(12) United States Patent
Albrecht et al.

(10) Patent No.: US 10,202,354 B2
(45) Date of Patent: Feb. 12, 2019

(54) THERAPEUTIC COMPOUNDS AND USES THEREOF

(71) Applicants: GENENTECH, INC., South San Francisco, CA (US); CONSTELLATION PHARMACEUTICALS, INC., Cambridge, MA (US)

(72) Inventors: Brian K. Albrecht, Cambridge, MA (US); Alexandre Cote, Cambridge, MA (US); Victor Gehling, Cambridge, MA (US); Vickie Hsiao-Wei Tsui, South San Francisco, CA (US); James Richard Jr. Kiefer, South San Francisco, CA (US); Jun Liang, South San Francisco, CA (US); Steven Magnuson, South San Francisco, CA (US); Christopher G. Nasveschuk, Cambridge, MA (US); F. Anthony Romero, South San Francisco, CA (US); Alexander M. Taylor, Cambridge, MA (US)

(73) Assignees: GENENTECH, INC., South San Francisco, CA (US); CONSTELLATION PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 15/643,805

(22) Filed: Jul. 7, 2017

(65) Prior Publication Data

US 2018/0022707 A1 Jan. 25, 2018

Related U.S. Application Data

(63) Continuation of application No. PCT/US2016/012588, filed on Jan. 8, 2016.

(60) Provisional application No. 62/101,933, filed on Jan. 9, 2015.

(51) Int. Cl.
| | | |
|---|---|---|
| *C07D 233/44* | (2006.01) | |
| *C07D 235/02* | (2006.01) | |
| *C07D 401/04* | (2006.01) | |
| *C07D 401/12* | (2006.01) | |
| *C07D 403/12* | (2006.01) | |
| *C07D 409/12* | (2006.01) | |
| *C07D 413/12* | (2006.01) | |
| *C07D 417/12* | (2006.01) | |
| *C07D 487/08* | (2006.01) | |

(52) U.S. Cl.
CPC ......... *C07D 233/44* (2013.01); *C07D 235/02* (2013.01); *C07D 401/04* (2013.01); *C07D 401/12* (2013.01); *C07D 403/12* (2013.01); *C07D 409/12* (2013.01); *C07D 413/12* (2013.01); *C07D 417/12* (2013.01); *C07D 487/08* (2013.01)

(58) Field of Classification Search
CPC .. C07D 233/44; C07D 235/02; C07D 401/04; C07D 401/12; C07D 403/12; C07D 409/12; C07D 413/12; C07D 417/12; C07D 487/08
See application file for complete search history.

(56) References Cited

FOREIGN PATENT DOCUMENTS

| WO | 2014027053 A1 | 2/2014 |
|---|---|---|
| WO | 2014151945 A1 | 9/2014 |
| WO | 2016112251 A1 | 7/2016 |

OTHER PUBLICATIONS

He, et al., "KDM2b/JHDM1b, an H3K36me2-specific demethylase, is required for initiation and maintenance of acute myeloid leukemia", Blood 117(14), 3869-3880 (2011).

(Continued)

*Primary Examiner* — Bruck Kifle
(74) *Attorney, Agent, or Firm* — Viksnins Harris Padys Malen LLP

(57) ABSTRACT

The present invention relates to compounds useful as inhibitors of one or more histone demethylses, such as KDM2b. The invention also provides pharmaceutically acceptable compositions comprising compounds of the present invention and methods of using said compositions in the treatment of various disorders.

16 Claims, No Drawings

(56) References Cited

OTHER PUBLICATIONS

He, et al., "The H3K36 demethylase Jhdm1b/Kdm2b regulates cell proliferation and senescence through p15Ink4b", Nature Structural & Molecular Biology 15(11), 1169-1175, Suppl Figures, 6 pages (2008).
Kottakis, et al., "NDY1/KDM2B Functions as a Master Regulator of Polycomb Complexes and Controls Self-Renewal of Breast Cancer Stem Cells", Cancer Res 74(14), 3935-3946 (2014).
Patent Cooperation Treaty, International Searching Authority, Search Report and Written Opinion for PCT/US2016/012588, 12 pages, dated Apr. 8, 2016.
Pfau, et al., "Members of a family of JmjC domain-containing oncoproteins immortalize embryonic fibroblasts via a JmjC domain-dependent process", PNAS 105(6), 1907-1912 (2008).
Suzuki, et al., "Identification of the KDM2/7 Histone Lysine Demethylase Subfamily Inhibitor and its Antiproliferative Activity", J Med Chem 56, 7222-7231 (2013).
Tzatsos, et al., "KDM2B promotes pancreatic cancer via Polycomb-dependent and -independent transcriptional programs", Journal of Clinical Investigation 123(2), 727-739, Supplemental Information 20 pages (2013).
Tzatsos, et al., "Ndy1/KDM2B immortalizes mouse embryonic fibroblasts by repressing the Ink4a/Arf locus", PNAS 106(8), 2641-2646, Supporting Information, 11 pages (2009).
Wagner, et al., "KDM2A promotes lung tumorigenesis by epigenetically enhancing ERK1/2 signaling", Journal of Clinical Investigation, doi:10.1172/JCI68642, 44 pages (2013).
Chem Abstracts, Chemistry Abstract Services Registry, 75 pages, Sep. 2014.

THERAPEUTIC COMPOUNDS AND USES THEREOF

CROSS-REFERENCE TO RELATED APPLICATION(S)

This patent application is a continuation of international application serial no. PCT/US2016/012588, filed Jan. 8, 2016, which claims the benefit of priority of U.S. provisional application Ser. No. 62/101,933, filed Jan. 9, 2015, which applications are herein incorporated by reference.

TECHNICAL FIELD

Compounds useful as inhibitors of histone demethylases, such as KDM2b are provided.

BACKGROUND

Packaging the 3 billion nucleotides of the human genome into the nucleus of a cell requires tremendous compaction. To accomplish this feat, DNA in our chromosomes is wrapped around spools of proteins called histones to form dense repeating protein/DNA polymers known as chromatin. Far from serving as mere packaging modules, chromatin templates form the basis of a newly appreciated and fundamentally important set of gene control mechanisms termed epigenetic regulation. By conferring a wide range of specific chemical modifications to histones and DNA, epigenetic regulators modulate the structure, function, and accessibility of our genome, thereby exerting a tremendous impact on gene expression. Hundreds of epigenetic effectors have recently been identified, many of which are chromatin-binding or chromatin-modifying enzymes. Significantly, an increasing number of these enzymes have been associated with a variety of disorders such as cancer. Thus, therapeutic agents directed against this emerging class of gene regulatory enzymes promise new approaches to the treatment of human diseases.

There is currently a need for compounds that inhibit of KDM2 demethylases for treating hyperproliferative diseases.

SUMMARY OF THE INVENTION

One aspect provides a compound of formula (I):

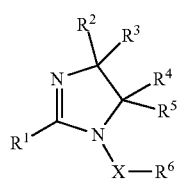

(I)

or a salt thereof, wherein:

X is C(=O) or S(O)$_2$;

R$^1$ is selected from the group consisting of N-linked piperazinyl, N-linked piperidine, and N-linked diazabicyclo[3.2.1]octane, wherein R$^1$ is optionally substituted with one or more groups independently selected from C$_{1-6}$alkyl, C$_{2-6}$alkenyl, C$_{2-6}$alkynyl, aryl, 3-10 membered heterocycle, and C$_{3-8}$cycloalkyl, wherein any aryl, 3-10 membered heterocycle, and C$_{3-8}$cycloalkyl is optionally substituted with one or more groups independently selected from halo, C$_{1-4}$alkyl, C$_{2-4}$alkenyl, and C$_{2-4}$alkynyl, and wherein any C$_{1-6}$alkyl, C$_{2-6}$alkenyl, and C$_{2-6}$alkynyl is optionally substituted with one or more groups independently selected from halo, C$_{1-4}$alkoxy, and C$_{3-8}$cycloalkyl that is optionally substituted with C$_{1-6}$alkyl;

R$^2$ and R$^3$ are each independently selected from H, C$_{1-6}$alkyl, C$_{2-6}$alkenyl, C$_{2-6}$alkynyl, and C$_{3-8}$cycloalkyl, wherein any C$_{1-6}$alkyl, C$_{2-6}$alkenyl, C$_{2-6}$alkynyl, and C$_{3-8}$cycloalkyl is optionally substituted with one or more groups independently selected from halo and oxo; or R$^2$ and R$^3$ taken together with the carbon to which they are attached form a 3-, 4-, 5-, or 6-membered carbocyclic ring that is optionally substituted with one or more groups independently selected from halo, oxo, C$_{1-4}$alkyl, C$_{2-4}$alkenyl, and C$_{2-4}$alkynyl;

R$^4$ and R$^5$ are each independently selected from H, C$_{1-6}$alkyl, C$_{2-6}$alkenyl, C$_{2-6}$alkynyl, and C$_{3-8}$cycloalkyl, wherein any C$_{1-6}$alkyl, C$_{2-6}$alkenyl, C$_{2-6}$alkynyl, and C$_{3-8}$cycloalkyl is optionally substituted with one or more groups independently selected from halo and oxo; or R$^4$ and R$^5$ taken together with the carbon to which they are attached form a 3-, 4-, 5-, or 6-membered carbocyclic ring that is optionally substituted with one or more groups independently selected from halo, oxo, C$_{1-4}$alkyl, C$_{2-4}$alkenyl, and C$_{2-4}$alkynyl;

R$^6$ is a 5-10 membered heteroaryl, 5-10 membered heterocycle, or a 6-10 membered aryl, which 5-10 membered heteroaryl, 5-10 membered heterocycle, and 6-10 membered aryl is optionally substituted with one or more groups independently selected from the group consisting of C$_{1-6}$alkyl, C$_{2-6}$alkenyl, C$_{2-6}$alkynyl, carbocycle, heterocycle, aryl, heteroaryl, halo, —NO$_2$, —N(R$^b$)$_2$, —CN, —C(O)—N(R$^b$)$_2$, —S(O)—N(R$^b$)$_2$, —S(O)$_2$—N(R$^b$)$^2$, —O—R$^b$, —S—R$^b$, —O—C(O)—R$^b$, —C(O)—R$^b$, —C(O)—OR$^b$, —S(O)—R$^b$, —S(O)$_2$—R$^b$, —N(R$^b$)—C(O)—R$^b$, —N(R$^b$)—S(O)—R$^b$, —N(R$^b$)—C(O)—N(R$^b$)$_2$, and —N(R$^b$)—S(O)$_2$—R$^b$; wherein each C$_{1-6}$alkyl, C$_{2-6}$alkenyl, C$_{2-6}$alkynyl, carbocycle, heterocycle, aryl, and heteroaryl is optionally substituted with one or more groups independently selected from the group consisting of halo, —NO$_2$, —N(R$^b$)$_2$, —CN, —C(O)—N(R$^b$)$_2$, —S(O)—N(R$^b$)$_2$, —S(O)$_2$—N(R$^b$)$_2$, —O—R$^b$, —S—R$^b$, —O—C(O)—R$^b$, —C(O)—R$^b$, —C(O)—OR$^b$, —S(O)—R$^b$, —S(O)$_2$—R$^b$, —N(R$^b$)—C(O)—R$^b$, —N(R$^b$)—S(O)—R$^b$, —N(R$^b$)—C(O)—N(R$^b$)$_2$, —N(R$^b$)—S(O)$_2$—R$^b$, and C$_{1-6}$alkyl that is optionally substituted with one or more groups independently selected from halo; each R$^b$ is independently selected from the group consisting of hydrogen, C$_{1-6}$alkyl, C$_{2-6}$alkenyl, aryl, and C$_{2-6}$alkynyl, wherein each C$_{1-6}$alkyl, C$_{2-6}$alkenyl, aryl, and C$_{2-6}$alkynyl is optionally substituted with one or more groups independently selected from the group consisting of halo, —N(R$^c$)$_2$, —CN, —C(O)—N(R$^c$)$_2$, —S(O)—N(R$^c$)$_2$, —S(O)$_2$—N(R$_c$)$_2$, —O—R$^c$, —S—R$^c$, —O—C(O)—R$^c$, —C(O)—R$^c$, —C(O)—OR$^c$, —S(O)—R$^c$, —S(O)$_2$—R$^c$, —N(R$^c$)—C(O)—R$^c$, —N(R$^c$)—S(O)—R$^c$, —N(R$^c$)—C(O)—N(R$^c$)$_2$, and —N(R$^c$)—S(O)$_2$-R$^c$; or two R$^b$ are taken together with the nitrogen to which they are attached to form a pyrrolidino, piperidino, or piperazino ring; and each R$^c$ is independently selected from the group consisting of hydrogen, C$_{1-6}$alkyl, C$_{2-6}$alkenyl, and C$_{2-6}$alkynyl, wherein each C$_{1-6}$alkyl, C$_{2-6}$alkenyl, and C$_{2-6}$alkynyl is optionally substituted with one or more groups independently selected from the group consisting of oxo, halo, amino, hydroxy, and C$_{1-6}$alkoxy; or two R$^c$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo.

Another aspect includes a composition, comprising a compound of formula (I), or a pharmaceutically acceptable salt thereof, and a pharmaceutically acceptable adjuvant, carrier, or vehicle.

Another aspect includes a method of treating a disease associated with KDM2b activity, comprising administering an therapeutically effective amount of a compound of formula (I), or a pharmaceutically acceptable salt thereof, to a patient in need thereof.

Another aspect includes the use of a compound of formula (I), or a pharmaceutically acceptable salt thereof, in therapy.

Another aspect includes the use of a compound of formula (I), or a pharmaceutically acceptable salt thereof, in treating a disease associated with KDM2b activity.

Another aspect includes the use of a compound of formula (I), or a pharmaceutically acceptable salt thereof, in the manufacture of a medicament for the treatment of a disease associated with KDM2b activity.

Another aspect includes a method of increasing the efficacy of a cancer treatment comprising a cancer therapy agent, comprising administering to a patient (a) an effective amount of a compound of formula (I), or a pharmaceutically acceptable salt thereof, and (b) an effective amount of the cancer therapy agent.

Another aspect includes a method of treating an individual with cancer who has an increased likelihood of developing resistance to a cancer therapy agent comprising administering to the individual (a) an effective amount of a compound of formula (I), or a pharmaceutically acceptable salt thereof, and (b) an effective amount of the cancer therapy agent.

Another aspect includes a method of treating cancer in a mammal in need thereof, comprising administering to the mammal, a compound of formula (I), or a pharmaceutically acceptable salt thereof.

Another aspect includes a method of inducing differentiation of a cancer stem/progenitor cell(s) in a mammal in need thereof, comprising administering to the mammal, an effective amount of a compound of formula (I), or a pharmaceutically acceptable salt thereof.

Another aspect includes a method of reducing activity of a cancer stem/progenitor cell(s) in a mammal in need thereof, comprising administering to the mammal, an effective amount of a compound of formula (I), or a pharmaceutically acceptable salt thereof.

Another aspect includes a method of depleting a cancer stem/progenitor cell in a mammal in need thereof, comprising administering to the mammal, an effective amount a compound of formula (I), or a pharmaceutically acceptable salt thereof. Another aspect includes a method of decreasing cancer initiation in a mammal in need thereof, comprising administering to the mammal, an effective amount of a compound of formula (I), or a pharmaceutically acceptable salt thereof.

Another aspect includes a compound of formula (I), or a pharmaceutically acceptable salt thereof for the therapeutic or prophylactic treatment of cancer. Another aspect includes a compound of formula (I), or a pharmaceutically acceptable salt thereof for inducing differentiation of a cancer stem/progenitor cell(s).

Another aspect includes a compound of formula (I), or a pharmaceutically acceptable salt thereof for reducing activity of a cancer stem/progenitor cell(s).

Another aspect includes a compound of formula (I), or a pharmaceutically acceptable salt thereof for depleting a cancer stem/progenitor cell.

Another aspect includes a compound of formula (I), or a pharmaceutically acceptable salt thereof for decreasing cancer initiation.

Another aspect includes the use of a compound of formula (I), or a pharmaceutically acceptable salt thereof to prepare a medicament for treating cancer in a mammal.

Another aspect includes the use of a compound of formula (I), or a pharmaceutically acceptable salt thereof to prepare a medicament for inducing differentiation of a cancer stem/progenitor cell(s) in a mammal.

Another aspect includes the use of a compound of formula (I), or a pharmaceutically acceptable salt thereof to prepare a medicament for reducing activity of a cancer stem/progenitor cell(s) in a mammal.

Another aspect includes the use of a compound of formula (I), or a pharmaceutically acceptable salt thereof to prepare a medicament for depleting a cancer stem/progenitor cell in a mammal.

Another aspect includes the use of a compound of formula (I), or a pharmaceutically acceptable salt thereof to prepare a medicament for decreasing cancer initiation in a mammal.

Another aspect includes a method of treating cancer in an individual in need thereof, comprising administering an effective amount of a KDM2 inhibitor to the individual.

Another aspect includes a method of inducing differentiation of a cancer stem/progenitor cell(s) in an individual in need thereof, comprising administering an effective amount of a KDM2 inhibitor to the individual.

Another aspect includes a method of reducing activity of a cancer stem/progenitor cell(s) in an individual in need thereof, comprising administering an effective amount of a KDM2 inhibitor to the individual.

Another aspect includes a method of depleting a cancer stem/progenitor cell population in an individual in need thereof, comprising administering an effective amount of a KDM2 inhibitor to the individual.

Another aspect includes a method of decreasing cancer initiation in an individual in need thereof, comprising administering an effective amount of a KDM2 inhibitor to the individual.

Another aspect includes a processes and synthetic intermediates that are useful for preparing a compound of formula (I), or a salt thereof.

Another aspect includes compounds for the study of histone demethylases, such as KDM2b, the study of intracellular signal transduction pathways mediated by such histone demethylases, and the comparative evaluation of modulators of these demethylases.

DETAILED DESCRIPTION

Definitions

Definitions of specific functional groups and chemical terms are described in more detail below. Chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry, Thomas Sorrell, University Science Books, Sausalito,* 1999; Smith and March *March's Advanced Organic Chemistry,* 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are included.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C- enriched carbon are included. Such compounds are useful, for example, as analytical tools, as probes in biological assays, or as therapeutic agents.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, IN 1972).

The term "a compound as described herein" includes the compounds described in the Examples herein and salts and free-bases thereof, as well as compounds of formula (I) and salts thereof.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

As used herein a "direct bond" or "covalent bond" refers to a single, double or triple bond. In certain embodiments, a "direct bond" or "covalent bond" refers to a single bond.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, alkynyl groups, and hybrids thereof such as (cycloalkyl) alkyl, (cycloalkenyl)alkyl or (cycloalkyl)alkenyl.

The term "unsaturated", as used herein, means that a moiety has one or more units of unsaturation.

The terms "cycloaliphatic", "carbocycle", "carbocyclyl", "carbocyclo", or "carbocyclic", used alone or as part of a larger moiety, refer to a saturated or partially unsaturated cyclic aliphatic monocyclic, bicyclic, or spior ring systems, as described herein, having from 3 to 10 members, wherein the aliphatic ring system is optionally substituted as described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons.

The term "alkyl," as used herein, refers to a monovalent saturated, straight- or branched-chain hydrocarbon radical derived from an aliphatic moiety containing between one and six carbon atoms by removal of a single hydrogen atom. In some embodiments, alkyl contains 1-5 carbon atoms. In another embodiment, alkyl contains 1-4 carbon atoms. In still other embodiments, alkyl contains 1-3 carbon atoms. In yet another embodiment, alkyl contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. In certain embodiments, alkenyl contains 2-6 carbon atoms. In certain embodiments, alkenyl contains 2-5 carbon atoms. In some embodiments, alkenyl contains 2-4 carbon atoms. In another embodiment, alkenyl contains 2-3 carbon atoms. Alkenyl groups include, for example, ethenyl ("vinyl"), propenyl ("allyl"), butenyl, 1-methyl-2-buten-1 yl, and the like.

The term "alkynyl," as used herein, refers to a monovalent group derived from a straight- or branched-chain aliphatic moiety having at least one carbon-carbon triple bond by the removal of a single hydrogen atom. In certain embodiments, alkynyl contains 2-6 carbon atoms. In certain embodiments, alkynyl contains 2-5 carbon atoms. In some embodiments, alkynyl contains 2-4 carbon atoms. In another embodiment, alkynyl contains 2-3 carbon atoms. Representative alkynyl groups include, but are not limited to, ethynyl, 2-propynyl ("propargyl"), 1-propynyl, and the like.

The term "aryl" used alone or as part of a larger moiety as in "aralkyl", "aralkoxy", or "aryloxyalkyl", refers to monocyclic and bicyclic ring systems having a total of 6,7,8,9, or 10 ring members, wherein at least one ring in the system is aromatic. The term "aryl" may be used interchangeably with the term "aryl ring". In certain embodiments, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic carbocyclic rings, such as indanyl, phthalimidyl, naphthimidyl, phenantriidinyl, or tetrahydronaphthyl, and the like. An aryl group may be attached at any atom in the ring system.

The terms "heteroaryl" and "heteroar-", used alone or as part of a larger moiety, e.g., "heteroaralkyl", or "heteroaralkoxy", refer to groups having 5 to 10 ring atoms, preferably 5,6, or 9 ring atoms; having 6,10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings. A heteroaryl group may be attached at any atom in the ring system. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted with one or more oxo (=O) groups. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl or cycloaliphatic rings, such as indolinyl, 3H-indolyl, chromanyl, phenanthridinyl, 2-azabicyclo[2.2.1]heptanyl, octahydroindolyl, or tetrahydroquinolinyl, where the radical or point of attachment is any atom in the heterocyclyl ringsystem. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms but is not aromatic. The term "partially unsaturated" is intended to encompass rings having multiple sites of unsaturation, but is not intended to include aryl or heteroaryl moieties, as herein defined.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

As used herein, the term "inhibitor" refers to a compound that binds to and inhibits a KDM2b enzyme with measurable affinity and activity. In certain embodiments, an inhibitor has an $IC_{50}$ and/or binding constant of less about 50 μM, less than about 1 μM, less than about 500 nM, less than about 100 nM, or less than about 10 nM.

The terms "measurable affinity" and "measurably inhibit," as used herein, refer to a measurable reduction in activity of a KDM2b enzyme between: (i) a sample comprising a compound as described herein and such KDM2b enzyme, and (ii) an equivalent sample comprising such KDM2b enzyme, in the absence of said compound.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, aralphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, tromethamine, dicyclohexylamine, choline, and caffeine.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "solvate" refers to an association or complex of one or more solvent molecules and a compound or pharmaceutically acceptable salt thereof as described herein. Examples of solvents include water, isopropanol, ethanol, methanol, DMSO, ethyl acetate, acetic acid and ethanolamine. The term "hydrate" refers to the complex where the solvent molecule is water.

"Therapeutically effective amount" refers to an amount of a a compound or pharmaceutically acceptable salt thereof as described herein that (i) treats the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. For cancer therapy, efficacy can, for example, be measured by assessing the time to disease progression (TTP) and/or determining the response rate (RR). In the case of immunological disorders, the therapeutic effective amount is an amount sufficient to decrease or alleviate an allergic disorder, the symptoms of an autoimmune and/or inflammatory disease, or the symptoms of an acute inflammatory reaction (e.g. asthma). In some embodiments, a therapeutically effective amount is an amount of a chemical entity described herein sufficient to significantly decrease the activity or number of drug tolerant or drug tolerant persisting cancer cells.

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include one or more of preventing occurrence or recurrence of disease, alleviation of symptoms, diminishment of any direct or indirect pathological consequences of the disease, stabilized (i.e., not worsening) state of disease, preventing metastasis, decreasing the rate of disease progression, amelioration or palliation of the disease state, prolonging survival as compared to expected survival if not receiving treatment and remission or improved prognosis. In certain embodiments, a compound as described herein is used to delay development of a disease or disorder or to slow the progression of a disease or disorder. Those individuals in need of treatment include those already with the condition or disorder as well as those prone to have the condition or disorder, (for example, through a genetic mutation or abberent expression of a gene or protein) or those in which the condition or disorder is to be prevented.

When $R^1$ is an "N-linked piperazinyl, N-linked piperidine, or N-linked diazabicyclo[3.2.1]octane", the $R^1$ group is linked to the 2-position of the imidazole ring shown in formula (I) through a nitrogen atom.

Examplary Values

In one embodiment the compound is a compound of formula (Ia):

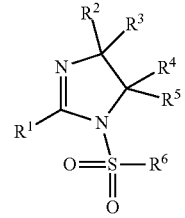

or a salt thereof

In one embodiment the compound is a compound of formula (Ia) or a salt thereof: provided that:
when $R^1$ is an optionally substituted piperazin-1-yl; and
$R^2$-$R^5$ are each H;
then $R^6$ is not: 2,5-dimethoxyphenyl, 3,4-dimethylphenyl, 4-ethylphenyl, 4-bromophenyl, 2,4-dimethylphenyl, 4-ethoxyphenyl, 4-chloro-2-methoxyphenyl, 4-propylphenyl, 2-(trifluoromethyl)phenyl, 2,4,5-trimethylphenyl, 3-methylphenyl, 2-(methylcarbonylamino)-5-methylphenyl, 4-chlorophenyl, 4-(isopropyl)phenyl, 3-chloro-4-fluorophenyl, 4-cyclohexylphenyl, 4-(isobutyl)phenyl, 2-methylphenyl, 4-acetylphenyl, 4-(tert-butyl)phenyl, 4-(methylcarbonylamino) phenyl, 2-fluorophenyl, phenyl, 3,5-dimethylphenyl, 4-methylphenyl, 5-fluoro-2-methylphenyl, 4-fluorophenyl, 5,6,7,8-tetrahydronaphthlene-2-yl, 2,4,6-trimethylphenyl, 3-chloro-4-fluorophenyl, 4-(ethoxycarbonylamino)phenyl, 2,5-difluorophenyl, 2-chlorophenyl, 3-chlorophenyl, 4-methoxyphenyl, 2-methoxy-4-chlorophenyl, or

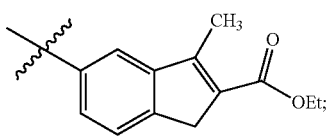 [SMILES: *c1ccc2c(c1)C(C)=C(C(=O)OCC)C2]

and provided that when:
$R^1$ is 4-benzylpiperidino; and
$R^2$-$R^5$ are each H;
then $R^6$ is not 4-methylphenyl.
In one embodiment the comopund is a compound of formula (Ia) or a salt thereof provided that:
when $R^6$ is an ontionally substituted phenyl or has the formula:

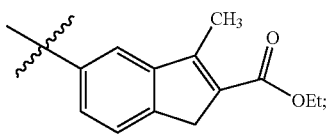 [SMILES: *c1ccc2c(c1)C(C)=C(C(=O)OCC)C2]

and
$R^2$-$R^5$ are each H;
then $R^1$ is not 4-benzylpiperidino or piperazin-1-yl that is substituted at the 4-position with a group selected from the group consisting of, methyl, ethyl, 3-chlorophenyl, 4-fluorophenyl, 2-chlorophenyl, 2-fluorophenyl, 4-methoxyphenyl, and 2-methoxyphenyl.

In one embodiment the compound is a compound of formula (Ib):

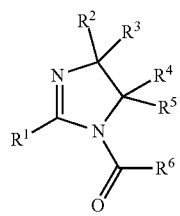

or a salt thereof.

In one embodiment the compound is a compound of formula (Ib) or a salt thereof: provided that:
when $R^1$ is an optionally substituted piperazin-1-yl; and
$R^2$-$R^5$ are each H;
then $R^6$ is not: 2-methoxyphenyl, 2-methylphenyl, 2-chlorophenyl, 4-ethylphenyl, 3,5-dimethylphenyl, 2,3-dimethoxyphenyl, 4-methylphenyl, 4-ethoxyphenyl, 3,4-dimethylphenyl, 2,3-benzodioxazol-5-yl, 3-chlorophenyl, 3-methylphenyl, 4-methoxyphenyl, 3,5-dimethoxyphenyl, 2-fluorophenyl, 4-fluorophenyl, 3-fluoro-4-methylphenyl, 2,3-dimethoxyphenyl, 4-(tert-butyl)phenyl, 3,4,5-trimethoxyphenyl, 2-bromophenyl, 4-chlorophenyl, 2-trifluoromethylphenyl, phenyl, 4-bromophenyl, 3,4-difluorophenyl, 2,6-difluorophenyl, 2-(dimethylamino)phenyl, 4-ethoxyphenyl, 3-fluoro-4-methylphenyl, 2,4-dimethylphenyl, 4-(trifluoromethyl)phenyl, 4-(dimethylamino)phenyl, 3-methoxyphenyl, 2-methoxy-4-chloro, or 3-(dimethylamino)phenyl.

In one embodiment the compound is a compound of formula (Ib) or a salt thereof: provided that: when $R^6$ is an optionally substituted phenyl or 2,3-benzodioxazol-5-yl; and
$R^2$-$R^5$ are each H;
then $R^1$ is not piperazin-1-yl that is substituted at the 4-position with a group selected from the group consisting of methyl, ethyl, 3-chlorophenyl, 2-fluorophenyl, 3-chlorophenyl, and 4-fluorophenyl.

In one embodiment $R^1$ is N-linked piperazinyl that is optionally substituted.

In one embodiment $R^1$ is, N-linked piperidine that is optionally substituted.

In one embodiment $R^1$ is N-linked diazabicyclo[3.2.1]octane that is optionally substituted.

In one embodiment $R^1$ is a piperazin-1-yl, which piperazin-1-yl is optionally substituted with one or more groups independently selected from $C_{1-6}$alkyl, $C_{2-6}$alkenyl, $C_{2-6}$alkynyl, aryl, and $C_{3-8}$cycloalkyl, wherein any aryl and $C_{3-8}$cycloalkyl is optionally substituted with one or more groups independently selected from halo, $C_{1-4}$alkyl, $C_{2-4}$alkenyl, and $C_{2-4}$alkynyl, and wherein any $C_{1-6}$alkyl, $C_{2-6}$alkenyl, and $C_{2-6}$alkynyl is optionally substituted with one or more groups independently selected from halo, $C_{1-4}$alkoxy, and $C_{3-8}$cycloalkyl.

In one embodiment $R^1$ is selected from the group consisting of N-linked piperazinyl, N-linked piperidine, and N-linked diazabicyclo[3.2.1]octane, wherein $R^1$ is optionally substituted with one or more groups independently selected from $C_{1-6}$alkyl, aryl, and $C_{3-8}$cycloalkyl, wherein any aryl and $C_{3-8}$cycloalkyl is optionally substituted with one or more groups independently selected from halo and $C_{1-4}$alkyl, and wherein any $C_{1-6}$alkyl is optionally substituted with one or more groups independently selected from halo, $C_{1-4}$alkoxy, and $C_{3-8}$cycloalkyl In one embodiment $R^1$ is a piperazin-1-yl that is substituted at the 4-position with a group selected from $C_{1-6}$alkyl, aryl, and $C_{3-8}$cycloalkyl, wherein any aryl and $C_{3-8}$cycloalkyl is optionally substituted with one or more groups independently selected from halo and $C_{1-4}$alkyl, and wherein any $C_{1-6}$alkyl is optionally substituted with one or more groups independently selected from halo, $C_{1-4}$alkoxy, and $C_{3-8}$cycloalkyl.

In one embodiment $R^1$ is selected from the group consisting of:

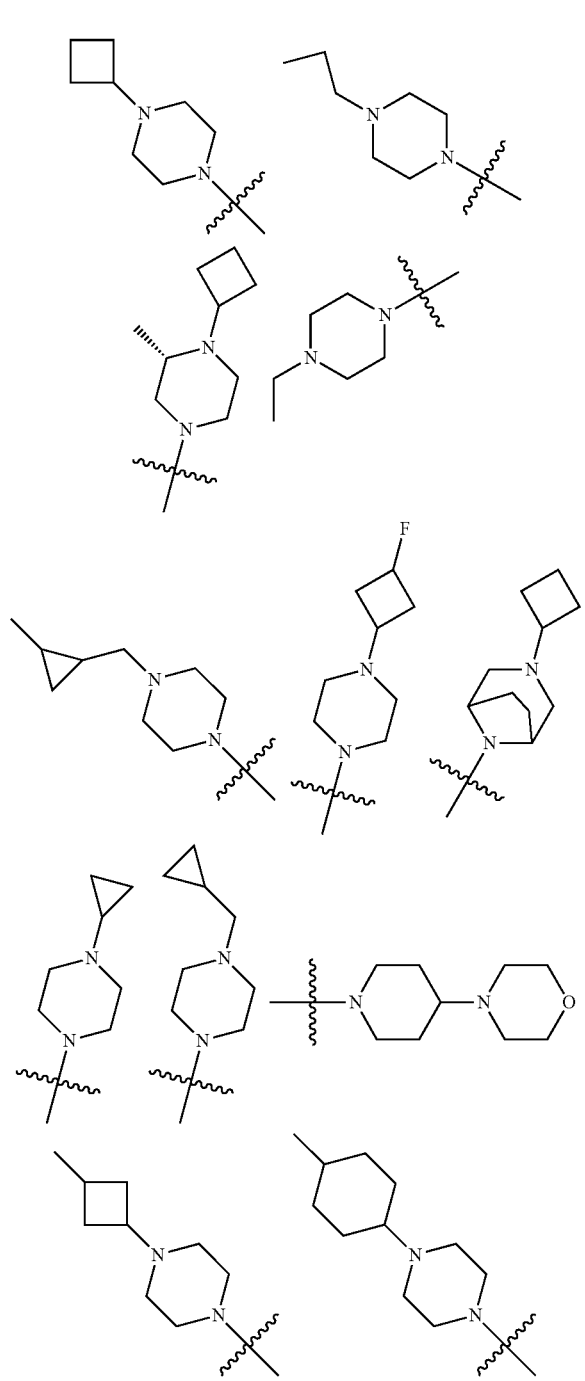

-continued

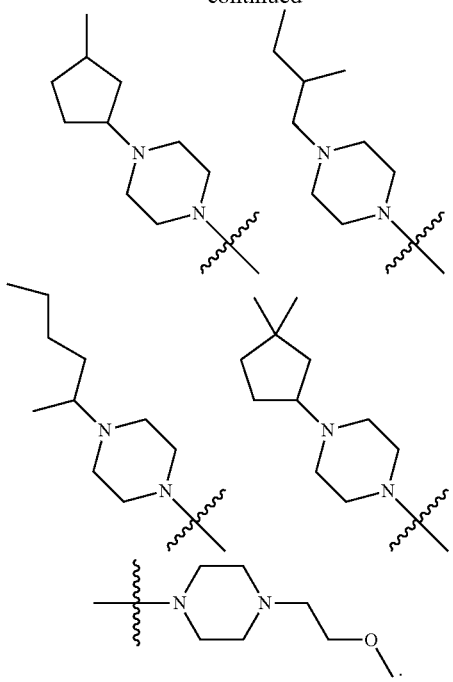

In one embodiment $R^2$ and $R^3$ are each H or wherein $R^2$ and $R^3$ taken together with the carbon to which they are attached form a 5-membered carbocyclic ring.

In one embodiment $R^4$ and $R^5$ are each H.

In one embodiment $R^6$ is a 6-10 membered aryl that is optionally substituted with one or more groups independently selected from the group consisting of $C_{1-6}$alkyl, $C_{2-6}$alkenyl, $C_{2-6}$alkynyl, carbocycle, heterocycle, aryl, heteroaryl, halo, —$NO_2$, —$N(R^b)_2$, —CN, —C(O)—$N(R^b)_2$, —S(O)—$N(R^b)_2$, —S(O)$_2$—$N(R^b)_2$, —O—$R^b$, —S—$R^b$, —O—C(O)—$R^b$, —C(O)—$R^b$, —C(O)—$OR^b$, —S(O)—$R^b$, —S(O)$_2$—$R^b$, —$N(R^b)$—C(O)—$R^b$, —$N(R^b)$—S(O)—$R^b$, —$N(R^b)$—C(O)—$N(R^b)_2$, and —$N(R^b)$—S(O)$_2$—$R^b$; wherein each $C_{1-6}$alkyl, $C_{2-6}$alkenyl, $C_{2-6}$alkynyl, carbocycle, heterocycle, aryl, and heteroaryl is optionally substituted with one or more groups independently selected from the group consisting of halo, —$NO_2$—$N(R^b)_2$, —CN, —C(O)—$N(R^b)_2$, —S(O)—$N(R^b)_2$, —S(O)$_2$—$N(R^b)_2$, —O—$R^b$, —S—$R^b$, —O—C(O)—$R^b$, —C(O)—$R^b$, —C(O)—$OR^b$, —S(O)—$R^b$, —S(O)$_2$—$R^b$, —$N(R^b)$—C(O)—$R^b$, —$N(R^b)$—S(O)—$R^b$, —$N(R^b)$—C(O)—$N(R^b)_2$, —$N(R^b)$—S(O)$_2$—$R^b$, and $C_{1-6}$alkyl that is optionally substituted with one or more groups independently selected from halo.

In one embodiment $R^6$ is phenyl that is substituted with phenyl that is optionally substituted with one or more groups independently selected from the group consisting of $C_{1-6}$alkyl, carbocycle, halo, —CN, —C(O)—$N(R^b)_2$, —O—$R^b$, —S(O)$_2$—$R^b$, and —$N(R^b)$—C(O)—$R^b$, wherein each $C_{1-6}$alkyl and carbocycle is optionally substituted with one or more groups independently selected from the group consisting of halo.

In one embodiment $R^6$ is phenyl that is optionally substituted with one or more groups independently selected from the group consisting of $C_{1-6}$alkyl, carbocycle, halo, —CN, —C(O)—$N(R^b)_2$, —O—$R^b$, —S(O)$_2$—$R^b$, —$N(R^b)$—C(O)—$R^b$, and —$N(R^b)$—C(O)—$N(R^b)_2$, wherein each $C_{1-6}$alkyl and carbocycle is optionally substituted with one or more groups independently selected from the group consisting of halo.

In one embodiment $R^6$ is selected from the group consisting of:

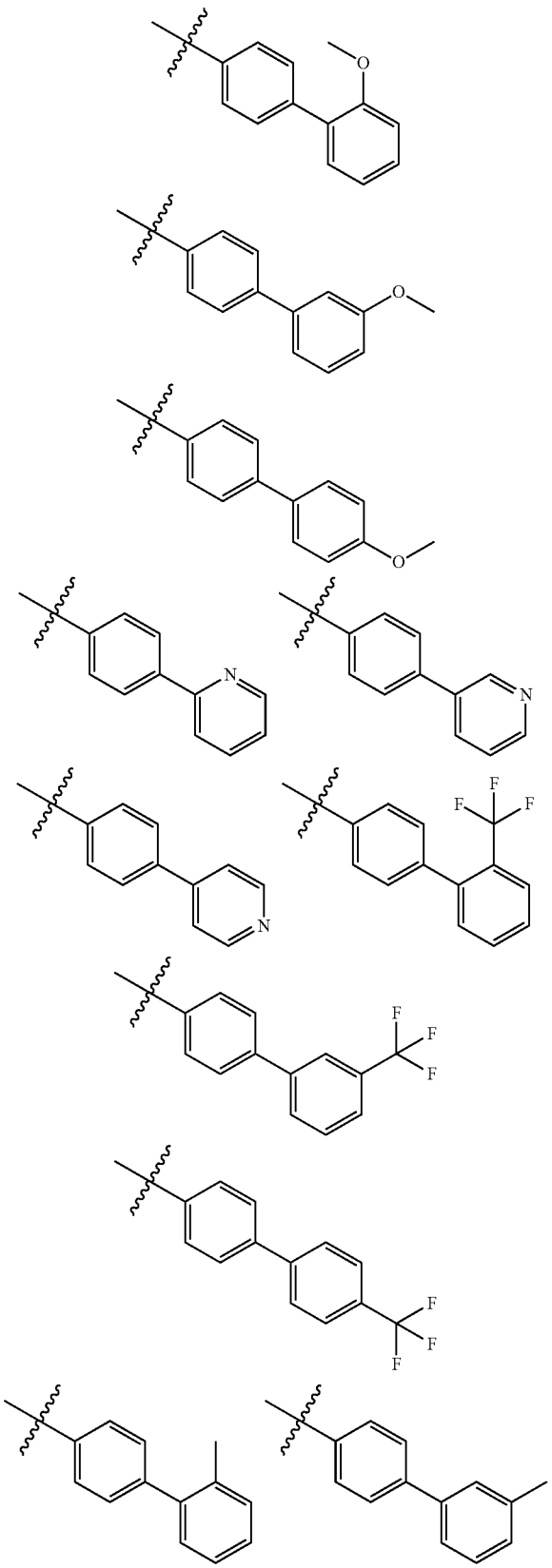

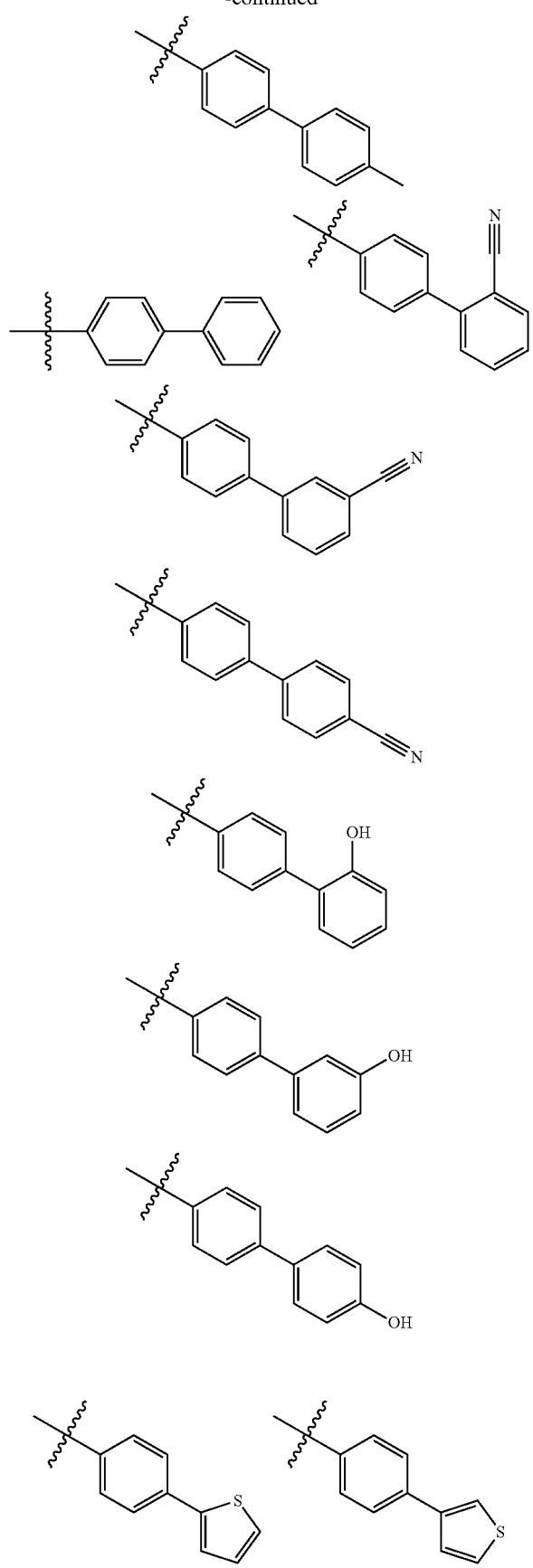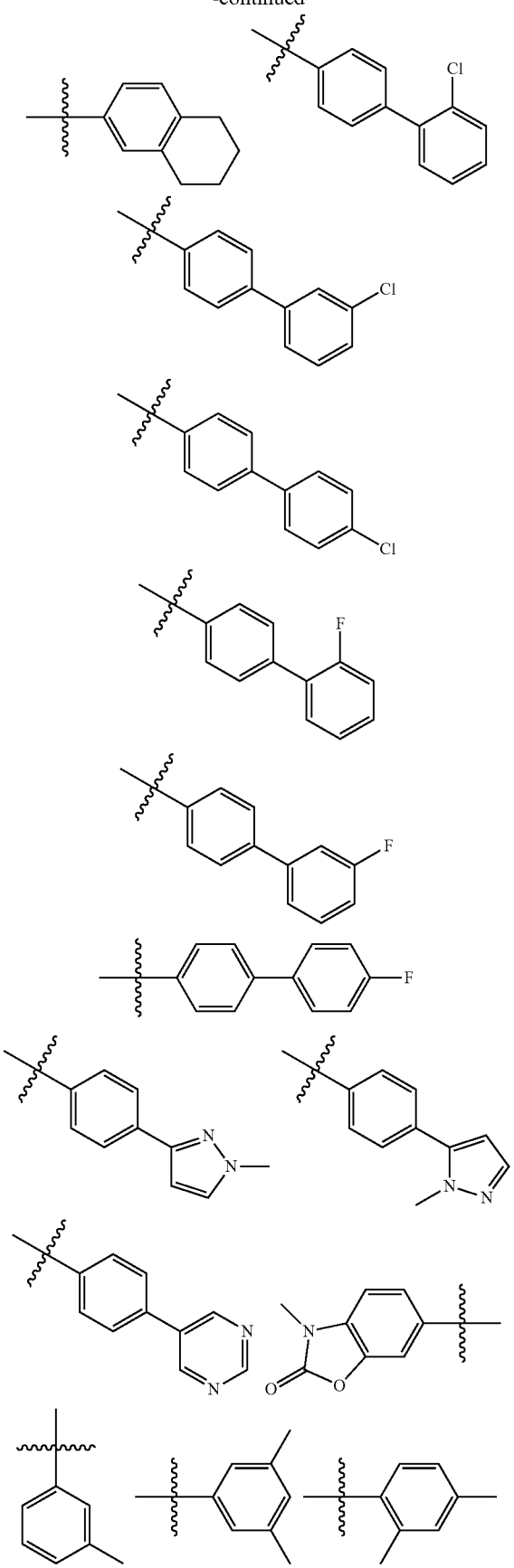

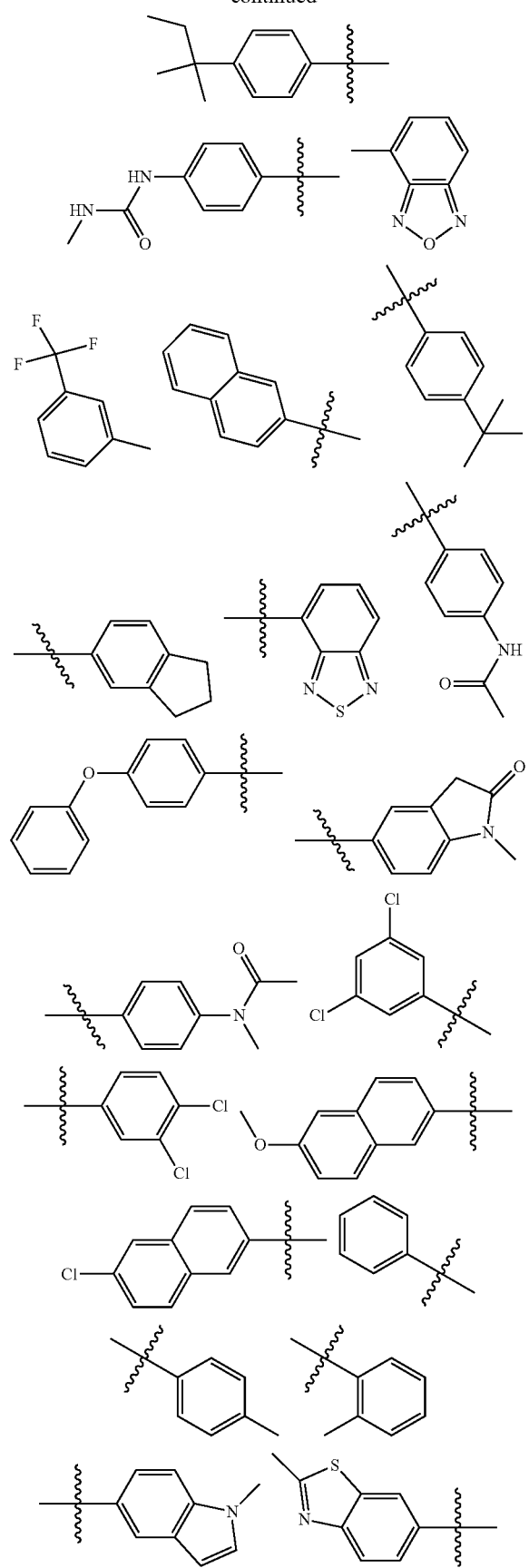
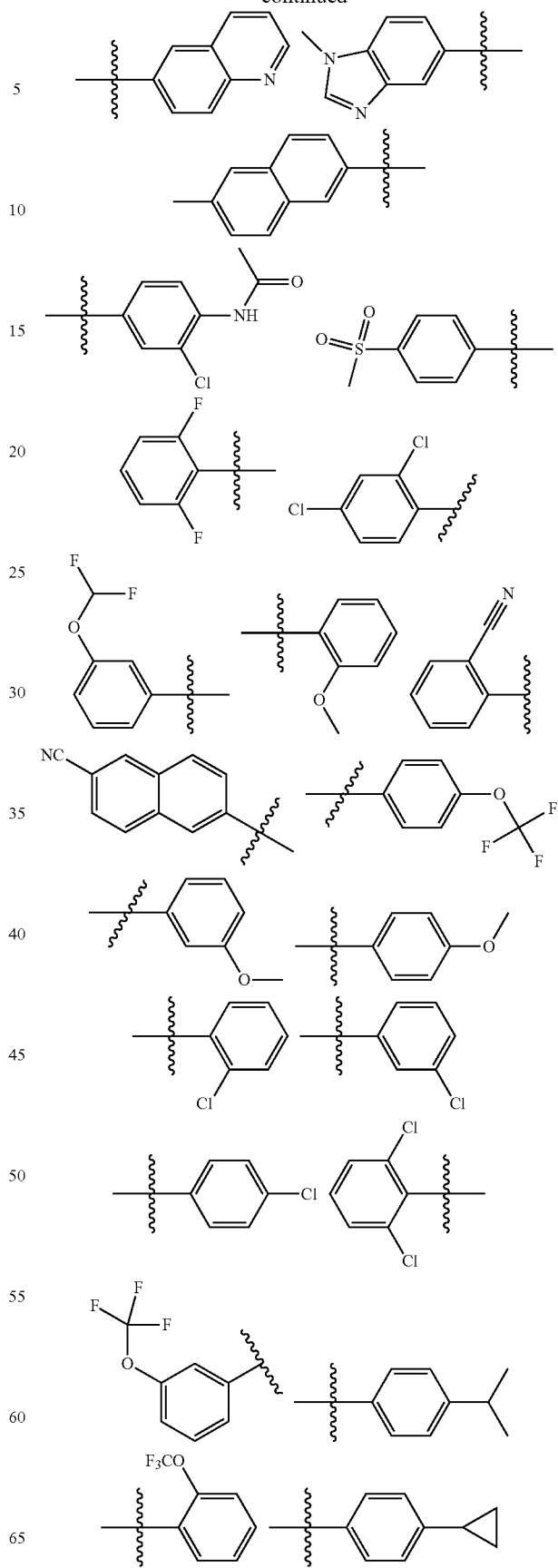

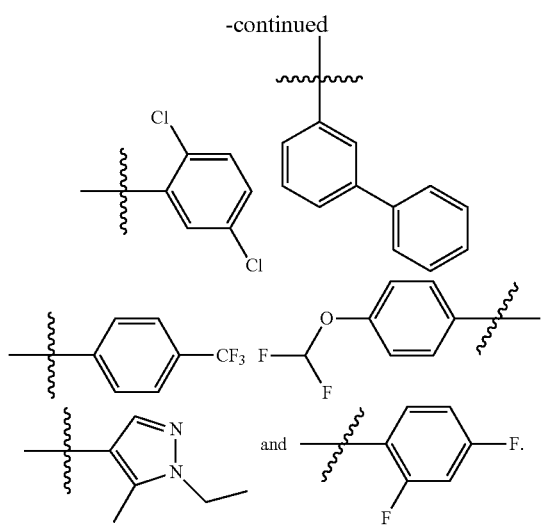

In one embodiment R⁶ is selected from the group consisting of:

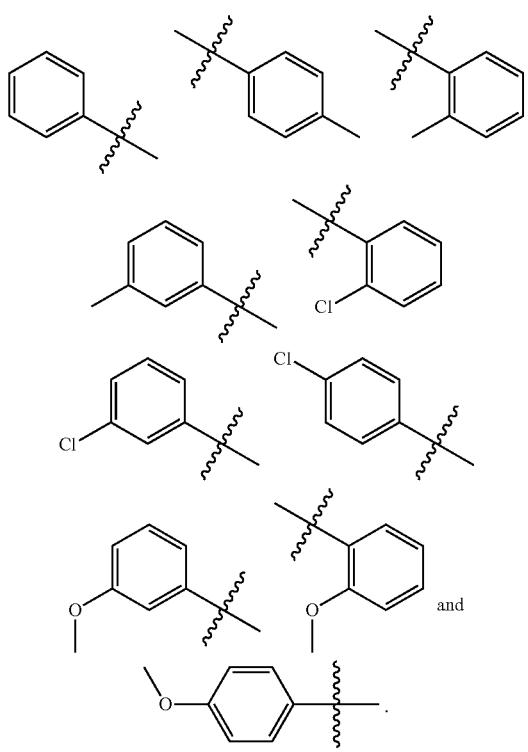

In one embodimen the compound is a compound of formula (Ia) wherein:

R¹ is selected from the group consisting of N-linked piperazinyl, N-linked piperidine, and N-linked diazabicyclo[3.2.1]octane, wherein R¹ is optionally substituted with one or more groups independently selected from $C_{1-6}$alkyl, aryl, and $C_{3-8}$cycloalkyl, wherein any aryl and $C_{3-8}$cycloalkyl is optionally substituted with one or more groups independently selected from halo and $C_{1-4}$alkyl, and wherein any $C_{1-6}$alkyl is optionally substituted with one or more groups independently selected from halo, $C_{1-4}$alkoxy, and $C_{3-8}$cycloalkyl;

R² and R³ are each H or R² and R³ taken together with the carbon to which they are attached form a 5-membered carbocyclic ring;

R⁴ and R⁵ are each H; and

R⁶ is a 6-10 membered aryl that is optionally substituted with one or more groups independently selected from the group consisting of $C_{1-6}$alkyl, $C_{2-6}$alkenyl, $C_{2-6}$alkynyl, carbocycle, heterocycle, aryl, heteroaryl, halo, —NO₂, —N(R^b)₂, —CN, —C(O)—N(R^b)₂, —S(O)—N(R^b)₂, —S(O)₂—N(R^b)₂, —S—R^b, —O—C(O)—R^b, —C(O)—R^b, —C(O)—OR^b, —S(O)—R^b, —S(O)₂—R^b, —N(R^b)—C(O)—R^b, —N(R^b)—S(O)—R^b, —N(R^b)—C(O)—N(R^b)₂, and —N(R^b)—S(O)₂—R^b; wherein each $C_{1-6}$alkyl, $C_{2-6}$alkenyl, $C_{2-6}$alkynyl, carbocycle, heterocycle, aryl, and heteroaryl is optionally substituted with one or more groups independently selected from the group consisting of halo, —NO₂, —N(R¹)₂, —CN, —C(O)—N(R^b)₂, —S(O)—N(R^b)₂, —S(O)₂—N(R^b)₂, —O—R^b, —S—R^b, —O—C(O)—R^b, —C(O)—R^b, —C(O)—OR^b, —S(O)—R^b, —S(O)₂—R^b, —N(R^b)—C(O)—R^b, —N(R^b)—S(O)—R^b, —N(R^b)—C(O)—N(R^b)₂, —N(R^b)—S(O)₂—R^b, and $C_{1-6}$alkyl that is optionally substituted with one or more groups independently selected from halo.

In one embodimen the compound is a compound of formula (Ia) wherein

R¹ is selected from the group consisting of:

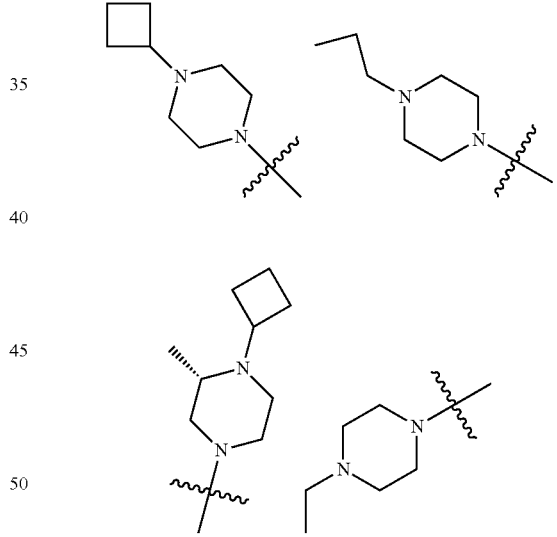

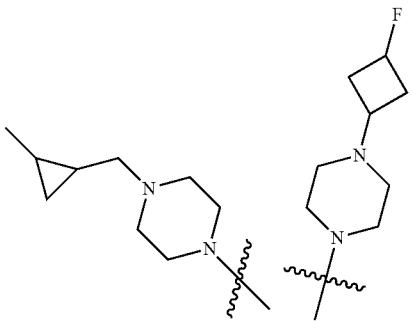

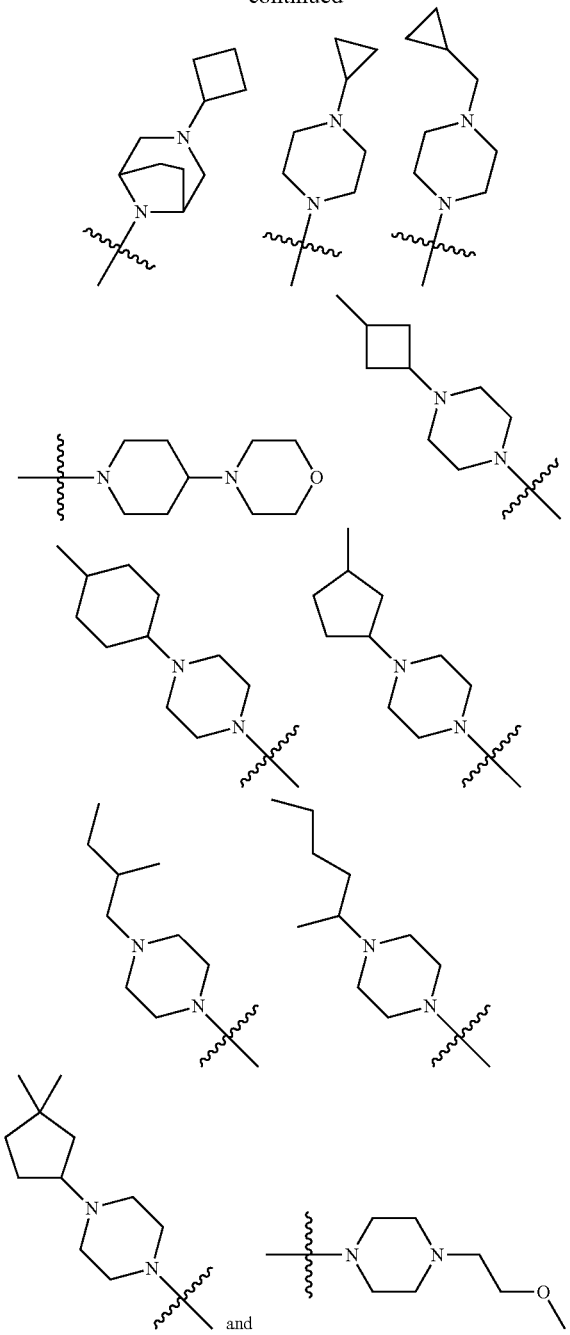

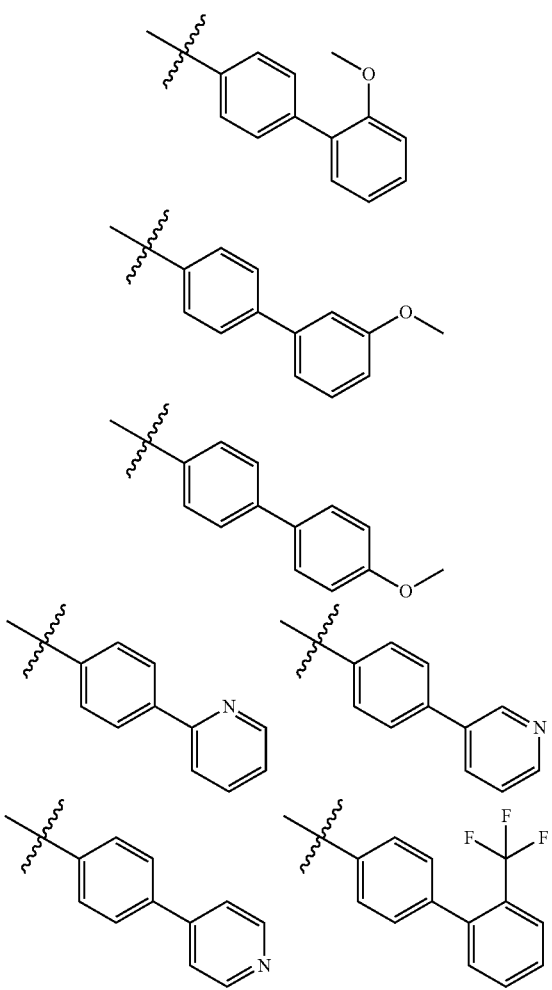

$R^2$ and $R^3$ are each H or $R^2$ and $R^3$ taken together with the carbon to which they are attached form a 5-membered carbocyclic ring;

$R^4$ and $R^5$ are each H; and $R^6$ is a 6-10 membered aryl that is optionally substituted with one or more groups independently selected from the group consisting of $C_{1-6}$alkyl, $C_{2-6}$alkenyl, $C_{2-6}$alkynyl, carbocycle, heterocycle, aryl, heteroaryl, halo, —$NO_2$, —$N(R^b)_2$, —CN, —C(O)—$N(R^b)_2$, —S(O)—$N(R^b)_2$, —$S(O)_2$—$N(R^b)_2$, —S—$R^b$, —O—C(O)—$R^b$, —C(O)—$R^b$, —C(O)—$OR^b$, —S(O)—$R^b$, —$S(O)_2$—$R^b$, —$N(R^b)$—C(O)—$R^b$, —$N(R^b)$—S(O)—$R^b$, —$N(R^b)$—C(O)—$N(R^b)_2$, and —$N(R^b)$—$S(O)_2$—$R^b$; wherein each $C_{1-6}$alkyl, $C_{2-6}$alkenyl, $C_{2-6}$alkynyl, carbocycle, hetero-cycle, aryl, and heteroaryl is optionally substituted with one or more groups independently selected from the group consisting of halo, —$NO_2$—$N(R^b)_2$, —CN, —C(O)—$N(R^b)_2$, —S(O)—$N(R^b)_2$, —$S(O)_2$—$N(R^b)_2$, —O—$R^b$, —S—$R^b$, —O—C(O)—$R^b$, —C(O)—$R^b$, —C(O)—$OR^b$, —S(O)—$R^b$, —$S(O)_2$—$R^b$, —$N(R^b)$—C(O)—$R^b$, —$N(R^b)$—S(O)—$R^b$, —$N(R^b)$—C(O)—$N(R^b)_2$, —$N(R^b)$—$S(O)_2$—$R^b$, and $C_{1-6}$alkyl that is optionally substituted with one or more groups independently selected from halo.

In one embodiment the compound is a compound of formula (Ia) wherein:

$R^1$ is selected from the group consisting of N-linked piperazinyl, N-linked piperidine, and N-linked diazabicyclo[3.2.1]octane, wherein $R^1$ is optionally substituted with one or more groups independently selected from $C_{1-6}$alkyl, aryl, and $C_{3-8}$cycloalkyl, wherein any aryl and $C_{3-8}$cycloalkyl is optionally substituted with one or more groups independently selected from halo and $C_{1-4}$alkyl, and wherein any $C_{1-6}$alkyl is optionally substituted with one or more groups independently selected from halo, $C_{1-4}$alkoxy, and $C_{3-8}$cycloalkyl;

$R^2$ and $R^3$ are each H or $R^2$ and $R^3$ taken together with the carbon to which they are attached form a 5-membered carbocyclic ring;

$R^4$ and $R^5$ are each H; and $R^6$ is selected from the group consisting of:

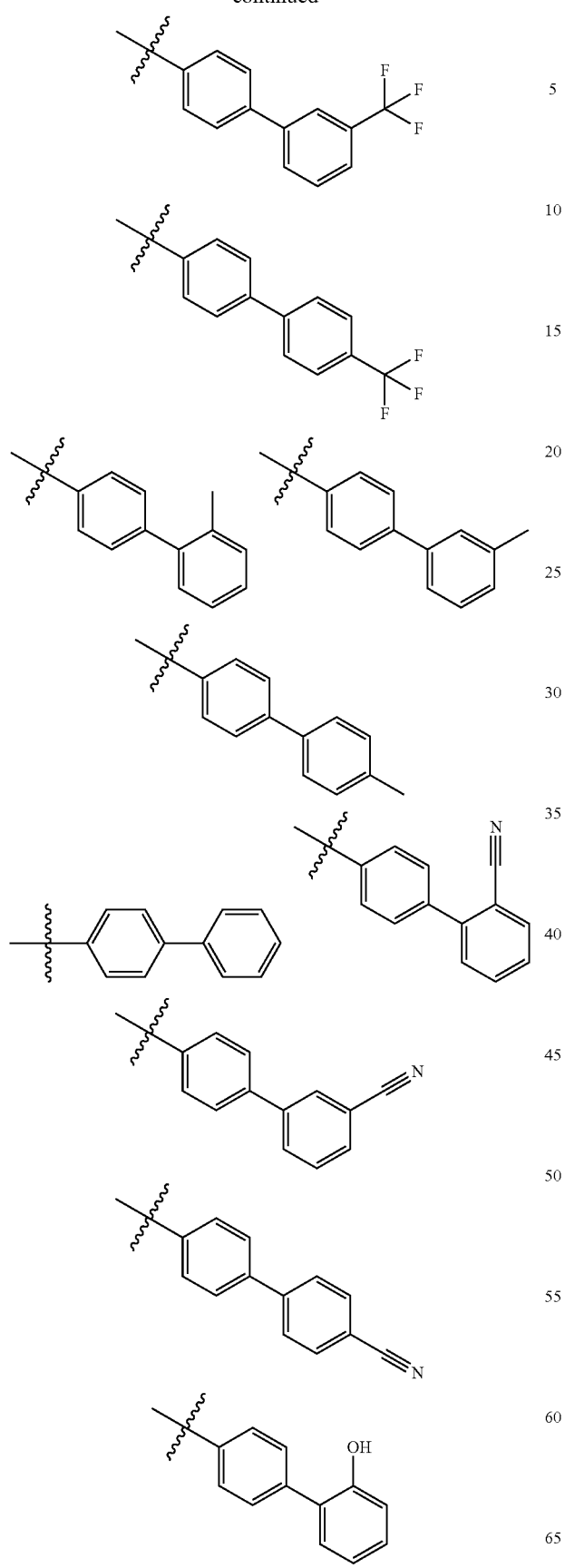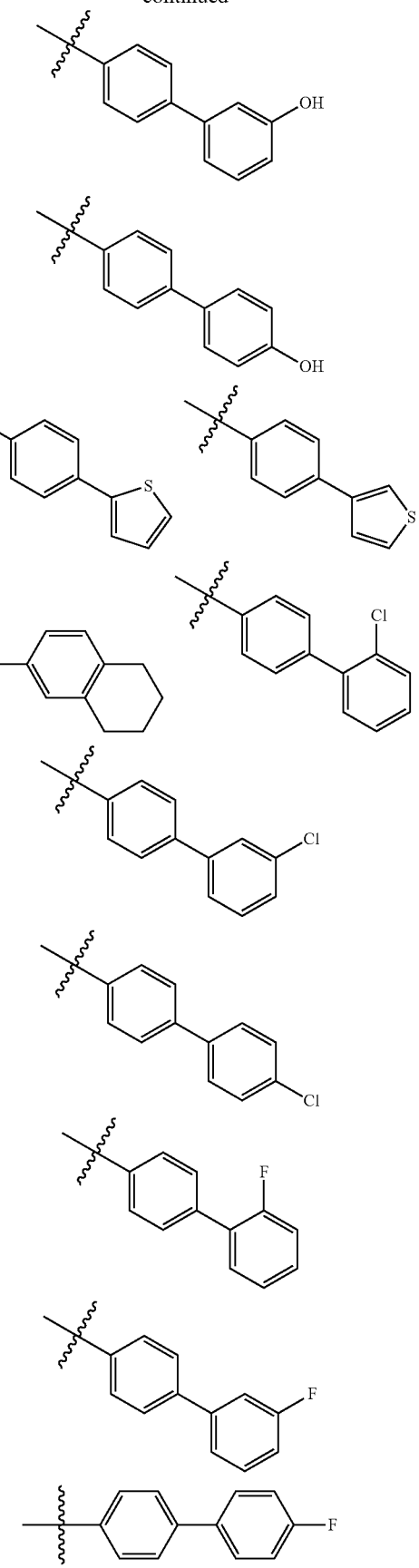

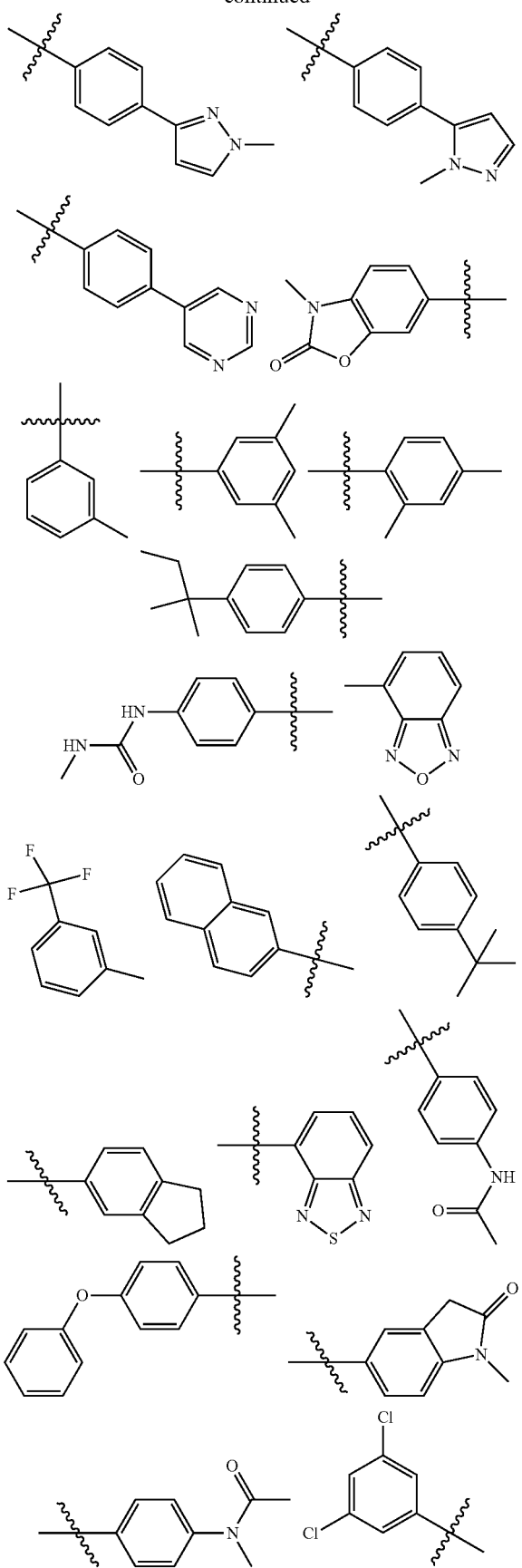
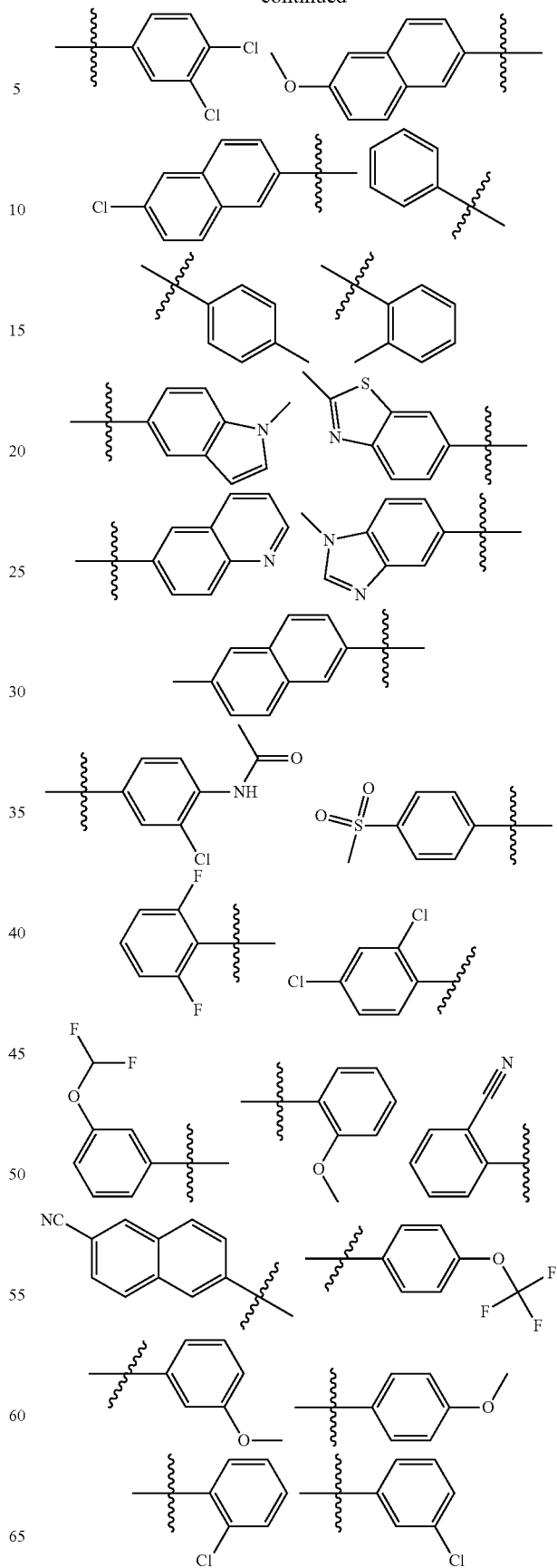

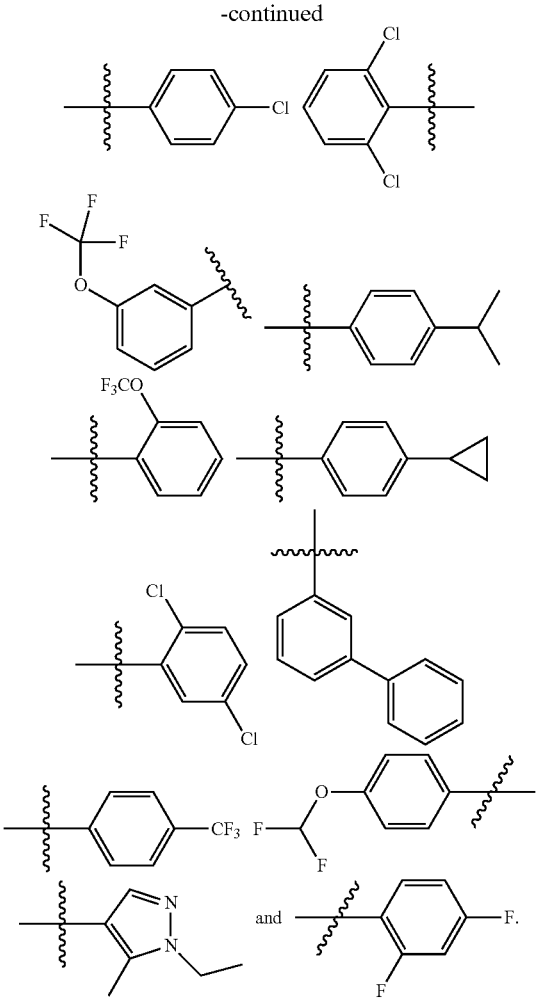

In one embodimen the compound is a compound of formula (Ib) wherein:

R$^1$ is:

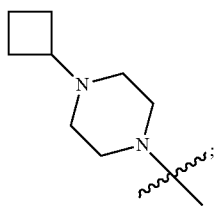 [SMILES: *N1CCN(C2CCC2)CC1]

R$^2$ and R$^3$ are each H or R$^2$ and R$^3$ taken together with the carbon to which they are attached form a 5-membered carbocyclic ring;
R$^4$ and R$^5$ are each H; and
R$^6$ is a phenyl that is optionally substituted with one or more groups independently selected from the group consisting of C$_{1-6}$alkyl, halo, CN, and —O—R$^b$, wherein each C$_{1-6}$alkyl is optionally substituted with one or more groups independently selected from the group consisting of halo.

In one embodimen the compound is a compound of formula (Ib) wherein:
R$^1$ is a piperazin-1-yl that is substituted at the 4-position with a group selected from C$_{1-6}$alkyl, aryl, and C$_{3-8}$cy-cloalkyl, wherein any aryl and C$_{3-8}$cycloalkyl is optionally substituted with one or more groups independently selected from halo and C$_{1-4}$alkyl, and wherein any C$_{1-6}$alkyl is optionally substituted with one or more groups independently selected from halo. C$_{1-4}$alkoxy, and C$_{3-8}$cycloalkyl;
R$^2$ and R$^3$ are each H;
R$^4$ and R$^5$ are each H; and
R$^6$ is selected from the group consisting of:

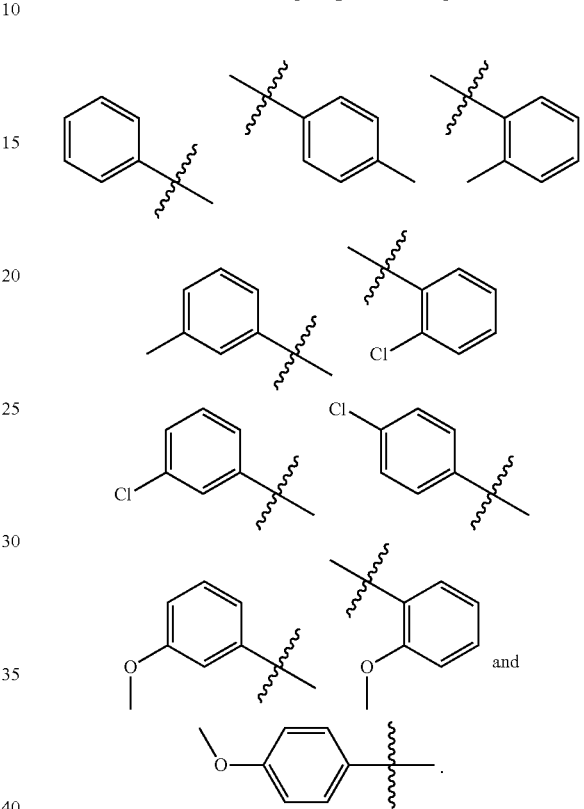

In one embodiment the compound is selected from:

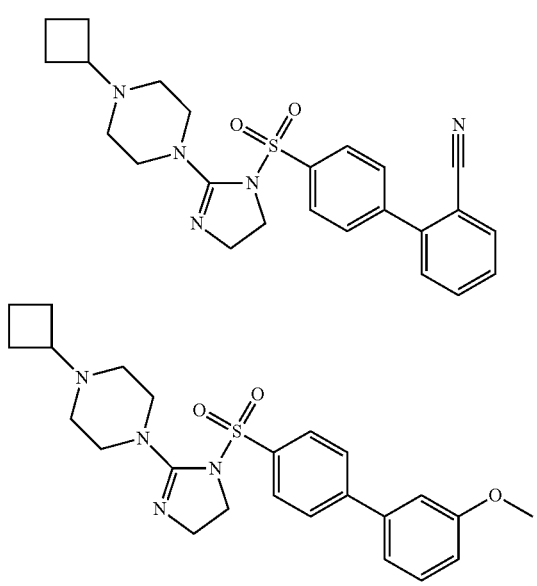

29
-continued
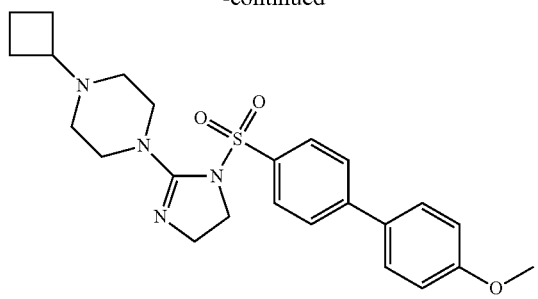
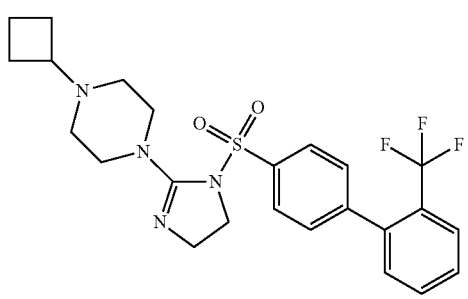
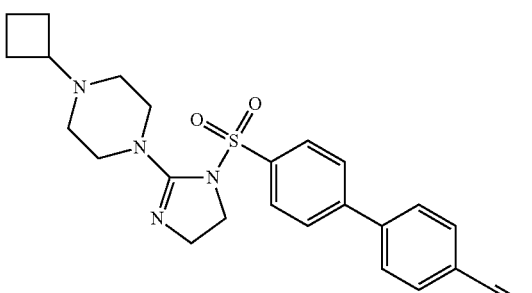
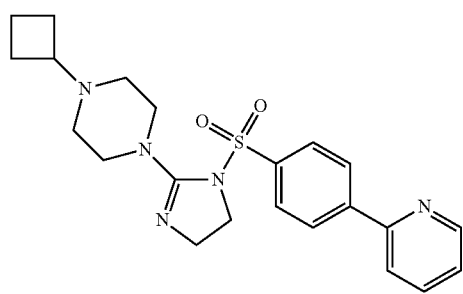
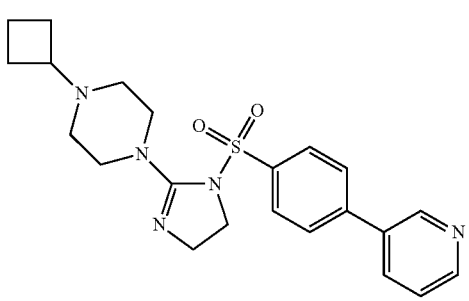
30
-continued
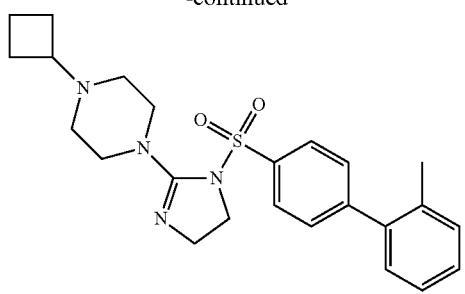
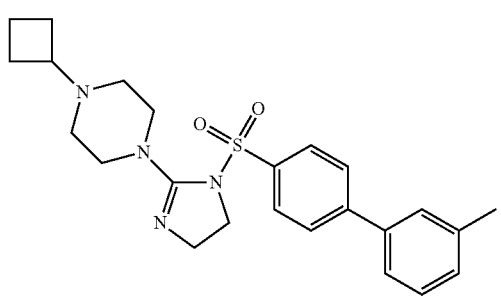
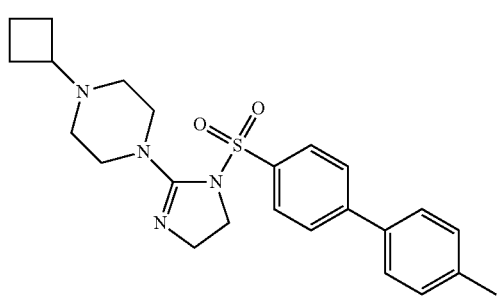
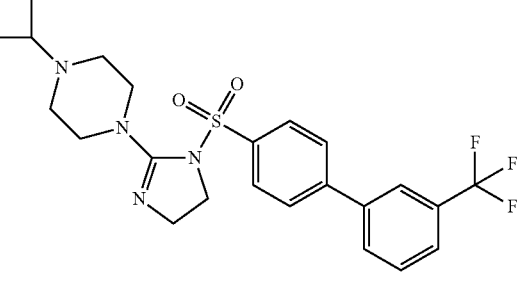
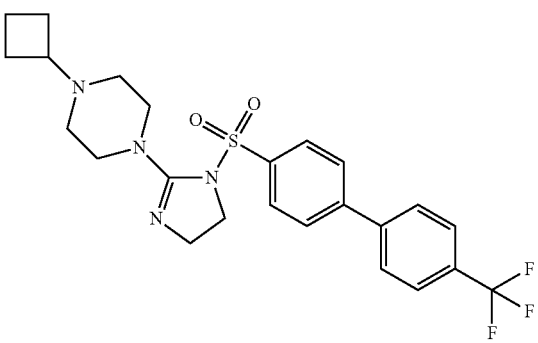

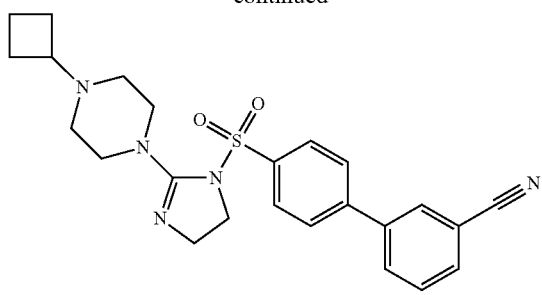
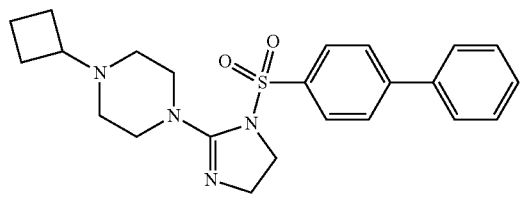
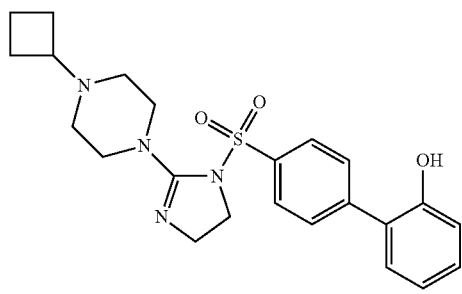
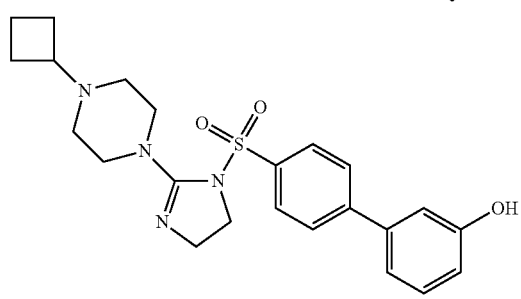
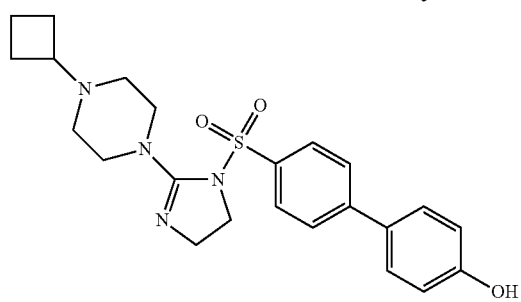
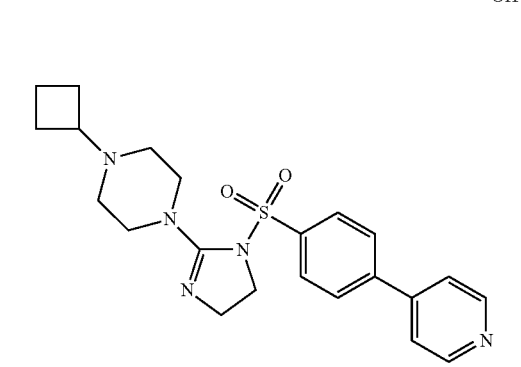
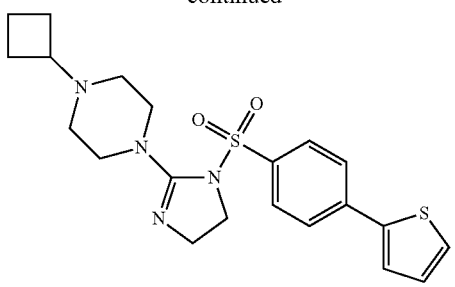
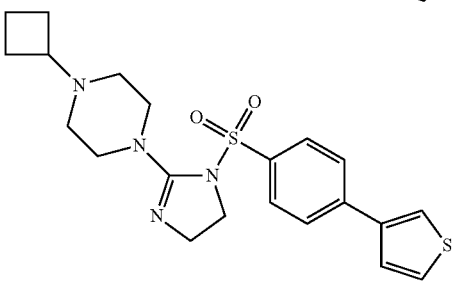
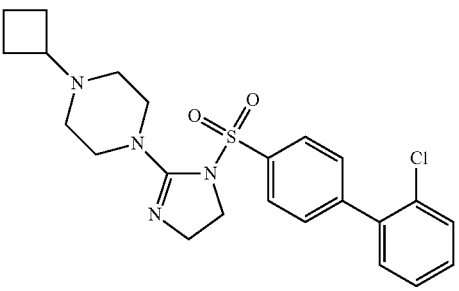
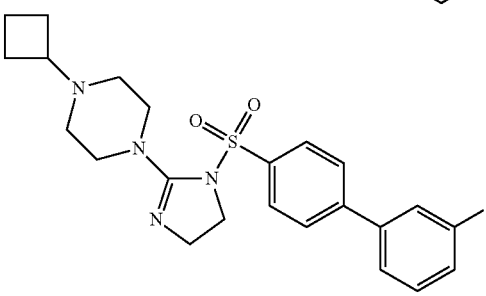
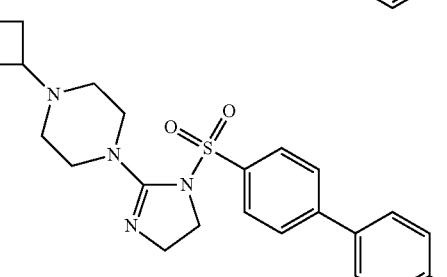
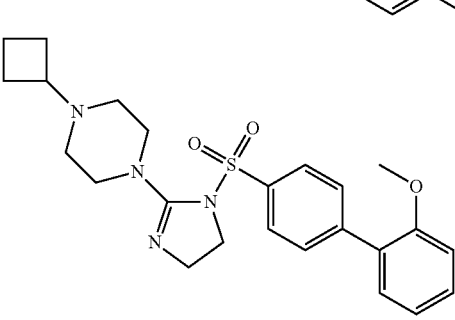

33
-continued
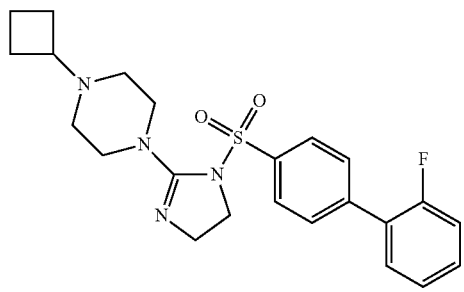
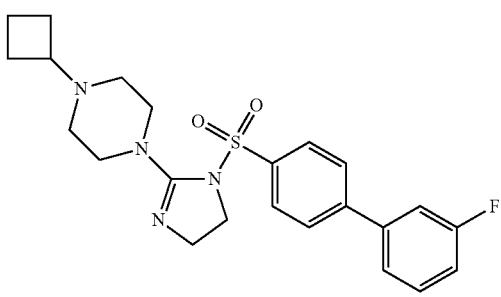
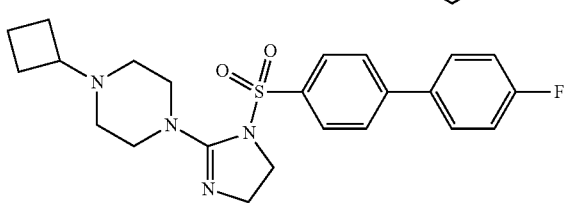
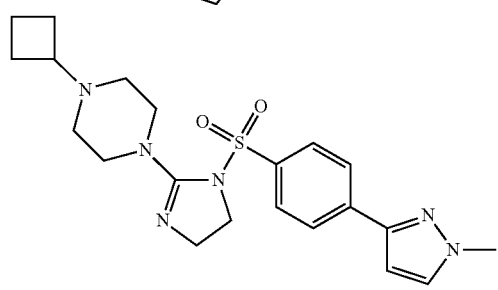
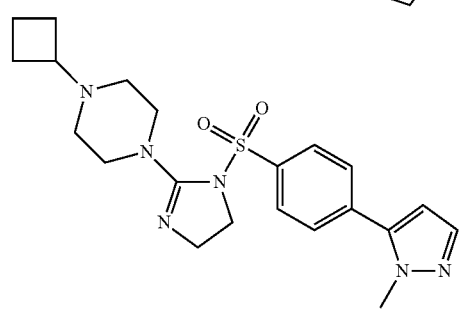
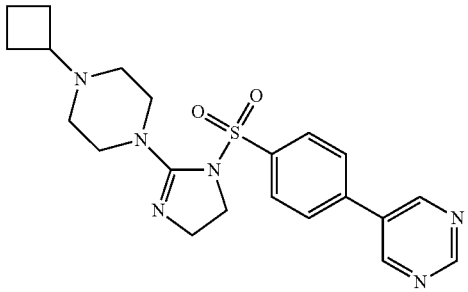
34
-continued
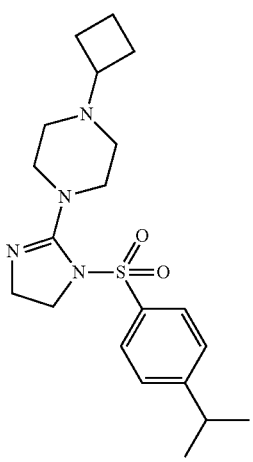
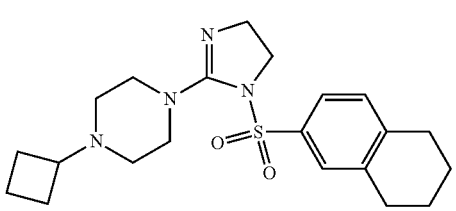
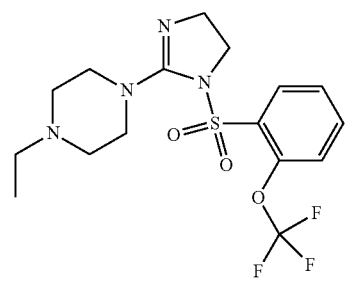
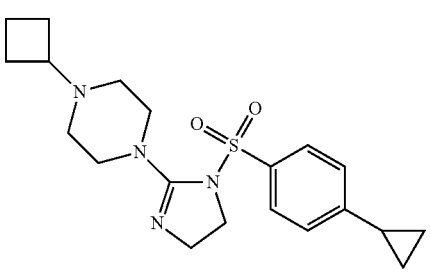
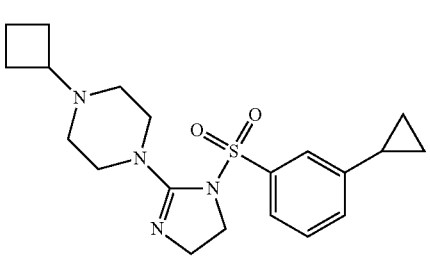

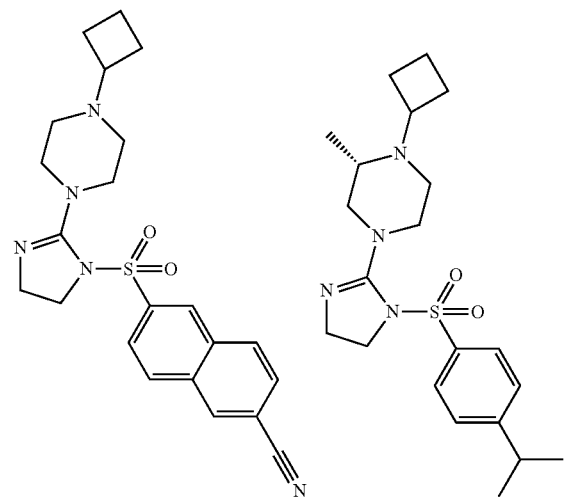
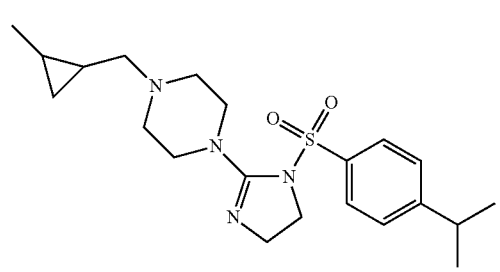
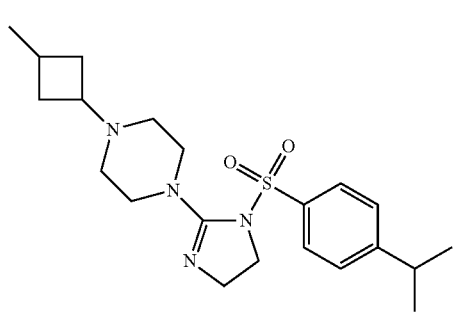
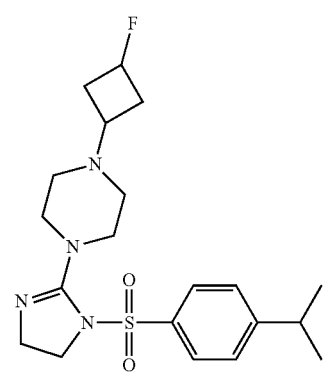
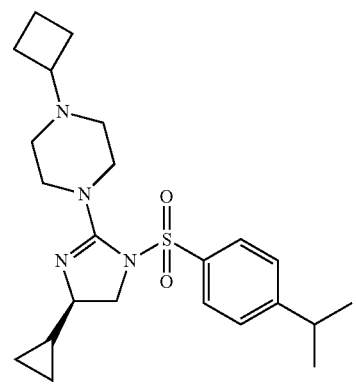
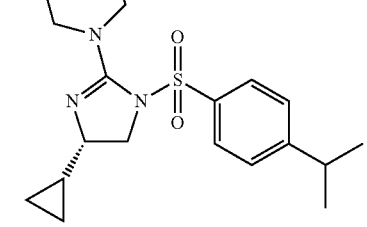
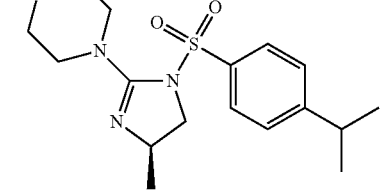
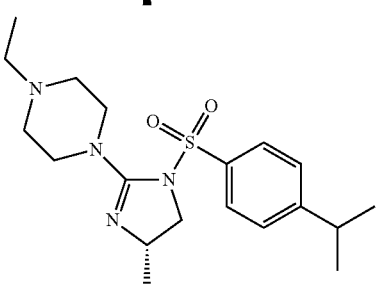
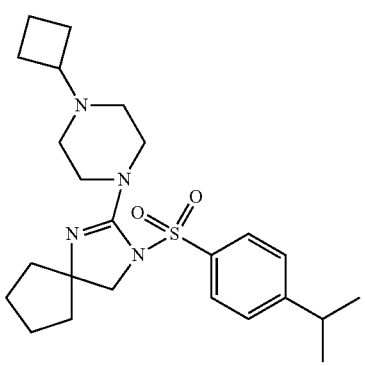

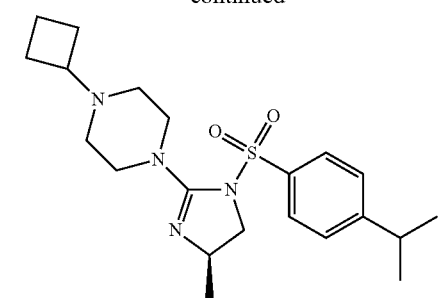
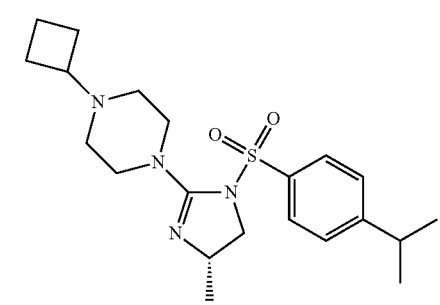
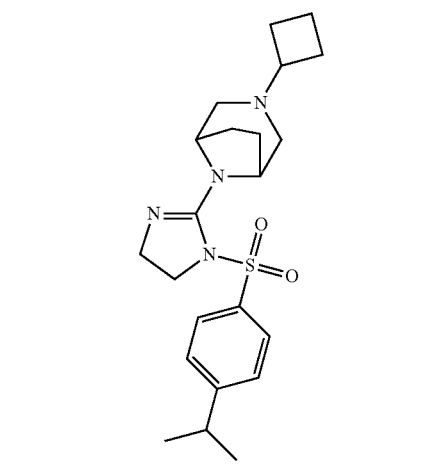
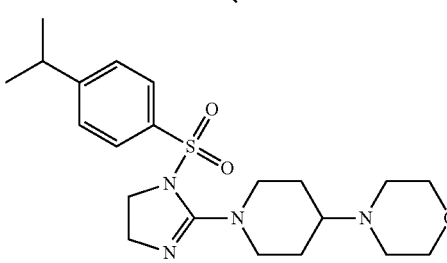
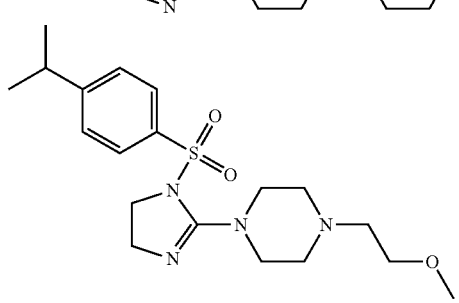
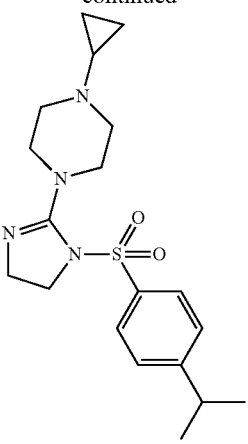
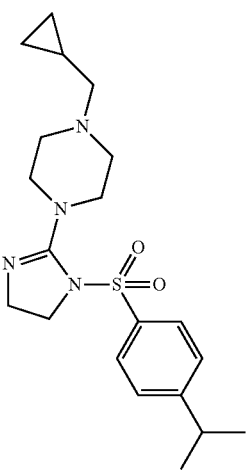
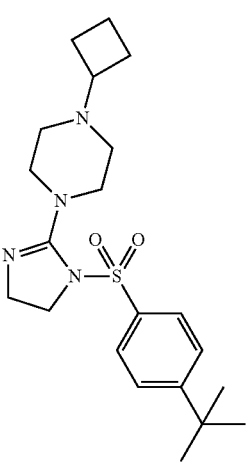
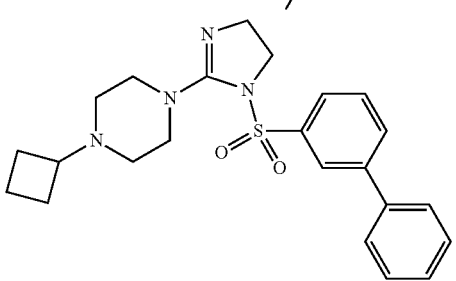

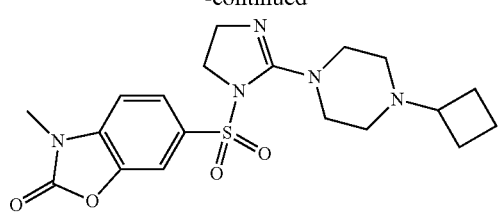
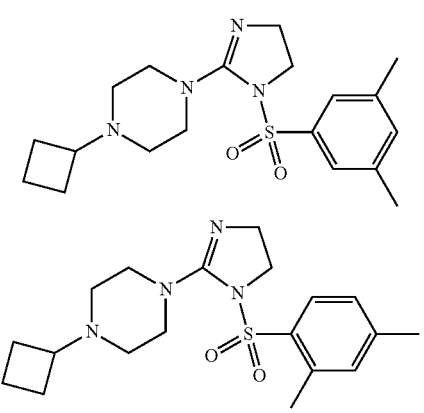
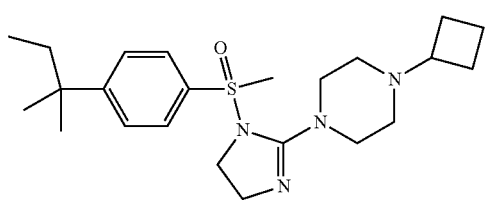
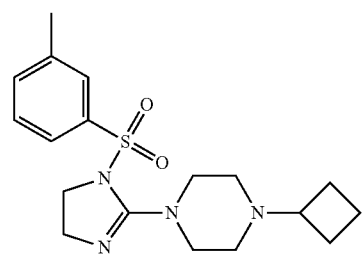
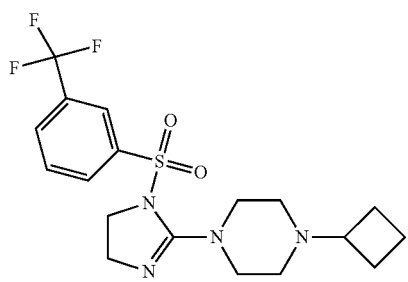
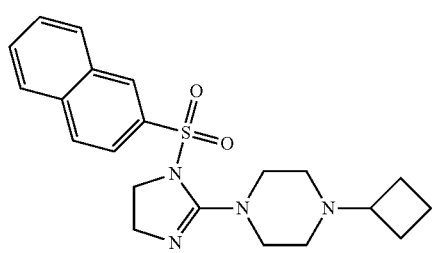
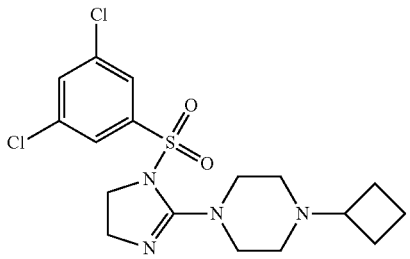
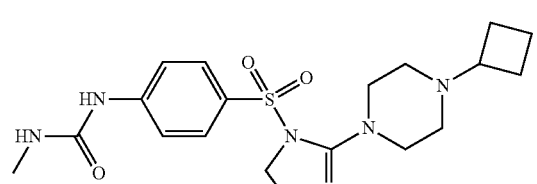
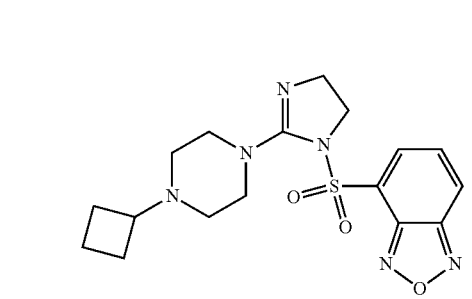
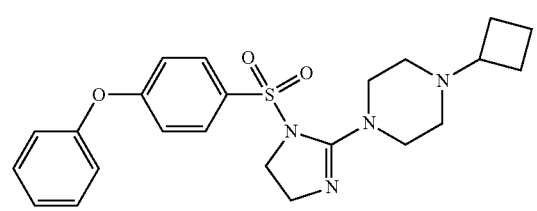
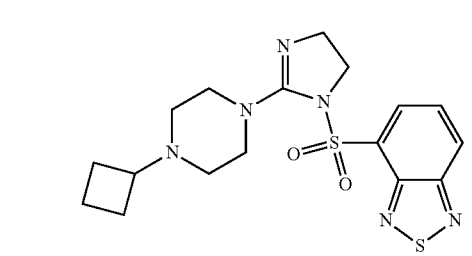
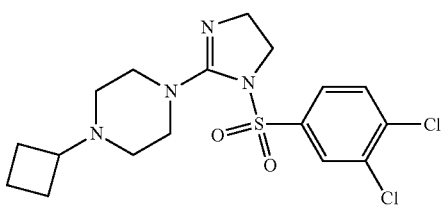

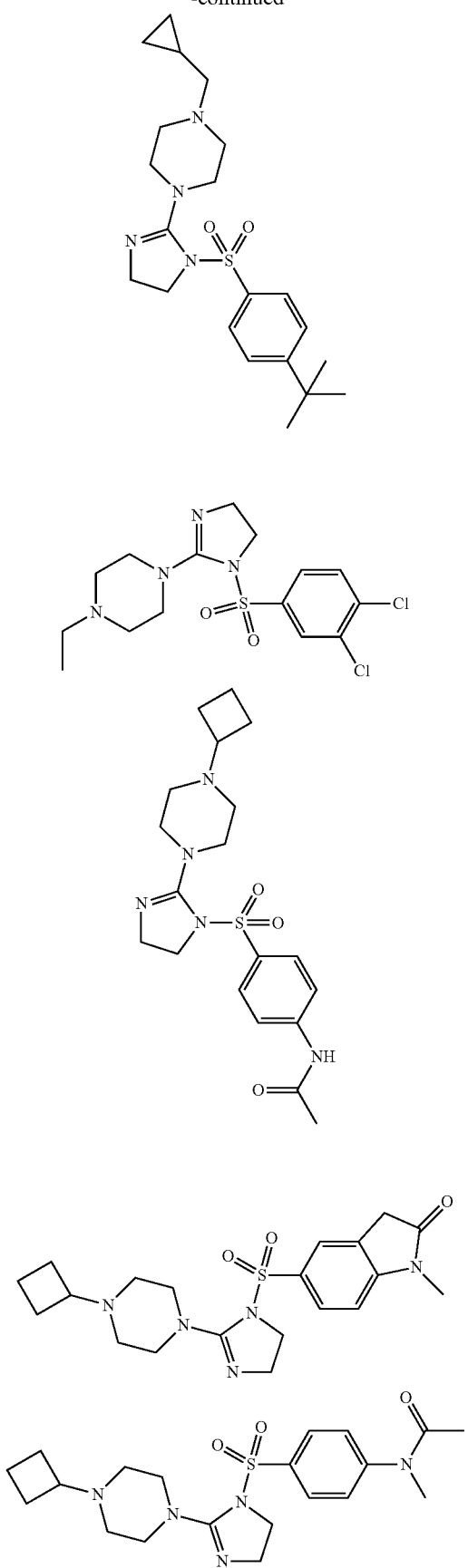
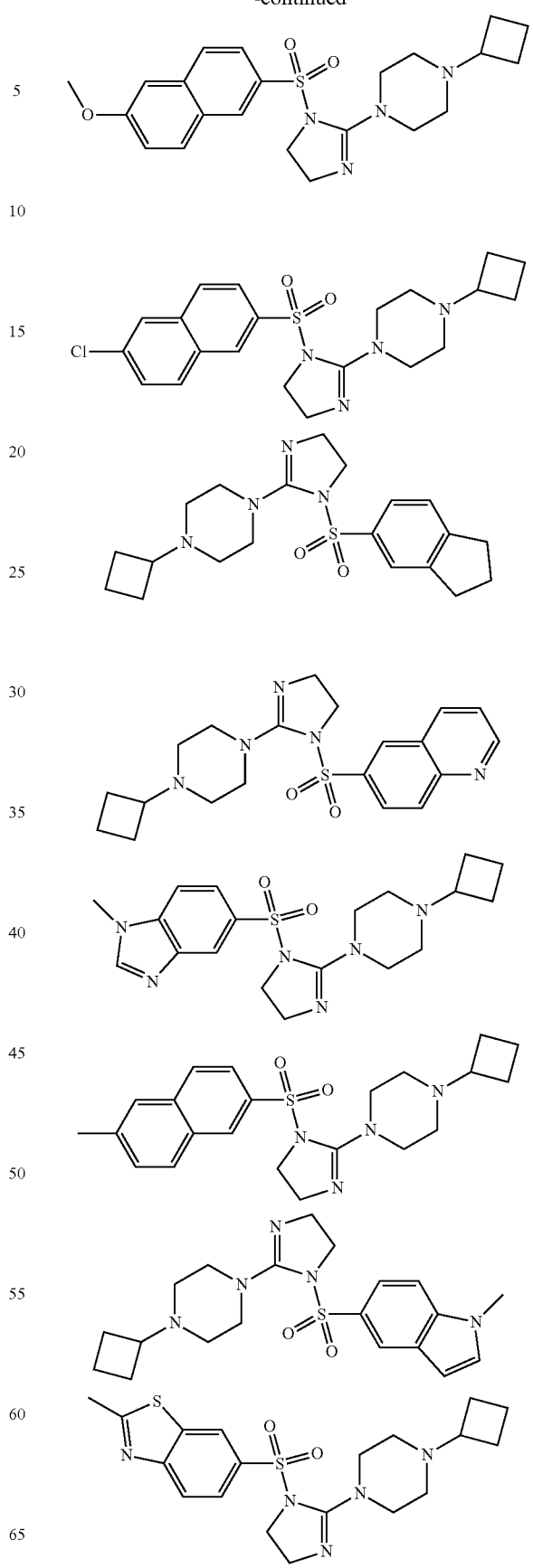

-continued

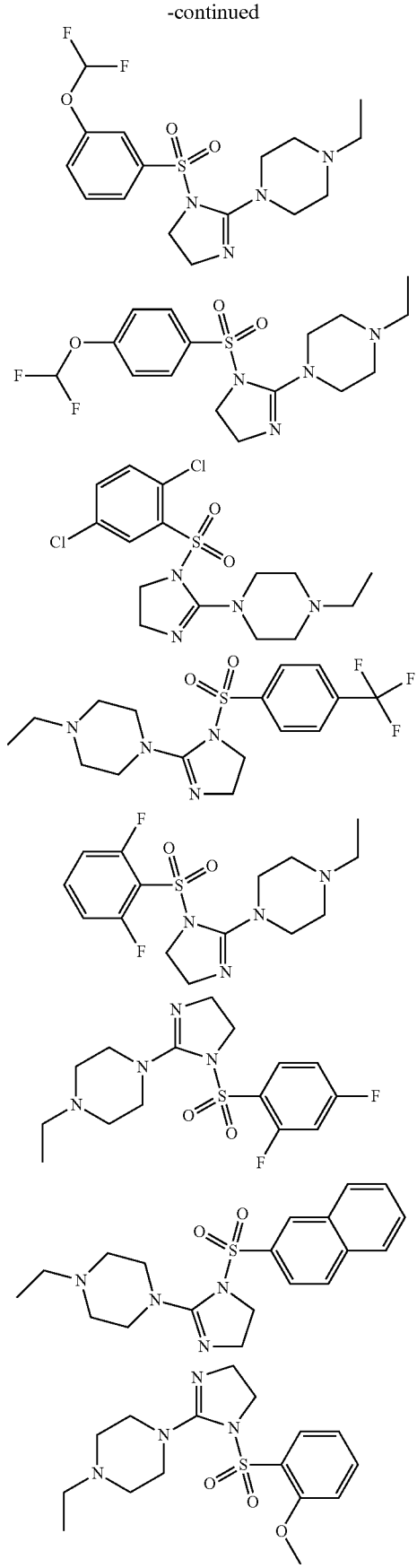
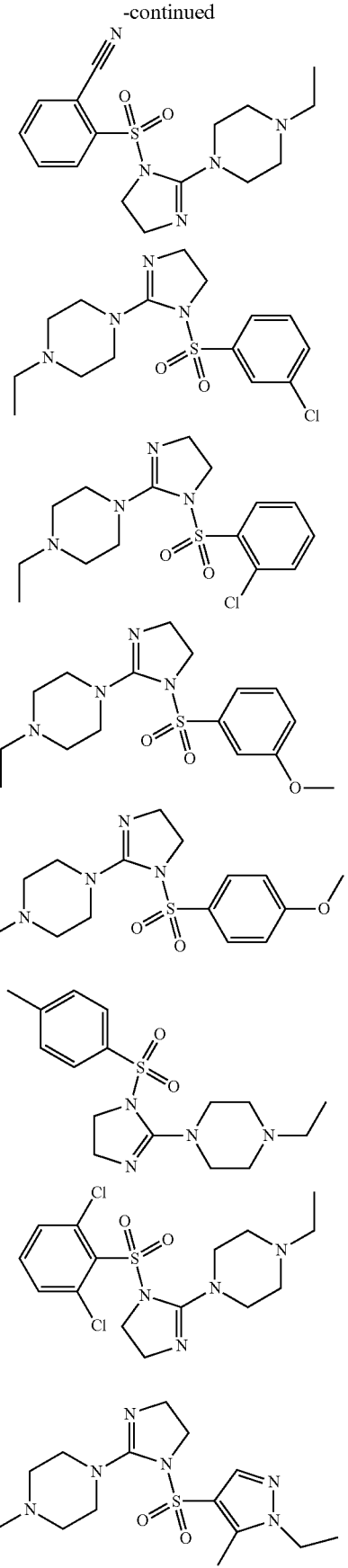

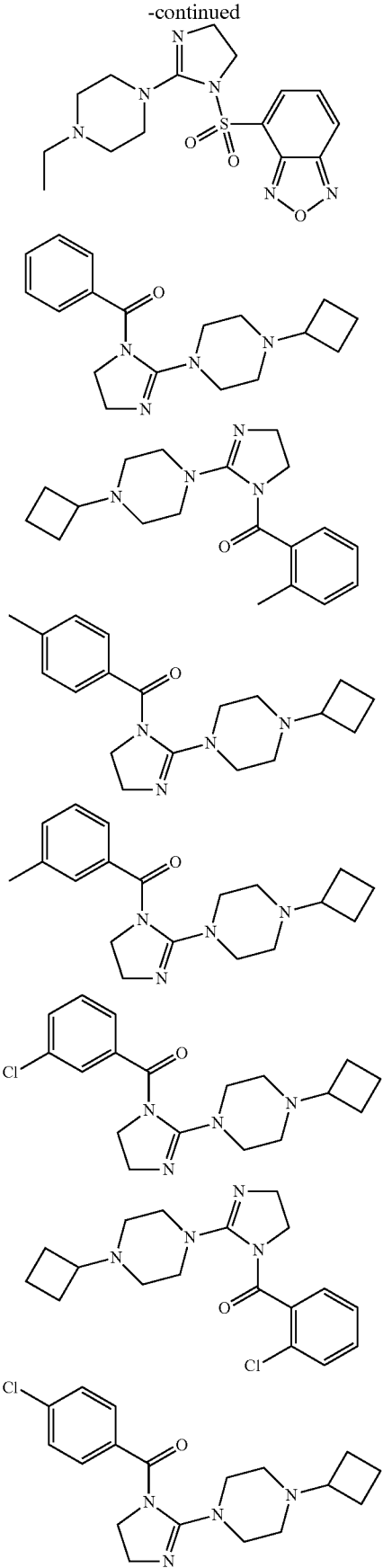
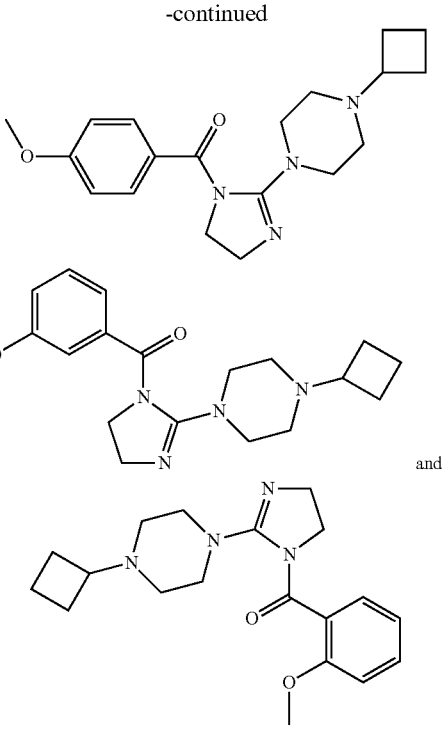
and salts thereof.
In one embodiment the compound is selected from:
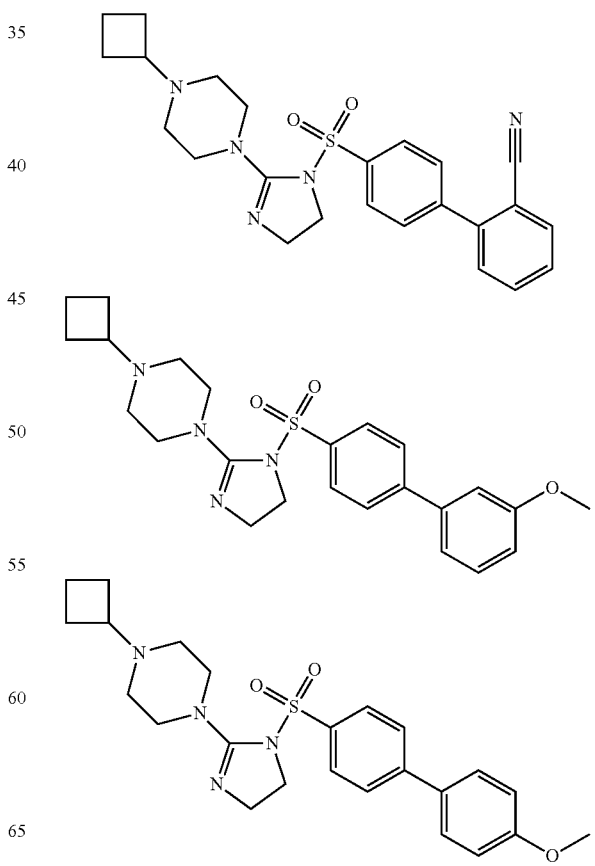

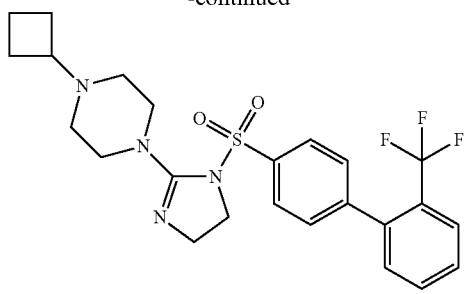
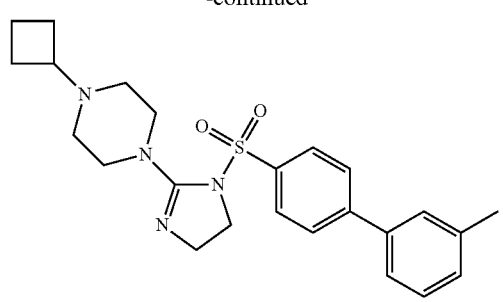
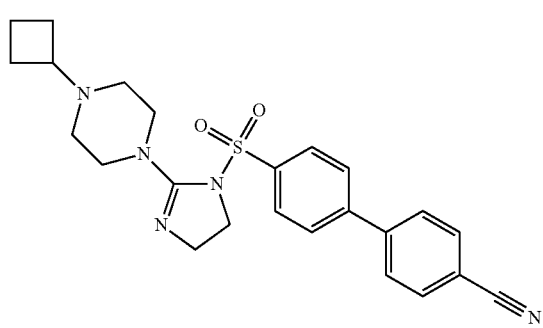
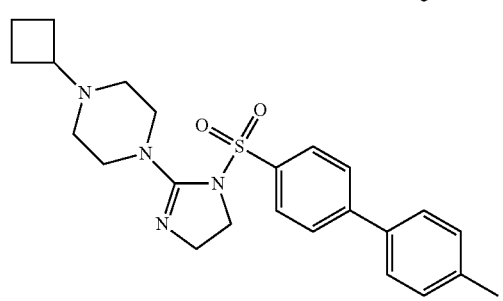
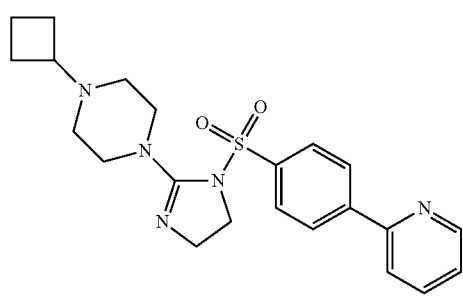
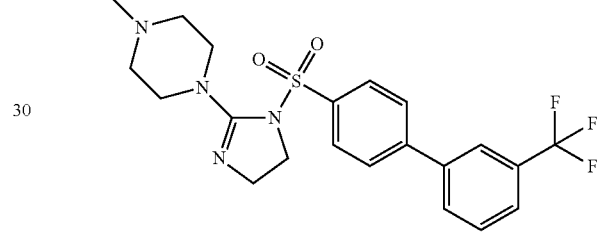
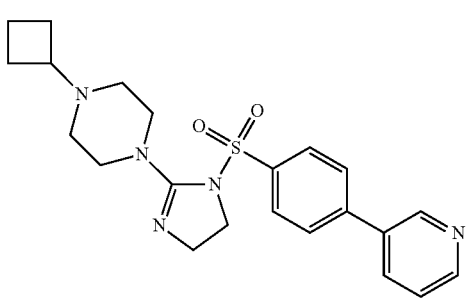
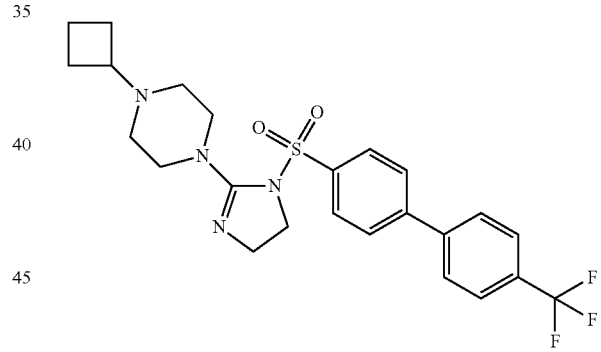
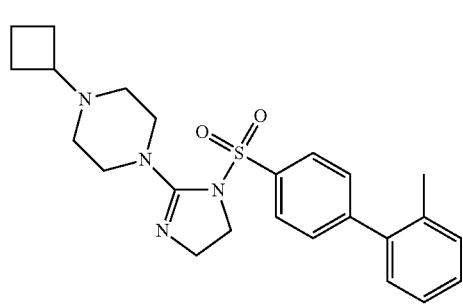
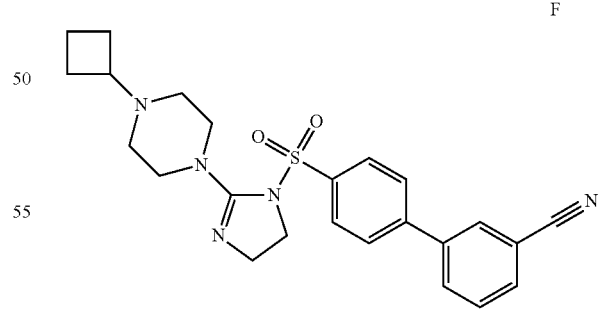

51
-continued
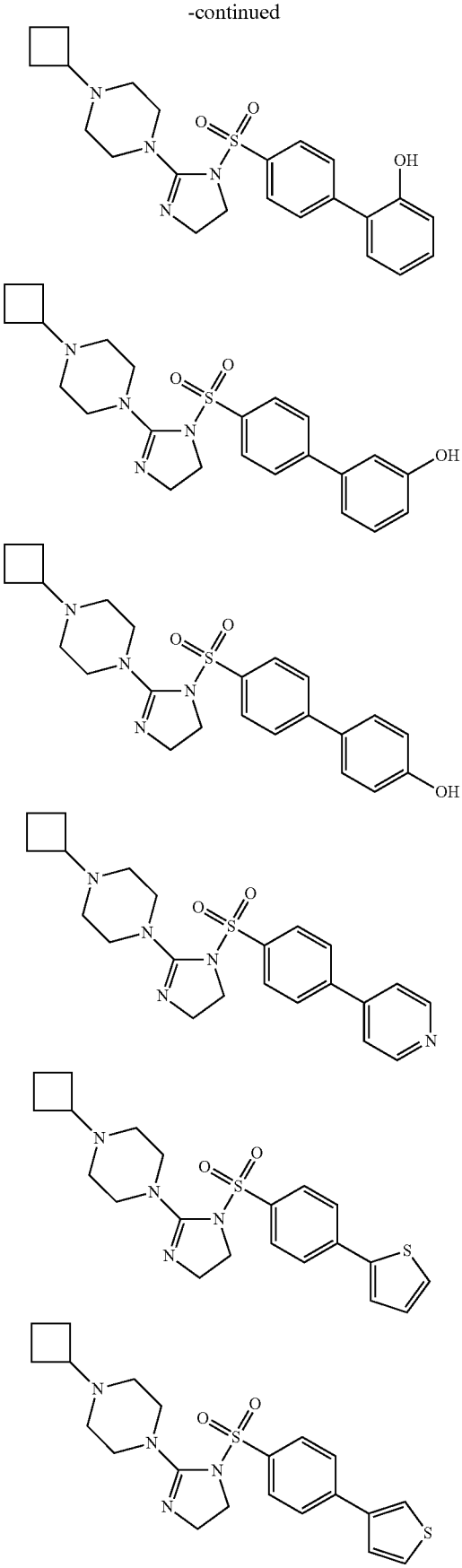
52
-continued
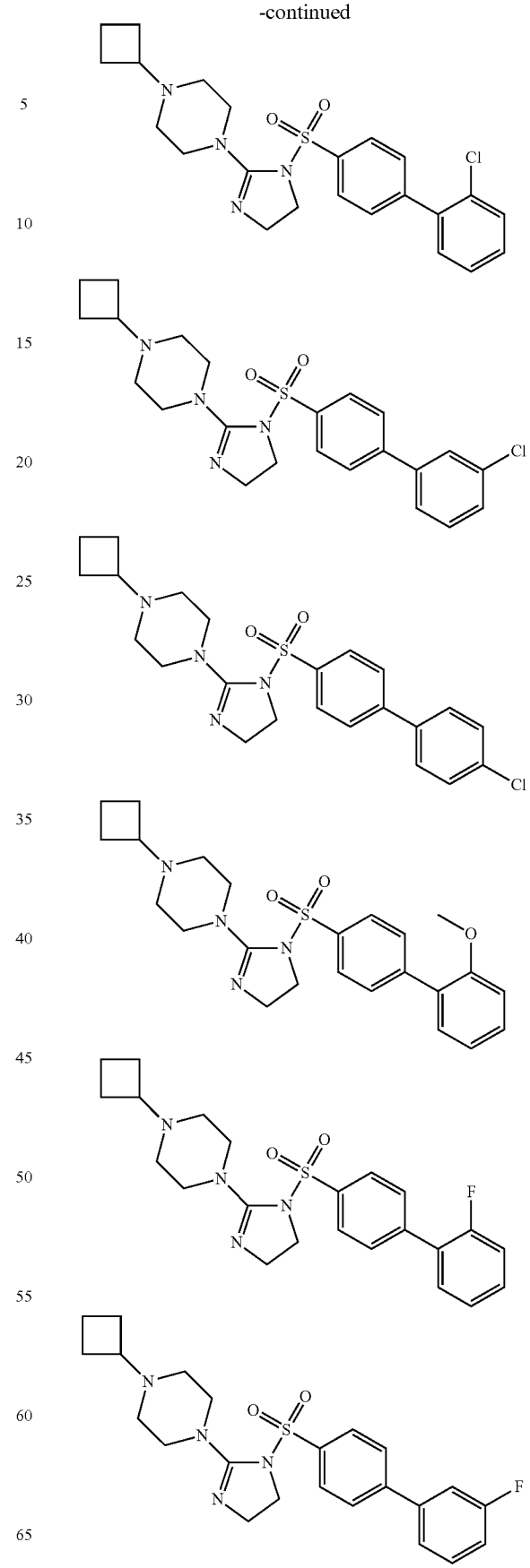

53
-continued
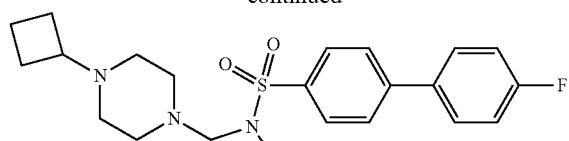
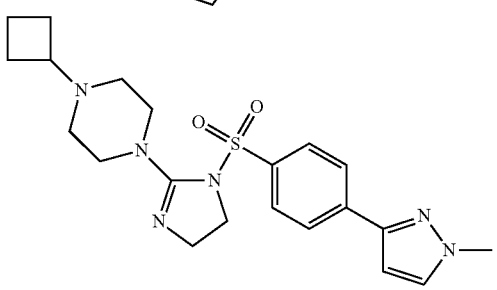
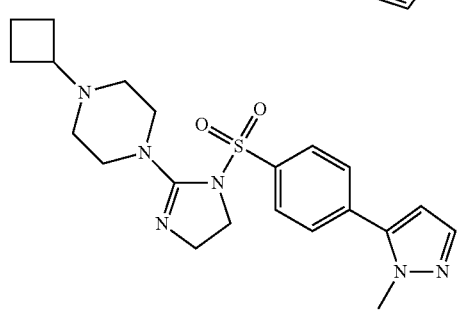
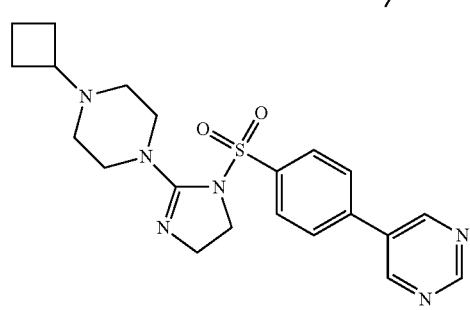
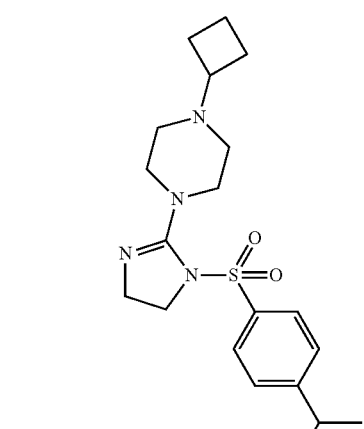
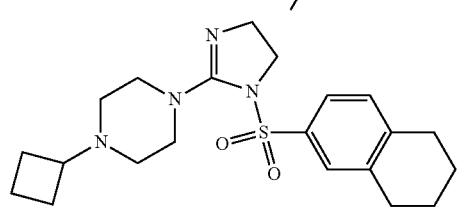
54
-continued
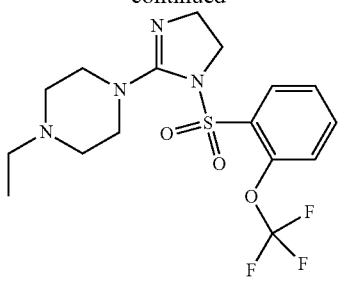
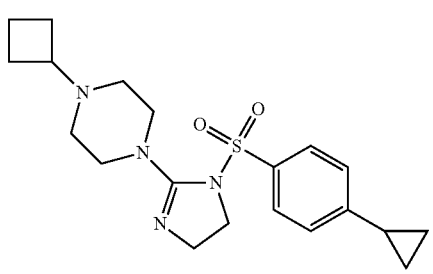
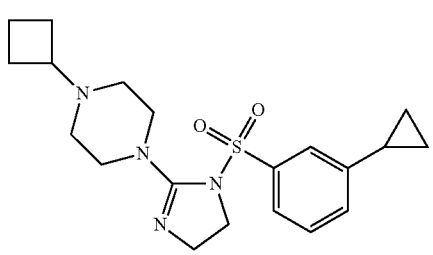
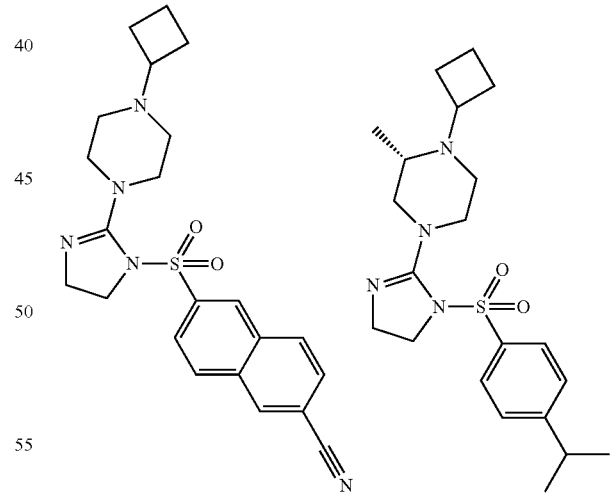
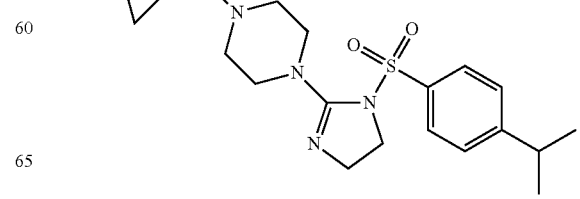

55
-continued
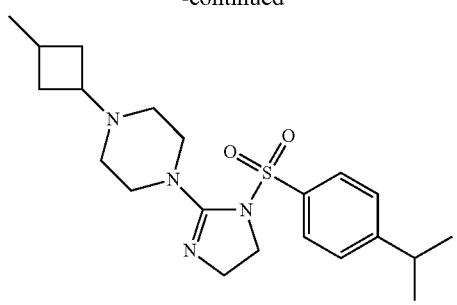
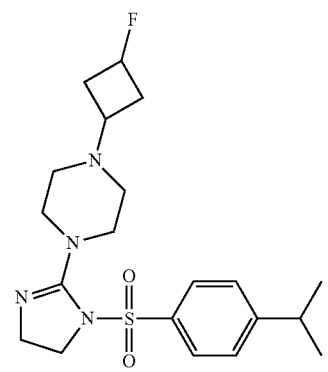
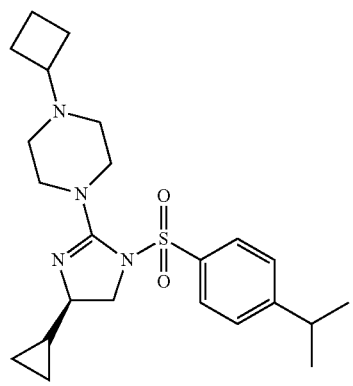
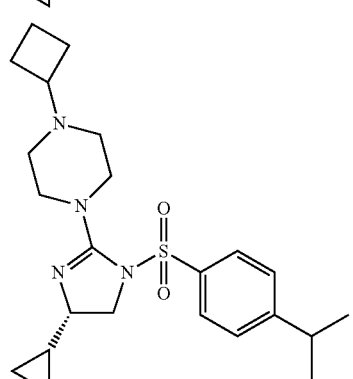
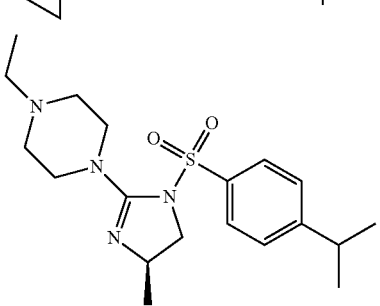
56
-continued
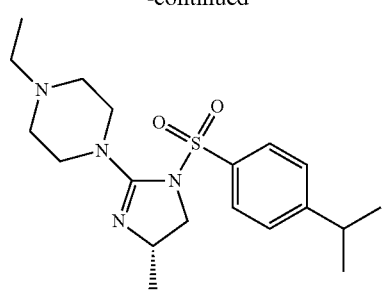
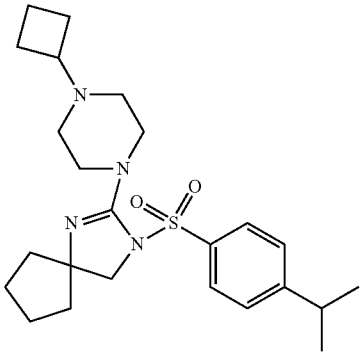
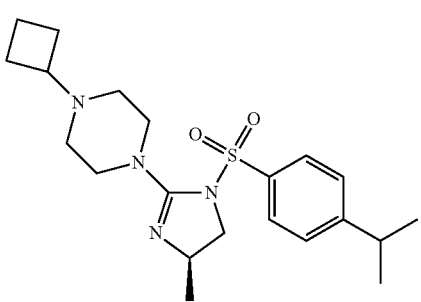
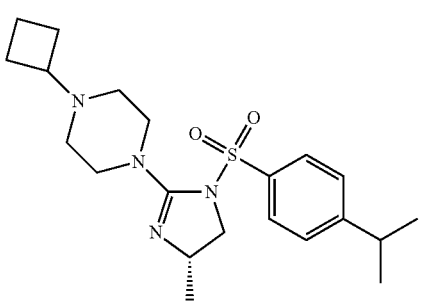
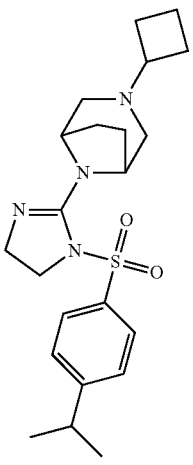

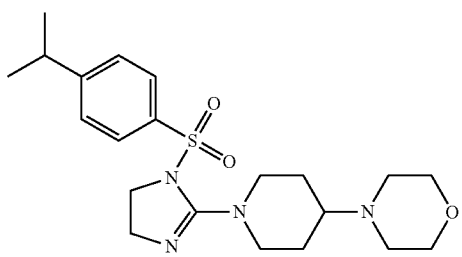
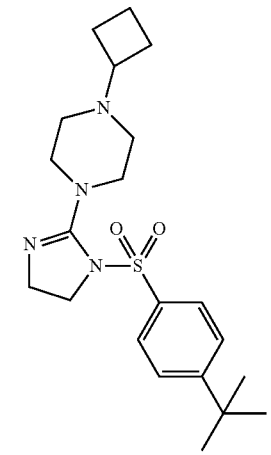
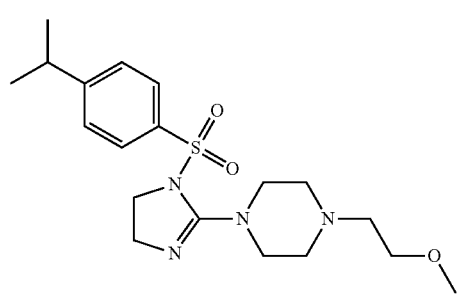
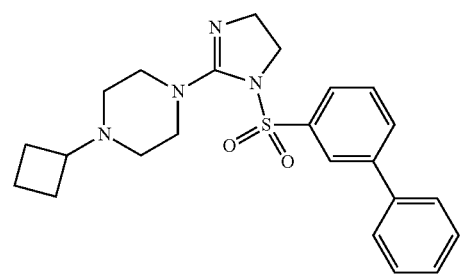
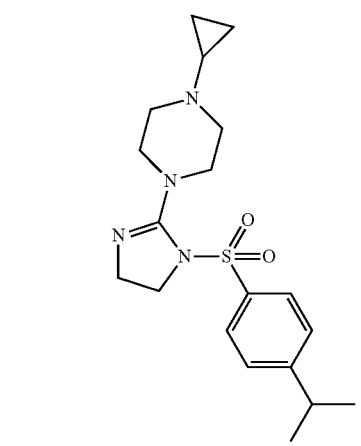
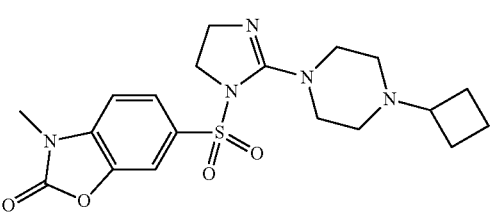
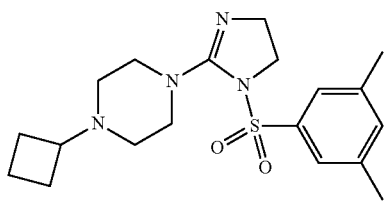
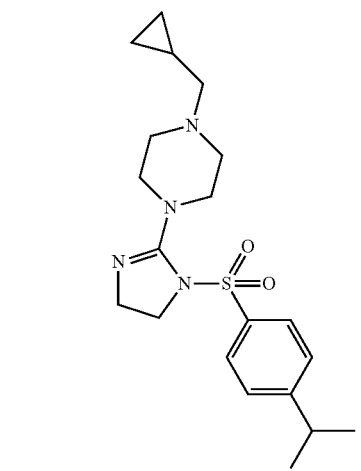
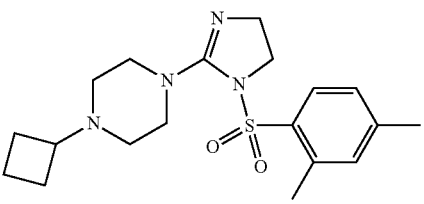
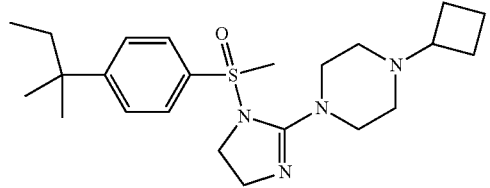

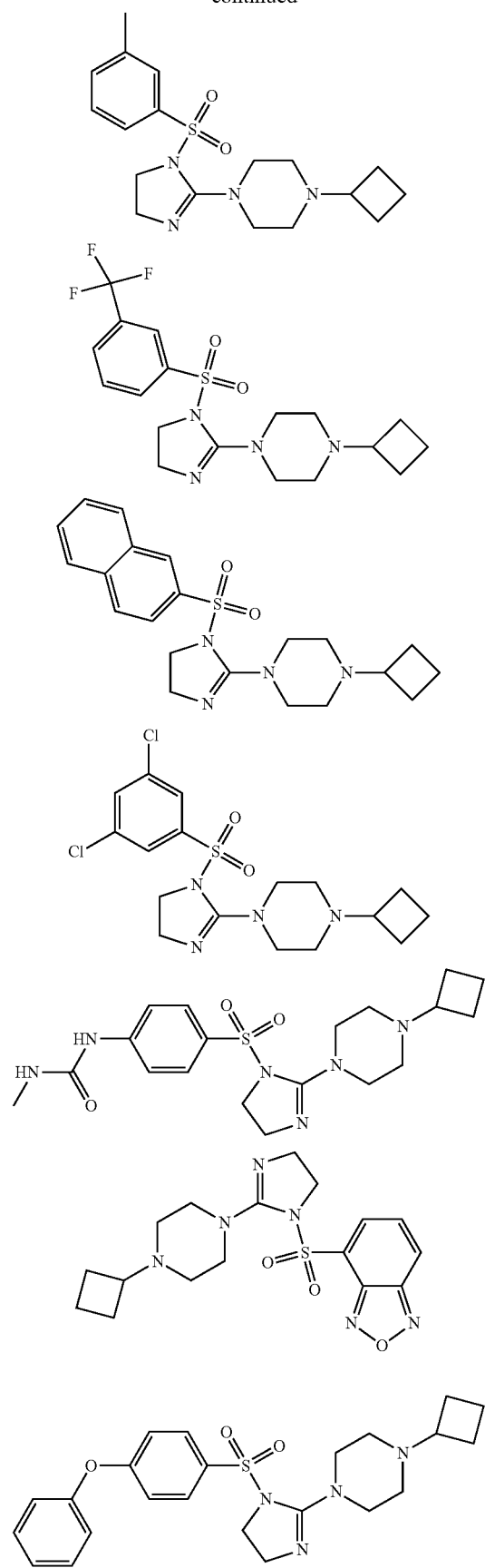
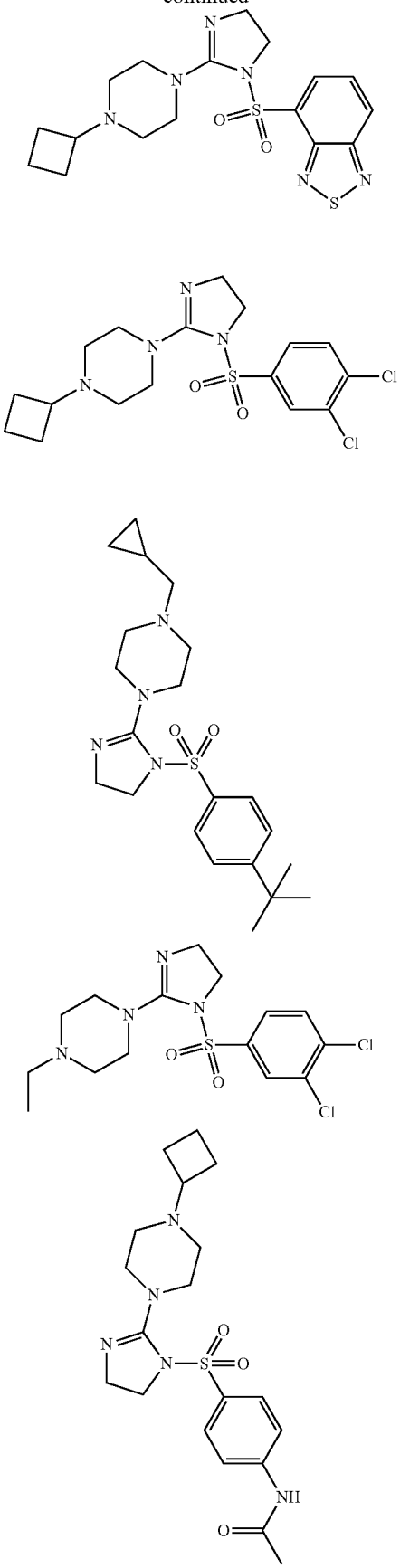

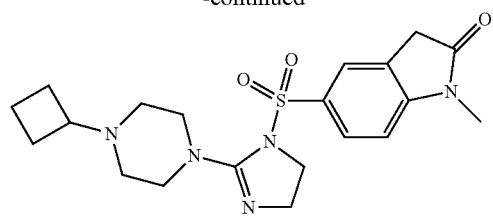
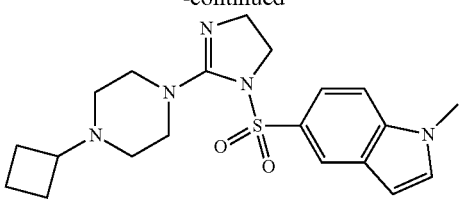
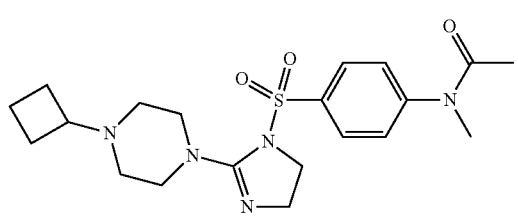
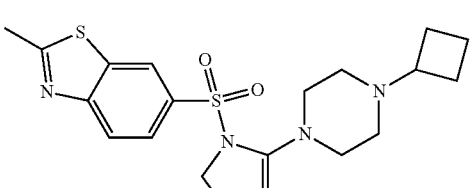
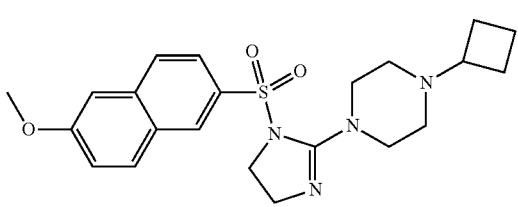
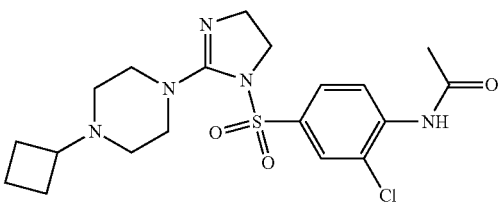
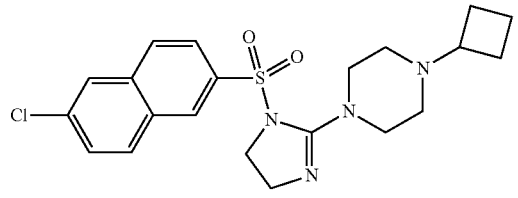
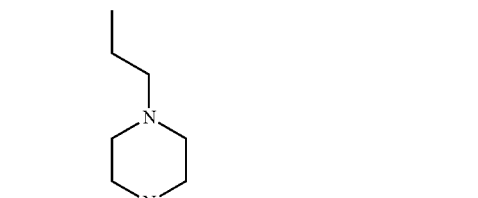
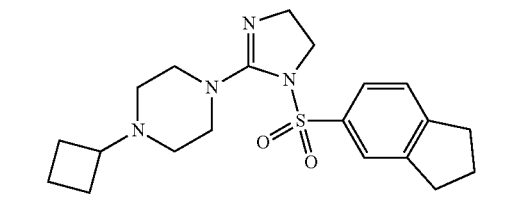
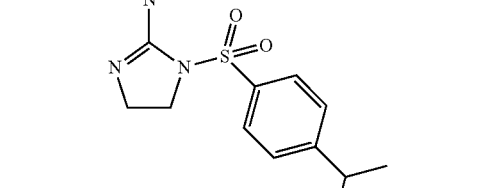
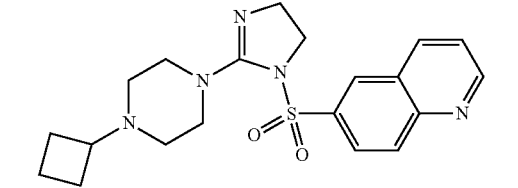
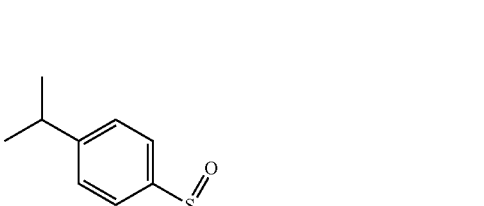
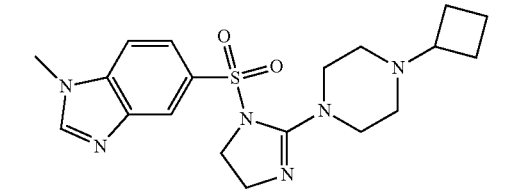
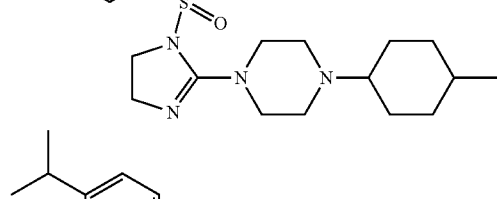
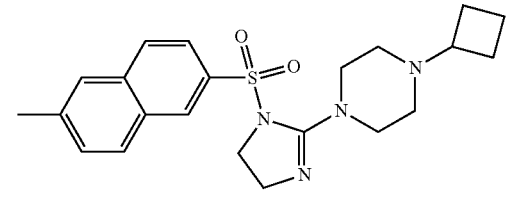
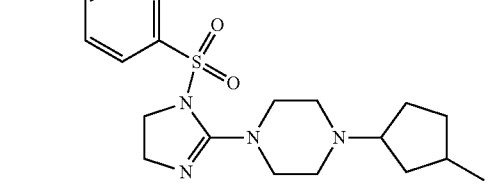

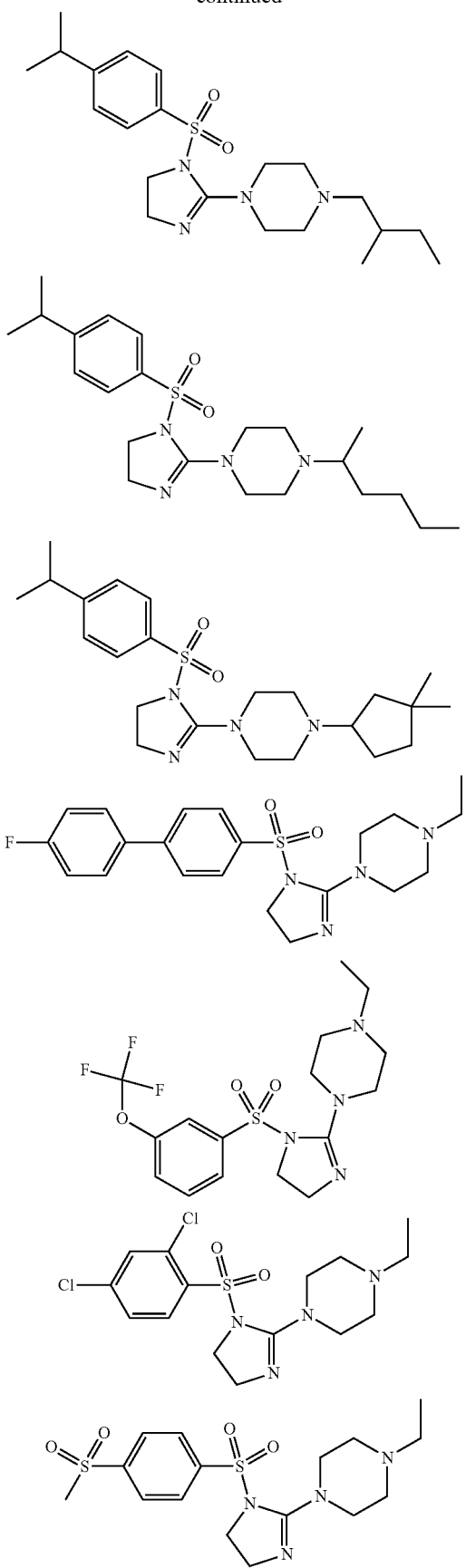
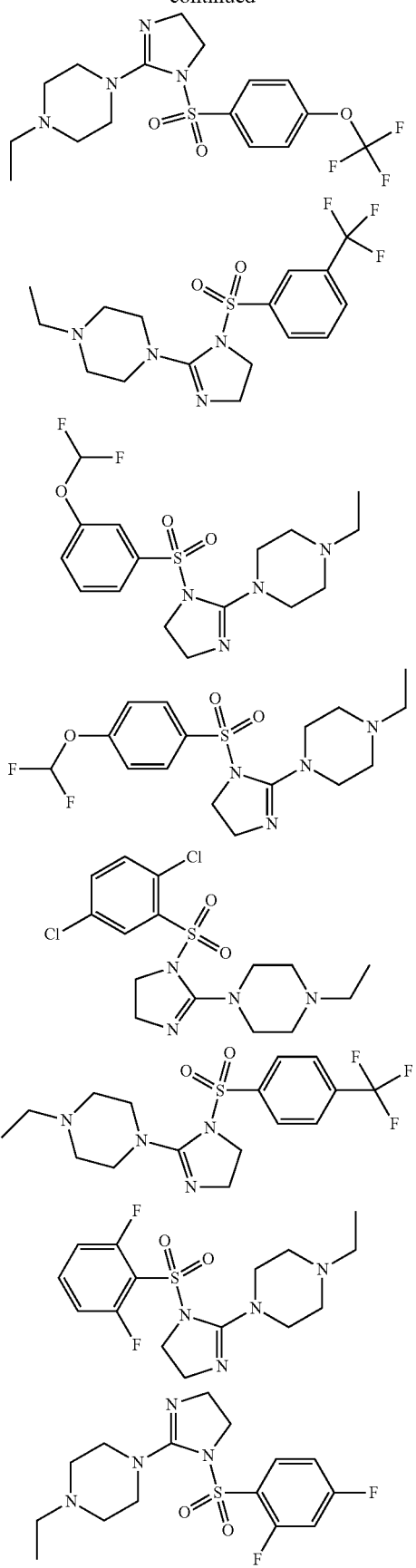

-continued
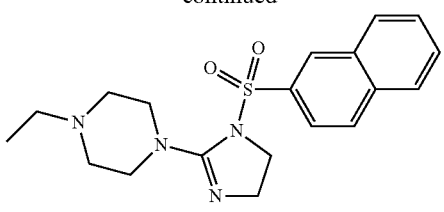
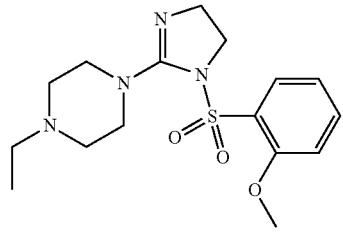
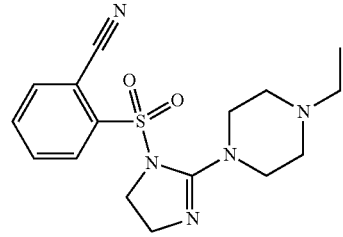
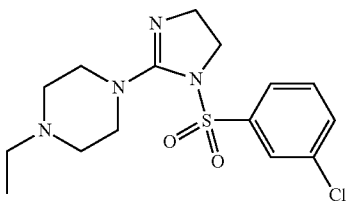
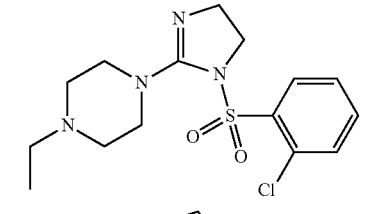
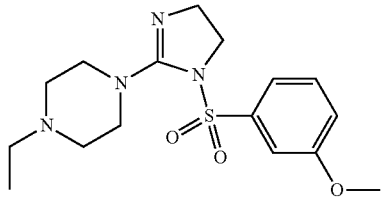
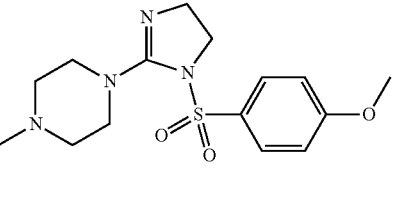
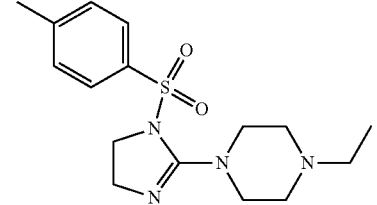
-continued
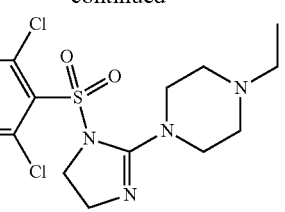
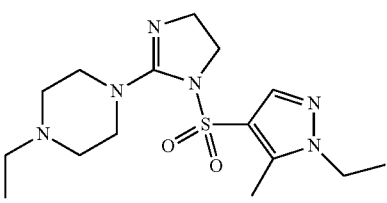
and
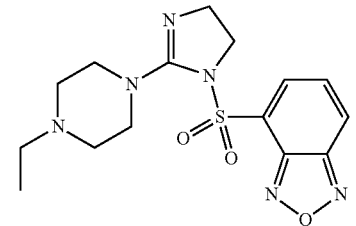
and salts thereof.
In one embodiment the compound is selected from:
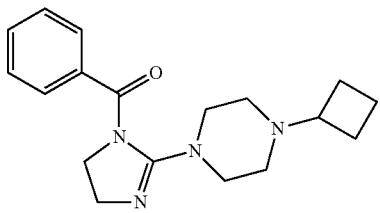
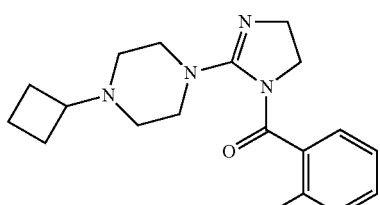
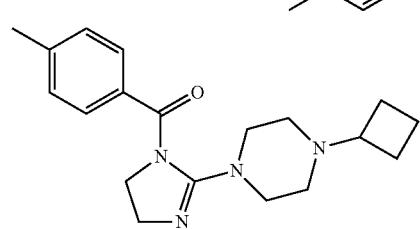

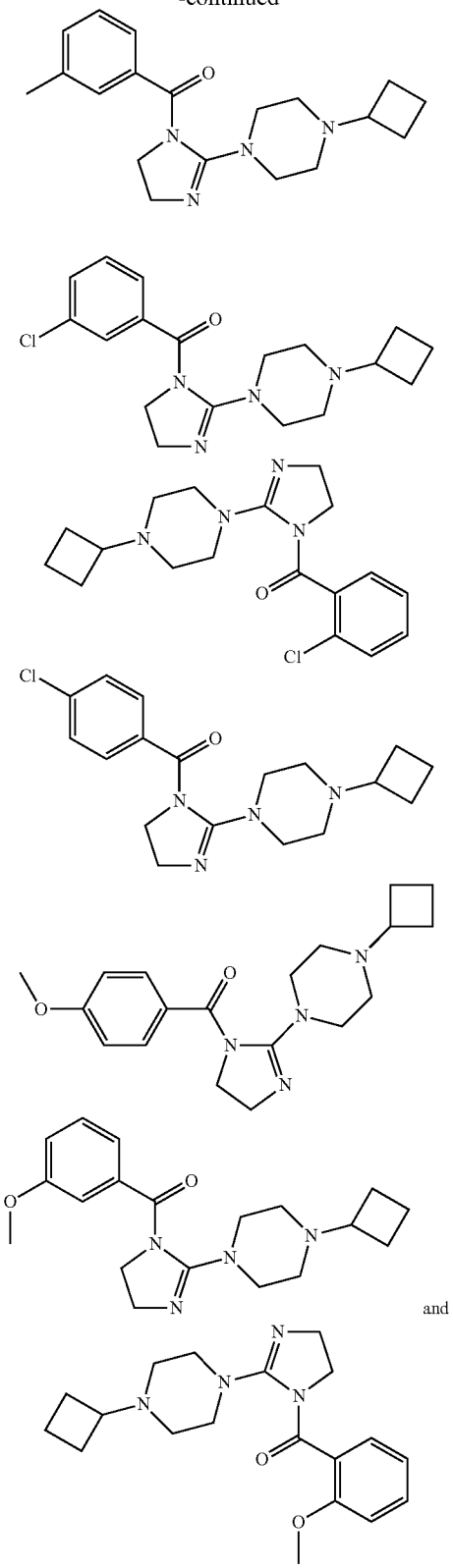

and salts thereof.

Uses, Formulation and Administration

Pharmaceutically Acceptable Compositions

Another aspect includes a pharmaceutical composition comprising a a compound as described herein or a pharma-ceutically acceptable salt thereof. In one embodiment, the composition further comprises a pharmaceutically acceptable carrier, adjuvant, or vehicle. In another embodiment, the composition further comprises an amount of the compound effective to measurably inhibit KDM2b. In certain embodiments, the composition is formulated for administration to a patient in need thereofcertain embodiments.

The term "patient" or "individual" as used herein, refers to an animal, such as a mammal, such as a human. In one embodiment, patient or individual refers to a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Compositions comprising a compound as described herein may be administered orally, parenterally, by inhalation spray, topically, transdermally, rectally, nasally, buccally, sublingually, vaginally, intraperitoneal, intrapulmonary, intradermal, epidural or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

In one embodiment, the composition comprising a compound as described herein is formulated as a solid dosage form for oral administration. Solid dosage forms for oral administration include capsules, tablets, pills, powders, and granules. In certain embodiments, the solid oral dosage form comprising a compound as described herein further comprises one or more of (i) an inert, pharmaceutically acceptable excipient or carrier, such as sodium citrate or dicalcium phosphate, and (ii) filler or extender such as starches, lactose, sucrose, glucose, mannitol, or silicic acid, (iii) binders such as carboxymethylcellulose, alginates, gelatin, polyvinylpyrrolidinone, sucrose or acacia, (iv) humectants such as glycerol, (v) disintegrating agent such as agar, calcium carbonate, potato or tapioca starch, alginic acid, certain silicates or sodium carbonate, (vi) solution retarding agents such as paraffin, (vii) absorption accelerators such as quaternary ammonium salts, (viii) a wetting agent such as cetyl alcohol or glycerol monostearate, (ix) absorbent such as kaolin or bentonite clay, and (x) lubricant such as talc, calcium stearate, magnesium stearate, polyethylene glycols or sodium lauryl sulfate. In certain embodiments, the solid oral dosage form is formulated as capsules, tablets or pills. In certain embodiments, the solid oral dosage form further comprises buffering agents. In certain embodiments, such compositions for solid oral dosage forms may be formulated as fillers in soft and hard-filled gelatin capsules comprising one or more excipients such as lactose or milk sugar, polyethylene glycols and the like.

In certain embodiments, tablets, dragees, capsules, pills and granules of the compositions comprising a compound as described herein optionally comprise coatings or shells such as enteric coatings. They may optionally comprise opacifying agents and can also be of a composition that they release the active ingredient(s) only, or preferentially, in a certain part of the intestinal tract, optionally, in a delayed manner. Examples of embedding compositions include polymeric substances and waxes, which may also be employed as fillers in soft and hard-filled gelatin capsules using such excipients as lactose or milk sugar as well as high molecular weight polethylene glycols and the like.

In another embodiment, a composition comprises microencapsulated compound as described herein, and optionally, further comprises one or more excipients.

In another embodiment, compositions comprise liquid dosage formulations comprising a compound as described herein for oral administration, and optionally further comprise one or more of pharmaceutically acceptable emulsions, microemulsions, solutions, suspensions, syrups and elixirs. In certain embodiments, the liquid dosage form optionally, further comprise one or more of an inert diluent such as water or other solvent, a solubilizing agent, and an emulsifier such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols or fatty acid esters of sorbitan, and mixtures thereof. In certain embodiments, liquid oral compositions optionally further comprise one or more adjuvant, such as a wetting agent, a suspending agent, a sweetening agent, a flavoring agent and a perfuming agent.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound as described herein, it may be desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In certain embodiments, the composition for rectal or vaginal administration are formulated as suppositories which can be prepared by mixing a compound as described herein with suitable non-irritating excipients or carriers such as cocoa butter, polyethylene glycol or a suppository wax, for example those which are solid at ambient temperature but liquid at body temperature and therefore melt in the rectum or vaginal cavity and release the compound.

Example dosage forms for topical or transdermal administration of a compound as described herein include ointments, pastes, creams, lotions, gels, powders, solutions, sprays, inhalants or patches. The compound as described herein is admixed under sterile conditions with a pharmaceutically acceptable carrier, and optionally preservatives or buffers. Additional formulation examples include an ophthalmic formulation, ear drops, eye drops, transdermal patches. Transdermal dosage forms can be made by dissolving or dispensing the compound as described herein in medium, for example ethanol or dimethylsulfoxide. Absorption enhancers can also be used to increase the flux of the compound across the skin. The rate can be controlled by either providing a rate controlling membrane or by dispersing the compound in a polymer matrix or gel.

Nasal aerosol or inhalation formulations of a compound as described herein may be prepared as solutions in saline, employing benzyl alcohol or other suitable preservatives, absorption promotors to enhance bioavailability, fluorocarbons, and/or other conventional solubilizing or dispersing agents.

In certain embodiments, pharmaceutical compositions may be administered with or without food. In certain embodiments, pharmaceutically acceptable compositions are administered without food. In certain embodiments, pharmaceutically acceptable compositions of this invention are administered with food.

Specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a compound as described herein in the composition will also depend upon the particular compound in the composition.

In one embodiment, the therapeutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 5 to about 100 mg of the compound of the invention.

An example tablet oral dosage form comprises about 2 mg, 5 mg, 25 mg, 50 mg, 100 mg, 250 mg or 500 mg of a compound as described herein, and further comprises about 95-30 mg anhydrous lactose, about 5-40 mg sodium croscarmellose, about 5-30 mg polyvinylpyrrolidone (PVP) K30 and about 1-10 mg magnesium stearate. The process of formulating the tablet comprises mixing the powdered ingredients together and further mixing with a solution of the PVP. The resulting composition can be dried, granulated, mixed with the magnesium stearate and compressed to tablet form using conventional equipment. An example of an aerosol formulation can be prepared by dissolving about 2-500 mg of a compound as described herein, in a suitable buffer solution, e.g. a phosphate buffer, and adding a tonicifier, e.g. a salt such sodium chloride, if desired. The solution may be filtered, e.g. using a 0.2 micron filter, to remove impurities and contaminants.

Uses of Compounds and Pharmaceutically Acceptable Compositions

Another aspect includes the use of a compound as described herein for the inhibition of KDM2b. Compounds as described herein may also be used to inhibit the removal of methyl marks on histone lysine residues, including inhibiting the removal of methyl marks from mono-, di- or tri-methylation of histones H1, H2A, H2B, H3 and H4, such as H3K36 (including for example the KDM2b substrate H3K36me2), thereby altering interactions of these histone proteins with DNA and/or other proteins, and altering certain subsequent genetic or protein expression. Compounds as described herein may also be used to inhibit KDM2b and reduce the activity of a cancer stem/progenitor cell population and/or deplete a cancer stem/progenitor cell population.

In certain embodiments, the binding or inhibition activity of a compound as described herein may be determined by running a competition experiment where the compound is incubated with the KDM2b enzyme bound to known radioligands. Detailed conditions for assaying a compound as an inhibitor of KDM2b or a mutant thereof are set forth in the Examples below.

In certain embodiments, detection of KDM2b activity is achieved with in vitro assays, which can be either direct binding (non-catalytic) or enzymatic (catalytic) asssays. Types of substrates that are used in such assays may include: short synthetic peptides corresponding to a number of residues from the N-terminus of histone sequences comprising the target lysine residue, single recombinant histone polypeptides, histone octamers reconstituted with recombinant histone proteins, and reconstituted nucleosomes (using reconstituted octamers and specific recombinant DNA fragments). The reconstituted nucleosomes may be mononucleosomes or oligonucleosomes.

Another aspect includes a method of treating or preventing a disease responsive to the inhibition of KDM2b activity in a patient. The method includes administering a therapeutically effective amount of a compound as described hereinto a patient in need thereof.

Another aspect includes the use of a compound as described herein, in therapy. Another aspect includes the use of a pharmaceutical composition comprising a compound as described herein, in therapy.

Another aspect includes the use of a compound as described herein, in treating a disease associated with KDM2b activity. Another aspect includes the use of a pharmaceutical composition comprising a compound as described herein, in treating a disease associated with KDM2b activity.

Another aspect includes the use of a compound as described herein, in the manufacture of a medicament for the treatment of a disease associated with KDM2b activity. Another aspect includes the use of a pharmaceutical composition comprising a compound as described herein, in the manufacture of a medicament for the treatment of a disease associated with KDM2b activity.

In certain embodiments, the disease or condition is a hyperproliferative disease, cancer, stroke, diabetes, hepatomegaly, cardiovascular disease, multiple sclerosis, Alzheimer's disease, cystic fibrosis, viral disease, autoimmune diseases, atherosclerosis, restenosis, psoriasis, rheumatoid arthritis, inflammatory bowel disease, asthma, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, liver disease, pathologic immune conditions involving T cell activation, CNS disorders or a myeloproliferative disorder.

In certain embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Another aspect includes a method for treating, ameliorating or preventing cancer, drug-resistant cancer or another proliferative disorder by administration of an effective amount of a compound as described herein to a mammal, for example a human, in need of such treatment. In certain embodiments, the disease to be treated is cancer.

Examples of cancers that may be treated using the compounds and methods described herein include, but are not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, androgen dependent cancer, angioimmunoblastic T-cell lymphoma, angiomyolipoma, angiosarcoma, astrocytoma, atypical teratoid rhabdoid tumor, B-cell chronic lymphocytic leukemia, B-cell lymphoma, basal cell carcinoma, biliary tract cancer, bladder cancer, blastoma, bone cancer, Brenner tumor, Brown tumor, Burkitt's lymphoma, breast cancer_(e.g., triple negative-breast cancer), brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, leukemia, leydig cell tumor, liposarcoma, lung cancer, lymphangioma, lymphangiosarcoma, lymphoepithelioma, lymphoma, acute lymphocytic leukemia (e.g., T-cell or B-cell), acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, acute myeloid leukemia, chronic myeloid leukemia, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor and Wilms' tumor.

Another embodiment includes a method for the treatment of benign proliferative disorders. Examples of benign proliferative disorders include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma and juvenile polyposis syndrome.

Another embodiment includes a therapeutic method useful for modulating protein methylation, gene expression, cell proliferation, cell differentiation and/or apoptosis in vivo in diseases mentioned above, in particular cancer, comprising administering to a patient in need of such therapy a pharmacologically active and therapeutically effective amount of one or more of the compounds as described herein.

Another embodiment includes a method for regulating endogenous or heterologous promotor activity by contacting a cell with a compound as described herein.

Another embodiment includes the use of a compound as described herein for the production of pharmaceutical compositions which are employed for the treatment and/or prophylaxis and/or amelioration of the diseases, disorders, illnesses and/or conditions as mentioned herein.

Another embodiment includes the use of a compound as described herein for the production of pharmaceutical compositions which are employed for the treatment and/or prophylaxis of diseases and/or disorders responsive or sensitive to the inhibition of histone demethylases, particularly those diseases mentioned above, such as e.g. cancer.

Compounds as described herein may be administered using any amount and any route of administration effective for treating or lessening the severity of the disorder. The exact amount required will vary from patient to patient, depending on the species, age, and general condition of the patient, for example the severity of the disorder, the particular compound, its mode of administration, and the like. The total daily usage of a compound as described herein by a given patient will be decided by the attending physician within the scope of sound medical judgment. The specific effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Another embodiment includes a method of inhibiting KDM2b activity in a biological sample comprising contacting said biological sample with a compound as described herein.

The term "biological sample", as used herein, includes, without limitation, a cell, cell cultures or extracts thereof; biopsied material obtained from a mammal or extracts thereof; and blood, saliva, urine, feces, semen, tears, or other body fluids or extracts thereof.

Co-Administration of Compounds and Other Agents

The compound as described herein may be employed alone or in combination with other agents for treatment. For example, the second agent of the pharmaceutical combination formulation or dosing regimen may have complementary activities to the compound as described herein such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer.

The term "co-administering" refers to either simultaneous administration, or any manner of separate sequential administration, of a compound as described herein, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Typically, any agent that has activity against a disease or condition being treated may be co-administered. Examples of such agents can be found in Cancer Principles and Practice of Oncology by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound as described herein and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $SM^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from antimicrotubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate salinosporamide A, carfilzomib, 17-AAG(geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CBI-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ11 and calicheamicin ω11 (Angew Chem. Intl. Ed Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)—imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and II-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imelone); panitumurnab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length $IgG_1$ λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (lmclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos: 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO 98/14451, WO 98/50038, WO 99/09016, and WO 99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839,gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner- Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFa) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) lockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTaI /β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi_{212}$, $P^{32}$, $Pb^{212}$ and radioactive isotopes of Lu); miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic. Chemotherapeutic agents also include treatments for Alzheimer's Disease such as donepezil hydrochloride and rivastigmine; treatments for Parkinson's Disease such as L-DOPA/carbidopa, entacapone, ropinrole, pramipexole, bromocriptine, pergolide, tribexephendyl, and amantadine; agents for treating multiple sclerosis (MS) such as beta interferon (e.g., Avonex® and Rebif®), glatiramer acetate, and mitoxantrone; treatments for asthma such as albuterol and montelukast sodium; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents;

agents for treating blood disorders such as corticosteroids, anti-leukemic agents, and growth factors; and agents for treating immunodeficiency disorders such as gamma globulin.

Additionally, chemotherapeutic agents include pharmaceutically acceptable salts, acids or derivatives of any of chemotherapeutic agents, described herein, as well as combinations of two or more of them.

The amount of both the compound as described herein and additional agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

The additional therapeutic agent and the compound as described herein may act synergistically. Therefore, the amount of additional therapeutic agent in such compositions may be less than that required in a monotherapy utilizing only that therapeutic agent, or there may be fewer side effects for the patient given that a lower dose is used. In certain embodiments, in such compositions a dosage of between 0.01-1,000 µg/kg body weight/day of the additional therapeutic agent can be administered.

In particular, provided herein are methods of treating cancer in an individual comprising administering to the individual (a) a compound as described herein and (b) a cytotoxic agent (e.g., targeted therapy, chemotherapy, and/or radiotherapy).

In certain embodiments of any of the methods, the cytotoxic agent is a targeted therapy. In certain embodiments, the targeted therapy is one or more of an EGFR antagonist, RAF inhibitor, and/or PI3K inhibitor.

In certain embodiments of any of the methods, the targeted therapy is an EGFR antagonist. In certain embodiments of any of the methods, the EGFR antagonist is N-(3-ethynylphenyl)-6,7-bis(2-methoxyethoxy)-4-quinazolinamine and/or a pharmaceutical acceptable salt thereof In certain embodiments, the EGFR antagonist is N-(3-ethynylphenyl)-6,7-bis(2-methoxyethoxy)-4-quinazolinamine. In certain embodiments, the EGFR antagonist is N-(4-(3-fluorobenzyloxy)-3-chlorophenyl)-6-(5-((2-(methylsulfonyl)ethylamino)methyl)furan-2-yl)quinazolin-4-amine,di4-methylbenzenesulfonate or a pharmaceutically acceptable salt thereof (e.g., lapatinib).

In certain embodiments of any of the methods, targeted therapy is a RAF inhibitor. In certain embodiments, the RAF inhibitor is a BRAF inhibitor. In certain embodiments, the RAF inhibitor is a CRAF inhibitor. In certain embodiments, the BRAF inhibitor is vemurafenib. In certain embodiments, the RAF inhibitor is 3-(2-cyanopropan-2-yl)-N-(4-methyl-3-(3-methyl-4-oxo-3,4-dihydroquinazolin-6-ylamino)phenyl)benzamide or a pharmaceutically acceptable salt thereof (e.g., AZ628 (CAS# 878739-06-1)).

In certain embodiments of any of the methods, the targeted therapy is a PI3 K inhibitor.

In certain embodiments of any of the methods, the cytotoxic agent is chemotherapy. In certain embodiments of any of the methods, the chemotherapy is a taxane. In certain embodiments, the taxane is paclitaxel. In certain embodiments, the taxane is docetaxel.

In certain embodiments of any of the methods, the cytotoxic agent is a platinum agent. In certain embodiments, the platinum agent is carboplatin. In certain embodiments, the platinum agent is cisplatin. In certain embodiments of any of the methods, the cytotoxic agent is a taxane and a platinum agent. In certain embodiments, the taxane is paclitaxel. In certain embodiments, the taxane is docetaxel. In certain embodiments, the platinum agent is carboplatin. In certain embodiments, the platinum agent is cisplatin.

In certain embodiments of any of the methods, the cytotoxic agent is a vinea alkyloid. In certain embodiments, the vinca alkyloid is vinorelbine. In certain embodiments of any of the methods, the chemotherapy is a nucleoside analog. In certain embodiments, the nucleoside analog is gemcitabine.

In certain embodiments of any of the methods, the cytotoxic agent is radiotherapy.

In certain embodiments of any of the methods, the compound as described herein is concomitantly administered with the cytotoxic agent (e.g, targeted therapy, chemotherapy, and/or radiotherapy). In certain embodiments, the compound as described herein is administered prior to and/or concurrently with the cytotoxic agent (e.g., targeted therapy, chemotherapy, and/or radiotherapy).

In certain embodiments of any of the methods, the cancer is lung cancer (e.g., non-small cell lung cancer), breast cancer (e.g., triple-negative breast cancer), pancreatic cancer, leukemia (e.g., AML, CML, ALL (e.g., T-cell or B-cell), MLL), lymphoma, bladder cancer, prostate cancer and/or seminoma. In certain embodiments, the cancer is lung. In certain embodiments, the lung cancer is NSCLC. In certain embodiments, the cancer is leukemia. In certain embodiments, the cancer is lymphoma.

EXEMPLIFICATION

As depicted in the Examples below, in certain exemplary embodiments, compounds are prepared according to the following general procedures. It will be appreciated that, although the general methods depict the synthesis of certain compounds, the following general methods, and other methods known to one of ordinary skill in the art, can typically be applied to all compounds and subclasses and species of each of these compounds, as described herein.

The general synthetic methods illustrated in Schemes 1-2 were used to prepare the compounds of the Examples as detailed below.

Scheme 1

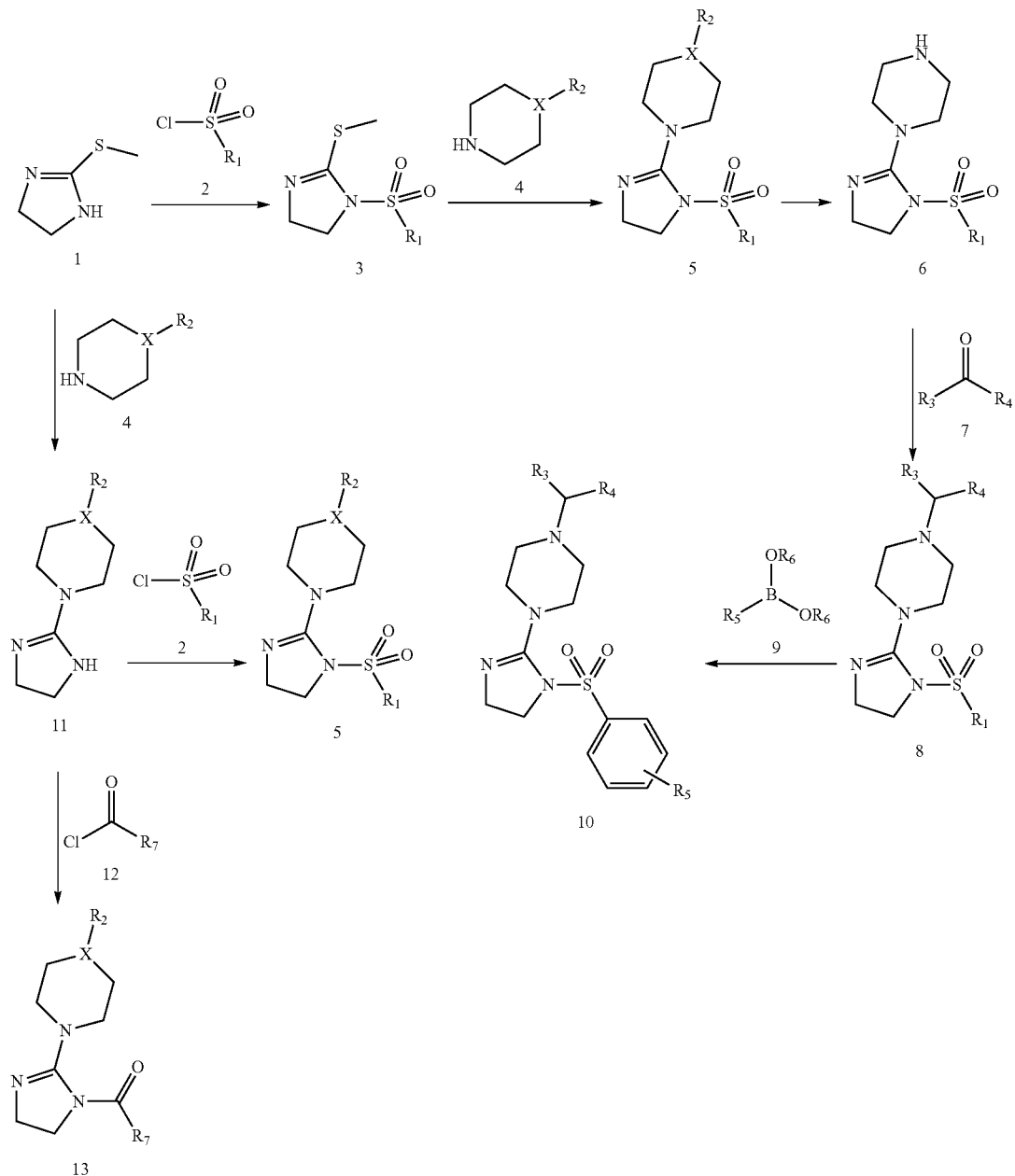

Compounds of formula (5), (8), (10) and (13) may be prepared by general synthetic methods as shown in Scheme 1.

Treatment of (1) with a substituted sulfonyl chloride (2) in an organic solvent such as, but not limited to, DCM in the presence of an inorganic base such as, but not limited to, diisopropylethylamine at a temperature of about room temperature and for a time varying from about 2 hours to 12 hours affords sulfonamide (3). Reaction between sulfonamide (3) and amine (4) neat at a temperature of about 110° C. to 130° C. and for a time varying from about 6 hours to 16 hours can afford compounds of formula (5). Alternatively, compounds of formula (5) can be accessed by treatment of (1) with amine (4) neat at a temperature of about 110° C. to 130° C. and for a time varying from about 6 hours to 16 hours gives imidazoline (11). Reaction of imidazoline (11) with a substituted sulfonyl chloride (2) in an organic solvent such as, but not limited to, DCM in the presence of an inorganic base such as, but not limited to, diisopropylethylamine at a temperature of about room temperature and for a time varying from about 2 hours to 12 hours can afford compounds of formula (5). Compounds of formula (5; X=NH, $R_2$=t-butyl carbamate) can be treated under acidic conditions with an acid such as, but not limited to, HCl or trifluoroacetic acid in an organic base such as, but not limited to, ethyl acetate or DCM at a temperature of about 0° C. to room temperature and for a time varying from about 2 hours to 10 hours affords piperazine (6). Treatment of piperazine (6) under reductive amination conditions with a variety of ketones or aldehydes (7) in the presence of a reducing agent such as, but not limited to, sodium triacetoxyborohydride or sodium cyanoborohydride in an organic solvent such as, but not limited to, DCM or DMF at a temperature of about room temperature can afford compounds of formula (8). Compounds for formula (8, $R_1$=an appropriately halogen substituted aromatic or heteroaromatic) can cross-couple with an aryl or heteroaryl boronic acid or boronate ester (9) under palladium catalyst conditions such as, but not limited to, 1,1'-[1,1'-bis(diphenylphosphino)ferrocene] dichloropalladium(II) in the presence of an inorganic base such as, but not limited to, potassium acetate, sodium carbonate or cesium carbonate in a suitable organic solvent such as, but not limited to, 1,4-dioxane in combination with water as a co-solvent at a temperature of about 110° C. and for a time varying from about 30 minutes to about 18 hours to yield compounds of formula (10). Imidazoline (11) can be treated with various acid chlorides (12) in an organic solvent such as, but not limited to, DCM in the presence of an inorganic base such as, but not limited to, triethylamine at a temperature of about room temperature and for a time varying from about 2 hours to 12 hours can afford compounds of formula (13).

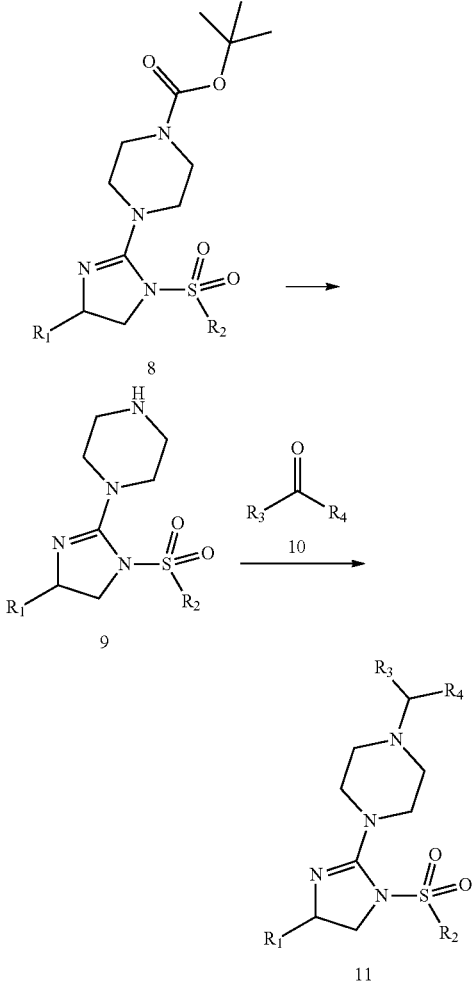

Compounds of formula (11) may be prepared by general synthetic methods as shown in Scheme 2.

A substituted 2-amino acetamide (1) could be converted to 1,2-diamine (2) under reduction conditions in the presence of a reducing agent such as, but not limited to, borane dimethylsulfide in a an organic solvent such as, but not limited to, THF at a temperature around reflux temperature for a time of about 5 hours. Treatment of 1,2-diamine (2) with carbon disulfide in a an organic solvent such as, but not limited to, ethanol and water as a cosolvent at a temperature around reflux temperature for a time of about 5 hours affords thiourea (3). Thiourea (3) can be treated with methyl iodide in a an organic solvent such as, but not limited to, methanol and at a temperature around 80° C. for a time of about 5 hours affords imidazoline (4). Reaction of imidazoline (4) with a substituted sulfonyl chloride (5) in an organic solvent such as, but not limited to, DCM in the presence of an inorganic base such as, but not limited to, diisopropylethylamine at a temperature of about room temperature and for a time varying from about 2 hours to 12 hours can afford sulfonamide (6). Reaction between sulfonamide (6) and piperazine (7) neat at a temperature of about 110° C. to 130° C. and for a time varying from about 6 hours to 16 hours can afford t-butyl carbamate piperazine (8). Compound t-butyl carbamate piperazine (8) can be treated under acidic conditions with an acid such as, but not limited to, HCl or trifluoroacetic acid in an organic base such as, but not

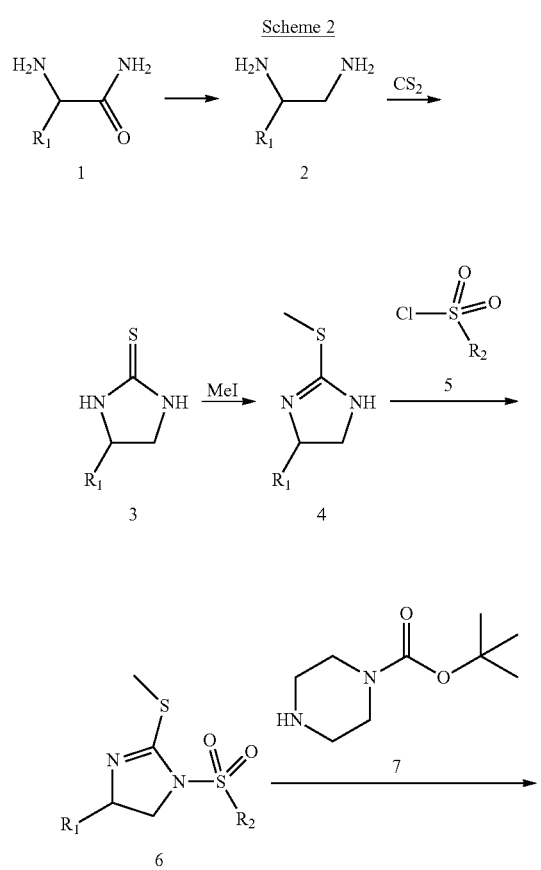

limited to, ethyl acetate or DCM at a temperature of about 0° C. to room temperature and for a time varying from about 2 hours to 10 hours affords piperazine (9). Treatment of piperazine (9) under reductive amination conditions with a variety of ketones or aldehydes (10) in the presence of a reducing agent such as, but not limited to, sodium triacetoxyborohydride or sodium cyanoborohydride in an organic solvent such as, but not limited to, DCM or DMF at a temperature of about room temperature can afford compounds of formula (11).

General Procedure for Intermediate A

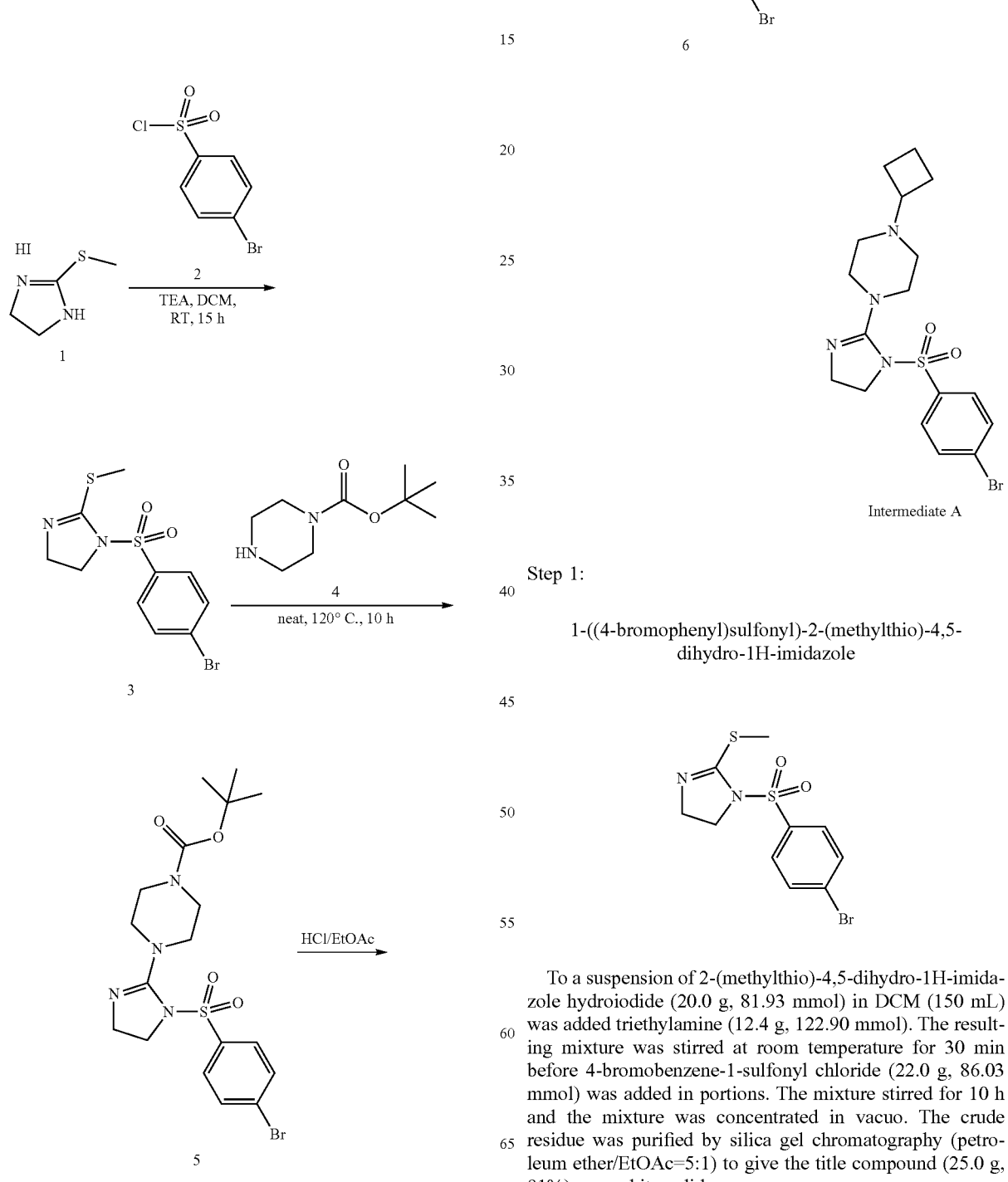

Step 1:

1-((4-bromophenyl)sulfonyl)-2-(methylthio)-4,5-dihydro-1H-imidazole

To a suspension of 2-(methylthio)-4,5-dihydro-1H-imidazole hydroiodide (20.0 g, 81.93 mmol) in DCM (150 mL) was added triethylamine (12.4 g, 122.90 mmol). The resulting mixture was stirred at room temperature for 30 min before 4-bromobenzene-1-sulfonyl chloride (22.0 g, 86.03 mmol) was added in portions. The mixture stirred for 10 h and the mixture was concentrated in vacuo. The crude residue was purified by silica gel chromatography (petroleum ether/EtOAc=5:1) to give the title compound (25.0 g, 91%) as a white solid.

Step 2:

tert-butyl 4-(1-((4-bromophenyl)sulfonyl)-4,5-di-hydro-1H-imidazol-2-yl)piperazine-1-carboxylate

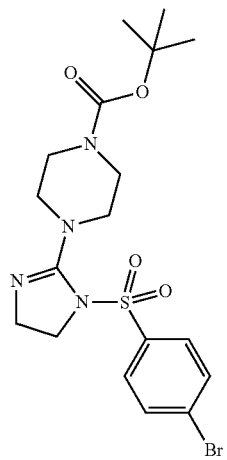 [SMILES: CC(C)(C)OC(=O)N1CCN(C2=NCCN2S(=O)(=O)c2ccc(Br)cc2)CC1]

A mixture of 1-((4-bromophenyl)sulfonyl)-2-(methylthio)-4,5-dihydro-1H-imidazole (20.0 g, 59.66 mmol) and tert-butyl piperazine-1-carboxylate (22.2 g, 119.32 mmol) was heated at 120° C. (neat) for 15 h. After cooling to room temperature, the residue was diluted with petroleum ether. The resulting precipitate was collected by filtration and dried in vacuo to give the title compound (21.0 g, 74%) as a white solid.

Step 3:

1-((4(4-bromophenyl)sulfonyl)-4,5-dihydro-1H-imidazol-2-yl)piperazine hydrochloride

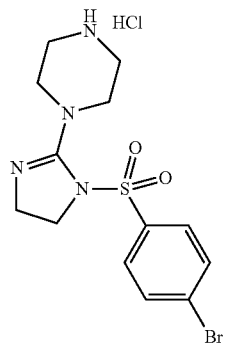 [SMILES: Cl ; O=S(=O)(c1ccc(Br)cc1)N1CCN=C1N1CCNCC1]

To a solution of tert-butyl 4-(1-((4-bromophenyl)sulfonyl)-4,5-dihydro-1H-imidazol-2-yl)piperazine-1-carboxylate (21.0 g, 44.36 mmol) in EtOAc (200 mL) was slowly added HCl (4 M in EtOAc, 50 mL, 200 mmol) at 0° C. After the addition, the mixture stirred at 0° C. for 2 h followed by room temperature for an additional 6 h. The solvent was removed in vacuo to give the crude product (17.0 g, 94%) as a white solid that required no further purification.

Step 4:

1-(1-((4-bromophenyl)sulfonyl)-4,5-dihydro-1H-imidazol-2-yl)-4-cyclobutylpiperazine

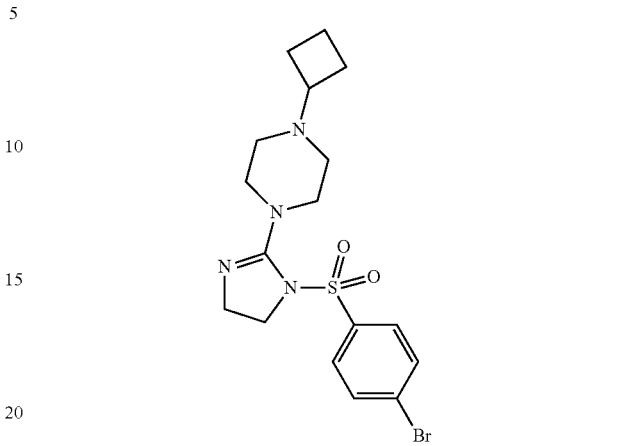

A solution of 1-(1-((4-bromophenyl)sulfonyl)-4,5-dihydro-1H-imidazol-2-yl)piperazine hydrochloride (15.0 g, 36.61 mmol) and cyclobutanone (10.3 g, 146.44 mmol) in DCM (180 mL) was stirred at room temperature for 1 h. Then NaBH(OAc)$_3$ (15.5 g, 73.22 mmol) was added in portions. After the addition, the reaction mixture was stirred for another 8 h and then quenched by the addition of a saturated aqueous NH$_4$Cl solution (40 mL). The mixture was extracted with DCM (100 mL×3). The combined organic layers were dried over anhydrous sodium sulfate and concentrated in vacuo. The crude product was purified by silica gel chromatography (petroleum ether/EtOAc=1:1) to give the title compound (Intermediate A) (11.0 g, 70%) as a white solid.

General Procedure for Intermediate B

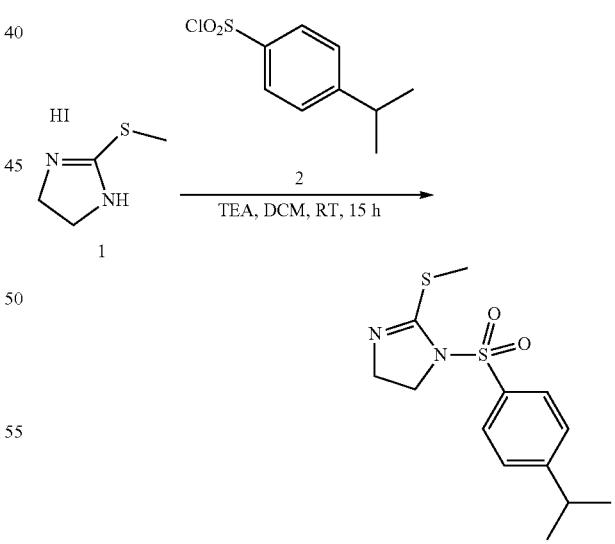

1-((4-isopropylphenyl)sulfonyl)-2-(methylthio)-4,5-dihydro-1H-imidazole

To a suspension of 2-(methylthio)-4,5-dihydro-1H-imidazole hydroiodide (10.0 g, 40.97 mmol) in DCM (150 mL)

was added triethylamine (9.1 g, 90.13 mmol). The resulting mixture was stirred at room temperature for 30 min before 4-isopropylbenzene-1-sulfonyl chloride (9.9 g, 45.06 mmol) was added portion-wise. The mixture stirred for 10 h before it was concentrated in vacuo. The crude product was purified by silica gel chromatography (petroleum ether/EtOAc=5:1) to give the title compound (10.0 g, 82%) as a white solid.

General Procedure for Intermediate C

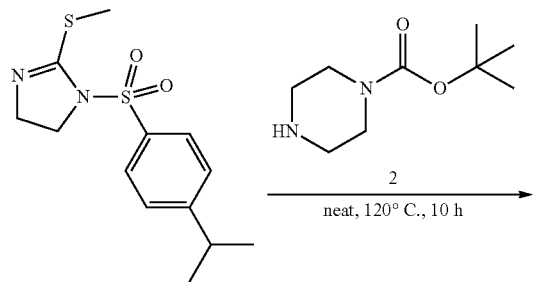

Intermediate B

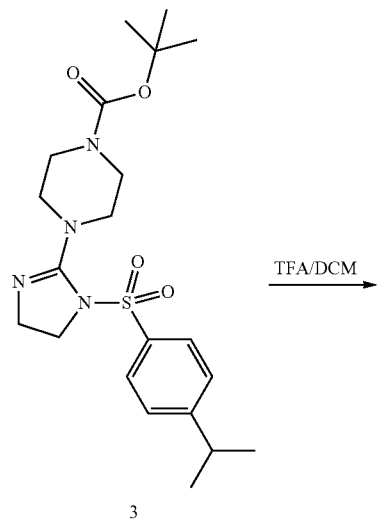

3

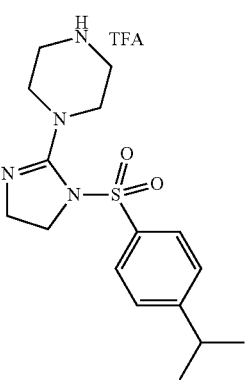

Intermediate C

Step 1:

tert-butyl 4-(1-((4-isopropylphenyl)sulfonyl)-4,5-dihydro-1H-imidazol-2-yl)piperazine-1-carboxylate

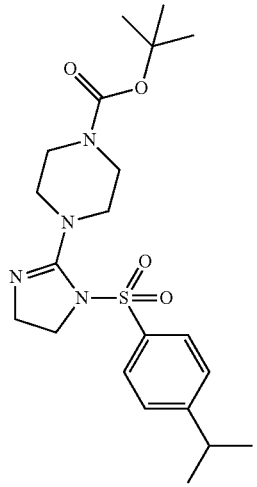 [SMILES: CC(C)c1ccc(S(=O)(=O)N2CCN=C2N2CCN(C(=O)OC(C)(C)C)CC2)cc1]

A mixture of 1-((4-isopropylphenyl)sulfonyl)-2-(methylthio)-4,5-dihydro-1H-imidazole (Intermediate B, 10.0 g, 33.51 mmol) and tert-butyl piperazine-1-carboxylate (12.5 g, 67.02 mmol) was heated at 130° C. (neat) for 12 h. After cooling to room temperature, the residue was purified by silica gel chromatography (petroleum ether/EtOAc=2:1) to give the title compound (8.5 g, 58%) as a brown solid.

Step 2:

1-(1-((4-isopropylphenyl)sulfonyl)-4,5-dihydro-1H-imidazol-2-piperazine

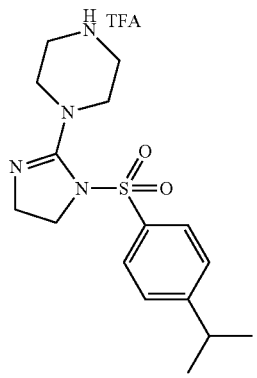 [SMILES: CC(C)c1ccc(S(=O)(=O)N2CCN=C2N2CCNCC2)cc1 ; "TFA"]

To a solution of tert-butyl 4-(1-((4-isopropylphenyl)sulfonyl)-4,5-dihydro-1H-imidazol-2-yl)piperazine-1-carboxylate (8.0 g, 18.32 mol) in DCM (50 mL) was added TFA (20 mL). The mixture was stirred at room temperature for 2 h. The solution was concentrated in vacuo to give the title compound (Intermediate C, 8.3 g, 100%) as a brown solid that required no further purification.

General Procedure for Intermediate D

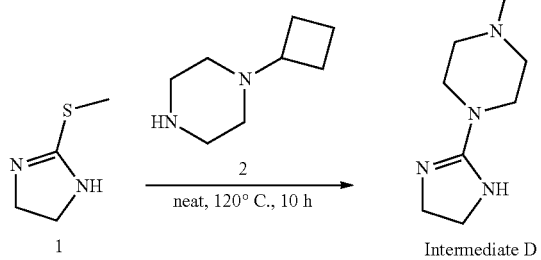

1-cyclobutyl-4-(4,5-dihydro-1H-imidazol-2-yl)piperazine

To a 40 mL vial was added 2-methylsulfanyl-4,5-dihydro-1H-imidazole (1000 mg, 8.61 mmol) and 1-cyclobutylpiperazine (1811 mg, 12.91 mmol). The mixture was heated without solvent at 120° C. overnight. Heptanes was added and a precipitate formed. The precipitate was collected by filtration to yield the title compound (1700 mg, 95%) as a brown-orange solid that required no further purification.

Example 1

2-[4-[[2-(4-cyclobutylpiperazin-1-yl)-4,5-dihydroimidazol-1-yl]sulfonyl]phenyl]benzonitrile

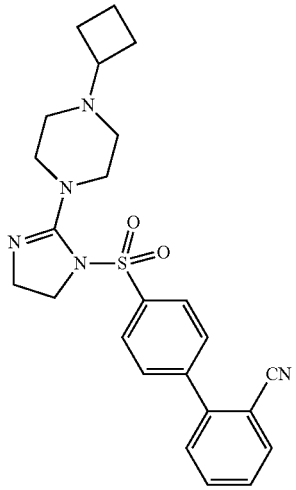 [SMILES: N#Cc1ccccc1-c1ccc(S(=O)(=O)N2CCN=C2N2CCN(C3CCC3)CC2)cc1]

A mixture of 1-(1-((4-bromophenyl)sulfonyl)-4,5-dihydro-1H-imidazol-2-yl)-4-cyclobutylpiperazine (Intermediate A, 100 mg, 0.234 mmol), (2-cyanophenyl)boronic acid (52 mg, 0.351 mmol), Pd(dppf)Cl$_2$ (17 mg, 0.023 mmol) and cesium carbonate (153 mg, 0.468 mmol) in dioxane (2.5 mL) and H$_2$O (0.5 mL) was irradiated at 110° C. in a microwave for 40 min. After cooling, the reaction mixture was diluted with EtOAc (20 mL) and washed with water (10 mL). The separated organic layer was dried over anhydrous sodium sulfate and concentrated in vacuo. The residue was purified by reverse phase chromatography (acetonitrile 42-52%/0.1% NH$_4$OH in water) to give the title compound (25 mg, 24%) as a white solid. $^1$H NMR (400 MHz, CD$_3$OD) δ 8.08-8.06 (m, 2H), 7.91-7.84 (m, 4H), 7.67-7.62 (m, 2H), 4.04-4.02 (m, 2H), 3.44-3.42 (m, 4H), 3.10-3.07 (m, 3H), 2.73-2.70 (m, 4H), 2.19-2.17 (m, 2H), 2.02-2.00 (m, 2H), 1.83-1.81 (m, 2H). LCMS M/Z (M+H) 450.

The following compounds were prepared in a similar fashion to Example 1:

Examples 2-30

| Example | Compound Name | NMR | m/z |
|---|---|---|---|
| Example 2 | 1-cyclobutyl-4-[1-[4-(3-methoxyphenyl)phenyl]sulfonyl-4,5-dihydroimidazol-2-yl]piperazine | $^1$H NMR (400 MHz, CD$_3$OD) δ 7.96 (d, J = 8.4 Hz, 2H), 7.85 (d, J = 8.4 Hz, 2H), 7.39-7.35 (m, 1H), 7.25-7.20 (m, 2H), 7.00-6.98 (m, 1H), 3.97 (t, J = 7.6 Hz, 2H), 3.85 (s, 3H), 3.39-3.37 (m, 4H), 3.03-2.99 (m, 2H), 2.90-2.75 (m, 1H), 2.51-2.48 (m, 4H), 2.12-2.09 (m, 2H), 1.97-1.85 (m, 2H), 1.80-1.70 (m, 2H) | 455 |
| Example 3 | 1-cyclobutyl-4-[1-[4-(4-methoxyphenyl)phenyl]sulfonyl-4,5-dihydroimidazol-2-yl]piperazine | $^1$H NMR (400 MHz, CD$_3$OD) δ 7.92 (d, J = 8.4 Hz, 2H), 7.82 (d, J = 8.0 Hz, 2H), 7.64 (d, J = 8.4 Hz, 2H), 7.03 (d, J = 8.8 Hz, 2H), 3.96 (t, J = 8.0 Hz, 2H), 3.84 (s, 3H), 3.45-3.35 (m, 4H), 3.04-2.95 (m, 2H), 2.87-2.83 (m, 1H), 2.52-2.50 (m, 4H), 2.11-2.07 (m, 2H), 1.95-1.92 (m, 2H), 1.77-1.70 (m, 2H) | 455 |
| Example 4 | 1-cyclobutyl-4-[1-[4-[2-(trifluoromethyl)phenyl]phenyl]sulfonyl-4,5-dihydroimidazol-2-yl]piperazine | $^1$H NMR (400 MHz, CD$_3$OD) δ 7.96 (d, J = 8.4 Hz, 2H), 7.81 (d, J = 8.0 Hz, 1H), 7.70-7.63 (m, 1H), 7.61-7.58 (m, 1H), 7.55 (d, J = 8.0 Hz, 2H), 7.39 (d, J = 7.6 Hz, 1H), 3.98 (t, J = 7.6 Hz, 2H), 3.39-3.37 (m, 4H), 3.01 (t, J = 7.2 Hz, 2H), 2.87-2.84 (m, 1H), 2.50-2.48 (m, 4H), 2.12-1.98 (m, 2H), 1.93-1.86 (m, 2H), 1.76-1.71 (m, 2H) | 493 |

-continued

| Example | Compound Name | NMR | m/z |
|---|---|---|---|
| Example 5 | 4-[4-[[2-(4-cyclobutylpiperazin-1-yl)-4,5-dihydroimidazol-1-yl]sulfonyl]phenyl]benzonitrile | 1H NMR (400 MHz, CD$_3$OD) δ 8.03 (d, J = 8.4 Hz, 2H), 7.94 (d, J = 8.4 Hz, 2H), 7.91-7.85 (m, 4H), 3.99 (t, J = 7.6 Hz, 2H), 3.39-3.31 (m, 4H), 3.03 (t, J = 7.6 Hz, 2H), 2.90-2.86 (m, 1H), 2.55-2.49 (m, 4H), 2.15-2.09 (m, 2H), 1.96-1.91 (m, 2H), 1.79-1.76 (m, 2H) | 450 |
| Example 6 | 1-cyclobutyl-4-[1-[4-(2-pyridyl)phenyl]sulfonyl-4,5-dihydroimidazol-2-yl]piperazine | $^1$H NMR (400 MHz, CD$_3$OD) δ 8.69 (d, J = 4.8 Hz, 1H), 8.23 (d, J = 8.4 Hz, 2H), 8.03 (d, J = 8.4 Hz, 2H), 7.97-7.93 (m, 2H), 7.46-7.43 (m, 1H), 4.00 (t, J = 7.6 Hz, 2H), 3.41-3.35 (m, 4H), 3.03 (t, J = 7.6 Hz, 2H), 2.89-2.87 (m, 1H), 2.52-2.49 (m, 4H), 2.12-2.10 (m, 2H), 1.96-1.92 (m, 2H), 1.79-1.77 (m, 2H) | 426 |
| Example 7 | 1-cyclobutyl-4-[1-[4-(3-pyridyl)phenyl]sulfonyl-4,5-dihydroimidazol-2-yl]piperazine | $^1$H NMR (400 MHz, CD$_3$OD) δ 8.90 (d, J = 1.6 Hz, 1H), 8.69-8.60 (m, 1H), 8.19 (d, J = 8.0 Hz, 1H), 8.04 (d, J = 8.4 Hz, 2H), 7.95 (d, J = 8.8 Hz, 2H), 7.60-7.52 (m, 1H), 4.00 (t, J = 7.6 Hz, 2H), 3.45-3.38 (m, 4H), 3.04 (t, J = 7.6 Hz, 2H), 2.89-2.84 (m, 1H), 2.52-2.48 (m, 4H), 2.18-2.08 (m, 2H), 1.94-1.88 (m, 2H), 1.79-1.77 (m, 2H) | 426 |
| Example 8 | 1-cyclobutyl-4-[1-[4-(o-tolyl)phenyl]sulfonyl-4,5-dihydroimidazol-2-yl]piperazine | $^1$H NMR (400 MHz, CD$_3$OD) δ 7.96 (d, J = 8.4 Hz, 2H), 7.55 (d, J = 8.4 Hz, 2H), 7.34-7.25 (m, 3H), 7.22-7.15 (m, 1H), 3.98 (t, J = 7.6 Hz, 2H), 3.39-3.37 (m, 4H), 3.03-3.01 (m, 2H), 2.87-2.85 (m, 1H), 2.52-2.50 (m, 4H), 2.21 (s, 3H), 2.10-2.03 (m, 2H), 1.95-1.87 (m, 2H), 1.77-1.70 (m, 2H) | 439 |
| Example 9 | 1-cyclobutyl-4-[1-[4-(m-tolyl)phenyl]sulfonyl-4,5-dihydroimidazol-2-yl]piperazine | $^1$H NMR (400 MHz, CD$_3$OD) δ 7.95 (d, J = 8.4 Hz, 2H), 7.83 (d, J = 8.4 Hz, 2H), 7.49-7.45 (m, 2H), 7.37-7.34 (m, 1H), 7.24-7.22 (m, 1H), 3.96 (t, J = 7.6 Hz, 2H), 3.37-3.30 (m, 4H), 3.02-2.99 (m, 2H), 2.87-2.80 (m, 1H), 2.51-2.45 (m, 4H), 2.41 (s, 3H), 2.10-2.03 (m, 2H), 1.94-1.85 (m, 2H), 1.82-1.71 (m, 2H) | 439 |
| Example 10 | 1-cyclobutyl-4-[1-[4-(p-tolyl)phenyl]sulfonyl-4,5-dihydroimidazol-2-yl]piperazine | $^1$H NMR (400 MHz, CD$_3$OD) δ 7.94 (d, J = 8.4 Hz, 2H), 7.84 (d, J = 8.4 Hz, 2H), 7.58 (d, J = 8.0 Hz, 2H), 7.30 (d, J = 8.4 Hz, 2H), 3.96 (t, J = 7.6 Hz, 2H), 3.38-3.36 (m, 4H), 3.02-2.99 (m, 2H), 2.89-2.80 (m, 1H), 2.51-2.49 (m, 4H), 2.38 (s, 3H), 2.12-2.09 (m, 2H), 1.95-1.85 (m, 2H), 1.77-1.70 (m, 2H) | 439 |
| Example 11 | 1-cyclobutyl-4-[1-[4-[3-(trifluoromethyl)phenyl]phenyl]sulfonyl-4,5-dihydroimidazol-2-yl]piperazine | $^1$H NMR (400 MHz, CD$_3$OD) δ 8.02-7.90 (m, 6H), 7.75-7.69 (m, 2H), 3.99 (t, J = 7.6 Hz, 2H), 3.38-3.36 (m, 4H), 3.02 (t, J = 7.6 Hz, 2H), 2.90-2.82 (m, 1H), 2.51-2.49 (m, 4H), 2.15-2.02 (m, 2H), 1.94-1.90 (m, 2H), 1.77-1.68 (m, 2H) | 493 |
| Example 12 | 1-cyclobutyl-4-[1-[4-[4-(trifluoromethyl)phenyl]phenyl]sulfonyl-4,5-dihydroimidazol-2-yl]piperazine | $^1$H NMR (400 MHz, CD$_3$OD) δ 8.03 (d, J = 8.4 Hz, 2H), 7.95-7.89 (m, 4H), 7.80 (d, J = 8.4 Hz, 2H), 4.00 (t, J = 7.6 Hz, 2H), 3.40-3.38 (m, 4H), 3.05-2.99 (m, 2H), 2.90-2.87 (m, 1H), 2.53-2.51 (m, 4H), 2.12-2.11 (m, 2H), 1.96-1.88 (m, 2H), 1.78-1.68 (m, 2H) | 493 |
| Example 13 | 3-[4-[[2-(4-cyclobutylpiperazin-1-yl])-4,5-dihydroimidazol-1-yl]sulfonyl]phenyl]benzonitrile | $^1$H NMR (400 MHz, CD$_3$OD) δ 8.09 (s, 1H), 8.01 (d, J = 8.4 Hz, 2H), 7.91 (d, J = 8.4 Hz, 2H), 7.79 (d, J = 7.6 Hz, 1H), 7.68 (t, J = 7.6 Hz, 1H), 3.97 (t, J = 7.6 Hz, 2H), 3.42-3.35 (m, 4H), 3.02 (t, J = 7.6 Hz, 2H), 2.87-2.82 (m, 1H), 2.51-2.45 (m, 4H), 2.13-2.02 (m, 2H), 1.95-1.87 (m, 2H), 1.80-1.69 (m, 2H). | 450 |
| Example 14 | 1-cyclobutyl-4-[1-(4-phenylphenyl)sulfonyl-4,5-dihydroimidazol-2-yl]piperazine | $^1$H NMR (400 MHz, CD$_3$OD) δ 7.97 (d, J = 8.8 Hz, 2H), 7.86 (d, J = 8.4 Hz, 2H), 7.68 (d, J = 7.2 Hz, 2H), 7.51-7.36 (m, 3H), 3.97 (t, J = 7.6 Hz, 2H), 3.42-3.35 (m, 4H), 3.05-2.95 (m, 2H), 2.89-2.83 (m, 1H), 2.52-2.45 (m, 4H), 2.11-2.03 (m, 2H), 1.95-1.87 (m, 2H), 1.78-1.68 (m, 2H). | 425 |

-continued

| Example | Compound Name | NMR | m/z |
|---|---|---|---|
| Example 15 | 2-[4-[[2-(4-cyclobutylpiperazin-1-yl)-4,5-dihydroimidazol-1-yl]sulfonyl]phenyl]phenol | ¹H NMR (400 MHz, CD₃OD) δ 7.89 (d, J = 8.8 Hz, 2H), 7.81 (d, J = 8.4 Hz, 2H), 7.29 (d, J = 7.6 Hz, 1H), 7.21-7.18 (m, 1H), 6.93-6.89 (m, 2H), 3.96 (t, J = 7.6 Hz, 2H), 3.42-3.34 (m, 4H), 3.04-2.98 (m, 2H), 2.90-2.82 (m, 1H), 2.55-2.48 (m, 4H), 2.15-2.02 (m, 2H), 1.95-1.88 (m, 2H), 1.80-1.70 (m, 2H) | 441 |
| Example 16 | 3-[4-[[2-(4-cyclobutylpiperazin-1-yl)-4,5-dihydroimidazol-1-yl]sulfonyl]phenyl]phenol | ¹H NMR (400 MHz, CD₃OD) δ 7.95 (d, J = 8.4 Hz, 2H), 7.82 (d, J = 8.4 Hz, 2H), 7.29 (t, J = 3.6 Hz, 1H), 7.12-7.06 (m, 2H), 6.84 (d, J = 6.4 Hz, 1H), 3.98 (t, J = 7.6 Hz, 2H), 3.40-3.31 (m, 4H), 3.04-3.00 (m, 2H), 2.92-2.89 (m, 1H), 2.52-2.45 (m, 4H), 2.13-2.09 (m, 2H), 1.98-1.88 (m, 2H), 1.78-1.70 (m, 2H) | 441 |
| Example 17 | 4-[4-[[2-(4-cyclobutylpiperazin-1-yl)-4,5-dihydroimidazol-1-yl]sulfonyl]phenyl]phenol | ¹H NMR (400 MHz, CD₃OD) δ 7.92 (d, J = 8.4 Hz, 2H), 7.80 (d, J = 8.4 Hz, 2H), 7.56 (d, J = 8.4 Hz, 2H), 6.90 (d, J = 8.8 Hz, 2H), 3.97 (t, J = 7.6 Hz, 2H), 3.40-3.36 (m, 4H), 3.04-2.94 (m, 3H), 2.57-2.50 (m, 4H), 2.15-2.08 (m, 2H), 1.98-1.93 (m, 2H), 1.80-1.72 (m, 2H) | 441 |
| Example 18 | 1-cyclobutyl-4-[1-[4-(4-pyridyl)phenyl]sulfonyl-4,5-dihydroimidazol-2-yl]piperazine | ¹H NMR (400 MHz, CD₃OD) δ 8.66 (d, J = 6.0 Hz, 2H), 8.07-8.00 (m, 4H), 7.79 (d, J = 6.0 Hz, 2H), 4.00 (t, J = 7.6 Hz, 2H), 3.45-3.30 (m, 4H), 3.05-3.01 (m, 2H), 2.90-2.82 (m, 1H), 2.53-2.45 (m, 4H), 2.15-2.02 (m, 2H), 1.98-1.90 (m, 2H), 1.80-1.71 (m, 2H) | 426 |
| Example 19 | 1-cyclobutyl-4-[1-[4-(2-thienyl)phenyl]sulfonyl-4,5-dihydroimidazol-2-yl]piperazine | ¹H NMR (400 MHz, CD₃OD) δ 7.93-7.87 (m, 4H), 7.61 (d, J = 3.6 Hz, 1H), 7.55 (d, J = 4.8 Hz, 1H), 7.15-7.12 (m, 1H), 3.97 (t, J = 7.6 Hz, 2H), 3.45-3.38 (m, 4H), 3.05-3.00 (m, 2H), 2.90-2.82 (m, 1H), 2.53-2.45 (m, 4H), 2.15-2.06 (m, 2H), 1.98-1.91 (m, 2H), 1.79-1.72 (m, 2H) | 431 |
| Example 20 | 1-cyclobutyl-4-[1-[4-(3-thienyl)phenyl]sulfonyl-4,5-dihydroimidazol-2-yl]piperazine | ¹H NMR (400 MHz, CD₃OD) δ 7.94-7.86 (m, 5H), 7.56 (d, J = 2.0 Hz, 2H), 3.97 (t, J = 7.6 Hz, 2H), 3.42-3.31 (m, 4H), 3.02-2.98 (m, 2H), 2.90-2.83 (m, 1H), 2.52-2.45 (m, 4H), 2.10-2.04 (m, 2H), 1.98-1.92 (m, 2H), 1.79-1.74 (m, 2H) | 431 |
| Example 21 | 1-[1-[4-(2-chlorophenyl)phenyl]sulfonyl-4,5-dihydroimidazol-2-yl]-4-cyclobutyl-piperazine | ¹H NMR (400 MHz, CD₃OD) δ 7.97 (d, J = 8.4 Hz, 2H), 7.65 (d, J = 8.4 Hz, 2H), 7.54-7.51 (m, 1H), 7.41-7.35 (m, 3H), 3.98 (t, J = 7.6 Hz, 2H), 3.42-3.35 (m, 4H), 3.04-2.98 (m, 2H), 2.87-2.82 (m, 1H), 2.52-2.43 (m, 4H), 2.09-2.03 (m, 2H), 1.92-1.85 (m, 2H), 1.76-1.65 (m, 2H). | 459 |
| Example 22 | 1-[1-[4-(3-chlorophenyl)phenyl]sulfonyl-4,5-dihydroimidazol-2-yl]-4-cyclobutyl-piperazine | ¹H NMR (400 MHz, CD₃OD) δ 7.97 (d, J = 8.0 Hz, 2H), 7.85 (d, J = 8.4 Hz, 2H), 7.70 (s, 1H), 7.61 (d, J = 7.6 Hz, 1H), 7.48-7.38 (m, 2H), 3.96 (t, J = 7.6 Hz, 2H), 3.42-3.35 (m, 4H), 3.03-2.98 (m, 2H), 2.87-2.77 (m, 1H), 2.52-2.43 (m, 4H), 2.10-2.00 (m, 2H), 1.95-1.86 (m, 2H), 1.77-1.71 (m, 2H) | 459 |
| Example 23 | 1-[1-[4-(4-chlorophenyl)phenyl]sulfonyl-4,5-dihydroimidazol-2-yl]-4-cyclobutyl-piperazine | ¹H NMR (400 MHz, CD₃OD) δ 7.97 (d, J = 8.4 Hz, 2H), 7.86 (d, J = 8.4 Hz, 2H), 7.69 (d, J = 8.8 Hz, 2H), 7.49 (d, J = 8.8 Hz, 2H), 3.97 (t, J = 7.6 Hz, 2H), 3.42-3.35 (m, 4H), 3.03-2.99 (m, 2H), 2.87-2.82 (m, 1H), 2.53-2.44 (m, 4H), 2.12-2.03 (m, 2H), 1.95-1.89 (m, 2H), 1.78-1.68 (m, 2H). | 459 |
| Example 24 G02848813 | 1-cyclobutyl-4-[1-[4-(2-methoxyphenyl)phenyl]sulfonyl-4,5-dihydroimidazol-2-yl]piperazine | ¹H NMR (400 MHz, CD₃OD) δ 7.89 (d, J = 8.4 Hz, 2H), 7.71 (d, J = 8.4 Hz, 2H), 7.37-7.35 (m, 1H), 7.32-7.30 (m, 1H), 7.12-7.08 (m, 1H), 7.05-6.98 (m, 1H), 3.95 (t, J = 7.6 Hz, 2H), 3.79 (s, 3H), 3.40-3.32 (m, 4H), 3.03-2.99 (m, 2H), 2.86-2.78 (m, 1H), 2.52-2.42 (m, 4H), 2.11-2.02 (m, 2H), 1.94-1.85 (m, 2H), 1.78-1.67 (m, 2H) | 455 |

-continued

| Example | Compound Name | NMR | m/z |
|---|---|---|---|
| Example 25 | 1-cyclobutyl-4-[1-[4-(2-fluorophenyl)phenyl]sulfonyl-4,5-dihydroimidazol-2-yl]piperazine | $^1$H NMR (400 MHz, CD$_3$OD) δ 7.98 (d, J = 8.4 Hz, 2H), 7.73 (d, J = 7.6 Hz, 2H), 7.55-7.40 (m, 2H), 7.31-7.18 (m, 2H), 3.97 (t, J = 7.6 Hz, 2H), 3.42-3.35 (m, 4H), 3.02 (t, J = 7.2 Hz, 2H), 2.90-2.78 (m, 1H), 2.54-2.45 (m, 4H), 2.10-2.02 (m, 2H), 1.97-1.85 (m, 2H), 1.78-1.66 (m, 2H) | 443 |
| Example 26 | 1-cyclobutyl-4-[1-[4-(3-fluorophenyl)phenyl]sulfonyl-4,5-dihydroimidazol-2-yl]piperazine | $^1$H NMR (400 MHz, CD$_3$OD) δ 8.01-7.95 (m, 2H), 7.93-7.88 (m, 2H), 7.55-7.41 (m, 3H), 7.18-7.10 (m, 1H), 4.04-3.90 (m, 2H), 3.44-3.35 (m, 4H), 3.01-2.95 (m, 2H), 2.90-2.82 (m, 1H), 2.52-2.45 (m, 4H), 2.11-2.05 (m, 2H), 1.95-1.85 (m, 2H), 1.79-1.72 (m, 2H) | 443 |
| Example 27 | 1-cyclobutyl-4-[1-[4-(4-fluorophenyl)phenyl]sulfonyl-4,5-dihydroimidazol-2-yl]piperazine | $^1$H NMR (400 MHz, CD$_3$OD) δ 7.96 (d, J = 8.4 Hz, 2H), 7.83 (d, J = 8.4 Hz, 2H), 7.74-7.68 (m, 2H), 7.22 (t, J = 8.8 Hz, 2H), 3.96 (t, J = 7.6 Hz, 2H), 3.42-3.33 (m, 4H), 3.01 (t, J = 7.6 Hz, 2H), 2.88-2.82 (m, 1H), 2.54-2.42 (m, 4H), 2.10-2.02 (m, 2H), 1.95-1.86 (m, 2H), 1.78-1.71 (m, 2H) | 443 |
| Example 28 | 1-cyclobutyl-4-[1-[4-(1-methylpyrazol-3-yl)phenyl]sulfonyl-4,5-dihydroimidazol-2-yl]piperazine | $^1$H NMR (400 MHz, CD$_3$OD) δ 8.03 (d, J = 8.4 Hz, 2H), 7.77 (d, J = 8.4 Hz, 2H), 7.54 (d, J = 1.6 Hz, 1H), 6.51 (d, J = 2.0 Hz, 1H), 3.99 (t, J = 7.6 Hz, 2H), 3.93 (s, 3H), 3.42-3.31 (m, 4H), 3.05-2.99 (m, 2H), 2.89-2.80 (m, 1H), 2.53-2.45 (m, 4H), 2.13-2.05 (m, 2H), 1.98-1.91 (m, 2H), 1.80-1.70 (m, 2H) | 429 |
| Example 29 | 1-cyclobutyl-4-[1-[4-(2-methylpyrazol-3-yl)phenyl]sulfonyl-4,5-dihydroimidazol-2-yl]piperazine | $^1$H NMR (400 MHz, CD$_3$OD) δ 8.03 (d, J = 8.4 Hz, 2H), 7.77 (d, J = 8.4 Hz, 2H), 7.55 (s, 1H), 6.52 (s, 1H), 3.99 (t, J = 7.2 Hz, 2H), 3.91 (s, 3H), 3.40-3.33 (m, 4H), 3.06-2.98 (m, 2H), 2.88-2.83 (m 1H), 2.52-2.44 (m, 4H), 2.13-2.04 (m, 2H), 1.96-1.88 (m, 2H), 1.82-1.74 (m, 2H) | 429 |
| Example 30 | 5-[4-[[2-(4-cyclobutylpiperazin-1-yl)-4,5-dihydroimidazol-1-yl]sulfonyl]phenyl]pyrimidine | $^1$H NMR (400 MHz, CD$_3$OD) δ 9.22 (s, 1H), 9.16 (s, 2H), 8.08 (d, J = 8.4 Hz, 2H), 8.01 (d, J = 8.0 Hz, 2H), 4.00 (t, J = 7.6 Hz, 2H), 3.45-3.31 (m, 4H), 3.02 (t, J = 7.6 Hz, 2H), 2.91-2.84 (m, 1H), 2.54 2.48 (m, 4H), 2.14-2.05 (m, 2H), 1.97-1.85 (m, 2H), 1.80-1.69 (m, 2H) | 427 |

Example 31

1-cyclobutyl-4-(1-((4-isopropylphenyl)sulfonyl)-4,5-dihydro-1H-imidazol-2-yl)piperazine

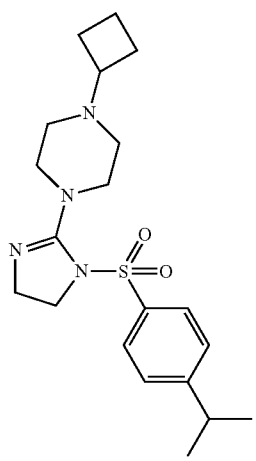 [SMILES: CC(C)c1ccc(S(=O)(=O)N2CCN=C2N2CCN(C3CCC3)CC2)cc1]

A solution of 1-(1-((4-isopropylphenyl)sulfonyl)-4,5-dihydro-1H-imidazol-2-yl)piperazine (Intermediate C, 5.0 g, 11.10 mmol), cyclobutanone (3.9 g, 55.50 mmol) and triethylamine (5.6 g, 55.50 mmol) in DCM (60 mL) was stirred at room temperature for 2 h before NaBH(AcO)$_3$ (9.4 g, 44.40 mmol) was added portion-wise. The reaction mixture was stirred for an additional 1 h and then quenched by the addition of saturated aqueous NH$_4$Cl (40 mL). The organic layer was separated before the aqueous layer was adjusted to pH 8-9 by the addition of saturated aqueous NaHCO$_3$. The aqueous mixture was extracted with DCM (100 mL×2). The combined organic layers were dried over anhydrous sodium sulfate and concentrated in vacuo. The residue was purified by silica gel chromatography (DCM/MeOH=20:1) to give the title compound (1.2 g, 27%) as a white solid. $^1$H NMR (400 MHz, CD$_3$OD) δ 7.84 (d, J=8.4 Hz, 2H), 7.50 (d, J=8.4 Hz, 2H), 3.94 (t, J=7.6 Hz, 2H), 3.60-3.40 (m, 5H), 3.05-2.90 (n, 7H), 2.29-2.23 (m, 2H), 2.17-2.05 (m, 2H), 1.87-1.73 (m, 2H), 1.27 (d, J=6.8 Hz, 6H). LCMS M/Z (M+H) 391.

The following compounds were prepared in a similar fashion to Example 31.

Examples 32-37

| Example | Compound Name | NMR | m/z |
|---|---|---|---|
| Example 32 | 1-cyclobutyl-4-(1-tetralin-6-ylsulfonyl-4,5-dihydroimidazol-2-yl)piperazine | $^1$H NMR (400 MHz, CD$_3$OD) δ 7.58-7.50 (m, 2H), 7.26 (d, J = 8.0 Hz, 1H), 3.91 (t, J = 7.6 Hz, 2H), 3.40-3.28 (m, 4H), 2.95 (t, J = 7.6 Hz, 2H), 2.90-2.75 (m, 5H), 2.50-2.43 (m, 4H), 2.13-2.03 (m, 2H), 1.96-1.85 (m, 2H), 1.84-1.81 (m, 4H), 1.77-1.70 (m, 2H) | 403 |
| Example 33 | 1-ethyl-4-[1-[2-(trifluoromethoxy)phenyl]sulfonyl-4,5-dihydroimidazol-2-yl]piperazine | $^1$H NMR (400 MHz, CD$_3$OD) δ 8.14 (d, J = 8.0 Hz, 1H), 7.82-7.75 (m, 1H), 7.60-7.52 (m, 2H), 3.98 (t, J = 7.6 Hz, 2H), 3.30-3.22 (m, 6H), 2.55-2.40 (m, 6H), 1.11 (t, J = 7.6 Hz, 3H) | 407 |
| Example 34 | 1-cyclobutyl-4-[1-(4-cyclopropylphenyl)sulfonyl-4,5-dihydroimidazol-2-yl]piperazine | $^1$H NMR (400 MHz, CD$_3$OD) δ 7.94 (d, J = 6.0 Hz, 2H), 7.40 (d, J = 6.0 Hz, 2H), 4.38-4.18 (m, 4H), 4.03-3.87 (m, 3H), 3.73-3.65 (m, 2H), 3.44-3.32 (m, 2H), 3.23-3.15 (m, 2H), 2.55-2.30 (m, 4H), 2.12-2.05 (m, 1H), 2.00-1.80 (m, 2H), 1.19-1.12 (m, 2H), 0.89-0.84 (m, 2H) | 389 |
| Example 35 | 1-cyclobutyl-4-[1-(3-cyclopropylphenyl)sulfonyl-4,5-dihydroimidazol-2-yl]piperazine | $^1$H NMR (400 MHz, CD$_3$OD) δ 7.82-7.77 (m, 2H), 7.65-7.60 (m, 1H), 7.54-7.48 (m, 1H), 4.37-4.18 (m, 4H), 3.98-3.84 (m, 3H), 3.75-3.65 (m, 2H), 3.42-3.29 (m, 2H), 3.22-3.15 (m, 2H), 2.50-2.27 (m, 4H), 2.15-2.06 (m, 1H), 1.95-1.80 (m, 2H), 1.14-1.08 (m, 2H), 0.83-0.77 (m, 2H) | 389 |
| Example 36 | 6-[[2-(4-cyclobutylpiperazin-1-yl)-4,5-dihydroimidazol-1-yl]sulfonyl]naphthalene-2-carbonitrile | $^1$H NMR (400 MHz, CD$_3$OD) δ 8.89 (s, 1H), 8.61 (s, 1H), 8.42-8.37 (m, 2H), 8.18-8.12 (m, 1H), 7.95-7.90 (m, 1H), 4.35-4.28 (m, 3H), 3.95-3.88 (m, 3H), 3.75-3.62 (m, 2H), 3.45-3.31 (m, 2H), 3.22-3.15 (m, 3H), 2.48-2.40 (m, 4H), 1.98-1.88 (m, 2H) | 424 |
| Example 37 | 1-cyclobutyl-4-[1-(4-isopropylphenyl)sulfonyl-4,5-dihydroimidazol-2-yl]-2-methyl-piperazine | $^1$H NMR (400 MHz, DMSO-d$_6$) δ 7.80 (d, J = 8.0 Hz, 2H), 7.51 (d, J = 8.4 Hz, 2H), 3.91-3.62 (m, 5H), 3.48-3.30 (m, 2H), 3.08-2.75 (m, 6H), 2.40-2.12 (m, 4H), 1.75-1.65 (m, 2H), 1.35-1.18 (m, 9H) | 405 |

Example 38

1-[1-(4-isopropylphenyl)sulfonyl-4,5-dihydroimidazol-2-yl]-4-[(2-methylcyclopropyl)methyl]piperazine

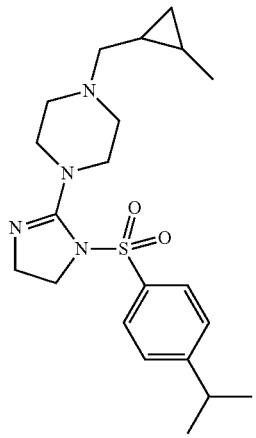 [SMILES: CC(C)c1ccc(S(=O)(=O)N2CCN=C2N2CCN(CC3CC3C)CC2)cc1]

To a solution of 1-(1-((4-isopropylphenyl)sulfonyl)-4,5-dihydro-1H-imidazol-2-yl) piperazine (Intermediate C, 200 mg, 0.44 mmol) in DCM (15 mL) was added DIPEA (143 mg, 1.11 mmol) and 1-(bromomethyl)-2-methylcyclopropane (132 mg, 0.89 mmol). The reaction mixture was stirred at room temperature for 6 h. The mixture concentrated in vacuo and the residue was purified by reverse phase chromatography (acetonitrile 25-55%/0.1% NH$_4$OH in water) to give the title compound (15 mg, 8%) as a white solid. $^1$H NMR (400 MHz, CD$_3$OD) δ 7.83 (d, J=8.4 Hz, 2H), 7.49 (d, J=8.4 Hz, 2H), 3.94 (t, J=7.6 Hz, 2H), 3.40-3.31 (m, 4H), 3.08-2.90 (m, 3H), 2.80-2.65 (m, 4H), 2.56-2.45 (m, 1H), 2.28-2.23 (m, 1H), 1.27 (d, J=6.8 Hz, 6H), 1.08 (d, J=5.2 Hz, 3H), 0.64-0.53 (m, 2H), 0.37-0.30 (m, 2H). LCMS M/Z (M+H) 405.

Example 39

1-[1-(4-isopropylphenyl)sulfonyl-4,5-dihydroimidazol-2-yl]-4-(3-methylcyclobutyl)piperazine

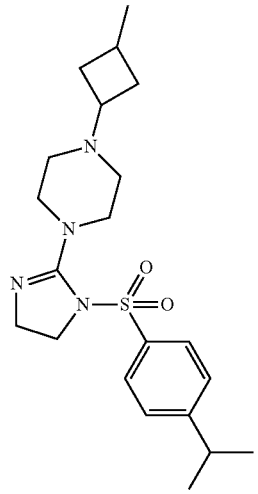

Step 1:

methyl 3-(4-(1-((4-isopropylphenyl)sulfonyl)-4,5-dihydro-1H-imidazol-2-yl)piperazin-1-yl)cyclobutanecarboxylate

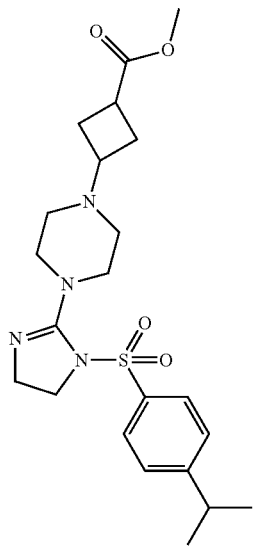 [SMILES: COC(=O)C1CC(N2CCN(C3=NCCN3S(=O)(=O)c3ccc(C(C)C)cc3)CC2)C1]

A solution of 1-(1-((4-isopropylphenyl)sulfonyl)-4,5-dihydro-1H-imidazol-2-yl)piperazine (Intermediate C, 500 mg, 1.11 mmol), methyl 3-oxocyclobutane carboxylate (284 mg, 2.22 mmol) and triethylamine (247 mg, 2.44 mmol) in DCM (20 mL) was stirred at room temperature for 2 h before NaBH(AcO)$_3$ (470 mg, 2.22 mmol) was added portionwise. The reaction mixture was stirred for an additional 1 h before being quenched by the addition of saturated aqueous NH$_4$Cl (10 mL). The organic layer was separated. The aqueous layer was adjusted to pH 8-9 by the addition of saturated aqueous NaHCO$_3$, and extracted with DCM (20 mL×2). The combined organic layers were dried over anhydrous sodium sulfate and concentrated in vacuo. The residue was purified by silica gel chromatography (DCM/MeOH=20:1) to give the title compound (400 mg, 80%) as a white solid.

Step 2:

(3-(4-(1-((4-isopropylphenyl)sulfonyl)-4,5-dihydro-1H-imidazol-2-yl)piperazin-1-yl)cyclobutyl)methanol

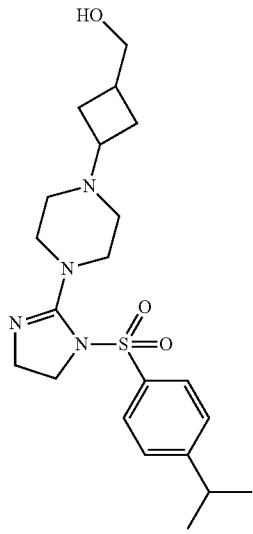 [SMILES: CC(C)c1ccc(S(=O)(=O)N2CCN=C2N2CCN(C3CC(CO)C3)CC2)cc1]

To a solution of methyl 3-(4-(1((4-isopropylphenyl)sulfonyl)-4,5-dihydro-1H-imidazol-2-yl)piperazin-1-yl)cyclobutanecarboxylate (400 mg, 0.89 mmol) in THF (20 mL) at 0° C. was added NaBH$_4$ (67 mg, 1.78 mmol) and LiCl (76 mg, 1.78 mmol). Ethanol (10 mL) was slowly added and the mixture stirred at room temperature for 5 h before being quenched by the addition of saturated aqueous NH$_4$Cl aqueous (5 mL). The solvent was removed in vacuo and the aqueous residue was adjusted to pH 8-9 by the addition of saturated aqueous NaHCO$_3$. The mixture was extracted with EtOAc (20 mL) and the combined organic layers were washed with water (10 mL×2), dried over anhydrous sodium sulfate and concentrated in vacuo. The residue was purified by silica gel chromatography (DCM/MeOH=20:1) to give the title compound (280 mg, 75%) as a white solid.

Step 3:

(3-(4-(1((4-isopropylphenyl)sulfonyl)-4,5-dihydro-1H-imidazol-2-yl)piperazin-1-yl)cyclobutyl)methyl methanesulfonate

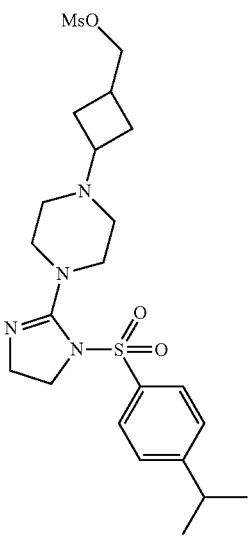 [SMILES: CC(C)c1ccc(S(=O)(=O)N2CCN=C2N2CCN(C3CC(COS(C)(=O)=O)C3)CC2)cc1]

To a solution of (3-(4-(1-((4-isopropylphenyl)sulfonyl)-4,5-dihydro-1H-imidazol-2-yl) piperazin-1-yl)cyclobutyl) methanol (200 mg, 0.48 mmol) in DCM (20 mL) was added triethylamine (72 mg, 0.71 mmol) and methanesulfonyl chloride (82 mg, 0.71 mmol). The reaction mixture was stirred at room temperature for 2 h. The reaction mixture was diluted with EtOAc (20 mL) and washed with water (10 mL×2). The separated organic layer was dried over sodium sulfate and concentrated to give the title compound (230 mg, 97%) as a white solid that required no further purification.

Step 4:

1-[1-(4-isopropylphenyl)sulfonyl-4,5-dihydroimidazol-2-yl]-4-(3-methylcyclobutyl)piperazine

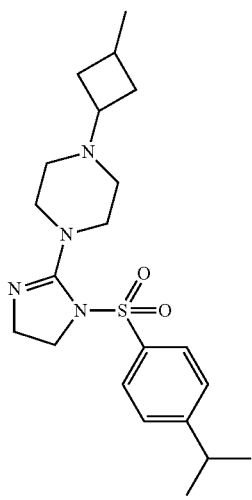 [SMILES: CC1CC(N2CCN(C3=NCCN3S(=O)(=O)c3ccc(C(C)C)cc3)CC2)C1]

To a solution of (3-(4-(1-((4-isopropylphenyl)sulfonyl)-4,5-dihydro-1H-imidazol-2-yl)piperazin-1-yl)cyclobutyl) methyl methanesulfonate (80 mg, 0.16 mmol) in DMF (8 mL) was added NaBH$_4$ (12 mg, 0.32 mmol). The reaction mixture was stirred at 80° C. for 8 h. After cooling, the solution was quenched by the addition of saturated aqueous NaHCO$_3$ (2 mL), and the mixture was extracted with EtOAc (10 mL×2). The combined organic layers were washed with water (6 mL×2), dried over anhydrous sodium sulfate and concentrated in vacuo. The residue was purified by reverse phase chromatography (acetonitrile 46-66%/0.1% NH$_4$OH in water) to give the title compound (10 mg, 15%) as a white solid. $^1$H NMR (400 MHz, CD$_3$OD) δ 7.80 (d, J=8.4 Hz, 2H), 7.70 (d, J=8.4 Hz, 2H), 3.91 (t,J=7.6 Hz, 2H), 3.45-3.35 (m, 4H), 3.04-2.82 (m, 3H), 2.70-2.58 (m, 1H), 2.55-2.40 (m, 4H), 2.33-2.23 (m, 2H), 2.15-2.03 (m, 1H), 1.52-1.41 (m, 2H), 1.32-1.25 (m, 6H), 1.80 (d, J=6.8 Hz, 3H). LCMS M/Z (M+H) 405.

Example 40

1-(3-fluorocyclobutyl)-4-[1-(4-isopropylphenyl)sulfonyl-4,5-dihydroimidazol-2-yl]piperazine

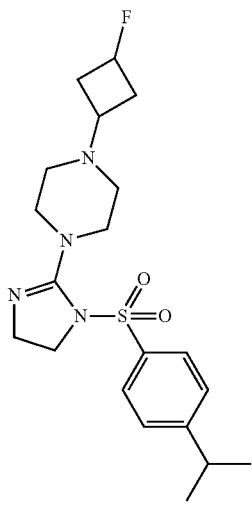 [SMILES: CC(C)c1ccc(S(=O)(=O)N2CCN=C2N2CCN(C3CC(F)C3)CC2)cc1]

Step 1:

1-(3-(benzyloxy)cyclobutyl)-4-(1-((4-isopropylphenyl)sulfonyl)-4,5-dihydro-1H-imidazol-2-yl)piperazine

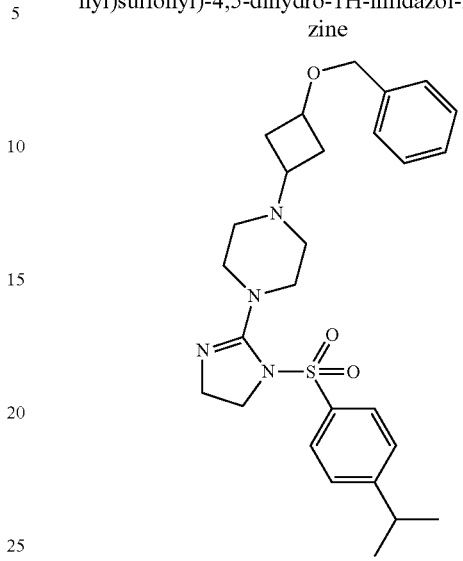

A solution of 1-(1-((4-isopropylphenyl)sulfonyl)-4,5-dihydro-1H-imidazol-2-yl)piperazine (Intermediate C, 500 mg, 1.11 mmol), 3-(benzyloxy)cyclobutanone (391 mg, 2.22 mmol) and triethylamine (247 mg, 2.44 mmol) in DCM (20 mL) was stirred at room temperature for 2 h before NaBH(AcO)$_3$(470 mg , 2.22 mmol) was added portion-wise. The reaction mixture stirred for an additional 1 h and then was quenched by the addition of saturated aqueous NH$_4$Cl (10 mL). The organic layer was separated. The aqueous layer was adjusted to pH 8-9 by addition of saturated aqueous NaHCO$_3$ and extracted with DCM (20 mL×2). The combined organic layers were dried over anhydrous sodium sulfate and concentrated in vacuo. The residue was purified by silica gel chromatography (DCM/MeOH=20:1) to give the title compound (420 mg, 76%) as a white solid.

Step 2:

3-(4-(1-((4-isopropylphenyl)sulfonyl)-4,5-dihydro-1H-imidazol-2-yl)piperazin-1-yl)cyclobutanol

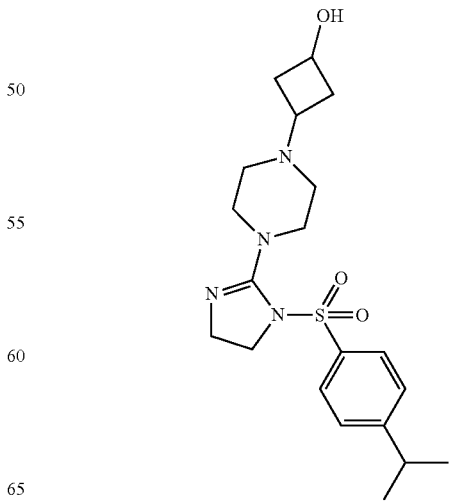

A solution of 1-(3-(benzyloxy)cyclobutyl)-4-(1-((4-isopropylphenyl)sulfonyl)-4,5-dihydro-1H-imidazol-2-yl)piperazine (420 mg, 0.85 mmol) in TFA (10 mL) was heated at 80° C. for 10 h. The mixture was concentrated in vacuo and the residue was dissolved in MeOH (20 mL) before K$_2$CO$_3$ (234 mg, 1.69 mmol) was added. The resulting mixture stirred at room temperature for 2 h and the mixture was concentrated in vacuo. The residue was dissolved in EtOAc (20 mL), washed with water (10 mL) and concentrated in vacuo. The crude product was purified by silica gel chromatography (petroleum ether/EtOAc=2:1) to afford the title compound (300 mg, 87%) as a white solid.

Step 3:

1-(3-fluorocyclobutyl)-4-[1-(4-isopropylphenyl)sulfonyl-4,5-dihydroimidazol-2-yl]piperazine

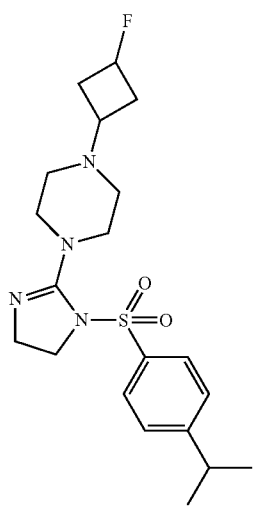 [SMILES: CC(C)c1ccc(S(=O)(=O)N2CCN=C2N2CCN(C3CC(F)C3)CC2)cc1]

To a solution of 3-(4-(1((4-isopropylphenyl)sulfonyl)-4,5-dihydro-1H-imidazo-2-yl) piperazin-1-yl)cyclobutanol (100 mg, 0.25 mmol) in DCM (8 mL) at 0° C. was added DAST (198 mg, 1.23 mmol). The reaction mixture stirred at 0° C. for 1 h and then at room temperature for 5 h. The reaction was quenched by the addition of MeOH (5 mL). The solvent was evaporated in vacuo and the crude product was purified by reverse phase chromatography (acetonitrile 49-59%/0.1% NH$_4$OH in water) to give the title compound (2 mg, 2%) as a white solid. $^1$H NMR (400 MHz, CD$_3$OD) δ 7.83 (d, J=8.4 Hz, 2H), 7.49 (d, J=8.4 Hz, 2H), 5.21-5.19 (m, 0.5H), 5.07-5.04 (m, 0.5H), 3.94 (d, J=7.6 Hz, 2H), 3.42-3.33 (m, 4H), 3.15-3.10 (m, 1H), 3.09-2.90 (m, 3H), 2.55-2.47 (m, 4H), 2.38-2.28 (m, 4H), 1.75 (d, J=6.8 Hz, 6H). LCMS M/Z (M+H) 409.

Examples 41 & 42

(R)-1-cyclobutyl-4-(4-cyclopropyl-1-((4-isopropylphenyl)sulfonyl)-4,5-dihydro-1H-imidazol-2-yl) piperazine & (S)-1-cyclobutyl-4-(4-cyclopropyl-1-((4-isopropylphenyl) sulfonyl)-4,5-dihydro-1H-imidazol-2-yl)piperazine

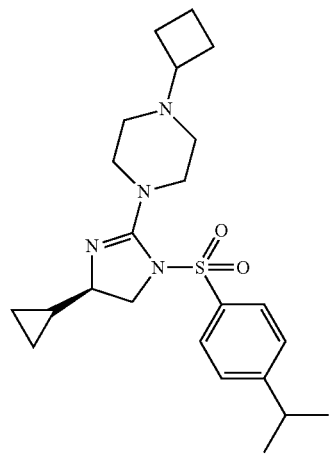

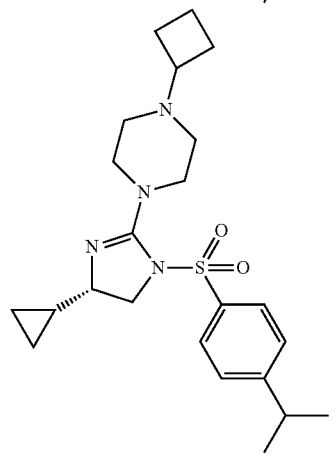

Step 1:

1-cyclopropylethane-1,2-diamine hydrochloride

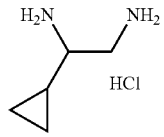

To a solution of 2-amino-2-cyclopropylacetamide (210 mg, 1.84 mmol) in THF (25 mL) was added borane (1M in Me$_2$S, 12 mL, 12.0 mmol) slowly at room temperature. The reaction mixture was heated at reflux temperature for 5 h. After cooling, the mixture was quenched by the slow addition of MeOH (12 mL) and HCl (10% in MeOH, 20 mL). The solvent was concentrated in vacuo to give the crude product (235 mg, 94%) as a white solid that required no further purification.

Step 2:

4-cyclopropylimidazolidine-2-thione

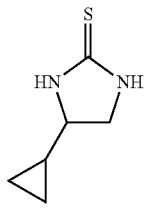

To a mixture of 1-cyclopropylethane-1,2-diamine hydrochloride (235 mg, 1.73 mmol) and triethylamine (640 mg, 6.34 mmol) in EtOH/H$_2$O (30 mL, 2:1) at room temperature was added CS$_2$ (685 mg, 9.0 mmol) dropwise. The resulting mixture was heated at 60° C. for 5 h before HCl (36%, 3 mL) was added and the mixture was heated at 95° C. for an additional 9 h. The solvent was evaporated in vacuo and the mixture was adjusted to pH 8-9 by the addition of saturated aqueous NaHCO$_3$. The solution was extracted with EtOAc (50 mL×3). The combined organic layers were dried over anhydrous sodium sulfate and concentrated in vacuo to give the title compound (150 mg, 61%) as a yellow solid.

Step 3:

5-cyclopropyl-2-(methylthio)-4,5-dihydro-1H-imidazole

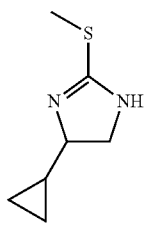

To a solution of 4-cyclopropylimidazolidine-2-thione (150 mg, 1.06 mmol) in MeOH (30 mL) at room temperature was added MeI (396 mg, 2.79 mmol). The resulting mixture stirred at 80° C. for 5 h. The mixture was concentrated in vacua to provide the title compound (155 mg, 94%) as a yellow solid.

Step 4:

4-cyclopropyl-1((4-isopropylphenyl)sulfonyl)-2-(methylthio)-4,5-dihydro-1H-imidazolle

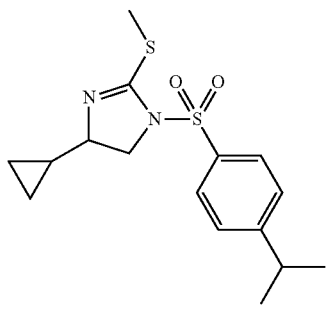 [SMILES: CSC1=NC(C2CC2)CN1S(=O)(=O)c1ccc(C(C)C)cc1]

To a solution of 5-cyclopropyl-2-(methylthio)-4,5-dihydro-1H-imidazole (155 mg, 0.94 mmol) and triethylamine (190 mg, 1.88 mmol) in DCM (20 mL) at ambient temperature was slowly added 4-isopropylbenzene-1-sulfonyl chloride (410 mg, 1.88 mmol). The mixture stirred for 5 h and then quenched by the addition of water (25 mL). The resulting solution was extracted with EtOAc (30 mL×3). The combined organic layers were dried over anhydrous sodium sulfate and concentrated in vacuo. The residue was purified by silica gel chromatography (petroleum ether/EtOAc=1:5) to provide the title compound (200 mg, 63%) as a yellow oil. LCMS M/Z (M+H) 339.

Step 5:

tert-butyl 4-(4-cyclopropyl-1((4-isopropylphenyl)sulfonyl)-4,5-dihydro-1H-imidazol-2-yl)piperazine-1-carboxylate

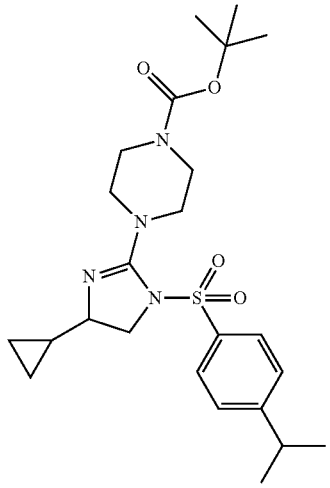 [SMILES: CC(C)c1ccc(S(=O)(=O)N2CC(C3CC3)N=C2N2CCN(C(=O)OC(C)(C)C)CC2)cc1]

A mixture of 4-cyclopropyl-1((4-isopropylphenyl)sulfonyl)-2-(methylthio)-4,5-dihydro-1H-imidazole (200 mg, 0.59 mmol) and tert-butyl piperazine-1-carboxylate (2.5 g, 13.44 mmol) was heated to 120° C. (neat) for 16 h. After cooling to room temperature, the mixture was purified by silica gel chromatography (petroleum ether/EtOAc=5:1) to provide the title compound (200 mg, 71%) as a yellow solid. $^1$H NMR (400 MHz, CDCl$_3$) δ 7.79 (d, J=8.4 Hz, 2H), 7.35 (d, J=8.4 Hz, 2H), 4.00 3.96 (m, 1H), 3.58-3.52 (m, 5H), 3.34-3.30 (m, 4H), 2.98-2.94 (m, 1H), 2.65-2.62 (m, 1H), 1.48 (s, 9H), 1.24 (d, J=6.8 Hz, 6H), 0.31-0.28 (m, 2H), 0.07-0.01 (m, 3H).

Step 6:

1-(4-cyclopropyl-1-((4-isopropylphenyl)sulfonyl)-4,5-dihydro-1H-imidazol-2-yl)piperazine hydrochloride

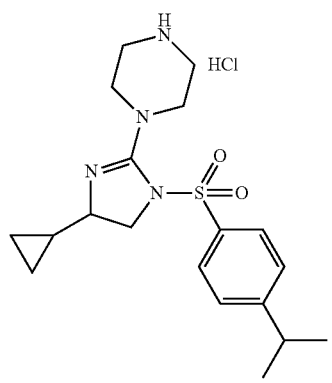 [SMILES: CC(C)c1ccc(S(=O)(=O)N2CC(C3CC3)N=C2N2CCNCC2)cc1 ; Cl]

To a solution of tert-butyl 4-(4-cyclopropyl-1-((4-isopropylphenyl)sulfonyl)-4,5-dihydro-1H-imidazol-2-yl)piperazine-1-carboxylate (200 mg, 0.42 mmol) in EtOAc (5 mL) at room temperature was added HCl (4M in EtOAc, 2 mL, 8.0 mmol). The resulting mixture was stirred at room temperature for 1 h and then concentrated in vacuo to provide the title compound (160 mg, 92%) as a yellow solid.

Step 7:

(R)-1-cyclobutyl-4-(4-cyclopropyl-1-((4-isopropylphenyl)sulfonyl)-4,5-dihydro-1H-imidazol-2-yl)piperazine & (S)-1-cyclobutyl-4-(4-cyclopropyl-1-((4-isopropylphenyl)sulfonyl)-4,5-dihydro-1H-imidazol-2-yl)piperazine

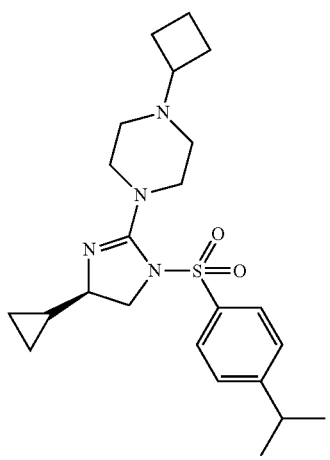

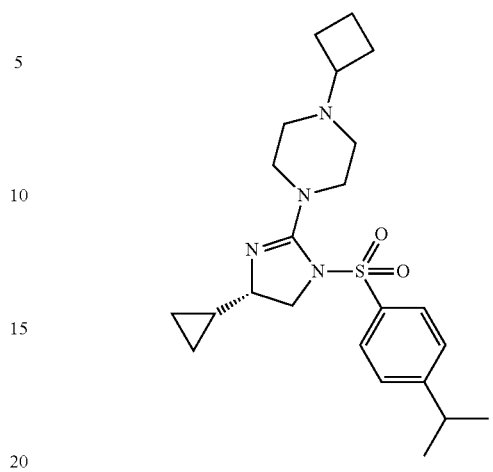

A solution of 1-(4-cyclopropyl-1((4-isopropylphenyl)sulfonyl)-4,5-dihydro-1H-imidazol-2-yl)piperazine hydrochloride (160 mg, 0.39 mmol) and cyclobutanone (1.0 mL) in DCE (20 mL) was stirred at room temperature for 20 min before NaBH(OAc)$_3$ (182 mg, 0.84 mmol) was added. The reaction mixture was stirred for an additional 3 h, quenched by the addition of water (20 mL) and extracted with EtOAc (25 mL×3). The combined organic layers were dried over anhydrous sodium sulfate and concentrated in vacuo. The residue was purified by reverse phase chromatography (acetonitrile 42-72%/0.1% NH$_4$OH in water) to provide the racemic product. The racemic product was further separated by SFC (chiral AD(250×30 mm,5 um), 25% IPA NH$_4$OH 60ML/MIN) to afford (R)-1-cyclobutyl-4-(4-cyclopropyl-1-((4-isopropylphenyl)sulfonyl)-4,5-dihydro-1H-imidazol-2-yl)piperazine (13.9 mg, 8.3%, first peak) and (S)-1-cyclobutyl-4-(4-cyclopropyl-1-((4-isopropylphenyl)sulfonyl)-4,5-dihydro-1H-imidazol-2-yl)piperazine (10.3 mg, 6.2%, second peak). Absolute configuration was arbitrarily assigned to each enantiomer. Example 41: $^1$H NMR (400 MHz, CDCl$_3$) δ 7.79 (d, J=8.0 Hz, 2H), 7.34 (d, J=8.4 Hz, 2H), 4.00-3.92 (m, 1H), 3.54-3.48 (m, 1H), 3.45-3.32 (m, 4H), 2.98-2.94 (m, 1H), 2.87-2.78 (m, 1H), 2.62-2.59 (m, 1H), 2.50-2.42 (m, 4H), 2.07-2.00 (m, 2H), 1.94-1.87 (m, 2H), 1.78-1.72 (m, 2H), 1.24 (d, J=7.2 Hz, 6H), 0.30-0.20 (m, 2H), 0.12-0.00 (m, 3H). LCMS M/Z (M+H) 431. Example 42: $^1$H NMR (400 MHz, CDCl$_3$) δ 7.79 (d, J=8.4 Hz, 2H), 7.34 (d, J=8.4 Hz, 2H), 4.00-3.93 (m, 1H), 3.54-3.48 (m, 1H), 3.45-3.30 (m, 4H), 2.97-2.94 (m, 1H), 2.87-2.78 (m, 1H), 2.62-2.59 (m, 1H), 2.50-2.43 (m, 4H), 2.07-2.04 (m, 2H), 1.94-1.89 (m, 2H), 1.76-1.73 (m, 2H), 1.24 (d, J=7.2 Hz, 6H), 0.32-0.24 (m, 2H), 0.07-0.00 (m, 3H). LCMS M/Z (M+H) 431.

The following compounds were prepared in a similar fashion to Examples 41 & 42. Absolute configuration was arbitrarily assigned to each enantiomer.

Examples 43-47

| Example | Compound Name | NMR | m/z |
|---------|---------------|-----|-----|
| Example 43 | (R)-1-ethyl-4-[1-(4-isopropylphenyl)sulfonyl-4-methyl-4,5-dihydroimidazol-2-yl]piperazine | $^1$H NMR (400 MHz, CD$_3$OD) δ 7.85 (d, J = 8.0 Hz, 2H), 7.52 (d, J = 8.0 Hz, 2H), 4.17-4.12 (m, 1H), 3.47-3.42 (m, 2H), 3.35-3.22 (m, 4H), 3.05-2.98 (m, 1H), 2.70-2.55 (m, 4H), 2.54-2.49 (m, 2H), 1.29 (d, J = 6.8 Hz, 6H), 1.17 (t, J = 7.2 Hz, 3H), 0.82 (d, J = 6.0 Hz, 3H) | 379 |
| Example 44 | (S)-1-ethyl-4-[1-(4-isopropylphenyl)sulfonyl-4-methyl-4,5-dihydroimidazol-2-yl]piperazine | $^1$H NMR (400 MHz, CD$_3$OD) δ 7.83 (d, J = 8.4 Hz, 2H), 7.50 (d, J = 8.4 Hz, 2H), 4.14-4.11 (m, 1H), 3.45-3.18 (m, 6H), 3.05-2.97 (m, 1H), 2.72-2.47 (m, 6H), 1.27 (d, J = 6.8 Hz, 6H), 1.15 (m, J = 7.2 Hz, 3H), 0.79 (d, J = 6.4 Hz, 3H) | 379 |
| Example 45 | 2-(4-cyclobutylpiperazin-1-yl)-3-(4-isopropylphenyl)sulfonyl-1,3-diazaspiro[4.4]non-1-ene | $^1$H NMR (400 MHz, CD$_3$OD) δ 7.81 (d, J = 8.4 Hz, 2H), 7.51 (d, J = 8.4 Hz, 2H), 3.68 (s, 2H), 3.32-3.28 (m, 2H), 3.03-2.85 (m, 2H), 2.57-2.48 (m, 4H), 2.12-2.05 (m, 2H), 1.95-1.90 (m, 2H), 1.80-1.70 (m, 2H), 1.56-1.45 (m, 2H), 1.43-1.38 (m, 2H), 1.25 (d, J = 6.8 Hz, 6H), 1.14-1.10 (m, 2H), 0.98-0.96 (m, 2H) | 445 |
| Example 46 | (R)-1-cyclobutyl-4-[1-(4-isopropylphenyl)sulfonyl-4-methyl-4,5-dihydroimidazol-2-yl]piperazine | $^1$H NMR (400 MHz, CD$_3$OD) δ 7.83 (d, J = 8.4 Hz, 2H), 7.50 (d, J = 8.0 Hz, 2H), 4.15-4.08 (m, 1H), 3.45-3.20 (m, 6H), 3.04-2.98 (m, 1H), 2.90-2.86 (m, 1H), 2.55-2.42 (m, 4H), 2.12-2.05 (m, 2H), 1.94-1.85 (m, 2H), 1.78-1.70 (m, 2H), 1.27 (d, J = 6.8 Hz, 6H), 0.80 (d, J = 6.0 Hz, 3H) | 405 |
| Example 47 | (S)-1-cyclobutyl-4-[1-(4-isopropylphenyl)sulfonyl-4-methyl-4,5-dihydroimidazol-2-yl]piperazine | $^1$H NMR (400 MHz, CD$_3$OD) δ 7.83 (d, J = 8.4 Hz, 2H), 7.50 (d, J = 8.4 Hz, 2H), 4.15-4.10 (m, 1H), 3.45-3.27 (m, 6H), 3.04-2.99 (m, 1H), 2.92-2.80 (m, 1H), 2.53-2.45 (m, 4H), 2.12-2.05 (m, 2H), 1.98-1.90 (m, 2H), 1.79-1.70 (m, 2H), 1.27 (d, J = 6.8 Hz, 6H), 0.80 (d, J = 6.4 Hz, 3H) | 405 |

Example 48

3-cyclobutyl-8-[1-(4-isopropylphenyl)sulfonyl-4,5-dihydroimidazol-2-yl]-3,8-diazabicyclo[3.2.1]octane

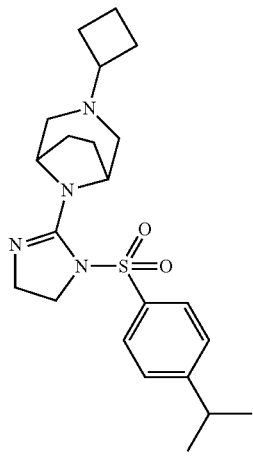 [SMILES: CC(C)c1ccc(S(=O)(=O)N2CCN=C2N2C3CCC2CN(C2CCC2)C3)cc1]

Step 1:

tert-butyl 8-((2-(((tert-butoxycarbonyl)amino)ethyl)carbamothioyl)-3,8-diazabicyclo[3.2.1]octane-3-carboxylate

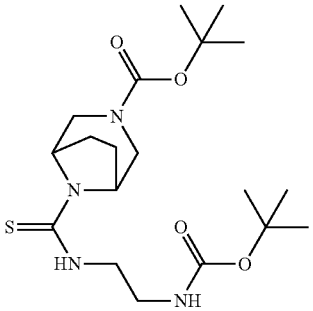 [SMILES: CC(C)(C)OC(=O)NCCNC(=S)N1C2CCC1CN(C(=O)OC(C)(C)C)C2]

To a solution of tert-butyl 3,8-diazabicyclo[3.2.1]octane-3-carboxylate (2.0 g, 9.42 mmol) in THF (50 mL) was added tert-butyl (2-isothiocyanatoethyl)carbamate (1.9 g, 9.42 mmol). The reaction mixture was stirred at room temperature for 2 h. The mixture was concentrated in vacua to afford the title compound (3.9 g, 100%) as a yellow oil that required no further purification.

Step 2:

(E)-tert-butyl 8-(11,11-dimethyl-9-oxo-10-oxa-3-thia-5,8-diazadodec-4-en-4-yl)-3,8-diazabicyclo[3.2.1]octane-3-carboxylate

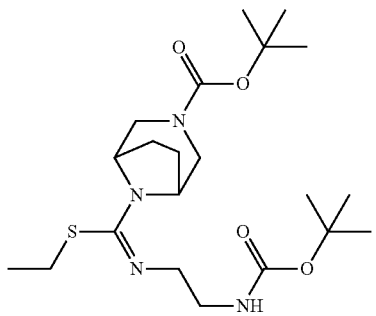 [SMILES: CCS/C(=N/CCNC(=O)OC(C)(C)C)N1C2CCC1CN(C(=O)OC(C)(C)C)C2]

To a solution of tert-butyl 8((2-((tert-butoxycarbonyl)amino)ethyl)carbamothioyl)-3,8-diazabicyclo[3.2.1]octane-3-carboxylate (3.9 g, 9.41 mmol) in EtOH (50 mL) was added iodoethane (1.5 g, 9.88 mmol). The reaction mixture was heated at reflux temperature for 8 h. The solvent was removed by concentration in vacuo and the residue was purified by silica gel chromatography (DCW/MeOH=10:1) to give the title compound (3.0 g, 72%) as a colorless oil.

Step 3:

(E)-ethyl N-(2-aminoethyl)-3,8-diazabicyclo[3.2.1]octane-8-carbimidothioate dihydrochloride

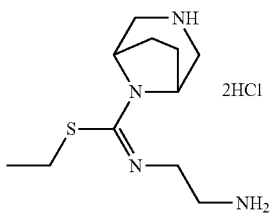 [SMILES: CCS/C(=N/CCN)N1C2CCC1CNC2]

To a solution of (E)-tert-butyl 8-(11,11-dimethyl-9-oxo-10-oxa-3-thia-5,8-diazadodec-4-en-4-yl)-3,8-diazabicyclo[3.2.1]octane-3-carboxylate (3.0 g , 6.78 mmol) in EtOAc (30 mL) was added HCl (4M in EtOAc, 20 mL, 80 mmol). The resulting mixture was stirred at room temperature for 2 h and then the solvent was concentrated in vacuo to give the title compound (2.1 g, 100%).

Step 4:

8-(4,5-dihydro-1H-imidazol-2-yl)-3,8-diazabicyclo[3.2.1]octane

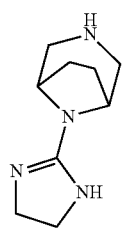

To a stirred solution of (E)-ethyl N-(2-aminoethyl)-3,8-diazabicyclo[3.2.1]octane-8-carbimidothioate dihydrochloride (2.0 g, 6.34 mmol) in EtOH (50 mL) and MeOH (10 mL) was added NaOEt (2.2 g, 31.72 mmol). The resulting mixture was stirred at room temperature for 12 h and then adjusted to pH 5-6 by the addition of 1N HCl (aq.). The solvent was removed by concentration in vacuo to give the title compound (1.0 g, 71%) as a yellow oil.

Step 5:

3-cyclobutyl-8-(4,5-dihydro-1H-imidazol-2-yl)-3,8-diazabicyclo[3.2.1]octane

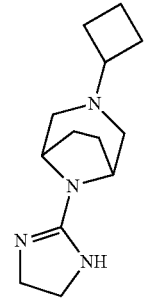 [SMILES: C1CC(N2CC3CCC(C2)N3C2=NCCN2)C1]

A solution of 8-(4,5-dihydro-1H-imidazol-2-yl)-3,8-diazabicyclo[3.2.1]octane (1.0 g, 5.55 mmol) and cyclobutanone (778 mg, 11.10 mmol) in DCM (20 mL) was stirred at room temperature for 1 h before NaBH(OAc)$_3$ (2.4 g, 11.10 mmol) was added. The reaction mixture was stirred for an additional 4 h and then concentrated in vacuo. The residue was purified by reverse phase chromatography (acetonitrile 0-30%/0.1% NH$_4$OH in water) to give the title compound (300 mg, 23%) as a colorless oil.

Step 6:

3-cyclobutyl-8-[1-(4-isopropylphenyl)sulfonyl-4,5-dihydroimidazol-2-yl]-3,8-diazabicyclo[3.2.1]octane

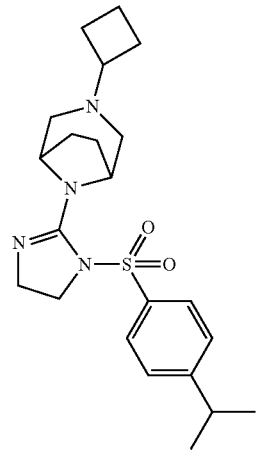 [SMILES: CC(C)c1ccc(S(=O)(=O)N2CCN=C2N2C3CCC2CN(C2CCC2)C3)cc1]

To a solution of 3-cyclobutyl-8-(4,5-dihydro-1H-imidazol-2-yl)-3,8-diazabicyclo [3.2.1]octane (200 mg, 0.85 mmol) in DMF (10 mL) was added triethylamine (173 mg, 1.71 mmol) and 4-isopropylbenzene-1-sulfonyl chloride (205 mg, 0.94 mmol). The reaction mixture was stirred at room temperature for 4 h. The solvent was removed in vacuo and the crude product was purified by reverse phase chromatography (acetonitrile 66-96%/0.1% NH$_4$OH in water) to give the title compound (5 mg, 1%) as a white solid. $^1$H NMR (400 MHz, CD$_3$OD) δ 7.84 (d, J=8.4 Hz, 2H), 7.48 (d, J=8.4 Hz, 2H), 4.26-4.24 (m, 2H), 3.92 (t, J=7.6 Hz, 2H), 3.02-2.93 (m, 3H), 2.85-2.80 (m, 1H), 2.68-2.62 (m, 2H), 2.29-2.25 (m, 2H), 2.00-1.99 (m, 2H), 1.93-1.85 (m, 6H), 1.78-1.71 (m, 2H), 1.27 (d, J=7.2 Hz, 6H). LCMS M/Z (M+H) 417.

Example 49

4-[1-[1-(4-isopropylphenyl)sulfonyl-4,5-dihydroimidazol-2-yl]-4-piperidyl]morpholine

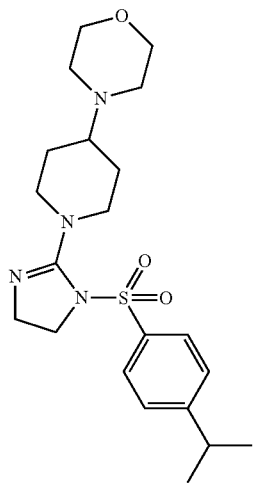 [SMILES: CC(C)c1ccc(S(=O)(=O)N2CCN=C2N2CCC(N3CCOCC3)CC2)cc1]

To a 1 dram vial was added 1-(4-isopropylphenyl)sulfonyl-2-methylsulfanyl-4,5-dihydroimidazole (Intermediate B, 40 mg, 0.134 mmol), 4-(piperidin-4-yl)morpholine (51.4 mg, 0.302 mmol) and DIEA (0.094 mL, 0.536 mmol). The vial was capped and the mixture was heated to 125° C. for 48 hrs. The crude residue was purified by reverse phase chromatography (acetonitrile 5-85%/0.1% formic acid in water) to give the title compound (45 mg, 71%). $^1$H NMR (400 MHz, DMSO-$d_6$) δ 7.78-7.74 (m, 2H), 7.54-7.48 (m, 2H), 3.82 (t, J=7.5 Hz, 2H), 3.78-3.67 (m, 2H), 3.61-3.49 (m, 2H), 3.06-2.94 (m, 1H), 2.87 (t, J=7.5 Hz, 2H), 2.71 (td, J=12.8, 11.9, 2.5 Hz, 2H), 2.49-2.42 (m, 6H), 2.35-2.24 (m, 1H), 1.87-1.74 (m, 2H), 1.57-1.40 (m, 2H), 1.26-1.16 (m, 6H). LCMS M/Z (M+H) 421.

The following compounds were prepared in a similar fashion to Example 49.

Examples 50-52

| Example | Compound Name | NMR | m/z |
|---|---|---|---|
| Example 50 | 1-[1-(4-isopropylphenyl)sulfonyl-4,5-dihydroimidazol-2-yl]-4-(2-methoxyethyl)piperazine | $^1$H NMR (400 MHz, DMSO-$d_6$) δ 7.81-7.75 (m, 2H), 7.53-7.48 (m, 2H), 3.83 (t, J = 7.6 Hz, 2H), 3.46 (t, J = 5.8 Hz, 2H), 3.24 (s, 3H), 3.21-3.14 (m, 4H), 3.05-2.95 (m, 1H), 2.88 (t, J = 7.6 Hz, 2H), 2.51-2.49 (m, 6H), 1.22 (d, J = 6.9 Hz, 6H) | 396 |
| Example 51 | 1-cyclopropyl-4-[1-(4-isopropylphenyl)sulfonyl-4,5-dihydroimidazol-2-yl]piperazine | $^1$H NMR (400 MHz, DMSO-$d_6$) δ 7.82-7.76 (m, 2H), 7.53-7.49 (m, 2H), 3.83 (t, J = 7.6 Hz, 2H), 3.20-3.12 (m, 4H), 3.06-2.95 (m, 1H), 2.88 (t, J = 7.5 Hz, 2H), 2.67-2.60 (m, 4H), 2.53-2.47 (m, 4H), 1.74-1.65 (m, 1H), 1.22 (d, J = 6.9 Hz, 6H) | 378 |
| Example 52 | 1-(cyclopropylmethyl)-4-[1-(4-isopropylphenyl)sulfonyl-4,5-dihydroimidazol-2-yl]piperazine | $^1$H NMR (400 MHz, DMSO-$d_6$) δ 7.80-7.75 (m, 2H), 7.52-7.48 (m, 2H), 3.82 (t, J = 7.6 Hz, 2H), 3.23-3.17 (m, 4H), 3.00 (p, J = 7.1 Hz, 1H), 2.88 (t, J = 7.5 Hz, 2H), 2.57-2.50 (m, 4H), 2.23 (d, J = 6.6 Hz, 2H), 1.22 (d, J = 6.9 Hz, 6H), 0.92-0.80 (m, 1H), 0.52-0.44 (m, 2H), 0.15-0.07 (m, 2H) | 392 |

Example 53

1-[4-tert-butylphenyl)sulfonyl-4,5-dihydroimidazol-2-yl]-4-cyclobutyl-piperazine

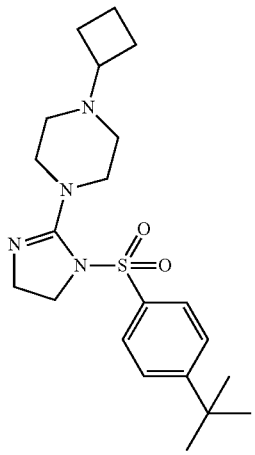 [SMILES: CC(C)(C)c1ccc(S(=O)(=O)N2CCN=C2N2CCN(C3CCC3)CC2)cc1]

To 1-cyclobutyl-4-(4,5-dihydro-1H-imidazol-2-yl)piperazine (Intermediate D, 25 mg, 0.120 mmol) in DMF (1 mL) was added 4-tert-butylbenzenesulfonyl chloride (30.7 mg, 0.132 mmol) and DIEA (34.1 mg, 0.264 mmol). The mixture stirred at 80° C. overnight. The mixture was concentrated in vacuo and the crude residue was purified by reverse phase chromatography (acetonitrile 30-70%/0.1% NH$_4$OH in water) to give the title compound (15.6 mg, 32%). $^1$H NMR (400 MHz, DMSO-d$_6$) δ 7.81-7.73 (m, 2H), 7.68-7.61 (m, 2H), 3.82 (t, J=7.5 Hz, 2H), 3.24-3.15 (m, 4H), 2.87 (t, J=7.5 Hz, 2H), 2.82-2.70 (m, 1H), 2.37-2.29 (m, 4H), 2.03-1.92 (m, 2H), 1.87-1.72 (m, 2H), 1.71-1.57 (m, 2H), 1.33-1.25 (m, 9H). LCMS M/Z (M+H) 406.

The following compounds were prepared in a similar fashion to Example 53. For Example 69, 1-(cyclopropylmethyl)-4-(4,5-dihydro-1H-imidazol-2-yl)piperazine was prepared in a similar fashion to Intermediate D.

Examples 54-68

| Example | Compound Name | NMR | m/z |
|---|---|---|---|
| Example 54 | 1-cyclobutyl-4-[1-(3-phenylphenyl)sulfonyl-4,5-dihydroimidazol-2-yl]piperazine | $^1$H NMR (400 MHz, DMSO-d$_6$) δ 8.07-8.02 (m, 2H), 7.92-7.84 (m, 1H), 7.77-7.66 (m, 3H), 7.56-7.49 (m, 2H), 7.48-7.42 (m, 1H), 3.92 (t, J = 7.6 Hz, 2H), 3.23-3.13 (m, 4H), 2.98-2.88 (m, 2H), 2.79-2.69 (m, 1H), 2.36-2.28 (m, 4H), 2.02-1.88 (m, 2H), 1.86-1.74 (m, 2H), 1.70-1.55 (m, 2H) | 426 |
| Example 55 | 6-[[2-(4-cyclobutylpiperazin-1-yl)-4,5-dihydroimidazol-1-yl]sulfonyl]-3-methyl-1,3-benzoxazol-2-one | $^1$H NMR (400 MHz, DMSO-d$_6$) δ 7.80-7.75 (m, 2H), 7.47 (d, J = 8.2 Hz, 1H), 3.89 (t, J = 7.6 Hz, 2H), 3.38 (s, 3H), 3.23-3.12 (m, 4H), 2.94 (t, J = 7.6 Hz, 2H), 2.84-2.72 (m, 1H), 2.39-2.30 (m, 4H), 2.05-1.93 (m, 2H), 1.87-1.73 (m, 2H), 1.70-1.58 (m, 2H) | 420 |
| Example 56 | 1-cyclobutyl-4-[1-(3,5-dimethylphenyl)sulfonyl-4,5-dihydroimidazol-2-yl]piperazine | $^1$H NMR (400 MHz, DMSO-d$_6$) δ 7.51-7.47 (m, 2H), 7.38-7.36 (m, 1H), 3.85 (t, J = 7.6 Hz, 2H), 3.20-3.11 (m, 4H), 2.93 (t, J = 7.6 Hz, 2H), 2.83-2.71 (m, 1H), 2.37-2.31 (m, 10H), 2.03-1.93 (m, 2H), 1.86-1.72 (m, 2H), 1.70-1.57 (m, 2H) | 378 |
| Example 57 | 1-cyclobutyl-4-[1-(2,4-dimethylphenyl)sulfonyl-4,5-dihydroimidazol-2-yl]piperazine | $^1$H NMR (400 MHz, DMSO-d$_6$) δ 7.78-7.74 (m, 1H), 7.44-7.39 (m, 1H), 7.32 (d, J = 7.8 Hz, 1H), 3.77 (t, J = 7.4 Hz, 2H), 3.18-3.11 (m, 4H), 3.01 (t, J = 7.4 Hz, 2H), 2.75-2.63 (m, 1H), 2.55 (s, 3H), 2.34 (s, 3H), 2.26-2.21 (m, 4H), 2.00-1.90 (m, 2H), 1.82-1.71 (m, 2H), 1.67-1.58 (m, 2H) | 378 |
| Example 58 | 1-cyclobutyl-4-[1-[4-(1,1-dimethylpropyl)phenyl]sulfonyl-4,5-dihydroimidazol-2-yl]piperazine | $^1$H NMR (400 MHz, DMSO-d$_6$) δ 7.79-7.75 (m, 2H), 7.60-7.55 (m, 2H), 3.81 (t, J = 7.6 Hz, 2H), 3.23-3.12 (m, 5H), 2.85 (t, J = 7.5 Hz, 2H), 2.37-2.27 (m, 4H), 2.04-1.92 (m, 2H), 1.86-1.70 (m, 2H), 1.69-1.57 (m, 5H), 1.27 (s, 6H), 0.57 (t, J = 7.4 Hz, 3H) | 420 |
| Example 59 | 1-cyclobutyl-4-[1-(m-tolylsulfonyl)-4,5-dihydroimidazol-2-yl]piperazine | $^1$H NMR (400 MHz, DMSO-d$_6$) δ 7.71-7.64 (m, 2H), 7.58-7.47 (m, 2H), 3.85 (t, J = 7.6 Hz, 2H), 3.19-3.12 (m, 4H), 2.95-2.87 (m, 2H), 2.83-2.71 (m, 1H), 2.41-2.31 (m, 7H), 2.03-1.93 (m, 2H), 1.86-1.73 (m, 2H), 1.69-1.58 (m, 2H) | 363 |

-continued

| Example | Compound Name | NMR | m/z |
|---|---|---|---|
| Example 60 | 1-cyclobutyl-4-[1-[3-(trifluoromethyl)phenyl]sulfonyl-4,5-dihydroimidazol-2-yl]-piperazine | $^1$H NMR (400 MHz, DMSO-$d_6$) δ 8.26-8.09 (m, 3H), 7.90 (t, J = 7.9 Hz, 1H), 3.94 (t, J = 7.6 Hz, 2H), 3.18-3.11 (m, 4H), 2.95 (t, J = 7.6 Hz, 2H), 2.81-2.70 (m, 1H), 2.38-2.30 (m, 4H), 2.04-1.93 (m, 2H), 1.86-1.73 (m, 2H), 1.70-1.58 (m, 2H) | 417 |
| Example 61 | 1-cyclobutyl-4-[1-(2-naphthylsulfonyl)-4,5-dihydroimidazol-2-yl]piperazine | $^1$H NMR (400 MHz, DMSO-$d_6$) δ 8.58 (d, J = 1.9 Hz, 1H), 8.16 (dd, J = 11.1, 8.0 Hz, 2H), 8.08 (dd, J = 8.1, 1.4 Hz, 1H), 7.86 (dd, J = 8.7, 1.9 Hz, 1H), 7.78-7.67 (m, 2H), 3.94 (t, J = 7.6 Hz, 2H), 3.22-3.14 (m, 4H), 2.89 (t, J = 7.6 Hz, 2H), 2.86-2.76 (m, 1H), 2.42-2.35 (m, 4H), 2.05-1.95 (m, 2H), 1.87-1.75 (m, 2H), 1.70-1.59 (m, 2H) | 400 |
| Example 62 | 1-cyclobutyl-4-[1-(3,5-dichlorophenyl)sulfonyl-4,5-dihydroimidazol-2-yl]piperazine | $^1$H NMR (400 MHz, DMSO-$d_6$) δ 8.10-8.07 (m, 1H), 7.90 (dd, J = 1.9, 0.7 Hz, 2H), 3.97 (t, J = 7.6 Hz, 2H), 3.16-3.13 (m, 4H), 3.06 (t, J = 7.6 Hz, 2H), 2.82-2.70 (m, 1H), 2.37-2.34 (m, 4H), 2.04-1.92 (m, 2H), 1.86-1.73 (m, 2H), 1.69-1.57 (m, 2H) | 417 |
| Example 63 | 1-[4-[[2-(4-cyclobutylpiperazin-1-yl)-4,5-dihydroimidazol-1-yl]sulfonyl]phenyl]-3-methyl-urea | $^1$H NMR (400 MHz, DMSO-$d_6$) δ 9.17 (s, 1H), 7.72-7.66 (m, 2H), 7.61-7.55 (m, 2H), 6.35 (q, J = 4.5 Hz, 1H), 3.81 (t, J = 7.6 Hz, 2H), 3.21-3.14 (m, 4H), 2.92 (t, J = 7.6 Hz, 2H), 2.81-2.72 (m, 1H), 2.65 (d, J = 4.5 Hz, 3H), 2.33 (dd, J = 6.1, 3.5 Hz, 4H), 2.03-1.93 (m, 2H), 1.85-1.74 (m, 2H), 1.70-1.57 (m, 2H) | 422 |
| Example 64 | 4-[[2-(4-cyclobutylpiperazin-1-yl)-4,5-dihydroimidazol-1-yl]sulfonyl]-2,1,3-benzoxadiazole | $^1$H NMR (400 MHz, DMSO-$d_6$) δ 8.47 (dd, J = 9.0, 0.7 Hz, 1H), 8.27 (d, J = 6.8 Hz, 1H), 7.83 (dd, J = 9.1, 6.8 Hz, 1H), 4.09 (t, J = 7.6 Hz, 2H), 3.13-3.06 (m, 4H), 3.02 (t, J = 7.6 Hz, 2H), 2.83-2.68 (m, 1H), 2.32-2.27 (m, 4H), 2.02-1.90 (m, 2H), 1.84-1.72 (m, 2H), 1.69-1.58 (m, 2H) | 391 |
| Example 65 | 1-cyclobutyl-4-[1-(4-phenoxyphenyl)sulfonyl-4,5-dihydroimidazol-2-yl]piperazine | $^1$H NMR (400 MHz, DMSO-$d_6$) δ 7.86-7.83 (m, 2H), 7.51-7.45 (m, 2H), 7.31-7.25 (m, 1H), 7.17-7.11 (m, 4H), 3.83 (t, J = 7.6 Hz, 2H), 3.21-3.15 (m, 4H), 2.95 (t, J = 7.6 Hz, 2H), 2.80-2.71 (m, 1H), 2.36-2.29 (m, 4H), 2.01-1.92 (m, 2H), 1.83-1.74 (m, 2H), 1.68-1.59 (m, 2H) | 442 |
| Example 66 | 4-[[2-(4-cyclobutylpiperazin-1-yl)-4,5-dihydroimidazol-1-yl]sulfonyl]-2,1,3-benzothiadiazole | $^1$H NMR (400 MHz, DMSO-$d_6$) δ 8.49 (dd, J = 8.8, 1.0 Hz, 1H), 8.37 (dd, J = 7.2, 1.0 Hz, 1H), 7.94 (dd, J = 8.8, 7.1 Hz, 1H), 4.24 (t, J = 7.7 Hz, 2H), 3.05-2.95 (m, 6H), 2.79-2.68 (m, 1H), 2.29-2.22 (m, 4H), 2.01-1.93 (m, 2H), 1.81-1.72 (m, 2H), 1.68-1.58 (m, 2H) | 408 |
| Example 67 | 1-cyclobutyl-4-[1-(3,4-dichlorophenyl)sulfonyl-4,5-dihydromidazol-2-yl]piperazine | $^1$H NMR (400 MHz, DMSO-$d_6$) δ 8.08 (d, J = 2.1 Hz, 1H), 7.93 (d, J = 8.5 Hz, 1H), 7.85 (dd, J = 8.5, 2.2 Hz, 1H), 3.94 (t, J = 7.6 Hz, 2H), 3.20-3.12 (m, 4H), 3.04 (t, J = 7.6 Hz, 2H), 2.82-2.73 (m, 1H), 2.38-2.31 (m, 4H), 2.03-1.93 (m, 2H), 1.84-1.75 (m, 2H), 1.68-1.60 (m, 2H) | 417 |
| Example 68 | 1-[1-(4-tert-butylphenyl)sulfonyl-4,5-dihydroimidazol-2-yl]-4-(cyclopropylmethyl)piperazine | $^1$H NMR (400 MHz, DMSO-$d_6$) δ 7.80-7.75 (m, 2H), 7.67-7.62 (m, 2H), 3.82 (t, J = 7.6 Hz, 2H), 3.24-3.18 (m, 4H), 2.87 (t, J = 7.5 Hz, 2H), 2.58-2.52 (m, 4H), 2.23 (d, J = 6.5 Hz, 2H), 1.30 (s, 9H), 0.90-0.79 (m, 1H), 0.52-0.44 (m, 2H), 0.13-0.07 (m, 2H) | 406 |

Example 69

1-[1-(3,4-dichlorophenyl)sulfonyl-4,5-dihydroimidazol-2-yl]-4-ethyl-piperazine

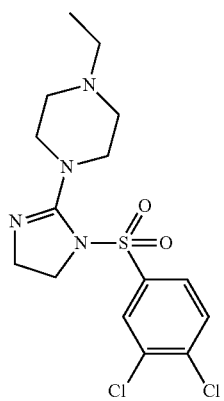 [SMILES: CCN1CCN(C2=NCCN2S(=O)(=O)c2ccc(Cl)c(Cl)c2)CC1]

To 1-(4,5-dihydro-1H-imidazol-2-yl)-4-ethyl-piperazine (made similarly to Intermediate D, 30 mg, 0.165 mmol) in DMF (1 mL) was added 3,4-dichlorobenzene-1-sulfonyl chloride (52.5 mg, 0.215 mmol) and DIEA (0.072 mL, 0.413 mmol). The mixture stirred at 80° C. overnight. The mixture was concentrated in vacuo and the crude residue was purified by reverse phase chromatography (acetonitrile 5-85%/0.1% NH$_4$OH in water) to give the title compound (6.7 mg, 7%). $^1$H NMR (400 MHz, DMSO-d$_6$) δ 8.09 (d, J=2.1 Hz, 1H), 7.94 (d, J=8.5 Hz, 1H), 7.86 (dd, J=8.5, 2.2 Hz, 1H), 3.94 (t,J=7.6 Hz, 2H), 3.21-3.12 (m, 4H), 3.04 (t,J=7.6 Hz, 2H), 2.48-2.43 (m, 4H), 2.38 (q, J=7.2 Hz, 2H), 1.02 (t,J=7.2 Hz, 3H). LCMS M/Z (M+H) 391.

Example 70

N-[4-[[2-(4-cyclobutylpiperazin-1-yl)-4,5-dihydroimidazol-1-yl]sulfonyl]phenyl]acetamide

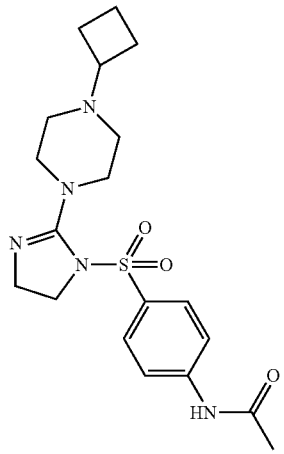 [SMILES: CC(=O)Nc1ccc(S(=O)(=O)N2CCN=C2N2CCN(C3CCC3)CC2)cc1]

To a 1 dram vial was added 2-methylsulfanyl-4,5-dihydro-1H-imidazole (50 mg, 0.430 mmol), 4-acetamidobenzenesulfonyl chloride (130.7 mg, 0.559 mmol), DIEA(111.3 mg, 0.861 mmol) and DMF (1.5 mL). The reaction mixture stirred at 80° C. overnight. The reaction mixture was concentrated in vacuo and the residue was dissolved in DCM and washed with water. The organic layer was concentrated in vacuo and to this residue was added DIEA (222.5 mg, 1.72 mmol) and 1-cyclobutylpiperazine (181.1 mg, 1.29 mmol). The reaction mixture was heated neat to 120° C. overnight. The crude residue was purified by reverse phase chromatography (acetonitrile 5-50%/0.1% NH$_4$OH in water) to give the title compound (18.3 mg, 10%). $^1$H NMR (400 MHz, DMSO-d$_6$) δ 10.37 (s, 1H), 7.78 (s, 4H), 3.82 (t,J=7.6 Hz, 2H), 3.20-3.14 (m, 4H), 2.92 (t,J=7.5 Hz, 2H), 2.82-2.72 (m, 1H), 2.36-2.31 (m, 4H), 2.09 (s, 3H), 2.02-1.95 (m, 2H), 1.84-1.75 (m, 2H), 1.69-1.61 (m, 2H). LCMS M/Z (M+H) 406.

The following compounds were prepared in a similar fashion to Example 70.

Examples 71-81

| Example | Compound Name | NMR | m/z |
| --- | --- | --- | --- |
| Example 71 | 5-[[2-(4-cyclobutylpiperazin-1-yl)-4,5-dihydroimidazol-1-yl]sulfonyl]-1-methyl-indolin-2-one | Not Determined | 419 |
| Example 72 | N-[4-[[2-(4-cyclobutylpiperazin-1-yl)-4,5-dihydroimidazol-1-yl]sulfonyl]phenyl]-N-methyl-acetamide | $^1$H NMR (400 MHz, DMSO-d$_6$) δ 7.90-7.86 (m, 2H), 7.63-7.58 (m, 2H), 3.87 (t, J = 7.6 Hz, 2H), 3.23 (s, 3H), 3.18 (s, 4H), 2.94 (t, J = 7.6 Hz, 2H), 2.82-2.71 (m, 1H), 2.38-2.30 (m, 4H), 2.03-1.89 (m, 5H), 1.86-1.73 (m, 2H), 1.70-1.58 (m, 2H) | 421 |
| Example 73 | 1-cyclobutyl-4-[1-[(6-methoxy-2-naphthyl)sulfonyl]-4,5-dihydroimidazol-2-yl]piperazine | $^1$H NMR (400 MHz, DMSO-d$_6$) δ 8.48 (d, J = 1.9 Hz, 1H), 8.03 (dd, J = 30.4, 8.9 Hz, 2H), 7.79 (dd, J = 8.7, 1.9 Hz, 1H), 7.47 (d, J = 2.5 Hz, 1H), 7.34 (dd, J = 9.0, 2.5 Hz, 1H), 3.96-3.85 (m, 5H), 3.21-3.13 (m, 4H), 2.88 (t, J = 7.6 Hz, 2H), 2.83-2.76 (m, 1H), 2.41-2.34 (m, 4H), 2.04-1.93 (m, 2H), 1.86-1.73 (m, 2H), 1.71-1.59 (m, 2H) | 430 |

-continued

| Example | Compound Name | NMR | m/z |
|---|---|---|---|
| Example 74 | 1-[1-[(6-chloro-2-naphthyl)sulfonyl]-4,5-dihydroimidazol-2-yl]-4-cyclobutyl-piperazine | $^1$H NMR (400 MHz, DMSO-d$_6$) δ 8.63 (d, J = 1.8 Hz, 1H), 8.26-8.22 (m, 2H), 8.13 (d, J = 8.8 Hz, 1H), 7.91 (dd, J = 8.7, 1.9 Hz, 1H), 7.73 (dd, J = 8.8, 2.1 Hz, 1H), 3.94 (t, J = 7.6 Hz, 2H), 3.19-3.14 (m, 4H), 2.90 (t, J = 7.6 Hz, 2H), 2.84-2.77 (m, 1H), 2.41-2.35 (m, 4H), 2.04-1.95 (m, 2H), 1.87-1.73 (m, 2H), 1.70-1.61 (m, 2H) | 433 |
| Example 75 | 1-cyclobutyl-4-(1-indan-5-ylsulfonyl-4,5-dihydroimidazol-2-yl)piperazine | $^1$H NMR (400 MHz, DMSO-d$_6$) δ 7.71 (d, J = 1.8 Hz, 1H), 7.62 (dd, J = 7.9, 1.8 Hz, 1H), 7.44 (d, J = 7.9 Hz, 1H), 3.84 (t, J = 7.6 Hz, 2H), 3.20-3.14 (m, 4H), 2.98-2.89 (m, 6H), 2.81-2.72 (m, 1H), 2.37-2.31 (m, 4H), 2.11-1.94 (m, 4H), 1.85-1.74 (m, 2H), 1.70-1.60 (m, 2H) | 390 |
| Example 76 | 6-[[2-(4-cyclobutylpiperazin-1-yl)-4,5-dihydroimidazol-1-yl]sulfonyl]quinoline | $^1$H NMR (400 MHz, DMSO-d$_6$) δ 9.10 (dd, J = 4.2, 1.7 Hz, 1H), 8.68 (d, J = 2.1 Hz, 1H), 8.66-8.62 (m, 1H), 8.21 (d, J = 8.9 Hz, 1H), 8.09 (dd, J = 8.9, 2.2 Hz, 1H), 7.73 (dd, J = 8.4, 4.2 Hz, 1H), 3.96 (t, J = 7.6 Hz, 2H), 3.22-3.15 (m, 4H), 2.91 (t, J = 7.6 Hz, 2H), 2.86-2.76 (m, 1H), 2.40-2.37 (m, 4H), 2.04-1.96 (m, 2H), 1.86-1.75 (m, 2H), 1.70-1.61 (m, 2H) | 401 |
| Example 77 | 5-[[2-(4-cyclobutylpiperazin-1-yl)-4,5-dihydroimidazol-1-yl]sulfonyl]-1-methyl-benzimidazole | $^1$H NMR (400 MHz, DMSO-d$_6$) δ 8.43 (s, 1H), 8.18-8.16 (m, 1H), 7.83-7.75 (m, 2H), 3.94-3.85 (m, 5H), 3.22-3.14 (m, 4H), 2.84-2.75 (m, 3H), 2.41-2.36 (m, 4H), 2.05-1.95 (m, 2H), 1.87-1.76 (m, 2H), 1.70-1.61 (m, 2H) | 404 |
| Example 78 | 1-cyclobutyl-4-[1-[(6-methyl-2-naphthyl)sulfonyl]-4,5-dihydroimidazol-2-yl]piperazine | $^1$H NMR (400 MHz, DMSO-d$_6$) δ 8.51 (d, J = 1.9 Hz, 1H), 8.05 (dd, J = 15.9, 8.6 Hz, 2H), 7.84 (s, 1H), 7.81 (dd, J = 8.7, 1.9 Hz, 1H), 7.55 (dd, J = 8.4, 1.7 Hz, 1H), 3.92 (t, J = 7.6 Hz, 2H), 3.19-3.15 (m, 4H), 2.91-2.75 (m, 3H), 2.53 (s, 3H), 2.41-2.34 (m, 4H), 2.04-1.95 (m, 2H), 1.86-1.75 (m, 2H), 1.70-1.60 (m, 2H) | 414 |
| Example 79 | 5-[[2-(4-cyclobutylpiperazin-1-yl)-4,5-dihydroimidazol-1-yl]sulfonyl]-1-methyl-indole | $^1$H NMR (400 MHz, DMSO-d$_6$) δ 8.23 (s, 1H), 8.15 (dd, J = 1.7, 0.7 Hz, 1H), 7.64-7.61 (m, 1H), 7.55 (d, J = 3.2 Hz, 1H), 6.66 (dd, J = 3.2, 0.8 Hz, 1H), 3.89-3.81 (m, 5H), 3.22-3.14 (m, 4H), 2.83-2.77 (m, 3H), 2.41-2.35 (m, 4H), 2.05-1.95 (m, 2H), 1.87-1.76 (m, 2H), 1.70-1.62 (m, 2H) | 403 |
| Example 80 | 6-[[2-(4-cyclobutylpiperazin-1-yl)-4,5-dihydroimidazol-1-yl]sulfonyl]-2-methyl-1,3-benzothiazole | $^1$H NMR (400 MHz, DMSO-d$_6$) δ 8.70 (d, J = 1.9 Hz, 1H), 8.09 (d, J = 8.6 Hz, 1H), 7.90 (dd, J = 8.6, 2.0 Hz, 1H), 3.91 (t, J = 7.6 Hz, 2H), 3.19-3.13 (m, 4H), 2.94-2.81 (m, 6H), 2.39-2.33 (m, 4H), 2.03-1.95 (m, 2H), 1.79 (dt, J = 11.1, 8.9 Hz, 2H), 1.69-1.61 (m, 2H) | 421 |
| Example 81 | N-[2-chloro-4-[[2-(4-cyclobutylpiperazin-1-yl)-4,5-dihydroimidazol-1-yl]sulfonyl]phenyl]acetamide | $^1$H NMR (400 MHz, DMSO-d$_6$) δ 8.19 (d, J = 8.7 Hz, 1H), 7.92 (d, J = 2.2 Hz, 1H), 7.81 (dd, J = 8.7, 2.2 Hz, 1H), 3.90 (t, J = 7.6 Hz, 2H), 3.20-3.12 (m, 4H), 3.00 (t, J = 7.6 Hz, 2H), 2.81-2.72 (m, 1H), 2.38-2.32 (m, 4H), 2.18 (s, 3H), 2.02-1.90 (m, 2H), 1.84-1.74 (m, 2H), 1.70-1.55 (m, 2H) | 440 |

Example 82

[2-(4-cyclobutylpiperazin-1-yl)-4,5-dihydroimidazol-1-yl]-phenyl-methanone

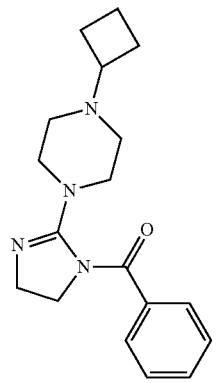 [SMILES: O=C(c1ccccc1)N1CCN=C1N1CCN(C2CCC2)CC1]

To benzoyl chloride (0.033 mL, 0.288 mmol) in a vial was added a solution of 1-cyclobutyl-4-(4,5-dihydro-1H-imidazol-2-yl)piperazine (Intermediate D, 50 mg, 0.240 mmol) and TEA (0.067 mL, 0.480 mmol) in DCM (1.5 mL). The mixture was stirred overnight at rt. The mixture was concentrated in vacuo and the crude residue was purified by reverse phase chromatography (acetonitrile 5-85%/0.1% $NH_4OH$ in water) to give the title compound (38 mg, 42%). $^1$H NMR (400 MHz, DMSO-$d_6$) δ 7.61-7.51 (m, 3H), 7.46 (ddt, J=83, 6.5, 1.2 Hz, 2H), 3.83 (t, J=7.5 Hz, 2H), 3.45 (t, J=7.5 Hz, 2H), 3.02 (t, J=4.9 Hz, 4H), 2.61-2.52 (m, 1H), 2.03-1.84 (m, 6H), 1.76-1.63 (m, 2H), 1.63-1.50 (m, 2H). LCMS M/Z (M+H) 313.

The following compounds were prepared in a similar fashion to Example 82.

Examples 83-91

| Example | Compound Name | NMR | m/z |
|---|---|---|---|
| Example 83 | [2-(4-cyclobutylpiperazin-1-yl)-4,5-dihydroimidazol-1-yl]-(o-tolyl)methanone | Not determined | 327 |
| Example 84 | [2-(4-cyclobutylpiperazin-1-yl)-4,5-dihydroimidazol-1-yl]-(p-tolyl)methanone | $^1$H NMR (400 MHz, DMSO-$d_6$) δ 7.53-7.46 (m, 2H), 7.29-7.24 (m, 2H), 3.81 (t, J = 7.5 Hz, 2H), 3.43 (t, J = 7.5 Hz, 2H), 3.03 (t, J = 4.9 Hz, 4H), 2.64-2.53 (m, 1H), 2.36 (s, 3H), 2.07-1.96 (m, 4H), 1.94-1.84 (m, 2H), 1.78-1.66 (m, 2H), 1.64-1.56 (m, 2H) | 327 |
| Example 85 | [2-(4-cyclobutylpiperazin-1-yl)-4,5-dihydroimidazol-1-yl]-(m-tolyl)methanone | $^1$H NMR (400 MHz, DMSO-$d_6$) δ 7.41-7.32 (m, 4H), 3.82 (t, J = 7.5 Hz, 2H), 3.44 (t, J = 7.5 Hz, 2H), 3.05-2.99 (m, 4H), 2.62-2.52 (m, 1H), 2.35 (s, 3H), 1.98 (s, 4H), 1.92-1.84 (m, 2H), 1.76-1.65 (m, 2H), 1.64-1.52 (m, 2H) | 327 |
| Example 86 | (3-chlorophenyl)-[2-(4-cyclobutylpiperazin-1-yl)-4,5-dihydroimidazol-1-yl]methanone | $^1$H NMR (400 MHz, DMSO-$d_6$) δ 7.63-7.58 (m, 2H), 7.57-7.46 (m, 2H), 3.83 (t, J = 7.5 Hz, 2H), 3.47 (t, J = 7.5 Hz, 2H), 2.98 (t, J = 4.9 Hz, 4H), 2.61-2.52 (m, 1H), 2.04-1.81 (m, 6H), 1.74-1.55 (m, 4H) | 347 |
| Example 87 | (2-chlorophenyl)-[2-(4-cyclobutylpiperazin-1-yl)-4,5-dihydroimidazol-1-yl]methanone | | 347 |
| Example 88 | (4-chlorophenyl)-[2-(4-cyclobutylpiperazin-1-yl)-4,5-dihydroimidazol-1-yl]methanone | $^1$H NMR (400 MHz, DMSO-$d_6$) δ 7.64-7.58 (m, 2H), 7.56-7.50 (m, 2H), 3.83 (t, J = 7.5 Hz, 2H), 3.46 (t, J = 7.4 Hz, 2H), 2.99 (t, J = 5.2 Hz, 4H), 2.62-2.52 (m, 1H), 2.01-1.86 (m, 6H), 1.77-1.66 (m, 2H), 1.63-1.55 (m, 2H) | 347 |
| Example 89 | [2-(4-cyclobutylpiperazin-1-yl)-4,5-dihydroimidazol-1-yl]-(4-methoxyphenyl)methanone | $^1$H NMR (400 MHz, DMSO-$d_6$) δ 7.61-7.56 (m, 2H), 7.02-6.97 (m, 2H), 3.86-3.77 (m, 5H), 3.43 (t, J = 7.3 Hz, 2H), 3.08-3.01 (m, 4H), 2.64-2.55 (m, 1H), 2.07-2.01 (m, 4H), 1.96-1.85 (m, 2H), 1.78-1.68 (m, 2H), 1.64-1.55 (m, 2H) | 343 |
| Example 90 | [2-(4-cyclobutylpiperazin-1-yl)-4,5-dihydroimidazol-1-yl]-(3-methoxyphenyl)methanone | $^1$H NMR (400 MHz, DMSO-$d_6$) δ 7.40-7.34 (m, 1H), 7.19-7.08 (m, 3H), 3.86-3.74 (m, 5H), 3.44 (t, J = 7.5 Hz, 2H), 3.04 (t, J = 5.0 Hz, 4H), 2.64-2.54 (m, 1H), 2.02 (s, 4H), 1.94-1.85 (m, 2H), 1.78-1.67 (m, 2H), 1.65-1.53 (m, 2H) | 343 |
| Example 91 | [2-(4-cyclobutylpiperazin-1-yl)-4,5-dihydroimidazol-1-yl]-(2-methoxyphenyl)methanone | | 343 |

Example 92

1-[1-(4-isopropylphenyl)sulfonyl-4,5-dihydroimidazol-2-yl]-4-propyl-piperazine

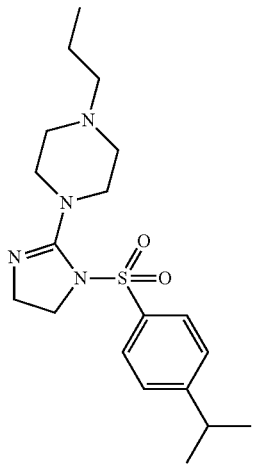 [SMILES: CCCN1CCN(C2=NCCN2S(=O)(=O)c2ccc(C(C)C)cc2)CC1]

To 1-[1-(4-isopropylphenyl)sulfonyl-4,5-dihydroimidazol-2-yl]piperazine (Intermediate C, 20 mg, 0.054 mmol) and propanal (6.23 mg, 0.107 mmol) in DMF was added sodium triacetoxyborohydride (45.47 mg, 0.215 mmol). The mixture stirred overnight at room temperature before being quenched with a small amount of 3N HCl. The mixture was then made basic with sat. aq. NaHCO$_3$ and was extracted with DCM. The combined organic layers were evaporated in vacuo. The crude residue was purified by reverse phase chromatography (acetonitrile 30-70%/0.1% NH$_4$OH in water) to give the title compound (10.1 mg, 50%). $^1$H NMR (400 MHz, DMSO-d$_6$) δ 7.81-7.75 (m, 2H), 7.53-7.47 (m, 2H), 3.83 (t,J=7.6 Hz, 2H), 3.23-3.15 (m, 4H), 3.05-2.95 (m, 1H), 2.88 (t,J=7.6 Hz, 2H), 2.46-2.42 (m, 4H), 2.31-2.25 (m, 2H), 1.52-1.40 (m, 2H), 1.22 (d, J=6.9 Hz, 6H), 0.87 (t,J=7.4 Hz, 3H). LCMS M/Z (M+H) 380.

The following compounds were prepared in a similar fashion to Example 92.

Examples 93-97

| Example | Compound Name | NMR | m/z |
| --- | --- | --- | --- |
| Example 93 | 1-[1-(4-isopropylphenyl)sulfonyl-4,5-dihydroimidazol-2-yl]-4-(4-methylcyclohexyl)piperazine | $^1$H NMR (400 MHz, DMSO-d$_6$) δ 7.77 (dd, J = 8.5, 2.6 Hz, 2H), 7.52-7.47 (m, 2H), 3.87-3.75 (m, 2H), 3.22-3.07 (m, 4H), 3.07-2.93 (m, 1H), 2.93-2.83 (m, 2H), 2.62-2.51 (m, 6H), 2.22 (ddd, J = 12.0, 9.2, 6.0 Hz, 1H), 1.86-1.60 (m, 4H), 1.52-1.33 (m, 2H), 1.33-1.13 (m, 6H), 0.99-0.78 (m, 4H) | 434 |
| Exmaple 94 | 1-[1-(4-isopropylphenyl)sulfonyl-4,5-dihydroimidazol-2-yl]-4-(3-methylcyclopentyl)piperazine | $^1$H NMR (400 MHz, DMSO-d$_6$) δ 7.82-7.73 (m, 2H), 7.54-7.45 (m, 2H), 3.82 (t, J = 7.6 Hz, 2H), 3.23-3.11 (m, 4H), 3.07-2.93 (m, 1H), 2.88 (t, J = 7.4 Hz, 2H), 2.74-2.61 (m, 1H), 2.48-2.41 (m, 4H), 2.07-1.60 (m, 4H), 1.56-1.26 (m, 2H), 1.21 (d, J = 6.9 Hz, 6H), 1.01-0.90 (m, 4H) | 420 |
| Example 95 | 1-[1-(4-isopropylphenyl)sulfonyl-4,5-dihydroimidazol-2-yl]-4-(2-methylbutyl)piperazine | $^1$H NMR (400 MHz, DMSO-d$_6$) δ 7.81-7.75 (m, 2H), 7.53-7.47 (m, 2H), 3.83 (t, J = 7.6 Hz, 2H), 3.23-3.14 (m, 4H), 3.05-2.95 (m, 1H), 2.89 (t, J = 7.6 Hz, 2H), 2.45-2.38 (m, 4H), 2.22-2.13 (m, 1H), 2.11-2.01 (m, 1H), 1.67-1.51 (m, 1H), 1.49-1.35 (m, 1H), 1.22 (d, J = 6.9 Hz, 6H), 1.14-1.02 (m, 1H), 0.92-0.83 (m, 6H) | 480 |
| Example 96 | 1-[1-(4-isopropylphenyl)sulfonyl-4,5-dihydroimidazol-2-yl]-4-(1-methylpentyl)piperazine | $^1$H NMR (400 MHz, DMSO-d$_6$) δ 7.82-7.74 (m, 2H), 7.53-7.47 (m, 2H), 3.82 (t, J = 7.5 Hz, 2H), 3.23-3.12 (m, 4H), 3.00 (p, J = 6.9 Hz, 1H), 2.87 (t, J = 7.5 Hz, 2H), 2.62-2.43 (m, 5H), 1.56-1.41 (m, 1H), 1.33-1.25 (m, 5H), 1.22 (d, J = 6.9 Hz, 6H), 0.94 (d, J = 6.5 Hz, 3H), 0.92-0.83 (m, 3H) | 422 |
| Example 97 | 1-(3,3-dimethylcyclopentyl)-4-[1-(4-isopropylphenyl)sulfonyl-4,5-dihydroimidazol-2-yl]piperazine | $^1$H NMR (400 MHz, DMSO-d$_6$) δ 7.80-7.76 (m, 2H), 7.52-7.48 (m, 2H), 3.83 (t, J = 7.6 Hz, 2H), 3.21-3.12 (m, 4H), 3.06-2.93 (m, 1H), 2.88 (t, J = 7.6 Hz, 2H), 2.73-2.59 (m, 1H), 2.48-2.41 (m, 4H), 1.85 (ddd, J = 11.4, 8.0, 4.5 Hz, 1H), 1.62 (dd, J = 12.2, 7.2 Hz, 1H), 1.57-1.32 (m, 3H), 1.22 (d, J = 6.9 Hz, 7H), 1.03 (s, 3H), 0.97 (s, 3H) | 434 |

The following compounds were prepared in a similar fashion to Example 69.

Examples 98-120

| Example | Compound Name | NMR | m/z |
|---|---|---|---|
| Example 98 | 1-ethyl-4-[1-[4-(4-fluorophenyl)phenyl]sulfonyl-4,5-dihydroimidazol-2-yl]piperazine | $^1$H NMR (400 MHz, DMSO-$d_6$) δ 7.96-7.90 (m, 4H), 7.86-7.80 (m, 2H), 7.38-7.32 (m, 2H), 3.90 (t, J = 7.6 Hz, 2H), 3.24-3.18 (m, 4H), 2.97 (t, J = 7.6 Hz, 2H), 2.49-2.45 (m, 4H), 2.39 (q, J = 7.2 Hz, 2H), 1.03 (t, J = 7.2 Hz, 3H) | 417 |
| Example 99 | 1-ethyl-4-[1-[3-(trifluoromethoxy)phenyl]sulfonyl-4,5-dihydroimidazol-2-yl]piperazine | $^1$H NMR (400 MHz, DMSO-$d_6$) δ 7.99-7.93 (m, 1H), 7.84-7.77 (m, 3H), 3.92 (t, J = 7.6 Hz, 2H), 3.21-3.14 (m, 4H), 2.95 (t, J = 7.6 Hz, 2H), 2.45 (t, J = 5.0 Hz, 4H), 2.37 (q, J = 7.2 Hz, 2H), 1.02 (t, J = 7.2 Hz, 3H) | 407 |
| Example 100 | 1-[1-(2,4-dichlorophenyl)sulfonyl-4,5-dihydroimidazol-2-yl]-4-ethyl-piperazine | $^1$H NMR (400 MHz, DMSO-$d_6$) δ 8.09 (d, J = 8.6 Hz, 1H), 7.94 (d, J = 2.1 Hz, 1H), 7.72 (dd, J = 8.6, 2.1 Hz, 1H), 3.93 (t, J = 7.5 Hz, 2H), 3.33-3.26 (m, 2H), 3.11-3.04 (m, 4H), 2.38-2.28 (m, 6H), 0.99 (t, J = 7.2 Hz, 3H) | 391 |
| Example 101 | 1-ethyl-4-[1-(4-methylsulfonylphenyl)sulfonyl-4,5-dihydroimidazol-2-yl]piperazine | $^1$H NMR (400 MHz, DMSO-$d_6$) δ 8.21-8.17 (m, 2H), 8.15-8.11 (m, 2H), 3.92 (t, J = 7.6 Hz, 2H), 3.33 (s, 3H), 3.22-3.15 (m, 4H), 2.98 (t, J = 7.6 Hz, 2H), 2.48-2.44 (m, 4H), 2.42-2.35 (m, 2H), 1.02 (t, J = 7.2 Hz, 3H) | 402 |
| Example 102 | 1-ethyl-4-[1-[4-(trifluoromethoxy)phenyl]sulfonyl-4,5-dihydroimidazol-2-yl]piperazine | $^1$H NMR (400 MHz, DMSO-$d_6$) δ 8.03-7.99 (m, 2H), 7.66-7.61 (m, 2H), 3.88 (t, J = 7.6 Hz, 2H), 3.21-3.15 (m, 4H), 2.95 (t, J = 7.6 Hz, 2H), 2.45 (t, J = 5.0 Hz, 4H), 2.38 (q, J = 7.2 Hz, 2H), 1.02 (t, J = 7.2 Hz, 3H) | 407 |
| Example 103 | 1-ethyl-4-[1-[3-(trifluoromethyl)phenyl]sulfonyl-4,5-dihydroimidazol-2-yl]piperazine | $^1$H NMR (400 MHz, DMSO-$d_6$) δ 8.26-8.22 (m, 1H), 8.19-8.15 (m, 1H), 8.14-8.11 (m, 1H), 7.94-7.88 (m, 1H), 3.95 (t, J = 7.6 Hz, 2H), 3.19-3.12 (m, 4H), 2.95 (t, J = 7.6 Hz, 2H), 2.48-2.43 (m, 4H), 2.37 (q, J = 7.2 Hz, 2H), 1.02 (t, J = 7.2 Hz, 3H) | 391 |
| Example 104 | 1-[1-[3-(difluoromethoxy)phenyl]sulfonyl-4,5-dihydroimidazol-2-yl]-4-ethyl-piperazine | $^1$H NMR (400 MHz, DMSO-$d_6$) δ 7.79-7.75 (m, 1H), 7.73-7.68 (m, 1H), 7.63-7.56 (m, 2H), 7.54-7.16 (m, 1H), 3.90 (t, J = 7.6 Hz, 2H), 3.18 (t, J = 5.1 Hz, 5H), 2.95 (t, J = 7.6 Hz, 2H), 2.47-2.43 (m, 4H), 2.37 (q, J = 7.2 Hz, 2H), 1.02 (t, J = 7.2 Hz, 3H) | 389 |
| Example 105 | 1-[1-[4-(difluoromethoxy)phenyl]sulfonyl-4,5-dihydroimidazol-2-yl]-4-ethyl-piperazine | $^1$H NMR (400 MHz, DMSO-$d_6$) δ 7.96-7.90 (m, 2H), 7.62-7.24 (m, 3H), 3.87 (t, J = 7.6 Hz, 2H), 3.22-3.15 (m, 4H), 2.95 (t, J = 7.6 Hz, 2H), 2.45 (t, J = 5.0 Hz, 4H), 2.38 (q, J = 7.2 Hz, 2H), 1.02 (t, J = 7.2 Hz, 3H) | 389 |
| Example 106 | 1-[1-(2,5-dichlorophenyl)sulfonyl-4,5-dihydroimidazol-2-yl]-4-ethyl-piperazine | $^1$H NMR (400 MHz, DMSO-$d_6$) δ 8.07 (d, J = 2.5 Hz, 1H), 7.83 (dd, J = 8.6, 2.5 Hz, 1H), 7.76 (d, J = 8.6 Hz, 1H), 4.01 (t, J = 7.6 Hz, 2H), 3.35 (t, J = 7.6 Hz, 2H), 3.03 (dd, J = 6.0, 3.9 Hz, 4H), 2.37-2.29 (m, 6H), 0.99 (t, J = 7.2 Hz, 3H) | 391 |
| Example 107 | 1-ethyl-4-[1-[4-(trifluoromethyl)phenyl]sulfonyl-4,5-dihydroimidazol-2-yl]piperazine | $^1$H NMR (400 MHz, DMSO-$d_6$) δ 8.13-8.08 (m, 2H), 8.07-8.02 (m, 2H), 3.91 (t, J = 7.6 Hz, 2H), 3.22-3.14 (m, 4H), 2.95 (t, J = 7.6 Hz, 2H), 2.48-2.44 (m, 4H), 2.38 (q, J = 7.2 Hz, 2H), 1.02 (t, J = 7.2 Hz, 3H) | 391 |
| Example 108 | 1-[1-(2,6-difluorophenyl)sulfonyl-4,5-dihydroimidazol-2-yl]-4-ethyl-piperazine | $^1$H NMR (400 MHz, DMSO-$d_6$) δ 7.86-7.78 (m, 1H), 7.39-6.60 (m, 2H), 4.00-3.93 (m, 2H), 3.34-3.31 (m, 2H), 3.09-3.03 (m, 4H), 2.37-2.30 (m, 6H), 0.98 (t, J = 7.2 Hz, 3H) | 359 |
| Example 109 | 1-[1-(2,4-difluorophenyl)sulfonyl-4,5-dihydroimidazol-2-yl]-4-ethyl-piperazine | $^1$H NMR (400 MHz, DMSO-$d_6$) δ 8.03-7.96 (m, 1H), 7.61 (ddd, J = 11.4, 9.2, 2.5 Hz, 1H), 7.42-7.33 (m, 1H), 3.91 (t, J = 7.7 Hz, 2H), 3.20 (t, J = 7.5 Hz, 2H), 3.11 (t, J = 5.0 Hz, 4H), 2.41-2.30 (m, 6H), 1.03-0.97 (m, 3H) | 359 |

| Example | Compound Name | NMR | m/z |
|---|---|---|---|
| Example 110 | 1-ethyl-4-[1-(2-naphthylsulfonyl)-4,5-dihydroimidazol-2-yl]piperazine | $^1$H NMR (400 MHz, DMSO-$d_6$) δ 8.59 (d, J = 1.9 Hz, 1H), 8.20-8.06 (m, 3H), 7.87 (dd, J = 8.7, 1.9 Hz, 1H), 7.79-7.68 (m, 2H), 3.94 (t, J = 7.6 Hz, 2H), 3.22-3.16 (m, 4H), 2.89 (t, J = 7.6 Hz, 2H), 2.53-2.45 (m, J = 2.5 Hz, 4H), 2.41 (q, J = 7.2 Hz, 2H), 1.04 (t, J = 7.2 Hz, 3H) | 373 |
| Example 111 | 1-ethyl-4-[1-(2-methoxyphenyl)sulfonyl-4,5-dihydroimidazol-2-yl]piperazine | $^1$H NMR (400 MHz, DMSO-$d_6$) δ 7.85 (dd, J = 7.9, 1.7 Hz, 1H), 7.66 (ddd, J = 8.4, 7.4, 1.8 Hz, 1H), 7.24 (dd, J = 8.5, 1.0 Hz, 1H), 7.15-7.10 (m, 1H), 3.91-3.86 (m, 5H), 3.33-3.25 (m, 2H), 3.02 (t, J = 5.1 Hz, 4H), 2.36-2.25 (m, 6H), 0.98 (t, J = 7.2 Hz, 3H) | 353 |
| Example 112 | 2-[[2-(4-ethylpiperazin-1-yl)-4,5-dihydroimidazol-1-yl]sulfonyl]benzonitrile | $^1$H NMR (400 MHz, DMSO-$d_6$) δ 8.18-8.14 (m, 2H), 8.00-7.91 (m, 2H), 4.00 (t, J = 7.5 Hz, 2H), 3.18-3.10 (m, 6H), 2.44-2.30 (m, 6H), 1.00 (t, J = 7.2 Hz, 3H) | 348 |
| Example 113 | 1-[1-(3-chlorophenyl)sulfonyl-4,5-dihydroimidazol-2-yl]-4-ethyl-piperazine | $^1$H NMR (400 MHz, DMSO-$d_6$) δ 7.90 (t, J = 1.9 Hz, 1H), 7.88-7.83 (m, 2H), 7.68 (t, J = 8.0 Hz, 1H), 3.95-3.87 (m, 2H), 3.20-3.13 (m, 4H), 3.02-2.95 (m, 2H), 2.48-2.44 (m, 4H), 2.38 (q, J = 7.2 Hz, 2H), 1.02 (t, J = 7.2 Hz, 3H). | 357 |
| Example 114 | 1-[1-(2-chlorophenyl)sulfonyl-4,5-dihydroimidazol-2-yl]-4-ethyl-piperazine | $^1$H NMR (400 MHz, DMSO-$d_6$) δ 8.13-8.09 (m, 1H), 7.73-7.70 (m, 2H), 7.61 (ddd, J = 7.9, 5.4, 3.3 Hz, 1H), 3.93 (t, J = 7.5 Hz, 2H), 3.28-3.24 (m, 2H), 3.10-3.03 (m, 4H), 2.35-2.28 (m, 6H), 0.98 (t, J = 7.2 Hz, 3H) | 357 |
| Example 115 | 1-ethyl-4-[1-(3-methoxyphenyl)sulfonyl-4,5-dihydroimidazol-2-yl]piperazine | $^1$H NMR (400 MHz, DMSO-$d_6$) δ 7.58-7.52 (m, 1H), 7.47-7.43 (m, 1H), 7.34-7.29 (m, 2H), 3.89-3.81 (m, 5H), 3.23-3.17 (m, 4H), 2.91 (t, J = 7.6 Hz, 2H), 2.45 (t, J = 4.9 Hz, 4H), 2.37 (q, J = 7.2 Hz, 2H), 1.02 (t, J = 7.2 Hz, 3H) | 353 |
| Example 116 | 1-ethyl-4-[1-(4-methoxyphenyl)sulfonyl-4,5-dihydroimidazol-2-yl]piperazine | $^1$H NMR (400 MHz, DMSO-$d_6$) δ 7.82-7.78 (m, 2H), 7.15-7.11 (m, 2H), 3.87-3.80 (m, 5H), 3.22-3.16 (m, 4H), 2.92 (t, J = 7.6 Hz, 2H), 2.47-2.43 (m, 4H), 2.37 (q, J = 7.2 Hz, 2H), 1.02 (t, J = 7.2 Hz, 3H) | 353 |
| Example 117 | 1-ethyl-4-[1-(p-tolylsulfonyl)-4,5-dihydroimidazol-2-yl]piperazine | $^1$H NMR (400 MHz, DMSO-$d_6$) δ 7.77-7.74 (m, 2H), 7.45-7.41 (m, 2H), 3.84 (t, J = 7.6 Hz, 2H), 3.22-3.15 (m, 4H), 2.94-2.87 (m, 2H), 2.45 (t, J = 5.0 Hz, 4H), 2.42-2.34 (m, 5H), 1.02 (t, J = 7.2 Hz, 3H) | 337 |
| Example 118 | 1-[1-(2,6-dichlorophenyl)sulfonyl-4,5-dihydroimidazol-2-yl]-4-ethyl-piperazine | $^1$H NMR (400 MHz, DMSO-$d_6$) δ 7.74-7.63 (m, 3H), 3.92 (t, J = 7.5 Hz, 2H), 3.42 (t, J = 7.5 Hz, 2H), 3.00-2.95 (m, 4H), 2.30-2.18 (m, 6H), 0.94 (t, J = 7.2 Hz, 3H) | 391 |
| Example 119 | 1-ethyl-4-[1-(1-ethyl-5-methyl-pyrazol-4-yl)sulfonyl-4,5-dihydroimidazol-2-yl]piperazine | $^1$H NMR (400 MHz, DMSO-$d_6$) δ 7.81 (s, 1H), 4.11 (q, J = 7.2 Hz, 2H), 3.83-3.76 (m, 2H), 3.26-3.18 (m, 4H), 2.99 (t, J = 7.5 Hz, 2H), 2.47 (s, 3H), 2.44-2.31 (m, 6H), 1.29 (t, J = 7.2 Hz, 3H), 1.01 (t, J = 7.2 Hz, 3H) | 355 |
| Example 120 | 4-[[2-(4-ethylpiperazin-1-yl)-4,5-dihydroimidazol-1-yl]sulfonyl]-2,1,3-benzoxadiazole | $^1$H NMR (400 MHz, DMSO-$d_6$) δ 8.48 (dd, J = 9.0, 0.7 Hz, 1H), 8.28 (dd, J = 6.9, 0.8 Hz, 1H), 7.83 (dd, J = 9.1, 6.8 Hz, 1H), 4.09 (t, J = 7.6 Hz, 2H), 3.13-3.07 (m, 4H), 3.02 (t, J = 7.6 Hz, 2H), 2.44-2.33 (m, 6H), 1.01 (t, J = 7.1 Hz, 3H) | 365 |

Example 121

KDM2B TR-FRET Assay for Determining Inhibitor IC$_{50}$

Full length KDM2B was cloned, expressed, and purified to homogeneity. Compound inhibition of KDM2B demethylase activity was assessed by monitoring the methylation status of a biotin-H3K36me2 peptide substrate (H2N-RK-SAPATGGV(KMe2)KPHRYRPGTV-NTPEGBiot; New England Peptide) in the presence of α-keotglutarate (2-OG) and iron (Fe$^{2+}$) using the TR-FRET assay technology (Cisbio). Specifically, in a 384 well ProxiPlate KDM2B (5 mM final), ascorbate (500 μM final) and DTT (2 mM final) were combined with the biotin-H3K36me2 peptide substrate (200 nM final), 2-OG (0.3 μM or 6 μM final; Sigma K2010) and Fe$^{2+}$ (100 μM final; Sigma F1543) in 50 mM HEPES (pH 6.5) and 0.01% Triton-X 100 either in the presence of DMSO (final 0.25% DMSO) or compound dilution series in DMSO and mixed. After a two hour incubation at room temperature, a mixture of EU-anti-H3K36me1 antibody (2 nM final; Cisbio #64CUSKAZ), and Streptavidin-d2 (50 nM final; Cisbio #64CUS000) in 200 mM KF, 200 mM EDTA, 0.1% BSA and 50 mM HEPES (pH 6.5) was added. After 1 hour incubation, the plates were read on an Envision instrument, the readouts were transformed into % inhibition, and $IC_{50}$ values were generated using a four parameter logistic model (XLFIT5). The KDM2B TR-FRET Assay described above represents an additional embodiment of the invention.

Data for representative compounds from the assay described in Example 121 is provided in the following Table.

TABLE

| Ex | Structure | KDM2B HTRF $IC_{50}$ (nM) |
|---|---|---|
| 1 | 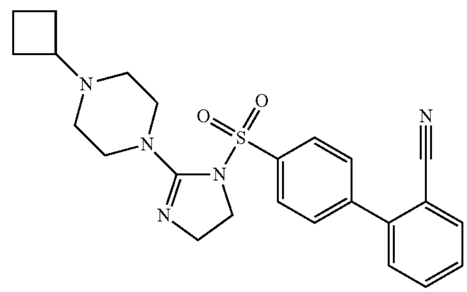 [SMILES: N#Cc1ccccc1-c1ccc(S(=O)(=O)N2CCN=C2N2CCN(C3CCC3)CC2)cc1] | 0.053 |
| 2 | 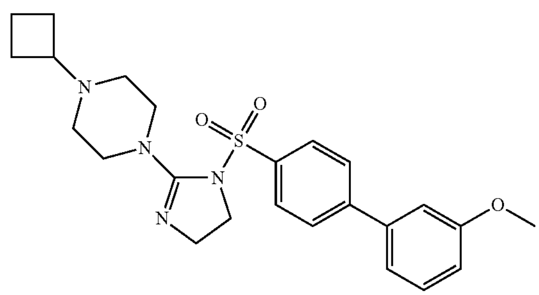 [SMILES: COc1cccc(-c2ccc(S(=O)(=O)N3CCN=C3N3CCN(C4CCC4)CC3)cc2)c1] | 0.098 |
| 3 | 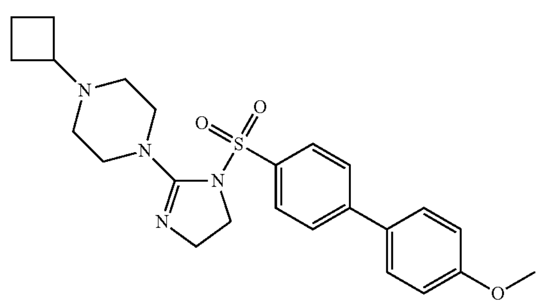 [SMILES: COc1ccc(-c2ccc(S(=O)(=O)N3CCN=C3N3CCN(C4CCC4)CC3)cc2)cc1] | 0.080 |
| 4 | 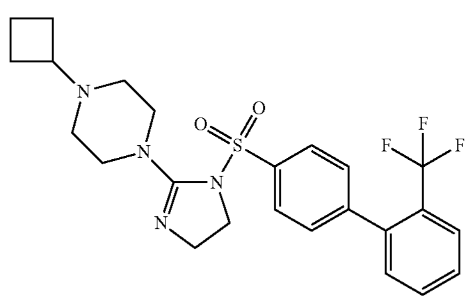 [SMILES: O=S(=O)(c1ccc(-c2ccccc2C(F)(F)F)cc1)N1CCN=C1N1CCN(C2CCC2)CC1] | 0.102 |

TABLE-continued
| Ex | Structure | KDM2B HTRF IC$_{50}$ (nM) |
|---|---|---|
| 5 | 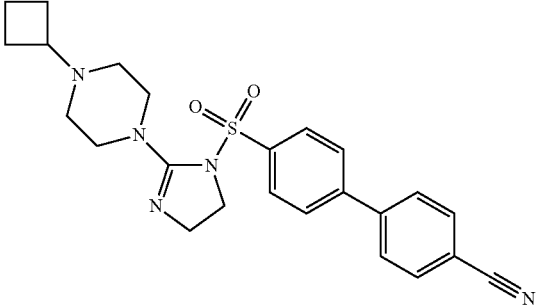 [SMILES: N#Cc1ccc(-c2ccc(S(=O)(=O)N3CCN=C3N3CCN(C4CCC4)CC3)cc2)cc1] | 0.097 |
| 6 | 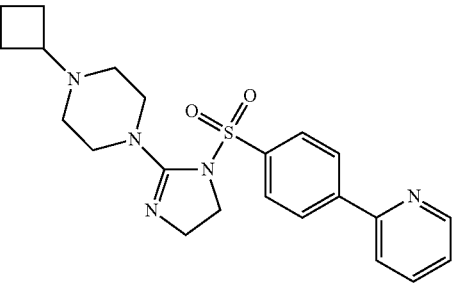 [SMILES: O=S(=O)(c1ccc(-c2ccccn2)cc1)N1CCN=C1N1CCN(C2CCC2)CC1] | 0.102 |
| 7 | 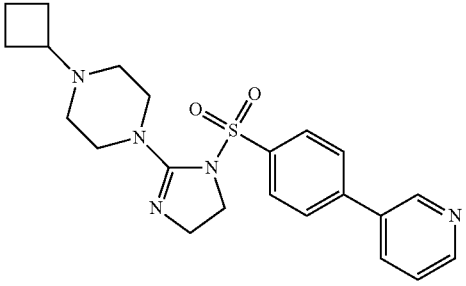 [SMILES: O=S(=O)(c1ccc(-c2cccnc2)cc1)N1CCN=C1N1CCN(C2CCC2)CC1] | 0.151 |
| 8 | 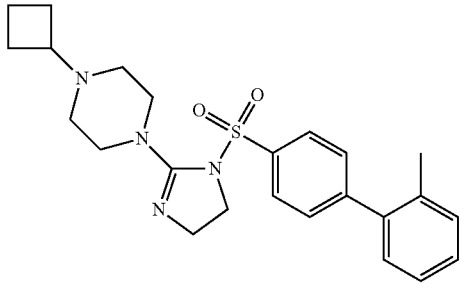 [SMILES: Cc1ccccc1-c1ccc(S(=O)(=O)N2CCN=C2N2CCN(C3CCC3)CC2)cc1] | 0.077 |
| 9 | 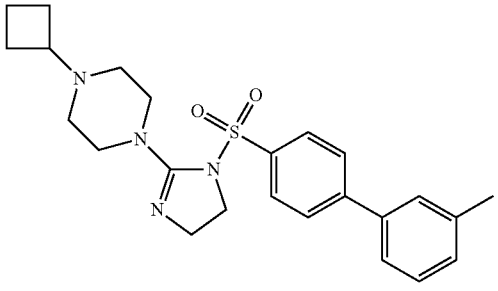 [SMILES: Cc1cccc(-c2ccc(S(=O)(=O)N3CCN=C3N3CCN(C4CCC4)CC3)cc2)c1] | 0.074 |

TABLE-continued

| Ex | Structure | KDM2B HTRF IC$_{50}$ (nM) |
|---|---|---|
| 10 | 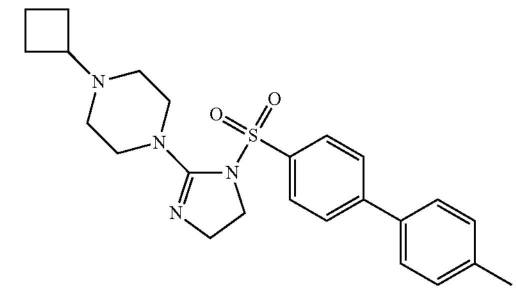 [SMILES: Cc1ccc(-c2ccc(S(=O)(=O)N3CCN=C3N3CCN(C4CCC4)CC3)cc2)cc1] | 0.145 |
| 11 | 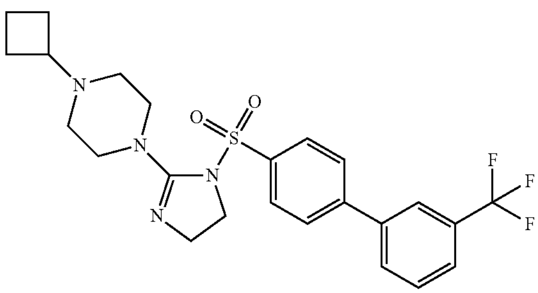 [SMILES: O=S(=O)(c1ccc(-c2cccc(C(F)(F)F)c2)cc1)N1CCN=C1N1CCN(C2CCC2)CC1] | 0.134 |
| 12 | 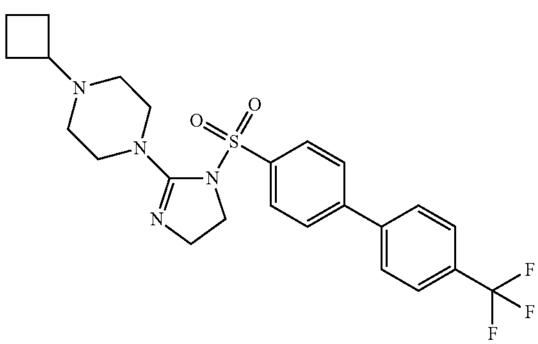 [SMILES: O=S(=O)(c1ccc(-c2ccc(C(F)(F)F)cc2)cc1)N1CCN=C1N1CCN(C2CCC2)CC1] | 0.380 |
| 13 | 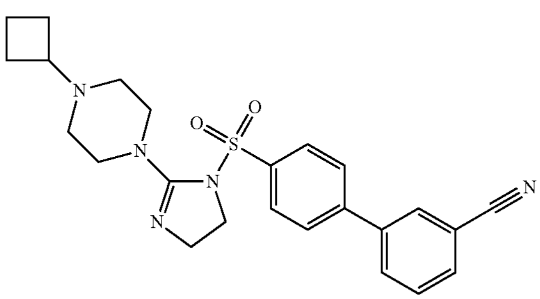 [SMILES: N#Cc1cccc(-c2ccc(S(=O)(=O)N3CCN=C3N3CCN(C4CCC4)CC3)cc2)c1] | 0.145 |
| 14 | 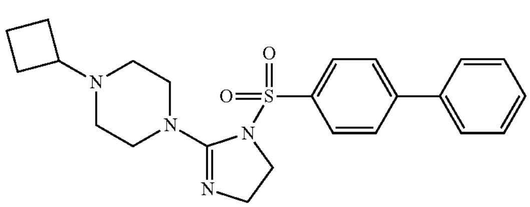 [SMILES: O=S(=O)(c1ccc(-c2ccccc2)cc1)N1CCN=C1N1CCN(C2CCC2)CC1] | 0.048 |

TABLE-continued

| Ex | Structure | KDM2B HTRF IC$_{50}$ (nM) |
|---|---|---|
| 15 | 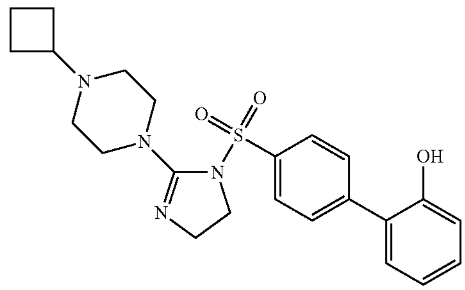 [SMILES: O=S(=O)(c1ccc(-c2ccccc2O)cc1)N1CCN=C1N1CCN(C2CCC2)CC1] | 0.037 |
| 16 | 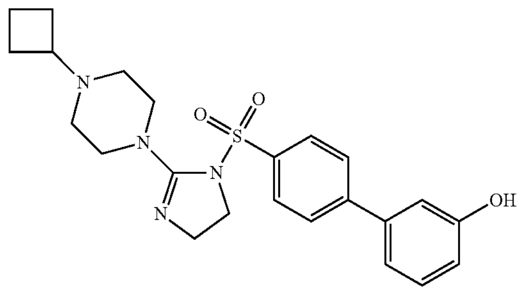 [SMILES: O=S(=O)(c1ccc(-c2cccc(O)c2)cc1)N1CCN=C1N1CCN(C2CCC2)CC1] | 0.034 |
| 17 | 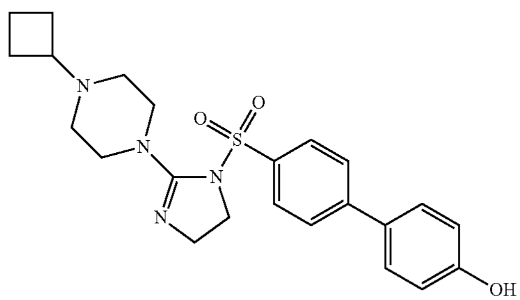 [SMILES: O=S(=O)(c1ccc(-c2ccc(O)cc2)cc1)N1CCN=C1N1CCN(C2CCC2)CC1] | 0.021 |
| 18 | 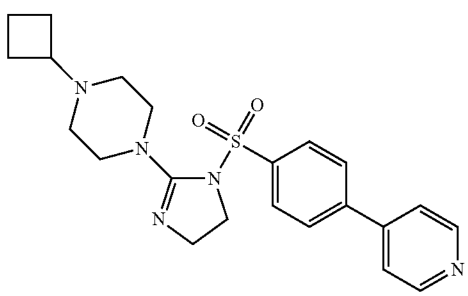 [SMILES: O=S(=O)(c1ccc(-c2ccncc2)cc1)N1CCN=C1N1CCN(C2CCC2)CC1] | 0.095 |
| 19 | 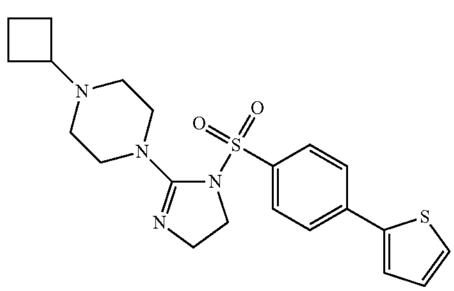 [SMILES: O=S(=O)(c1ccc(-c2cccs2)cc1)N1CCN=C1N1CCN(C2CCC2)CC1] | 0.027 |

TABLE-continued

| Ex | Structure | KDM2B HTRF IC$_{50}$ (nM) |
|---|---|---|
| 20 | 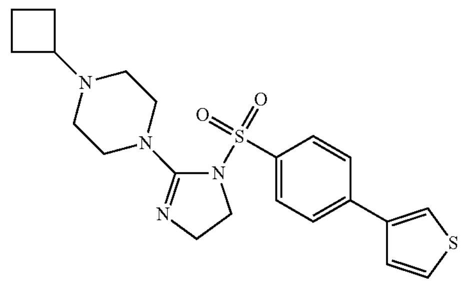 [SMILES: O=S(=O)(c1ccc(-c2ccsc2)cc1)N1CCN=C1N1CCN(C2CCC2)CC1] | 0.021 |
| 21 | 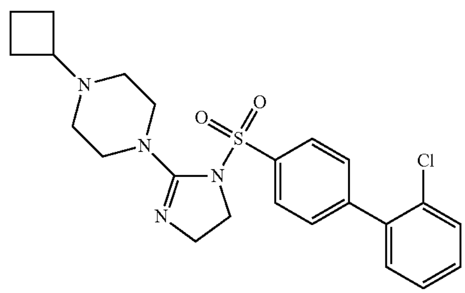 [SMILES: O=S(=O)(c1ccc(-c2ccccc2Cl)cc1)N1CCN=C1N1CCN(C2CCC2)CC1] | 0.084 |
| 22 | 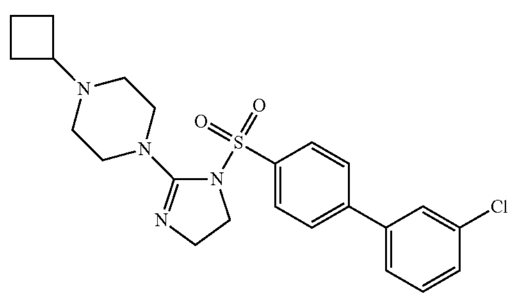 [SMILES: O=S(=O)(c1ccc(-c2cccc(Cl)c2)cc1)N1CCN=C1N1CCN(C2CCC2)CC1] | 0.120 |
| 23 | 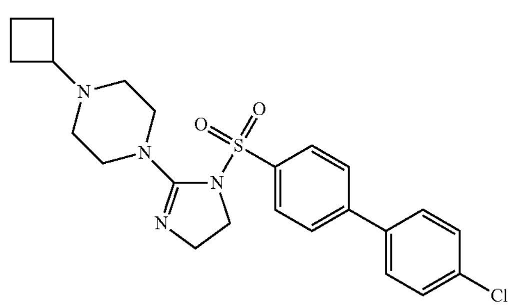 [SMILES: O=S(=O)(c1ccc(-c2ccc(Cl)cc2)cc1)N1CCN=C1N1CCN(C2CCC2)CC1] | 0.275 |
| 24 | 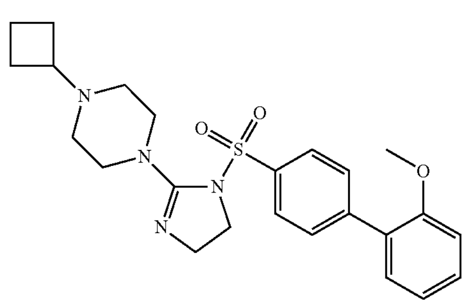 [SMILES: COc1ccccc1-c1ccc(S(=O)(=O)N2CCN=C2N2CCN(C3CCC3)CC2)cc1] | 0.050 |

TABLE-continued
| Ex | Structure | KDM2B HTRF IC$_{50}$ (nM) |
| --- | --- | --- |
| 25 | 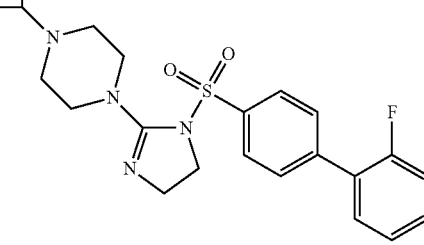 | 0.046 |
| 26 | 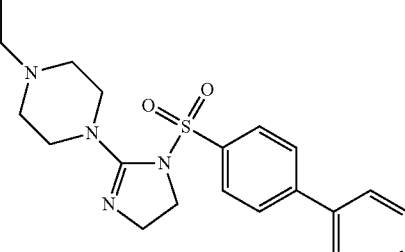 | 0.138 |
| 27 | 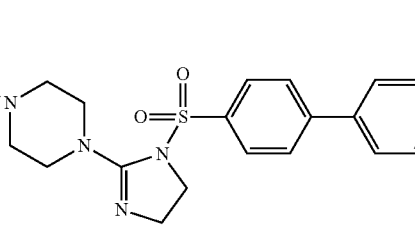 | 0.071 |
| 28 | 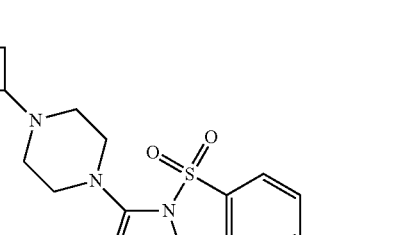 | 0.049 |
| 29 | 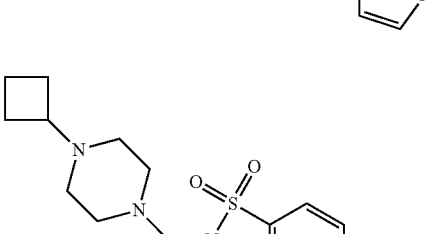 | 0.049 |

TABLE-continued

| Ex | Structure | KDM2B HTRF IC$_{50}$ (nM) |
|---|---|---|
| 30 | 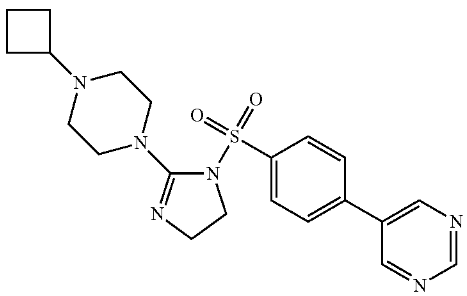 [SMILES: O=S(=O)(c1ccc(-c2cncnc2)cc1)N1CCN=C1N1CCN(C2CCC2)CC1] | 0.060 |
| 31 | 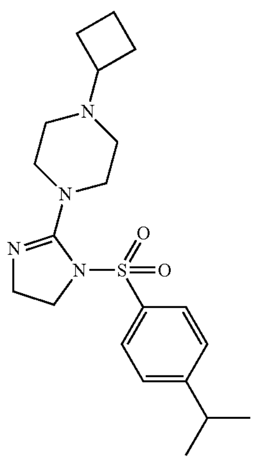 [SMILES: CC(C)c1ccc(S(=O)(=O)N2CCN=C2N2CCN(C3CCC3)CC2)cc1] | 0.043 |
| 32 | 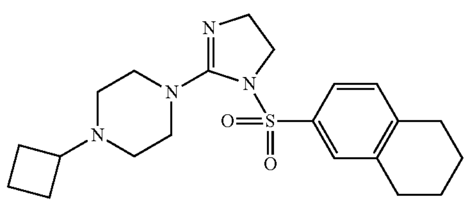 [SMILES: O=S(=O)(c1ccc2c(c1)CCCC2)N1CCN=C1N1CCN(C2CCC2)CC1] | 0.016 |
| 33 | 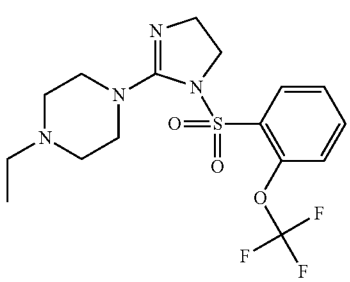 [SMILES: CCN1CCN(C2=NCCN2S(=O)(=O)c2ccccc2OC(F)(F)F)CC1] | 8.507 |
| 34 | 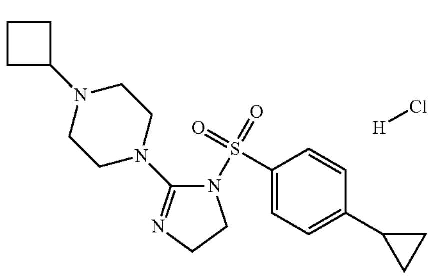 | 0.058 |

TABLE-continued

| Ex | Structure | KDM2B HTRF IC$_{50}$ (nM) |
|---|---|---|
| 35 | 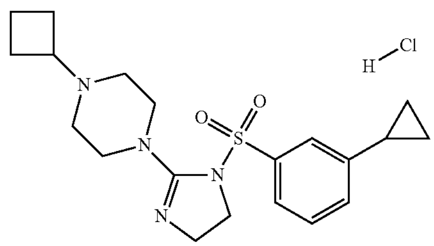 | 0.087 |
| 36 | 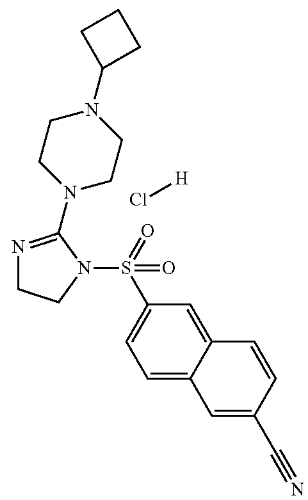 | 0.130 |
| 37 | 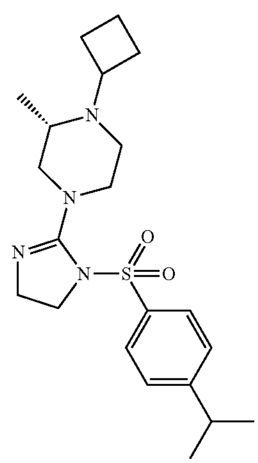 [SMILES: CC(C)c1ccc(S(=O)(=O)N2CCN=C2N2CCN(C3CCC3)[C@@H](C)C2)cc1] | 0.689 |
| 38 | 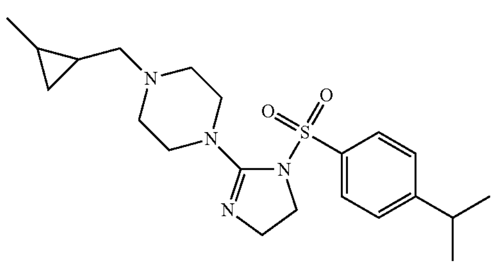 [SMILES: CC(C)c1ccc(S(=O)(=O)N2CCN=C2N2CCN(CC3CC3C)CC2)cc1] | 0.492 |

TABLE-continued
| Ex | Structure | KDM2B HTRF IC$_{50}$ (nM) |
|---|---|---|
| 39 | 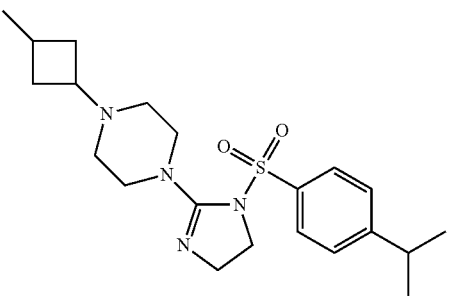 [SMILES: CC1CC(N2CCN(C3=NCCN3S(=O)(=O)c3ccc(C(C)C)cc3)CC2)C1] | 0.860 |
| 40 | 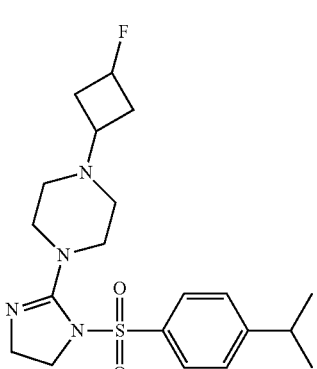 | 0.391 |
| 41 | 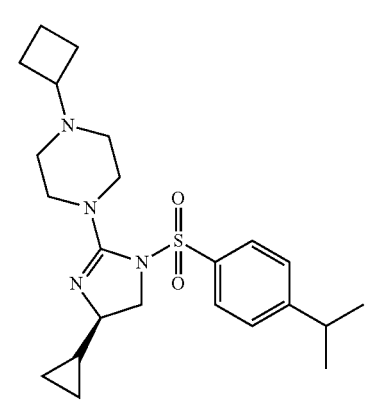 [SMILES: CC(C)c1ccc(S(=O)(=O)N2C[C@@H](C3CC3)N=C2N2CCN(C3CCC3)CC2)cc1] | 0.039 |
| 42 | 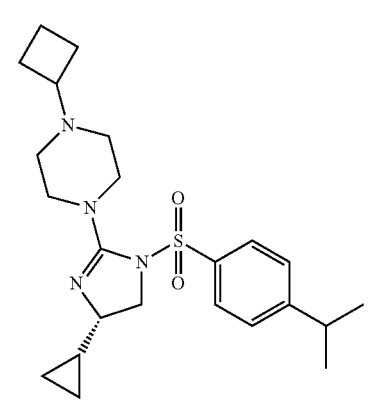 [SMILES: CC(C)c1ccc(S(=O)(=O)N2C[C@H](C3CC3)N=C2N2CCN(C3CCC3)CC2)cc1] | 0.047 |

TABLE-continued

| Ex | Structure | KDM2B HTRF IC$_{50}$ (nM) |
|---|---|---|
| 43 | 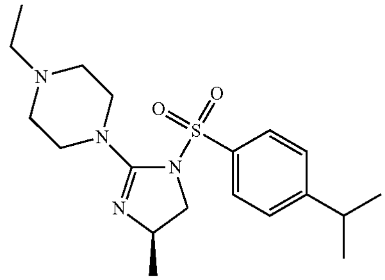 [SMILES: CCN1CCN(C2=N[C@H](C)CN2S(=O)(=O)c2ccc(C(C)C)cc2)CC1] | 8.755 |
| 44 | 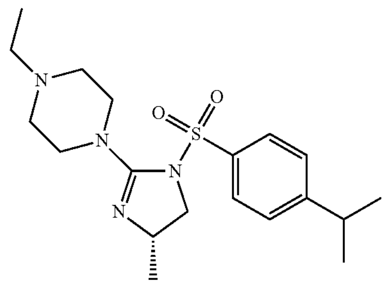 [SMILES: CCN1CCN(C2=N[C@@H](C)CN2S(=O)(=O)c2ccc(C(C)C)cc2)CC1] | 0.519 |
| 45 | 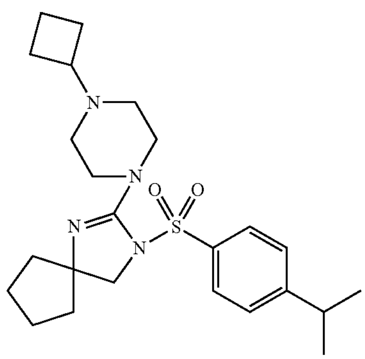 [SMILES: CC(C)c1ccc(S(=O)(=O)N2CC3(CCCC3)N=C2N2CCN(C3CCC3)CC2)cc1] | 0.049 |
| 46 | 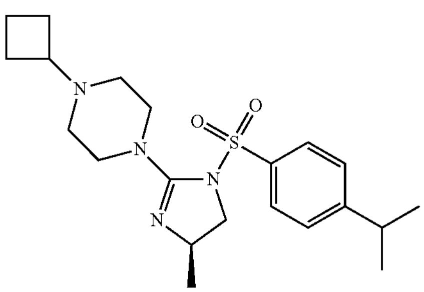 [SMILES: CC(C)c1ccc(S(=O)(=O)N2C[C@@H](C)N=C2N2CCN(C3CCC3)CC2)cc1] | 0.054 |
| 47 | 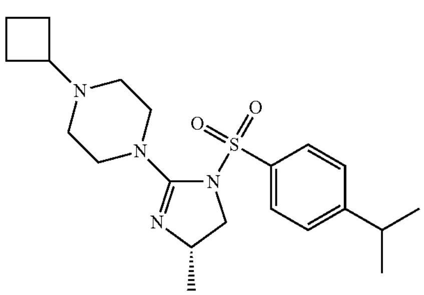 [SMILES: CC(C)c1ccc(S(=O)(=O)N2C[C@H](C)N=C2N2CCN(C3CCC3)CC2)cc1] | 0.114 |

TABLE-continued
| Ex | Structure | KDM2B HTRF IC$_{50}$ (nM) |
|---|---|---|
| 48 | 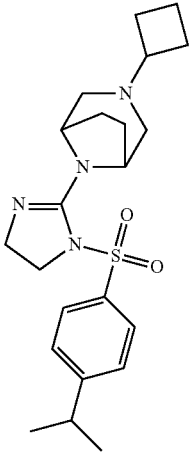 [SMILES: CC(C)c1ccc(S(=O)(=O)N2CCN=C2N2C3CCC2CN(C2CCC2)C3)cc1] | 1.187 |
| 49 | 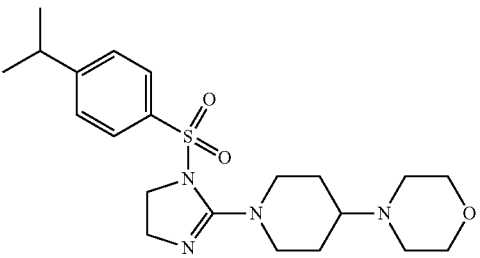 [SMILES: CC(C)c1ccc(S(=O)(=O)N2CCN=C2N2CCC(N3CCOCC3)CC2)cc1] | 4.222 |
| 50 | 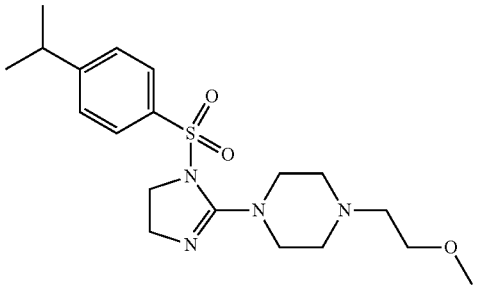 [SMILES: COCCN1CCN(C2=NCCN2S(=O)(=O)c2ccc(C(C)C)cc2)CC1] | 2.909 |
| 51 | 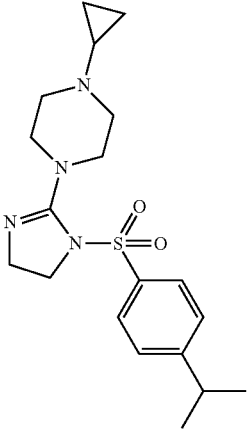 [SMILES: CC(C)c1ccc(S(=O)(=O)N2CCN=C2N2CCN(C3CC3)CC2)cc1] | 0.321 |

TABLE-continued
| Ex | Structure | KDM2B HTRF IC$_{50}$ (nM) |
|---|---|---|
| 52 | 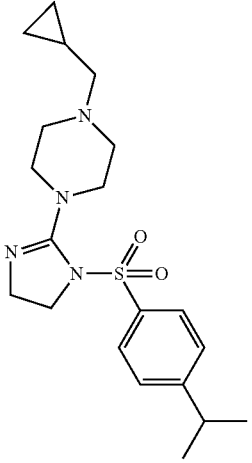 [SMILES: CC(C)c1ccc(S(=O)(=O)N2CCN=C2N2CCN(CC3CC3)CC2)cc1] | 0.198 |
| 53 | 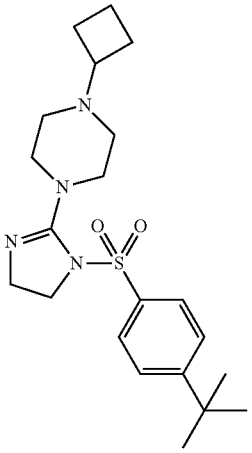 [SMILES: CC(C)(C)c1ccc(S(=O)(=O)N2CCN=C2N2CCN(C3CCC3)CC2)cc1] | 0.081 |
| 54 | 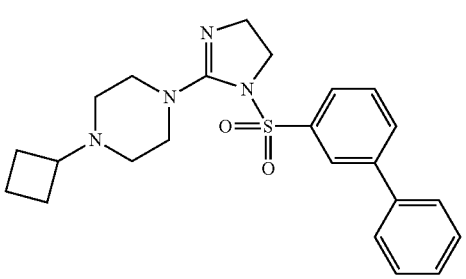 [SMILES: O=S(=O)(c1cccc(-c2ccccc2)c1)N1CCN=C1N1CCN(C2CCC2)CC1] | 0.049 |
| 55 | 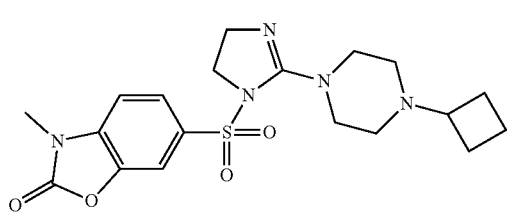 [SMILES: Cn1c(=O)oc2cc(S(=O)(=O)N3CCN=C3N3CCN(C4CCC4)CC3)ccc21] | 0.360 |

TABLE-continued

| Ex | Structure | KDM2B HTRF IC$_{50}$ (nM) |
|---|---|---|
| 56 | 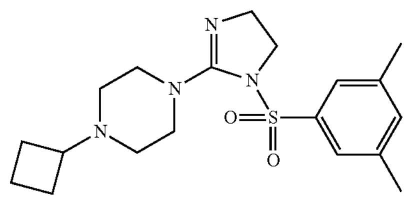 [SMILES: Cc1cc(C)cc(S(=O)(=O)N2CCN=C2N2CCN(C3CCC3)CC2)c1] | 0.088 |
| 57 | 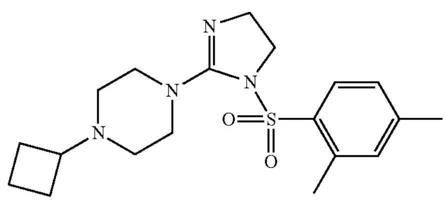 [SMILES: Cc1ccc(S(=O)(=O)N2CCN=C2N2CCN(C3CCC3)CC2)c(C)c1] | 0.139 |
| 58 | 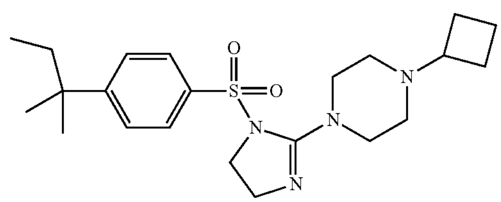 [SMILES: CCC(C)(C)c1ccc(S(=O)(=O)N2CCN=C2N2CCN(C3CCC3)CC2)cc1] | 0.035 |
| 59 | 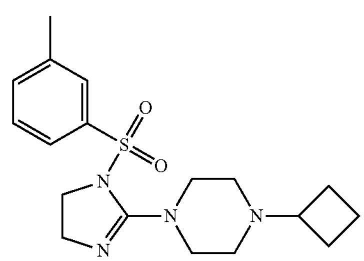 [SMILES: Cc1cccc(S(=O)(=O)N2CCN=C2N2CCN(C3CCC3)CC2)c1] | 0.146 |
| 60 | 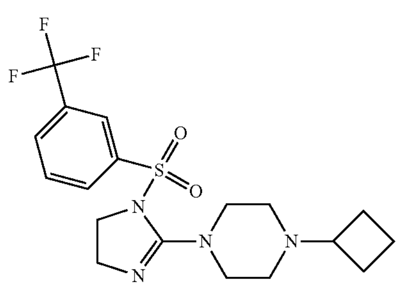 [SMILES: O=S(=O)(c1cccc(C(F)(F)F)c1)N1CCN=C1N1CCN(C2CCC2)CC1] | 0.278 |
| 61 | 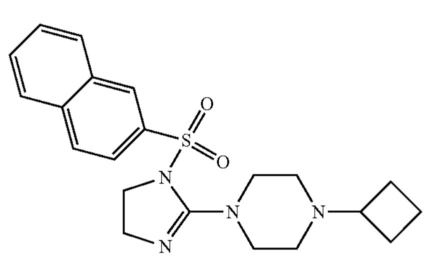 [SMILES: O=S(=O)(c1ccc2ccccc2c1)N1CCN=C1N1CCN(C2CCC2)CC1] | 0.062 |

TABLE-continued

| Ex | Structure | KDM2B HTRF IC$_{50}$ (nM) |
|---|---|---|
| 62 | 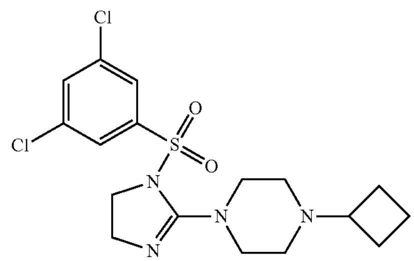 [SMILES: O=S(=O)(c1cc(Cl)cc(Cl)c1)N1CCN=C1N1CCN(C2CCC2)CC1] | 0.306 |
| 63 | 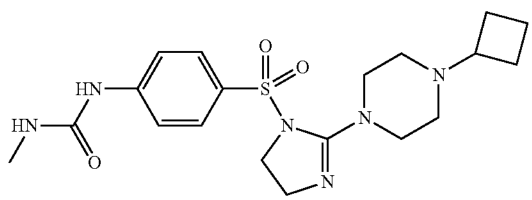 [SMILES: CNC(=O)Nc1ccc(S(=O)(=O)N2CCN=C2N2CCN(C3CCC3)CC2)cc1] | 0.138 |
| 64 | 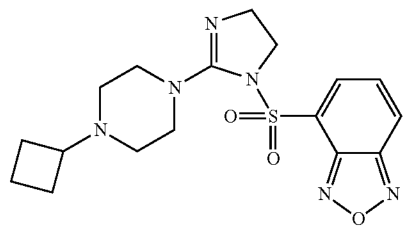 | 0.500 |
| 65 | 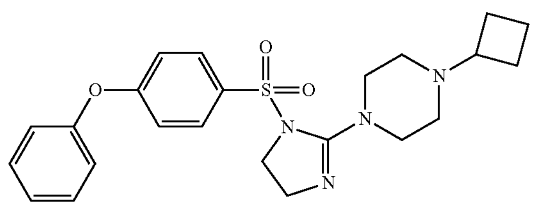 [SMILES: O=S(=O)(c1ccc(Oc2ccccc2)cc1)N1CCN=C1N1CCN(C2CCC2)CC1] | 0.050 |
| 66 | 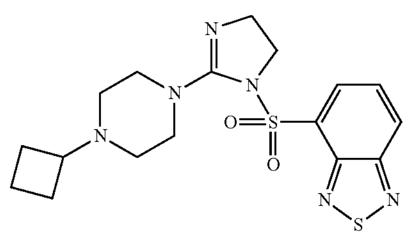 [SMILES: O=S(=O)(c1cccc2nsnc12)N1CCN=C1N1CCN(C2CCC2)CC1] | 0.141 |
| 67 | 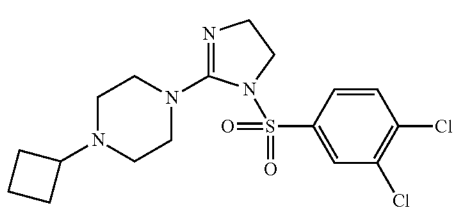 [SMILES: O=S(=O)(c1ccc(Cl)c(Cl)c1)N1CCN=C1N1CCN(C2CCC2)CC1] | 0.136 |

TABLE-continued
| Ex | Structure | KDM2B HTRF IC$_{50}$ (nM) |
|---|---|---|
| 68 | 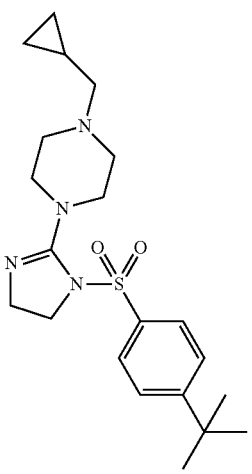 [SMILES: CC(C)(C)c1ccc(S(=O)(=O)N2CCN=C2N2CCN(CC3CC3)CC2)cc1] | 0.201 |
| 69 | 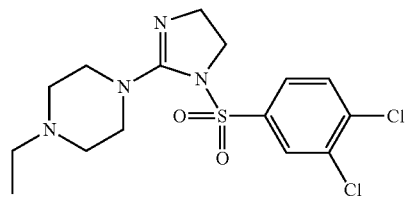 [SMILES: CCN1CCN(C2=NCCN2S(=O)(=O)c2ccc(Cl)c(Cl)c2)CC1] | 11.462 |
| 70 | 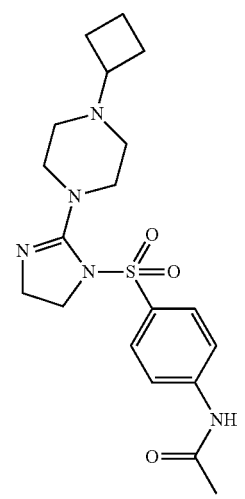 [SMILES: CC(=O)Nc1ccc(S(=O)(=O)N2CCN=C2N2CCN(C3CCC3)CC2)cc1] | 0.094 |
| 71 | 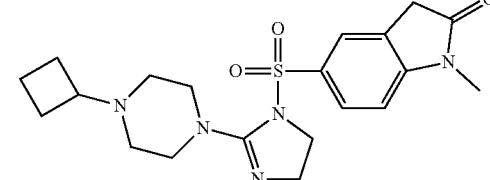 | 5.697 |

TABLE-continued
| Ex | Structure | KDM2B HTRF IC$_{50}$ (nM) |
|---|---|---|
| 72 | 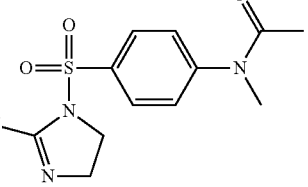 | 0.209 |
| 73 | 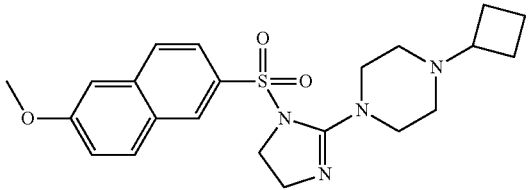 [SMILES: COc1ccc2cc(S(=O)(=O)N3CCN=C3N3CCN(C4CCC4)CC3)ccc2c1] | 0.041 |
| 74 | 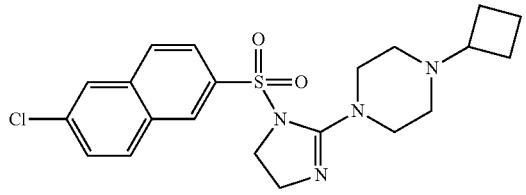 [SMILES: O=S(=O)(c1ccc2cc(Cl)ccc2c1)N1CCN=C1N1CCN(C2CCC2)CC1] | 0.041 |
| 75 | 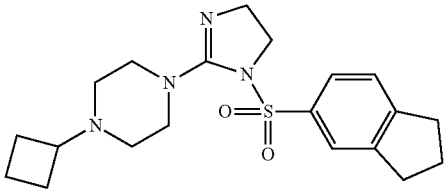 [SMILES: O=S(=O)(c1ccc2c(c1)CCC2)N1CCN=C1N1CCN(C2CCC2)CC1] | 0.031 |
| 76 | 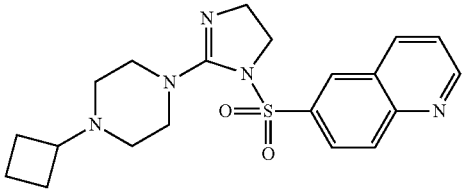 [SMILES: O=S(=O)(c1ccc2ncccc2c1)N1CCN=C1N1CCN(C2CCC2)CC1] | 0.174 |
| 77 | 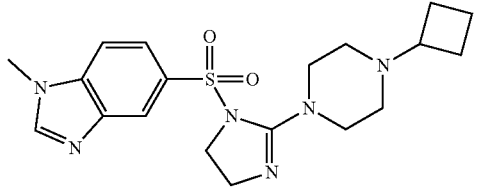 [SMILES: Cn1cnc2cc(S(=O)(=O)N3CCN=C3N3CCN(C4CCC4)CC3)ccc21] | 0.195 |
| 78 | 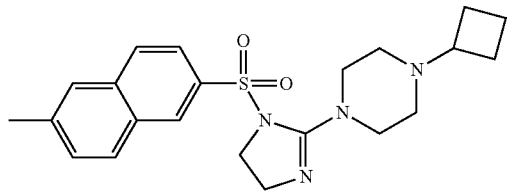 [SMILES: Cc1ccc2cc(S(=O)(=O)N3CCN=C3N3CCN(C4CCC4)CC3)ccc2c1] | 0.077 |

TABLE-continued

| Ex | Structure | KDM2B HTRF IC$_{50}$ (nM) |
|---|---|---|
| 79 | 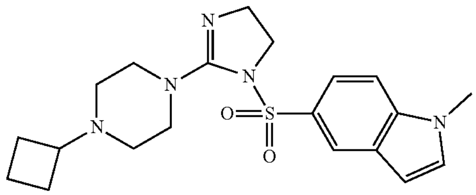 [SMILES: Cn1ccc2cc(S(=O)(=O)N3CCN=C3N3CCN(C4CCC4)CC3)ccc21] | 0.062 |
| 80 | 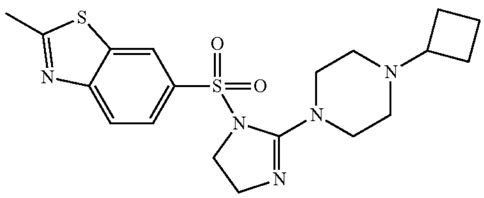 [SMILES: Cc1nc2ccc(S(=O)(=O)N3CCN=C3N3CCN(C4CCC4)CC3)cc2s1] | 0.112 |
| 81 | 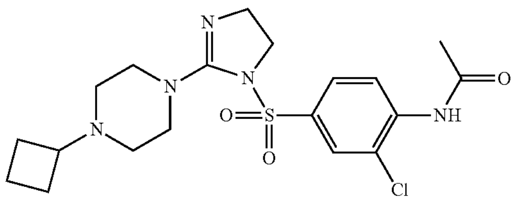 [SMILES: CC(=O)Nc1ccc(S(=O)(=O)N2CCN=C2N2CCN(C3CCC3)CC2)cc1Cl] | 0.127 |
| 82 | 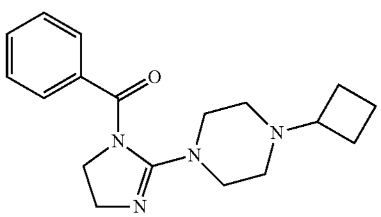 [SMILES: O=C(c1ccccc1)N1CCN=C1N1CCN(C2CCC2)CC1] | 7.004 |
| 83 | 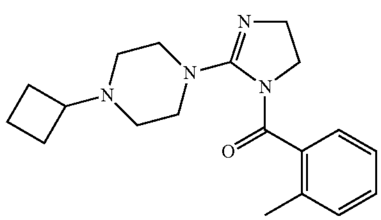 [SMILES: Cc1ccccc1C(=O)N1CCN=C1N1CCN(C2CCC2)CC1] | 3.066 |
| 84 | 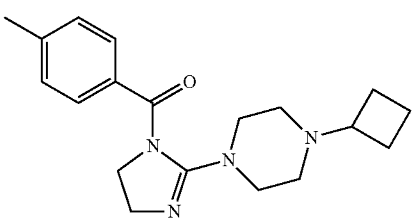 [SMILES: Cc1ccc(C(=O)N2CCN=C2N2CCN(C3CCC3)CC2)cc1] | 2.698 |
| 85 | 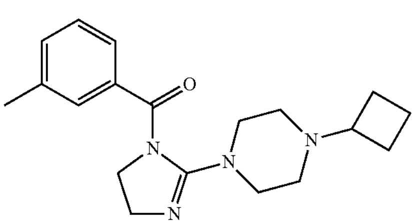 [SMILES: Cc1cccc(C(=O)N2CCN=C2N2CCN(C3CCC3)CC2)c1] | 3.125 |

TABLE-continued

| Ex | Structure | KDM2B HTRF IC$_{50}$ (nM) |
|---|---|---|
| 86 | 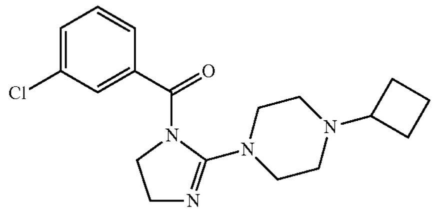 [SMILES: O=C(c1cccc(Cl)c1)N1CCN=C1N1CCN(C2CCC2)CC1] | 2.041 |
| 87 | 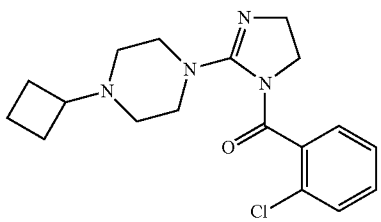 [SMILES: O=C(c1ccccc1Cl)N1CCN=C1N1CCN(C2CCC2)CC1] | 2.225 |
| 88 | 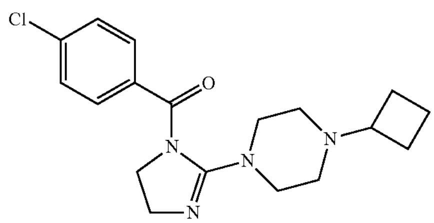 [SMILES: O=C(c1ccc(Cl)cc1)N1CCN=C1N1CCN(C2CCC2)CC1] | 2.212 |
| 89 | 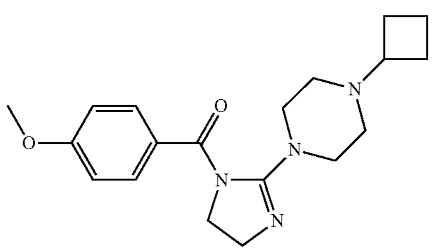 [SMILES: COc1ccc(C(=O)N2CCN=C2N2CCN(C3CCC3)CC2)cc1] | 4.384 |
| 90 | 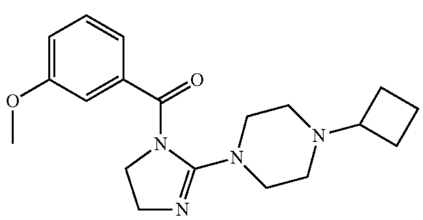 [SMILES: COc1cccc(C(=O)N2CCN=C2N2CCN(C3CCC3)CC2)c1] | 2.290 |
| 91 | 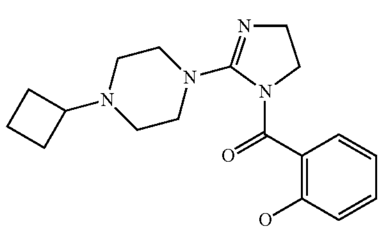 [SMILES: O=C(c1ccccc1O)N1CCN=C1N1CCN(C2CCC2)CC1] | 11.477 |

TABLE-continued

| Ex | Structure | KDM2B HTRF IC$_{50}$ (nM) |
|---|---|---|
| 92 | 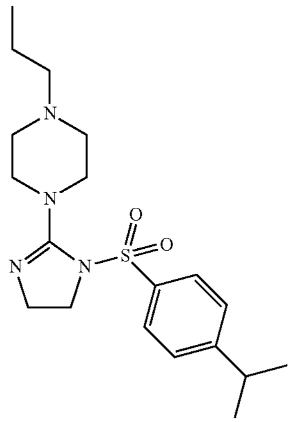 [SMILES: CCCN1CCN(C2=NCCN2S(=O)(=O)c2ccc(C(C)C)cc2)CC1] | 0.150 |
| 93 | 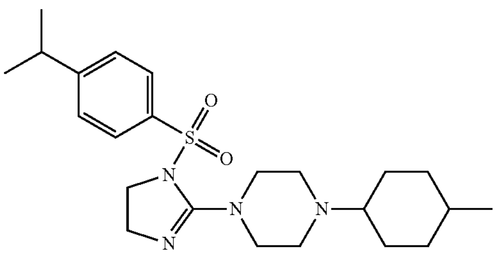 [SMILES: CC1CCC(N2CCN(C3=NCCN3S(=O)(=O)c3ccc(C(C)C)cc3)CC2)CC1] | 2.261 |
| 94 | 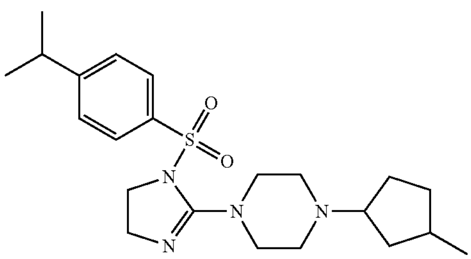 [SMILES: CC1CCC(N2CCN(C3=NCCN3S(=O)(=O)c3ccc(C(C)C)cc3)CC2)C1] | 1.417 |
| 95 | 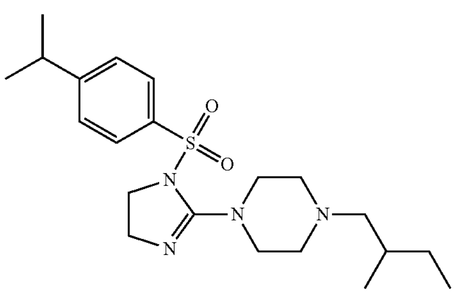 [SMILES: CCC(C)CN1CCN(C2=NCCN2S(=O)(=O)c2ccc(C(C)C)cc2)CC1] | 0.585 |
| 96 | 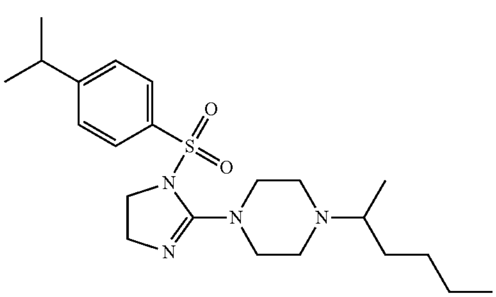 [SMILES: CCCCC(C)N1CCN(C2=NCCN2S(=O)(=O)c2ccc(C(C)C)cc2)CC1] | 3.246 |

TABLE-continued

| Ex | Structure | KDM2B HTRF IC$_{50}$ (nM) |
|---|---|---|
| 97 | 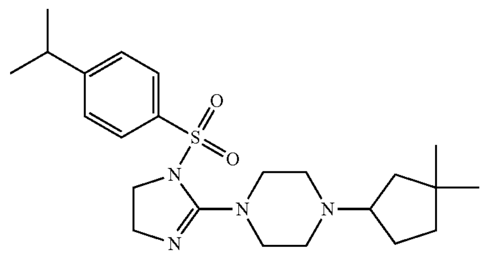 [SMILES: CC(C)c1ccc(S(=O)(=O)N2CCN=C2N2CCN(C3CCC(C)(C)C3)CC2)cc1] | 10.462 |
| 98 | 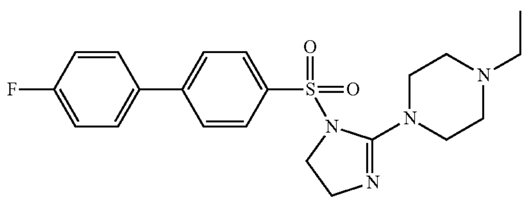 [SMILES: CCN1CCN(C2=NCCN2S(=O)(=O)c2ccc(-c3ccc(F)cc3)cc2)CC1] | 1.020 |
| 99 | 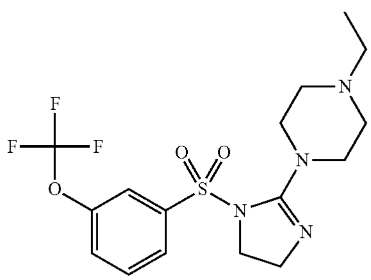 [SMILES: CCN1CCN(C2=NCCN2S(=O)(=O)c2cccc(OC(F)(F)F)c2)CC1] | 6.222 |
| 100 | 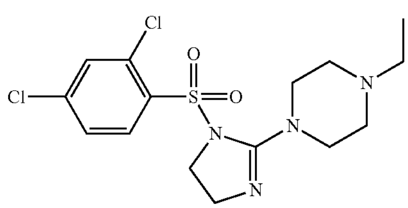 [SMILES: CCN1CCN(C2=NCCN2S(=O)(=O)c2ccc(Cl)cc2Cl)CC1] | 2.831 |
| 101 | 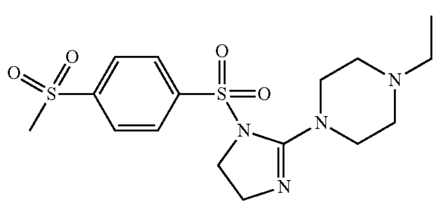 [SMILES: CCN1CCN(C2=NCCN2S(=O)(=O)c2ccc(S(C)(=O)=O)cc2)CC1] | 1.119 |
| 102 | 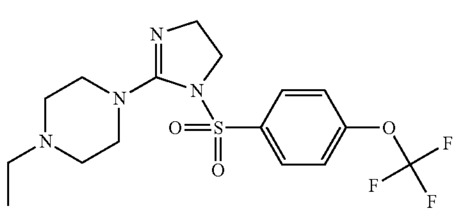 [SMILES: CCN1CCN(C2=NCCN2S(=O)(=O)c2ccc(OC(F)(F)F)cc2)CC1] | 1.655 |

TABLE-continued

| Ex | Structure | KDM2B HTRF IC$_{50}$ (nM) |
|---|---|---|
| 103 | 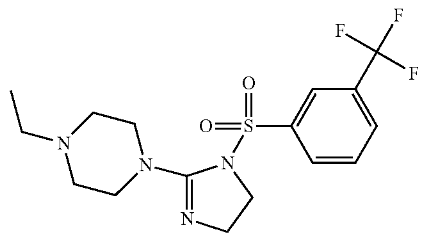 [SMILES: CCN1CCN(C2=NCCN2S(=O)(=O)c2cccc(C(F)(F)F)c2)CC1] | 6.992 |
| 104 | 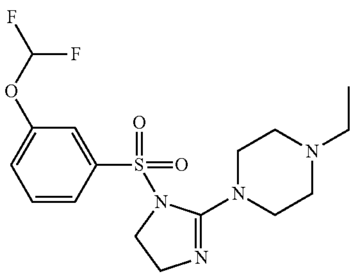 [SMILES: CCN1CCN(C2=NCCN2S(=O)(=O)c2cccc(OC(F)F)c2)CC1] | 7.759 |
| 105 | 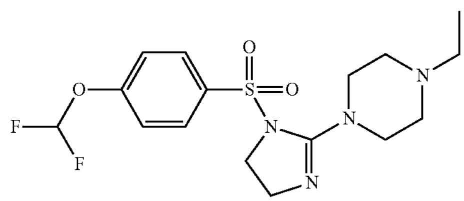 [SMILES: CCN1CCN(C2=NCCN2S(=O)(=O)c2ccc(OC(F)F)cc2)CC1] | 3.307 |
| 106 | 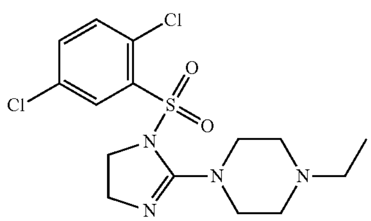 [SMILES: CCN1CCN(C2=NCCN2S(=O)(=O)c2cc(Cl)ccc2Cl)CC1] | 3.569 |
| 107 | 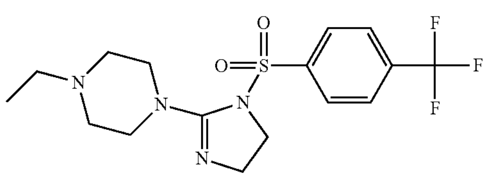 [SMILES: CCN1CCN(C2=NCCN2S(=O)(=O)c2ccc(C(F)(F)F)cc2)CC1] | 3.915 |
| 108 | 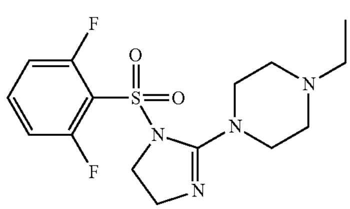 [SMILES: CCN1CCN(C2=NCCN2S(=O)(=O)c2c(F)cccc2F)CC1] | 12.844 |
| 109 | 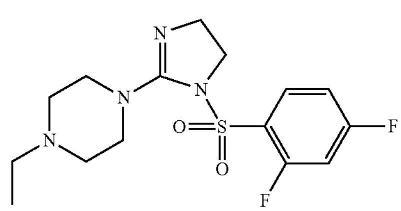 [SMILES: CCN1CCN(C2=NCCN2S(=O)(=O)c2ccc(F)cc2F)CC1] | 6.329 |

TABLE-continued

| Ex | Structure | KDM2B HTRF IC$_{50}$ (nM) |
|---|---|---|
| 110 | 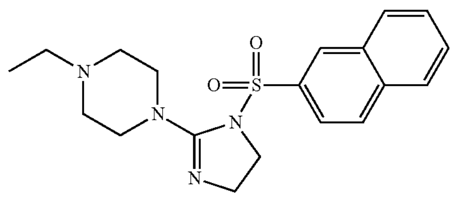 [SMILES: CCN1CCN(C2=NCCN2S(=O)(=O)c2ccc3ccccc3c2)CC1] | 0.998 |
| 111 | 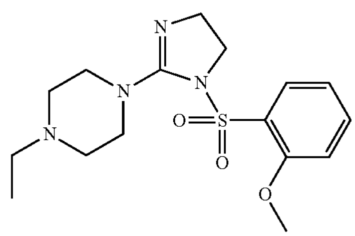 [SMILES: CCN1CCN(C2=NCCN2S(=O)(=O)c2ccccc2OC)CC1] | 13.288 |
| 112 | 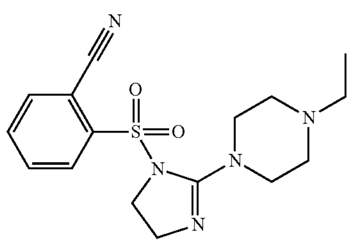 [SMILES: CCN1CCN(C2=NCCN2S(=O)(=O)c2ccccc2C#N)CC1] | 9.813 |
| 113 | 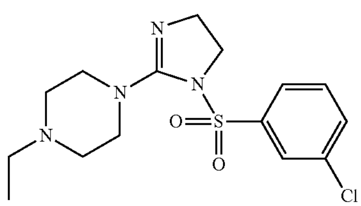 [SMILES: CCN1CCN(C2=NCCN2S(=O)(=O)c2cccc(Cl)c2)CC1] | 9.064 |
| 114 | 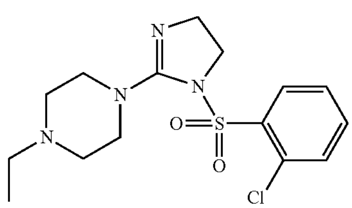 [SMILES: CCN1CCN(C2=NCCN2S(=O)(=O)c2ccccc2Cl)CC1] | 2.805 |
| 115 | 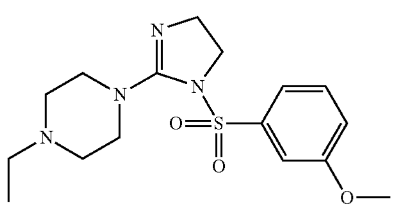 [SMILES: CCN1CCN(C2=NCCN2S(=O)(=O)c2cccc(OC)c2)CC1] | 3.573 |
| 116 | 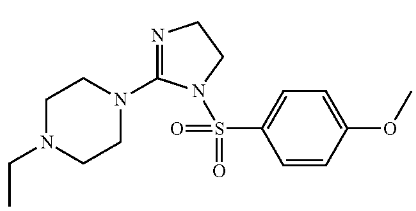 [SMILES: CCN1CCN(C2=NCCN2S(=O)(=O)c2ccc(OC)cc2)CC1] | 5.453 |

TABLE-continued

| Ex | Structure | KDM2B HTRF IC$_{50}$ (nM) |
|---|---|---|
| 117 | 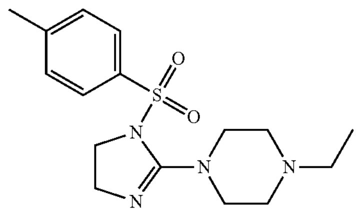 [SMILES: CCN1CCN(C2=NCCN2S(=O)(=O)c2ccc(C)cc2)CC1] | 3.758 |
| 118 | 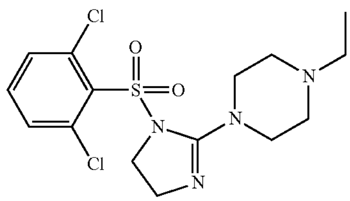 [SMILES: CCN1CCN(C2=NCCN2S(=O)(=O)c2c(Cl)cccc2Cl)CC1] | 1.023 |
| 119 | 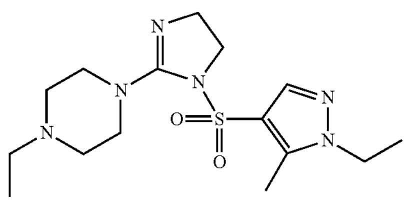 [SMILES: CCN1CCN(C2=NCCN2S(=O)(=O)c2cnn(CC)c2C)CC1] | 11.405 |
| 120 | 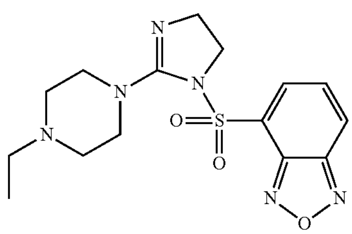 [SMILES: CCN1CCN(C2=NCCN2S(=O)(=O)c2cccc3nonc23)CC1] | 13.314 |

While a number of embodiments have been described, these examples may be altered to provide other embodiments that utilize the compounds and methods described herein. Therefore, the scope of this invention is to be defined by the appended claims rather than by the specific embodiments that have been represented by way of example.

We claim:

1. A compound of formula (I):

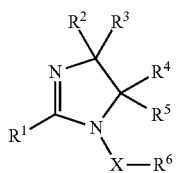

or a salt thereof, wherein:

X is C(=O) or S(O)$_2$;

R$^1$ is selected from the group consisting of N-linked piperazinyl, N-linked piperidine, and N-linked diazabicyclo[3.2.1]octane, wherein R$^1$ is optionally substituted with one or more groups independently selected from C$_{1-6}$alkyl, C$_{2-6}$alkenyl, C$_{2-6}$alkynyl, aryl, 3-10 membered monocyclic or bicyclic staturated or partially unsaturated heterocycle having one to four heteroatoms selected from oxygen, sulfur, nitrogen phosphorous, and silicon wherein the heteroatoms may be oxidized, and C$_{3-8}$cycloalkyl, wherein any aryl, 3-10 membered monocyclic or bicyclic staturated or partially unsaturated heterocycle, and C$_{3-8}$cycloalkyl is optionally substituted with one or more groups independently selected from halo, C$_{1-4}$alkyl, C$_{2-4}$alkenyl, and C$_{2-4}$alkynyl, and wherein any C$_{1-6}$alkyl, C$_{2-6}$alkenyl, and C$_{2-6}$alkynyl is optionally substituted with one or more groups independently selected from halo, C$_{1-4}$alkoxy, and C$_{3-8}$cycloalkyl that is optionally substituted with C$_{1-6}$alkyl;

R$^2$ and R$^3$ are each independently selected from H, C$_{1-6}$alkyl, C$_{2-6}$alkenyl, C$_{2-6}$alkynyl, and C$_{3-8}$cycloalkyl, wherein any C$_{1-6}$alkyl, C$_{2-6}$alkenyl, C$_{2-6}$alkynyl, and C$_{3-8}$cycloalkyl is optionally substituted with one or more groups independently selected from halo and oxo; or R$^2$ and R$^3$ taken together with the carbon to which they are attached form a 3-, 4-, 5-, or 6-membered monocyclic saturated or partially unsaturated carbocyclic ring that is optionally substituted with one or more groups independently selected from halo, oxo, C$_{1-4}$alkyl, C$_{2-4}$alkenyl, and C$_{2-4}$alkynyl;

R$^4$ and R$^5$ are each independently selected from H, C$_{1-6}$alkyl, C$_{2-6}$alkenyl, C$_{2-6}$alkynyl, and C$_{3-8}$cycloalkyl, wherein any $C_{1-6}$alkyl, $C_{2-6}$alkenyl, $C_{2-6}$alkynyl, and $C_{3-8}$cycloalkyl is optionally substituted with one or more groups independently selected from halo and oxo; or $R_4$ and $R^5$ taken together with the carbon to which they are attached form a 3-, 4-, 5-, or 6-membered monocyclic saturated or partially unsaturated carbocyclic ring that is optionally substituted with one or more groups independently selected from halo, oxo, $C_{1-4}$alkyl, $C_{2-4}$alkenyl, and $C_{2-4}$alkynyl;

$R^6$ is a 5-10 membered monocyclic or bicyclic heteroaryl having one to five heteroatoms selected from the group consisting of nitrogen, oxygen, and sulfur, wherein the heteroatoms may be oxidized, 5-10 membered monocyclic or bicyclic heterocycle having one to four heteroatoms selected from oxygen, sulfur, nitrogen phosphorous, and silicon wherein the heteroatoms may be oxidized, or a 6-10 membered aryl, which 5-10 membered monocyclic or bicyclic heteroaryl, 5-10 membered monocyclic or bicyclic heterocycle, and 6-10 membered aryl is optionally substituted with one or more groups independently selected from the group consisting of $C_{1-6}$alkyl, $C_{2-6}$alkenyl, $C_{2-6}$alkynyl, 3-10 membered saturated or partially unsaturated monocyclic or bicyclic carbocycle, 3-8 membered monocyclic saturated or partially unsaturated heterocycle having one to four heteroatoms selected from oxygen, sulfur, nitrogen phosphorous, and silicon wherein the heteroatoms may be oxidized, aryl, 5-10 membered monocyclic or bicyclic heteroaryl having one to five heteroatoms selected from the group consisting of nitrogen, oxygen, and sulfur, wherein the heteroatoms may be oxidized, halo, $-NO_2$, $-N(R^b)_2$, $-CN$, $-C(O)-N(R^b)_2$, $-S(O)-N(R^b)_2$, $-S(O)_2-N(R^b)_2$, $-O-R^b$, $-S-R^b$, $-O-C(O)-R^b$, $-C(O)-R^b$, $-S(O)-R^b$, $-S(O)_2-R^b$, $-N(R^b)-C(O)-R^b$, $-N(R^b)-S(O)-R^b$, $-N(R^b)-C(O)-N(R^b)_2$, and $-N(R^b)-S(O)_2-R^b$; wherein each $C_{1-6}$alkyl, $C_{2-6}$alkenyl, $C_{2-6}$alkynyl, 3-10 membered saturated or partially unsaturated monocyclic or bicyclic carbocycle, 3-8 membered monocyclic saturated or partially unsaturated heterocycle, aryl, and 5-10 membered monocyclic or bicyclic heteroaryl is optionally substituted with one or more groups independently selected from the group consisting of halo, $-NO_2-N(R^b)_2$, $-CN$, $-C(O)-N(R^b)_2$, $-S(O)-N(R^b)_2$, $-S(O)_2-N(R^b)_2$, $-O-R^b$, $-S-R^b$, $-O-C(O)-R^b$, $-C(O)-R^b$, $-C(O)-OR^b$, $-S(O)-R^b$, $-S(O)_2-R^b$, $-N(R^b)-C(O)-R^b$, $-N(R^b)-S(O)-R^b$, $-N(R^b)-C(O)-N(R^b)_2$, $-N(R^b)-S(O)_2-R^b$, and $C_{1-6}$alkyl that is optionally substituted with one or more groups independently selected from halo;

each $R^b$ is independently selected from the group consisting of hydrogen, $C_{1-6}$alkyl, $C_{2-6}$alkenyl, aryl, and $C_{2-6}$alkynyl, wherein each $C_{1-6}$alkyl, $C_{2-6}$alkenyl, aryl, and $C_{2-6}$alkynyl is optionally substituted with one or more groups independently selected from the group consisting of halo, $-N(R^c)_2$, $-CN$, $-C(O)-N(R^c)_2$, $-S(O)-N(R^c)_2$, $-S(O)_2-N(R^c)_2$, $-O-R^c$, $-S-R^c$, $-O-C(O)-R^c$, $-C(O)-R^c$, $-C(O)-OR^c$, $-S(O)-R^c$, $-S(O)_2-R^c$, $-N(R^c)-C(O)-R^c$, $-N(R^c)-S(O)-R^c$, $-N(R^c)-C(O)-N(R^c)_2$, and $-N(R^c)-S(O)_2-R^c$; or two $R^b$ are taken together with the nitrogen to which they are attached to form a pyrrolidino, piperidino, or piperazino ring; and each $R^c$ is independently selected from the group consisting of hydrogen, $C_{1-6}$alkyl, $C_{2-6}$alkenyl, and $C_{2-6}$alkynyl, wherein each $C_{1-6}$alkyl, $C_{2-6}$alkenyl, and $C_{2-6}$alkynyl is optionally substituted with one or more groups independently selected from the group consisting of oxo, halo, amino, hydroxy, and $C_{1-6}$alkoxy; or two $R^c$ are taken together with the nitrogen to which they are attached to form a 3-8 membered monocyclic saturated or partially unsaturated heterocyclyl having one to four heteroatoms selected from oxygen, sulfur, nitrogen phosphorous, and silicon wherein the heteroatoms may be oxidized that is optionally substituted with one or more groups independently selected from the group consisting of oxo, halo and $C_{1-3}$alkyl that is optionally substituted with one or more groups independently selected from the group consisting of oxo and halo;

provided that when:

X is $S(O)_2$;

$R^1$ is an optionally substituted piperazin-1-yl; and $R^2$—$R^5$ are each H;

then $R^6$ is not: 2,5-dimethoxyphenyl, 3,4-dimethylphenyl, 4-ethylphenyl, 4-bromophenyl, 2,4-dimethylphenyl, 4-ethoxyphenyl, 4-chloro-2-methoxyphenyl, 4-propylphenyl, 2-(trifluoromethyl)phenyl, 2,4,5-trimethylphenyl, 3-methylphenyl, 2-(methylcarbonylamino)-5-methylphenyl, 4-chlorophenyl, 4-(i sopropyl)phenyl, 3-chloro-4-fluorophenyl, 4-cyclohexylphenyl, 4-(isobutyl)phenyl, 2-methylphenyl, 4-acetylphenyl, 4-(tert-butyl)phenyl, 4-(methylcarbonylamino) phenyl, 2-fluorophenyl, phenyl, 3,5-dimethylphenyl, 4- methylphenyl, 5-fluoro-2-methylphenyl, 4-fluorophenyl, 5,6,7,8-tetrahydronaphthlene-2-yl, 2,4,6-trimethylphenyl, 3-chloro-4-fluorophenyl, 4-(ethoxycarbonylamino)phenyl, 2,5-difluorophenyl, 2-chlorophenyl, 3-chlorophenyl, 4-methoxyphenyl, or 2-methoxy-4-chlorophenyl and provided that when:

X is C(=O);

$R^1$ is an optionally substituted piperazin-1-yl; and $R^2$—$R^5$ are each H;

then $R^6$ is not: 2-methoxyphenyl, 2-methylphenyl, 2-chlorophenyl, 4-ethylphenyl, 3,5-dimethylphenyl, 2,3-dimethoxyphenyl, 4-methylphenyl, 4-ethoxyphenyl, 3,4-dimethylphenyl, 2,3-benzodioxazol-5-yl, 3-chlorophenyl, 3-methylphenyl, 4-methoxyphenyl, 3,5-dimethoxyphenyl, 2-fluorophenyl, 4-fluorophenyl, 3-fluoro-4-methylphenyl, 2,3-dimethoxyphenyl, 4-(tert-butyl)phenyl, 3,4,5-trimethoxyphenyl, 2-bromophenyl, 4-chlorophenyl, 2-trifluoromethylphenyl, phenyl, 4-bromophenyl, 3,4-difluorophenyl, 2,6-difluorophenyl, 2-(dimethylamino)phenyl, 4-ethoxyphenyl, 3-fluoro-4-methylphenyl, 2,4-dimethylphenyl, 4-(trifluoromethyl)phenyl, 4-(dimethylamino)phenyl, 3-methoxyphenyl, 2-methoxy-4-chloro, or 3-(dimethylamino)phenyl.

2. The compound of claim 1 which is a compound of formula (Ia):

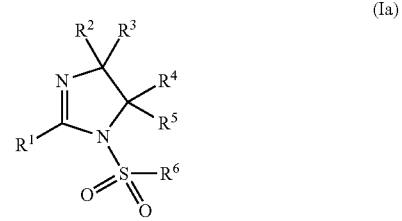

or a salt thereof.

3. The compound of claim 2 wherein:
R² and R³ are each H or wherein R² and R³ taken together with the carbon to which they are attached form a 5-membered saturated or partially unsaturated carbocyclic ring ; and
R⁴ and R⁵ are each H.

4. The compound of claim 2 provided that:
when R⁶ is an optionally substituted phenyl or has the formula:

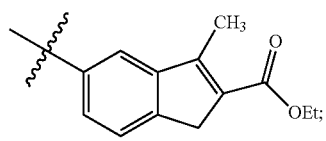 [SMILES: *c1ccc2c(c1)C(C)=C(C(=O)OCC)C2]

and
R²-R⁵ are each H;
then R¹ is not piperazin-1-yl that is substituted at the 4-position with a group selected from the group consisting of, methyl, ethyl, 3-chlorophenyl, 4-fluorophenyl, 2-chlorophenyl, 2-fluorophenyl, 4-methoxyphenyl, and 2-methoxyphenyl.

5. The compound of claim 1 which is a compound of formula (Ib):

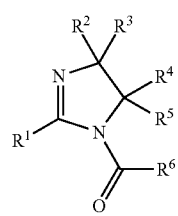

(Ib)

or a salt thereof.

6. The compound of claim 5 wherein:
R² and R³ are each H or wherein R² and R³ taken together with the carbon to which they are attached form a 5-membered saturated or partially unsaturated carbocyclic ring; and
R⁴ and R⁵ are each H.

7. The compound of claim 5 provided that:
when R⁶ is an optionally substituted phenyl or 2,3-benzodioxazol-5-yl; and
R²-R⁵ are each H;
then R¹ is not piperazin-1-yl that is substituted at the 4-position with a group selected from the group consisting of methyl, ethyl, 3-chlorophenyl, 2-fluorophenyl, 3-chlorophenyl, and 4-fluorophenyl.

8. The compound of claim 1 wherein R¹ is selected from the group consisting of N-linked piperazinyl, N-linked piperidine, and N-linked diazabicyclo[3.2.1]octane, wherein R¹ is optionally substituted with one or more groups independently selected from $C_{1-6}$alkyl, aryl, and $C_{3-8}$cycloalkyl, wherein any aryl and $C_{3-8}$cycloalkyl is optionally substituted with one or more groups independently selected from halo and $C_{1-4}$alkyl, and wherein any $C_{1-6}$alkyl is optionally substituted with one or more groups independently selected from halo, $C_{1-4}$alkoxy, and $C_{3-8}$cycloalkyl.

9. The compound of claim 1 wherein R¹ is selected from the group consisting of:

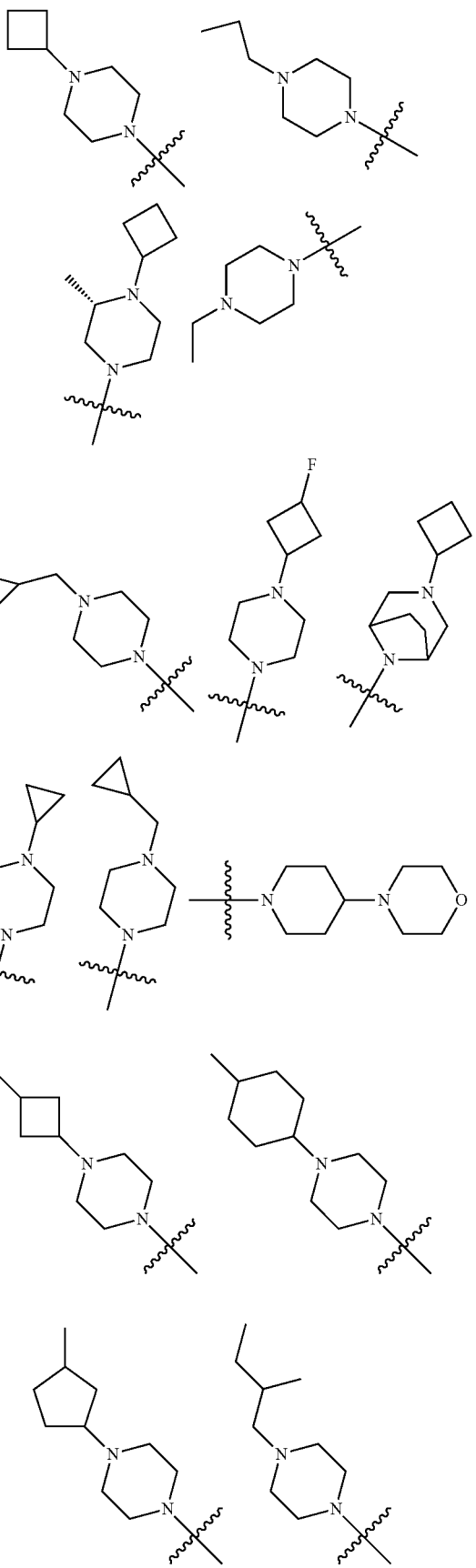

-continued

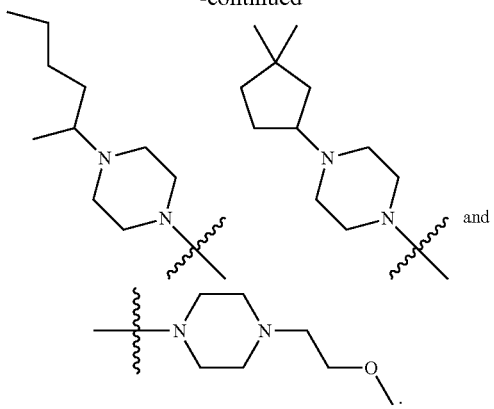

10. The compound of claim 1 wherein $R^6$ is a 6-10 membered aryl that is optionally substituted with one or more groups independently selected from the group consisting of $C_{1-6}$alkyl, $C_2$alkenyl, $C_{2-6}$alkynyl, 3-10 membered saturated or partially unsaturated monocyclic or bicyclic carbocycle, 3-8 membered monocyclic saturated or partially unsaturated heterocycle having one to four heteroatoms selected from oxygen, sulfur, nitrogen phosphorous, and silicon wherein the heteroatoms may be oxidized, aryl, 5-10 membered monocyclic or bicyclic heteroaryl having one to five heteroatoms selected from the group consisting of nitrogen, oxygen, and sulfur, wherein the heteroatoms may be oxidized, halo, —NO$_2$, —N(R$^b$)$_2$, —CN, —C(O)—N(R$^b$)$_2$, —S(O)—N(R$^b$)$_2$, —S(O)$_2$—N(R$^b$)$_2$, —O—R$^b$, —S—R$^b$, —O—C(O)—R$^b$, —C(O)—R$^b$, —C(O)—OR$^b$, —S(O)—R$^b$, —S(O)$_2$—R$^b$, —N(R$^b$)—C(O)—R$^b$, —N(R$^b$)—S(O)—R$^b$, —N(R$^b$)—C(O)—N(R$^b$)$_2$ and —N(R$^b$)—S(O)$_2$—R$^b$; wherein each $C_{1-6}$alkyl, $C_{2-6}$alkenyl, $C_{2-6}$alkynyl, -10 membered saturated or partially unsaturated monocyclic or bicyclic carbocycle, 3-8 membered monocyclic saturated or partially unsaturated heterocycle, aryl, and 5-10 membered monocyclic or bicyclic heteroaryl is optionally substituted with one or more groups independently selected from the group consisting of halo, —NO$_2$, —N(R$^b$)$_2$, —CN, —C(O)—N(R$^b$)$_2$, —S(O)—N(R$^b$)$_2$, —S(O)$_2$—N(R$^b$)$_2$, —O—R$^b$, —S—R$^b$, —O—C(O)—R$^b$, —C(O)—R$^b$, —C(O)—OR$^b$, —S(O)—R$^b$, —S(O)$_2$—R$^b$, —N(R$^b$)—C(O)—R$^b$,—N (R$^b$)—S(O)—R$^b$, —N(R$^b$)—C(O)—N(R$^b$)$_2$, —N(R$^b$)—S(O)$_2$—R$^b$, and $C_{1-6}$alkyl that is optionally substituted with one or more groups independently selected from halo.

11. The compound of claim 1 wherein $R^6$ is phenyl that is substituted with phenyl that is optionally substituted with one or more groups independently selected from the group consisting of $C_{1-6}$alkyl, 3-10 membered saturated or partially unsaturated monocyclic or bicyclic carbocycle, halo, —CN, —C(O)—N(R$^b$)$_2$, —O—R$^b$, —S(O)$_2$—R$^b$ and —N(R$^b$)—C(O)—R$^b$ wherein each $C_{1-6}$alkyl and 3-10 membered saturated or partially unsaturated monocyclic or bicyclic carbocycle is optionally substituted with one or more groups independently selected from the group consisting of halo.

12. The compound of claim 1 wherein $R^6$ is phenyl that is optionally substituted with one or more groups independently selected from the group consisting of $C_{1-6}$alkyl, 3-10 membered saturated or partially unsaturated monocyclic or bicyclic carbocycle, halo, —CN, —C(O)—N(R$^b$)$_2$, —O—R$^b$, —S(O)$_2$—R$^b$, —N(R$^b$)—C(O)—R$^b$, and —N(R$^b$)—C(O)—N(R$^b$)$_2$, wherein each $C_{1-6}$alkyl and 3-10 membered saturated or partially unsaturated monocyclic or bicyclic carbocycle is optionally substituted with one or more groups independently selected from the group consisting of halo.

13. The compound of claim 1 wherein $R^6$ is selected from the group consisting of:

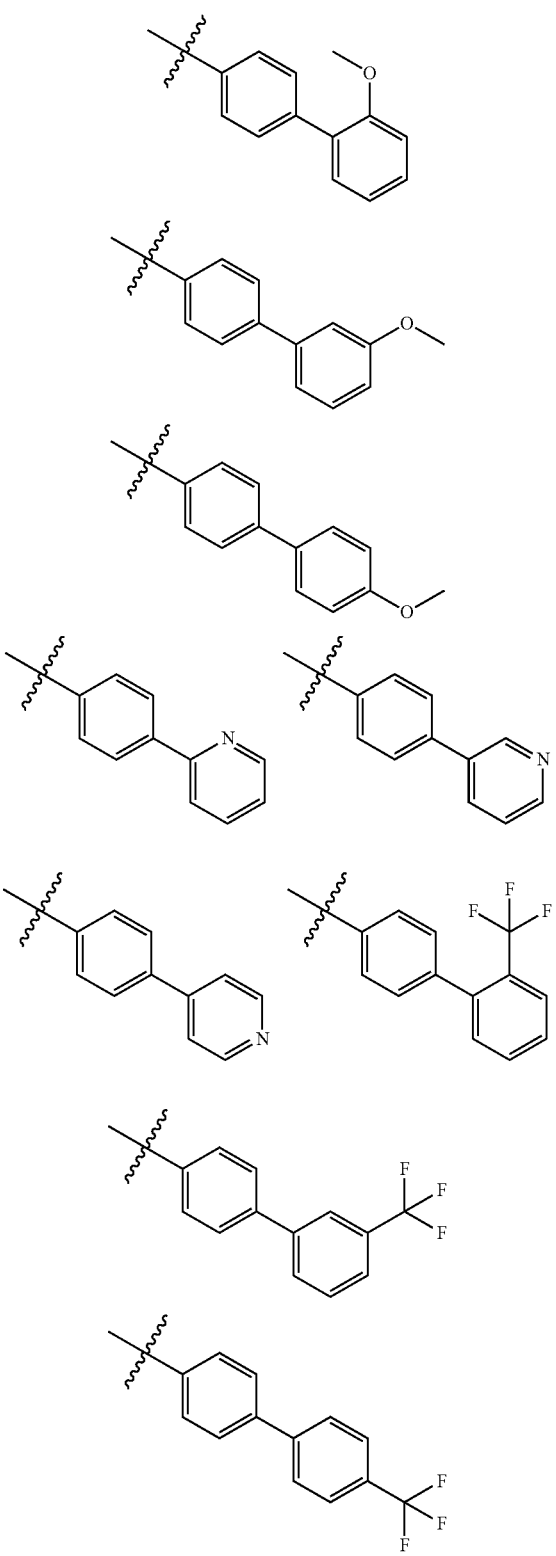

-continued
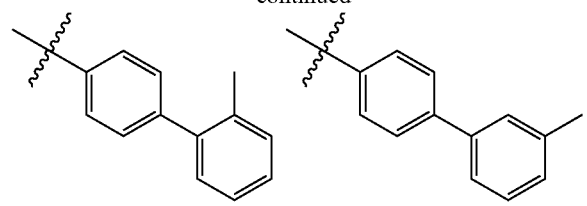
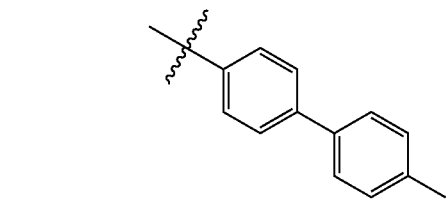
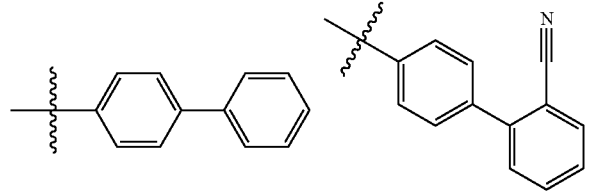
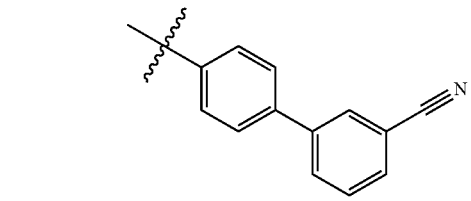
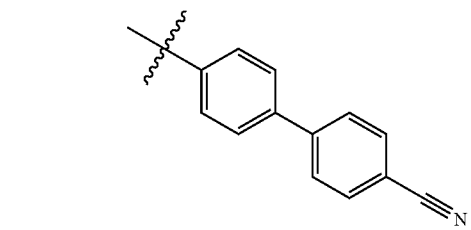
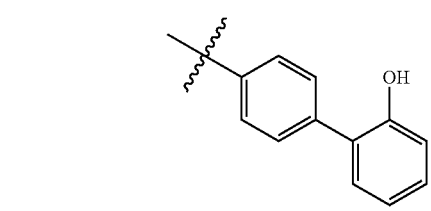
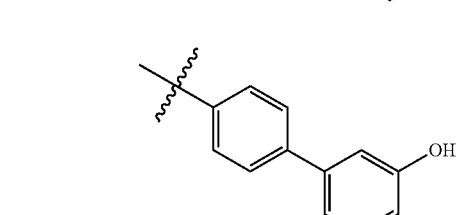
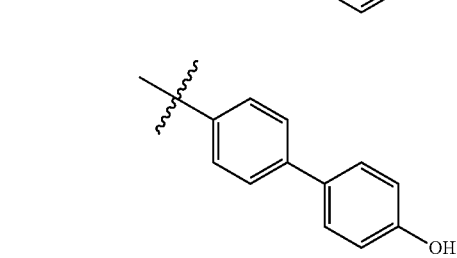
-continued
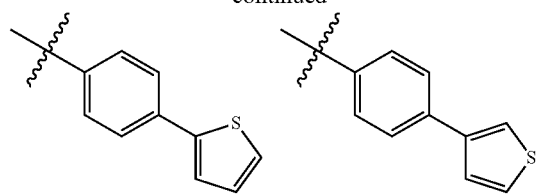
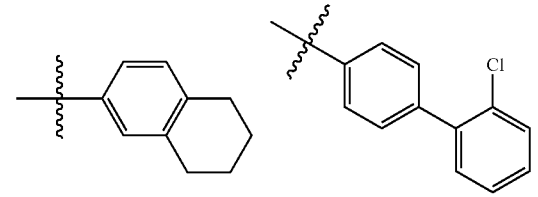
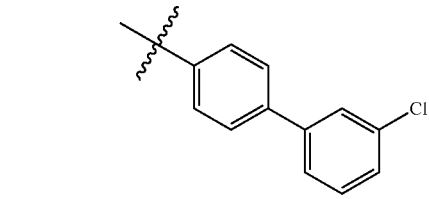
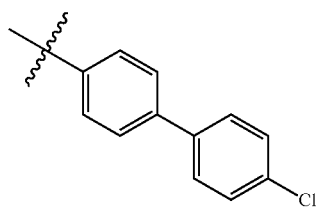
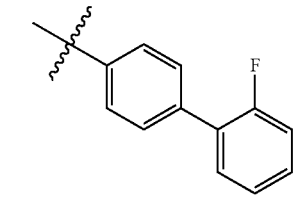
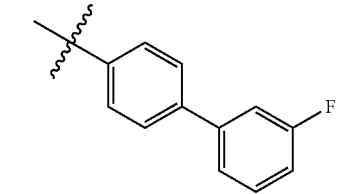
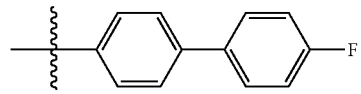
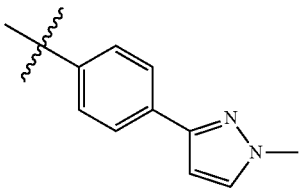
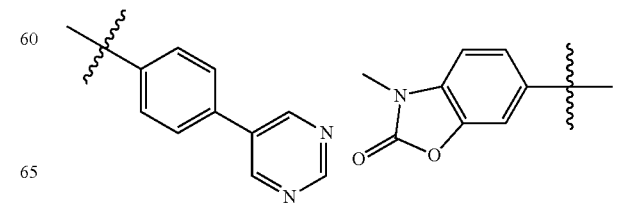

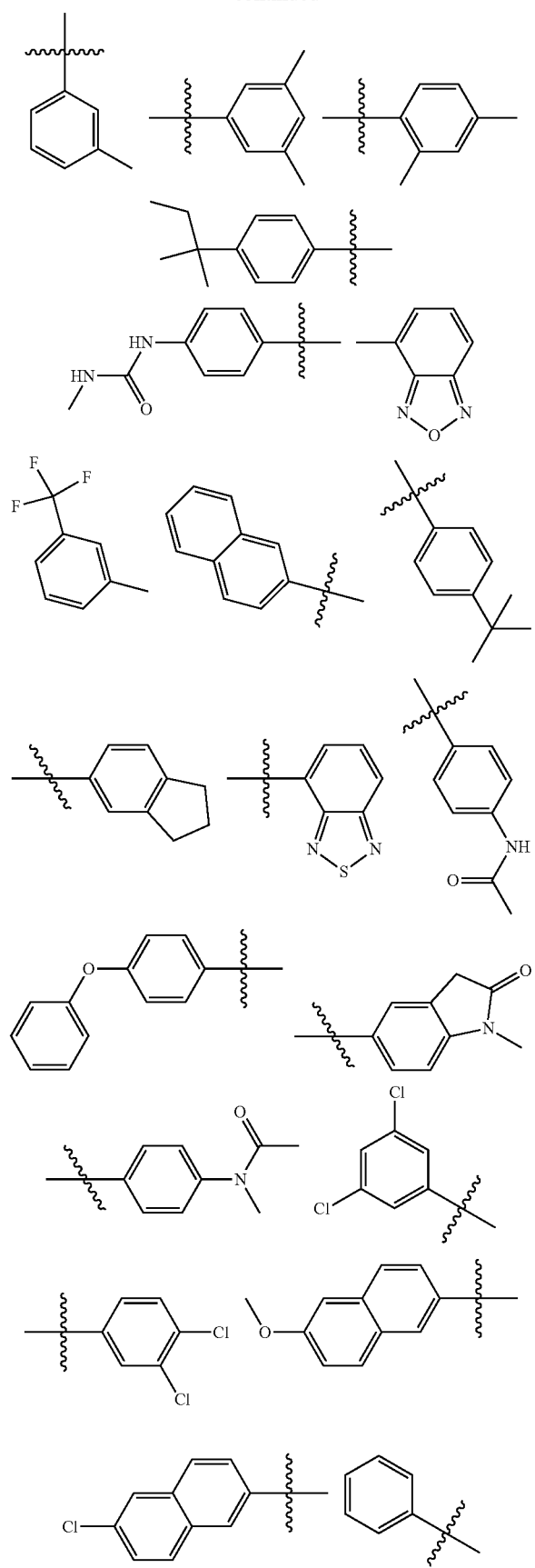
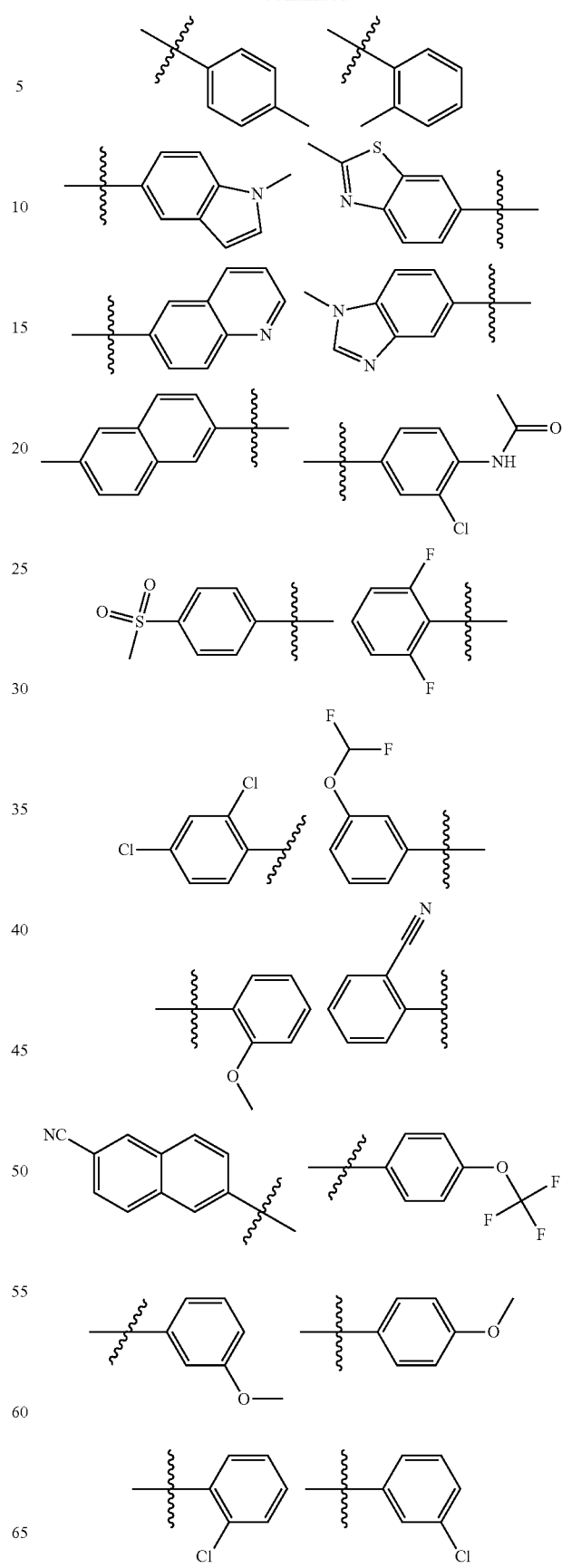

191
-continued
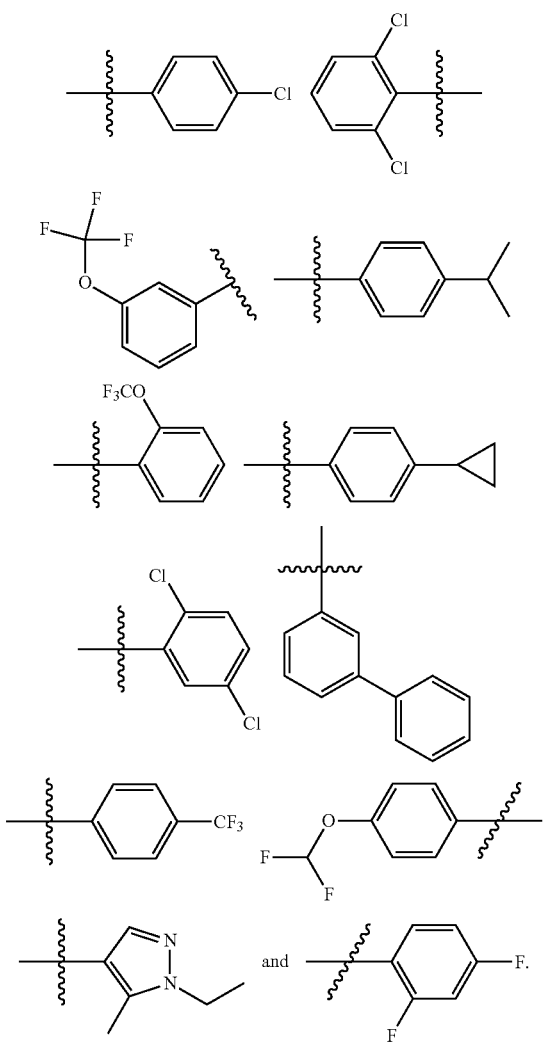
14. The compound of claim 1 wherein $R^6$ is selected from the group consisting of:
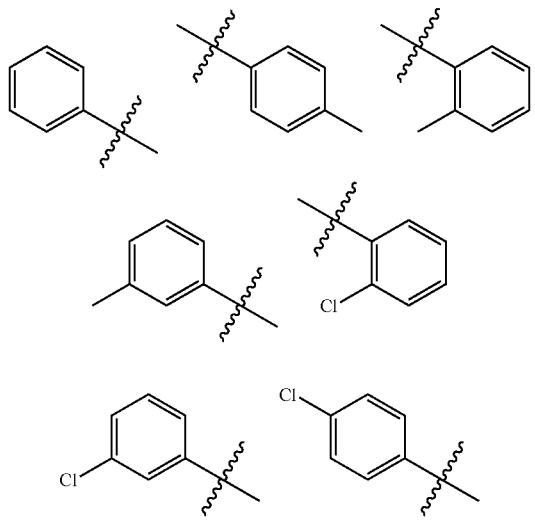
192
-continued
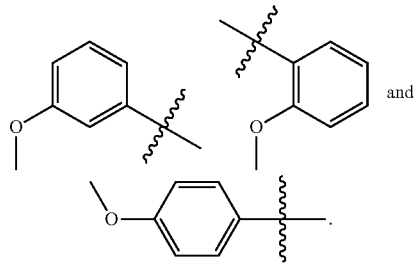
15. The compound of claim 1 which is selected from:
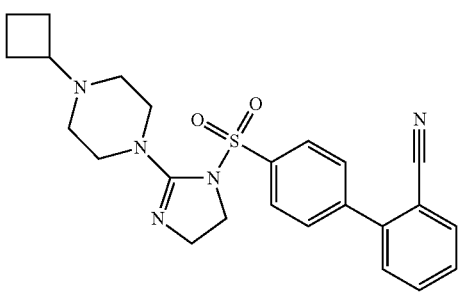
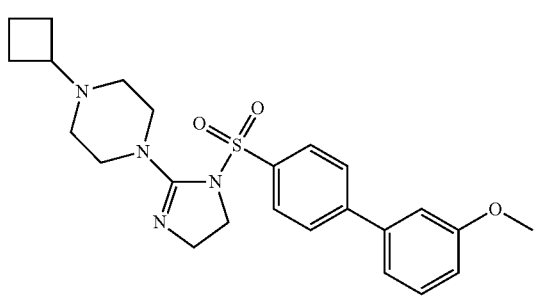
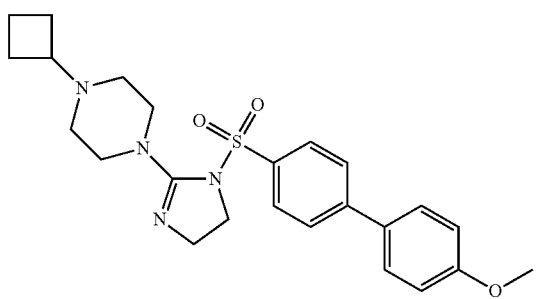
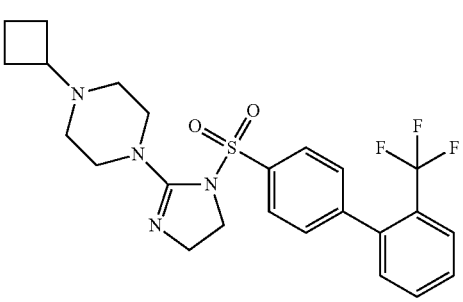

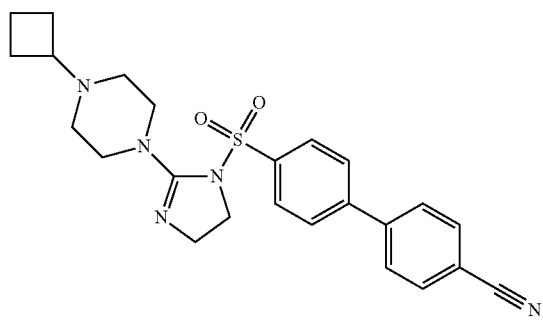
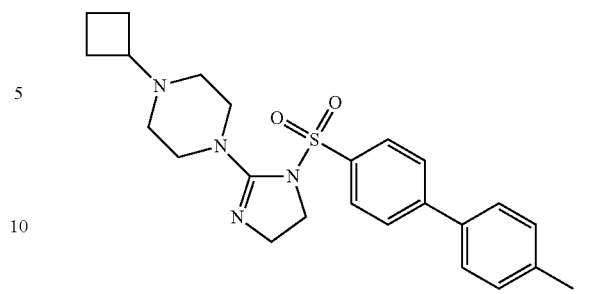
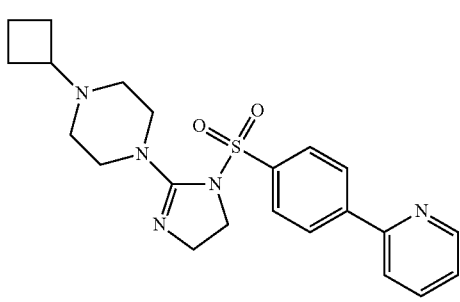
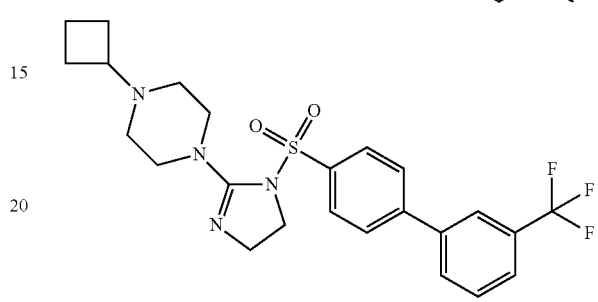
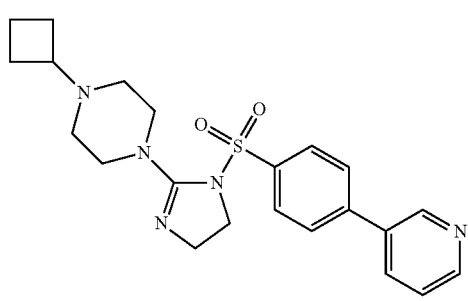
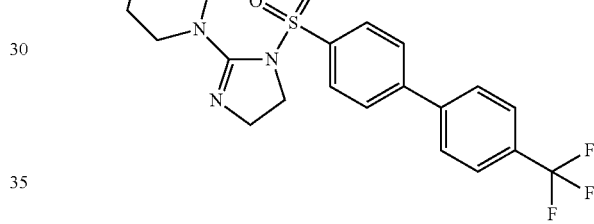
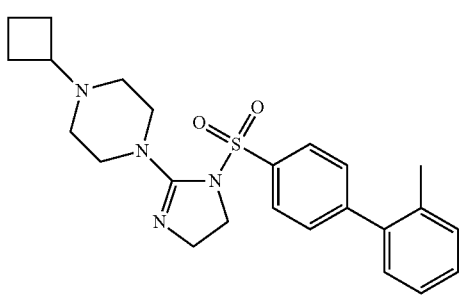
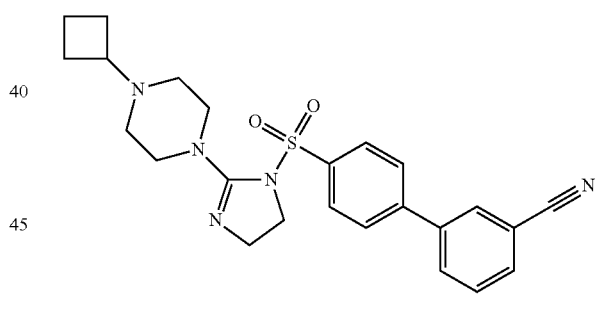
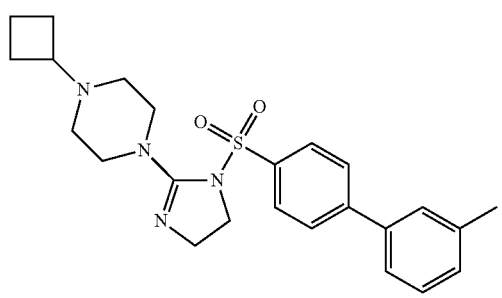
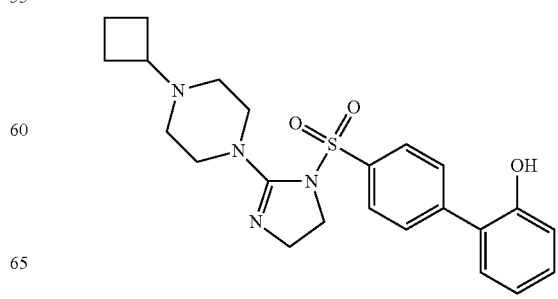

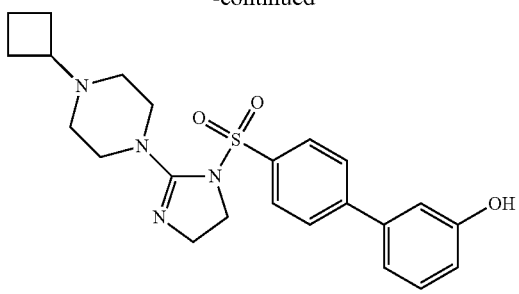
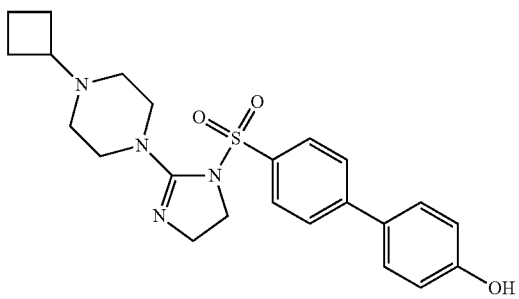
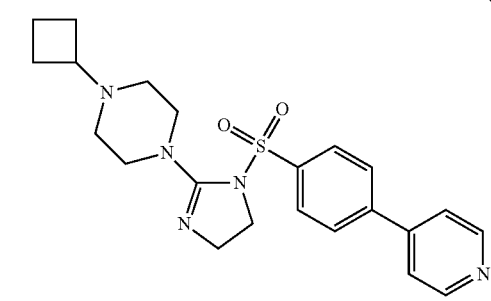
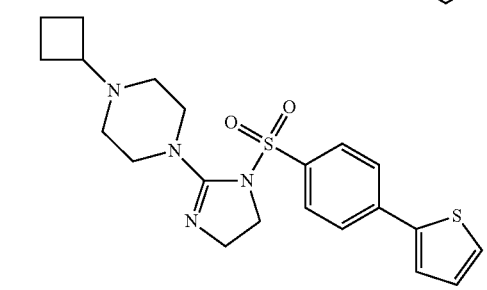
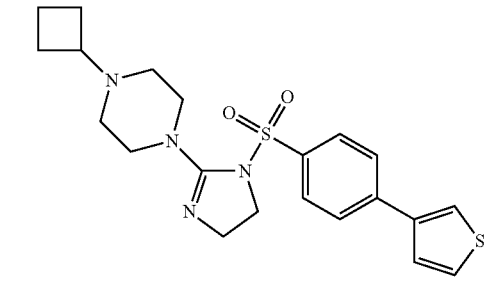
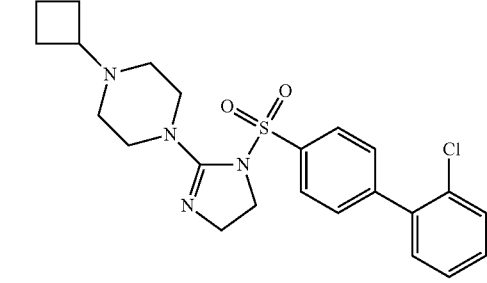
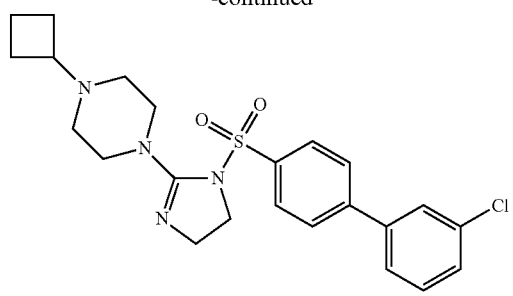
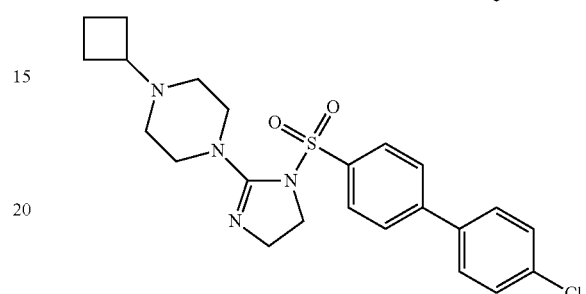
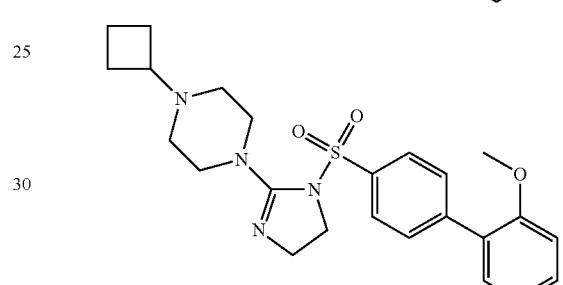
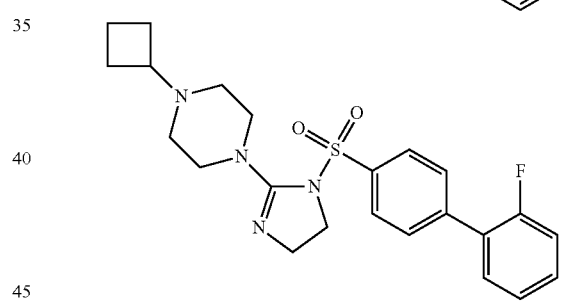
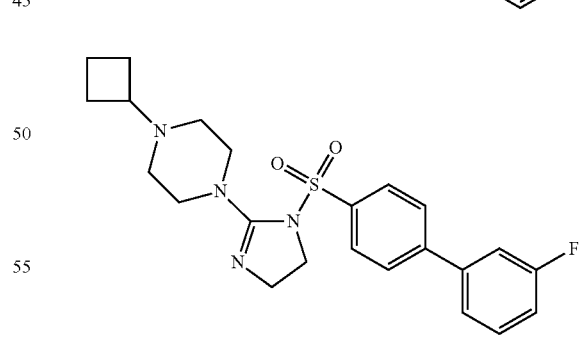
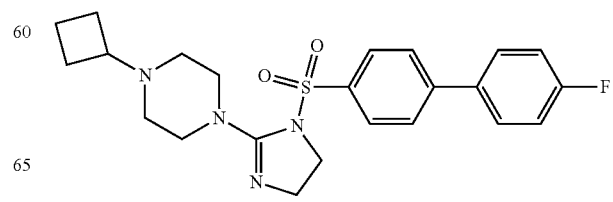

197
-continued
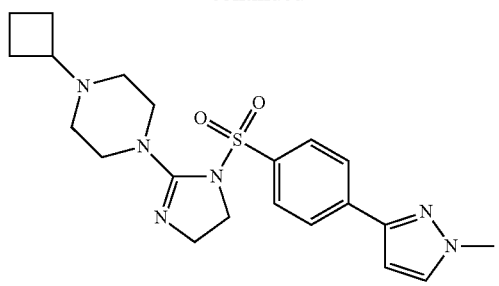
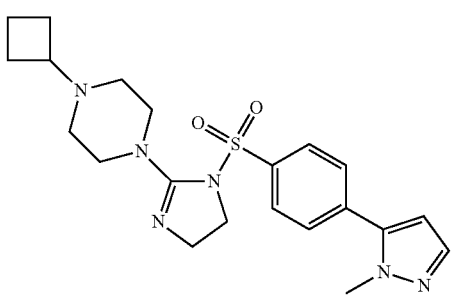
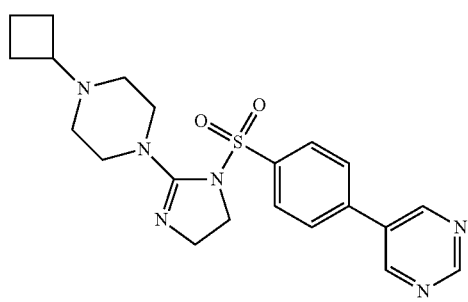
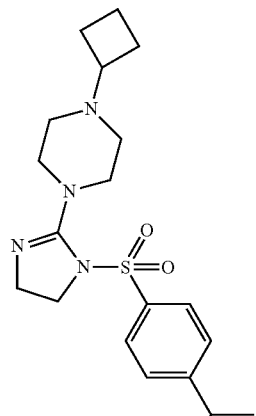
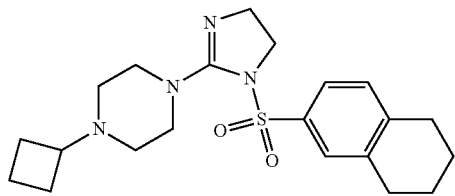
198
-continued
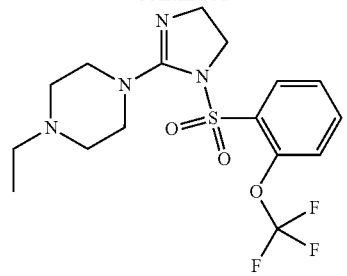
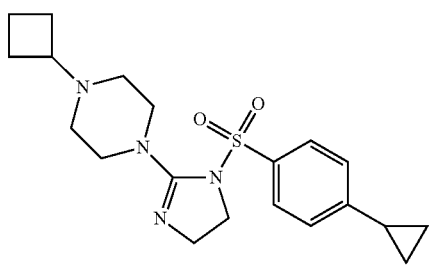
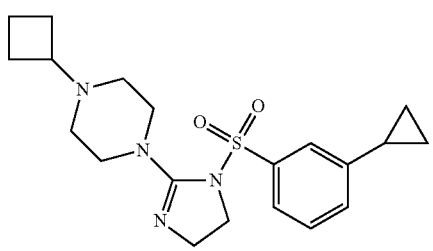
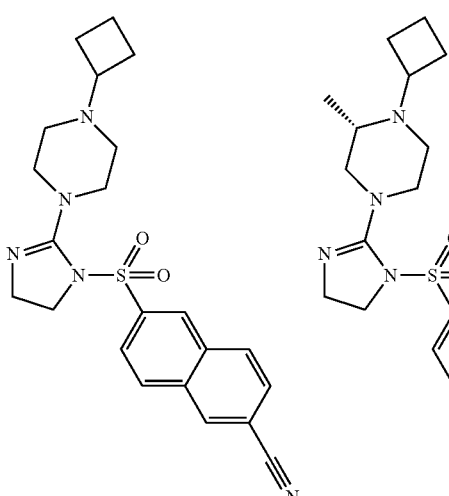
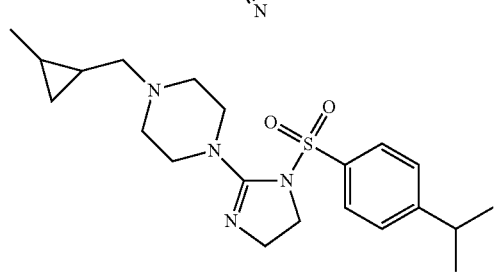

199
-continued
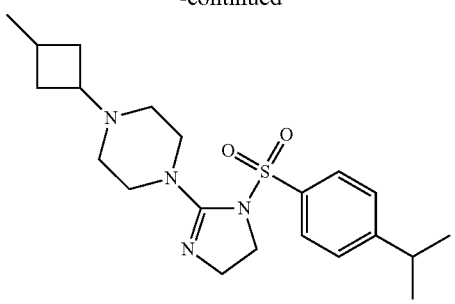
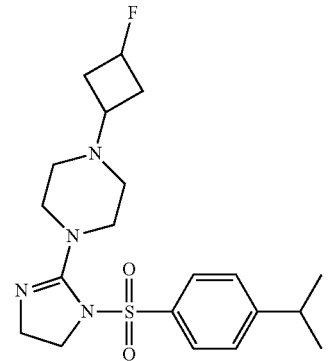
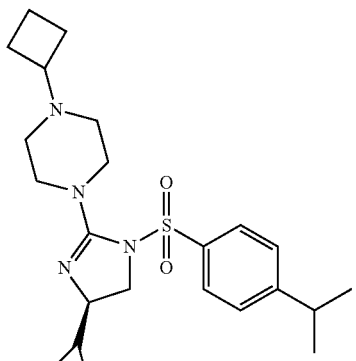
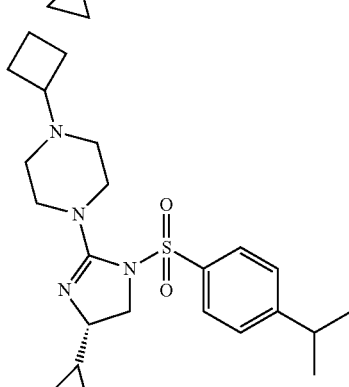
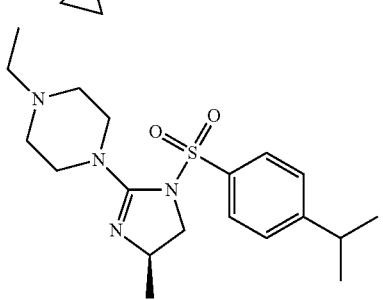
200
-continued
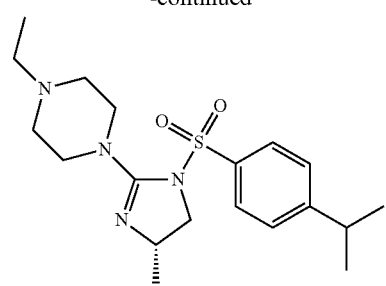
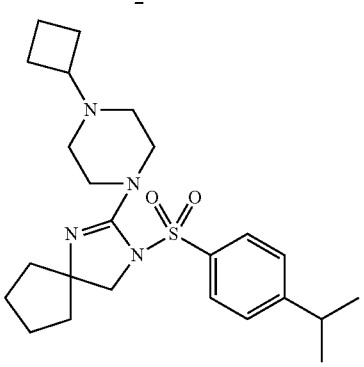
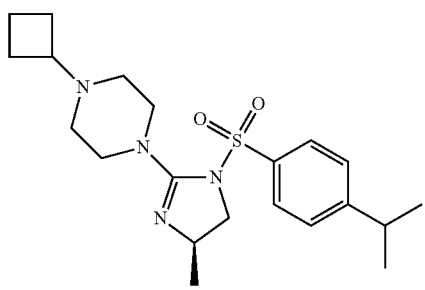
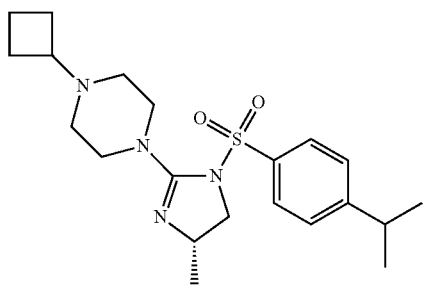
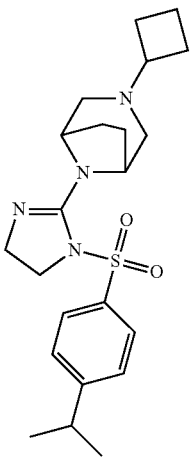

-continued
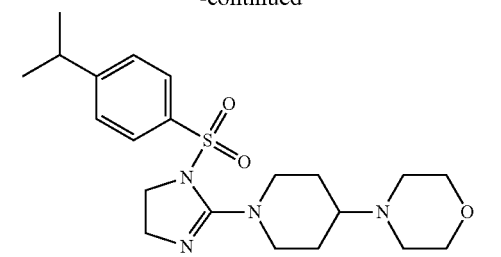
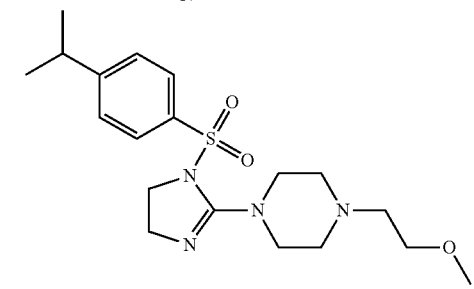
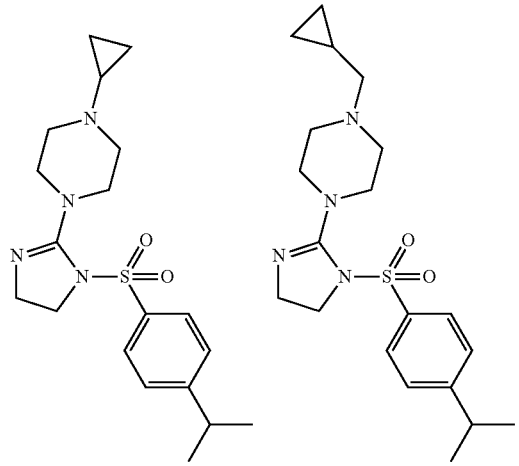
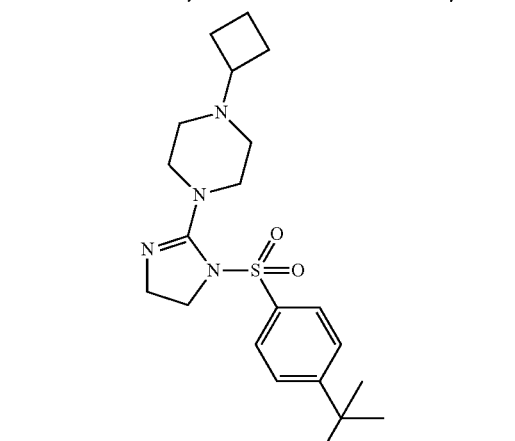
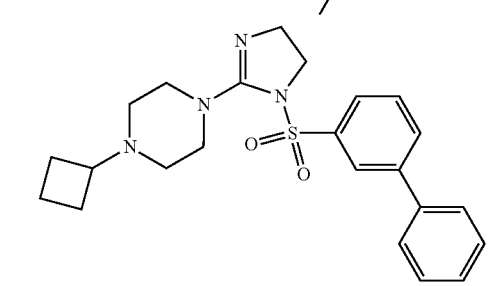
-continued
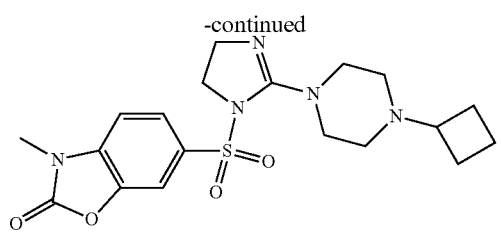
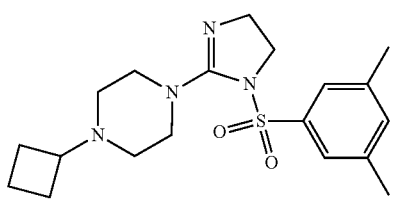
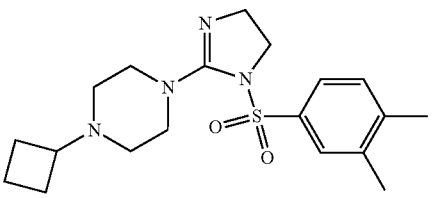
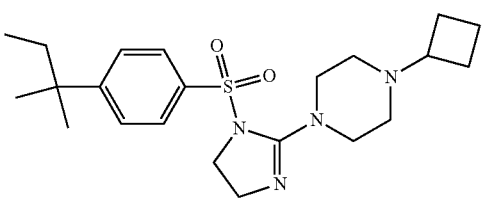
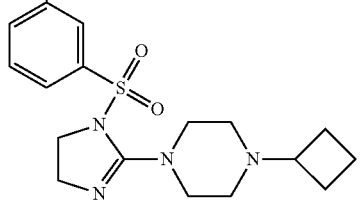
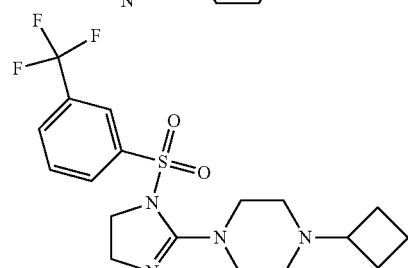
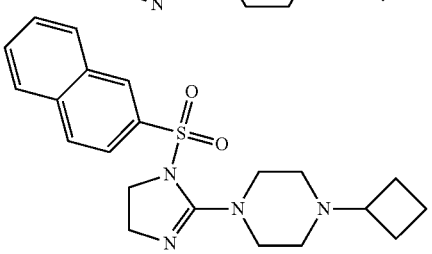

203
-continued
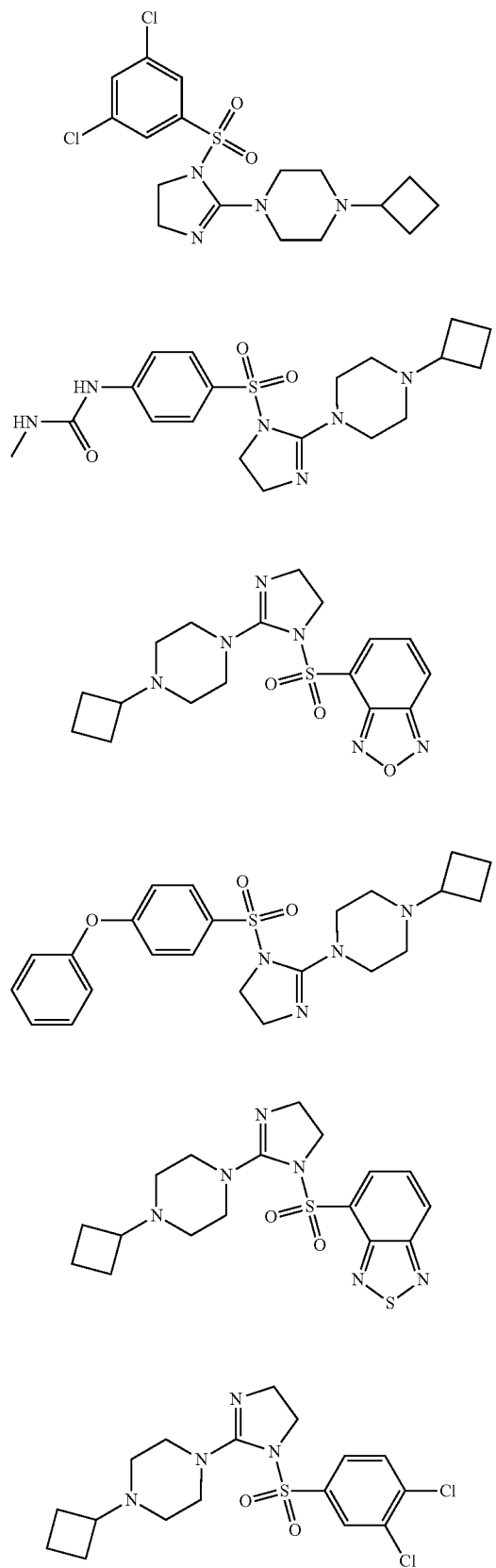
204
-continued
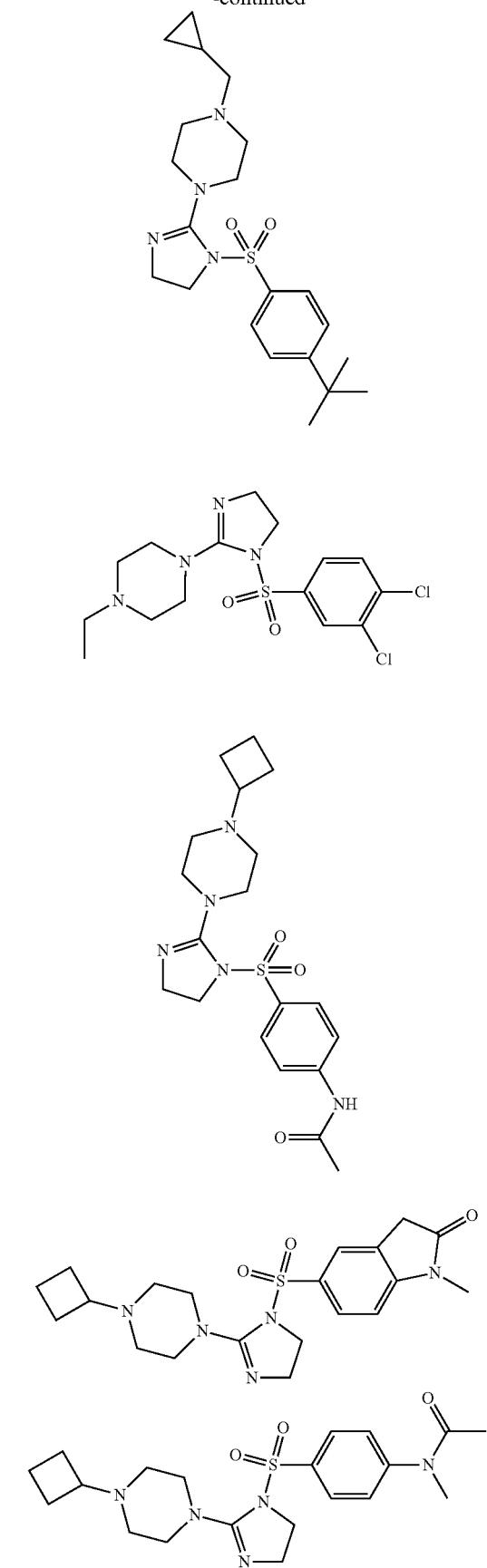

205
-continued
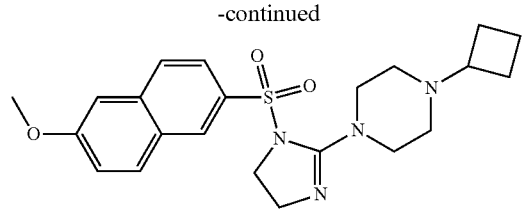
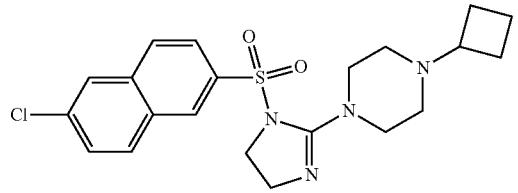
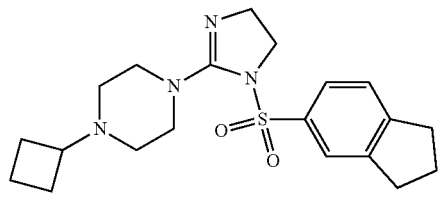
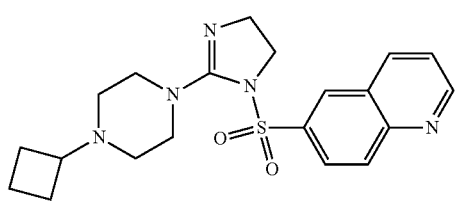
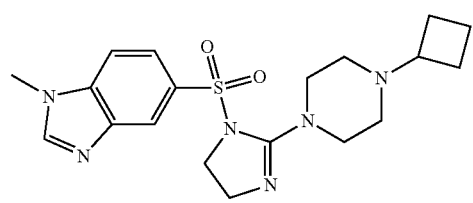
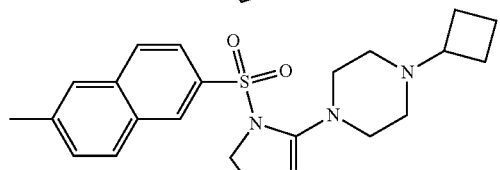
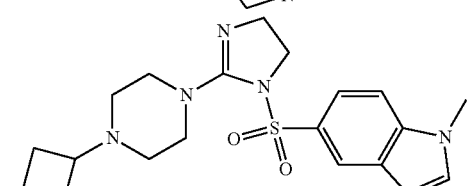
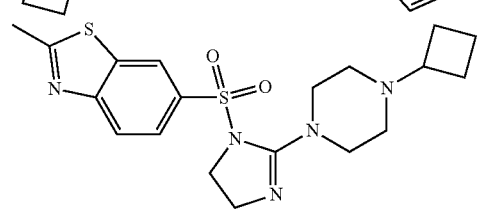
206
-continued
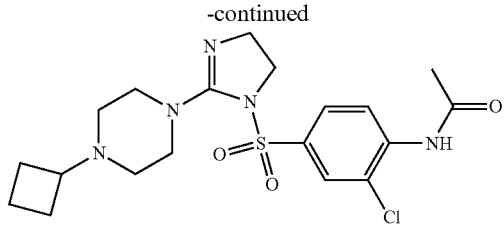
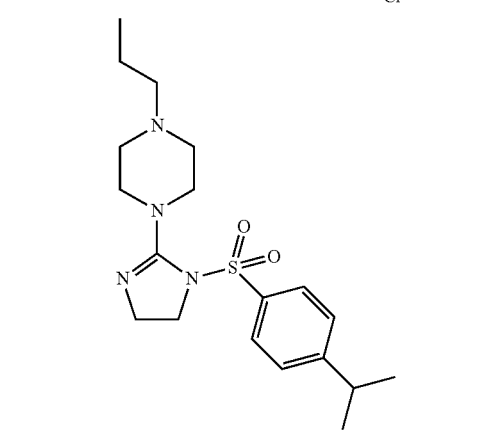
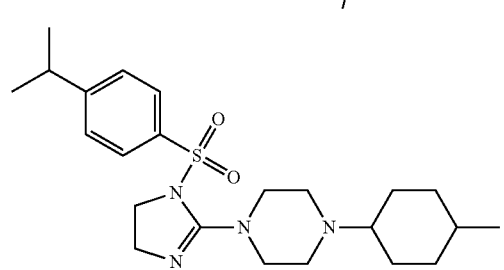
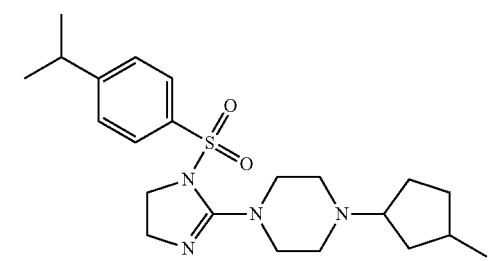
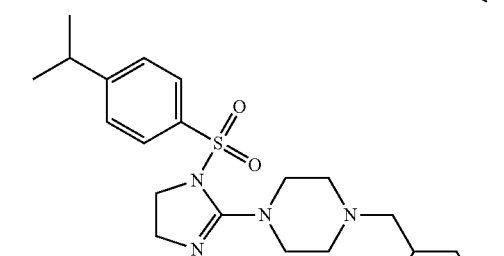
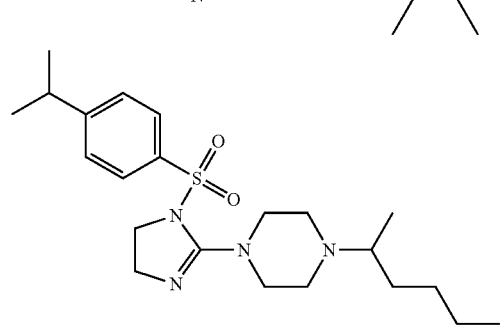

207
-continued
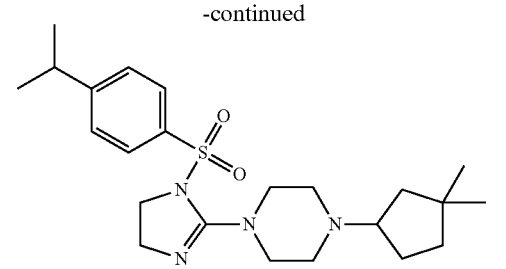
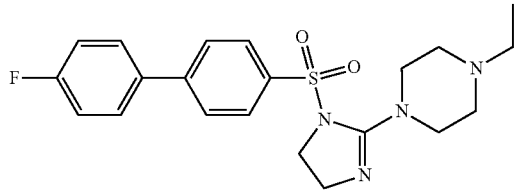
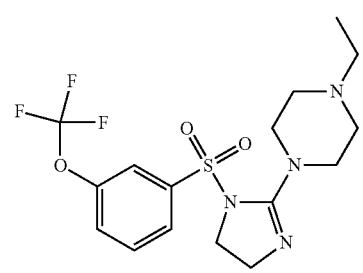
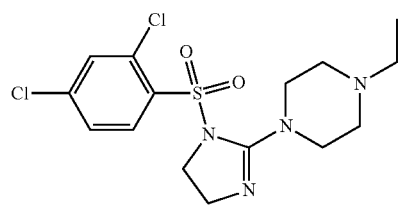
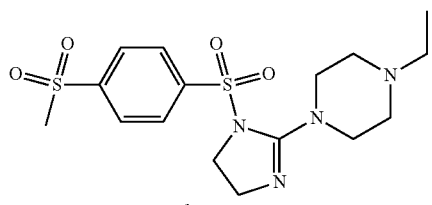
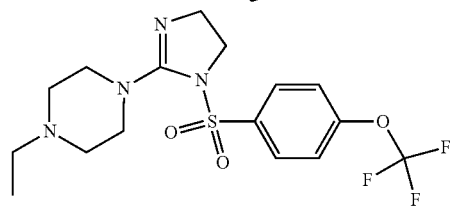
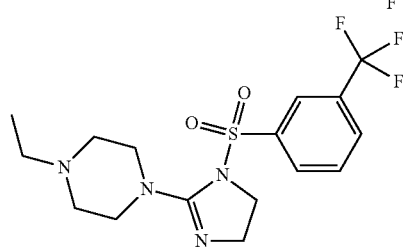
208
-continued
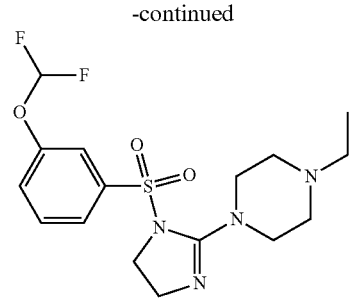
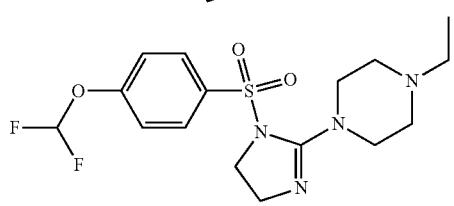
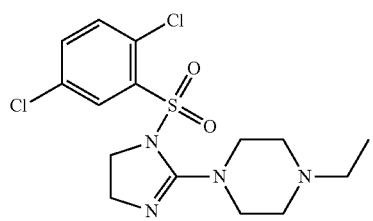
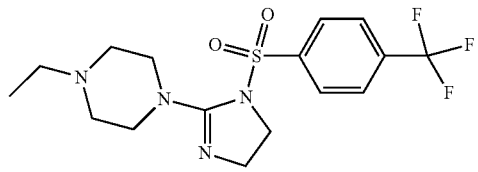
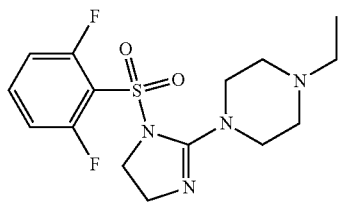
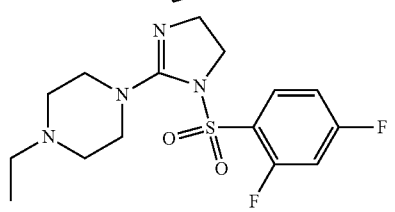
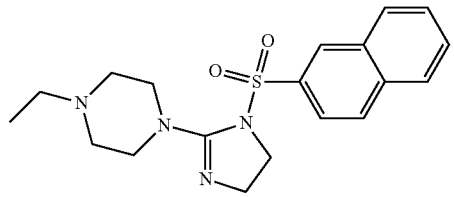

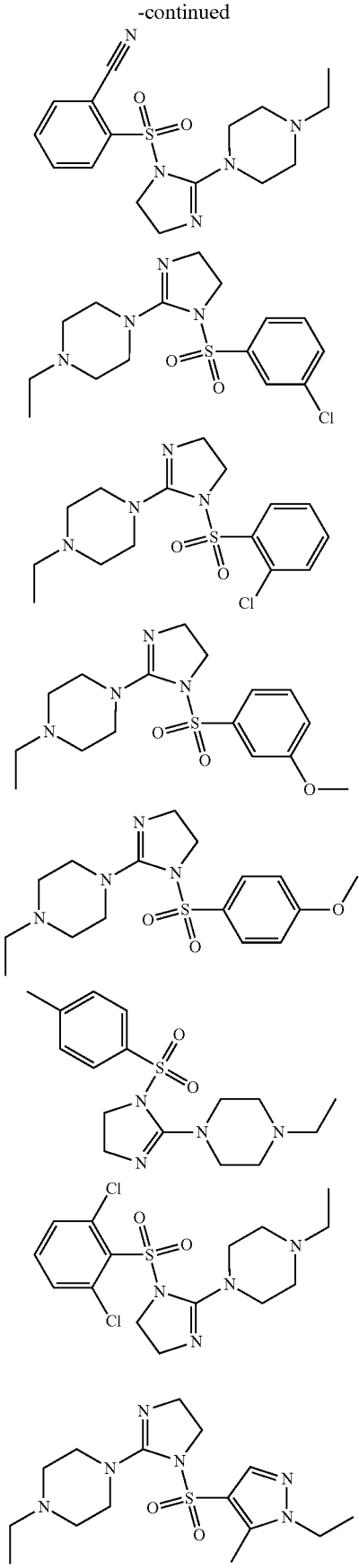
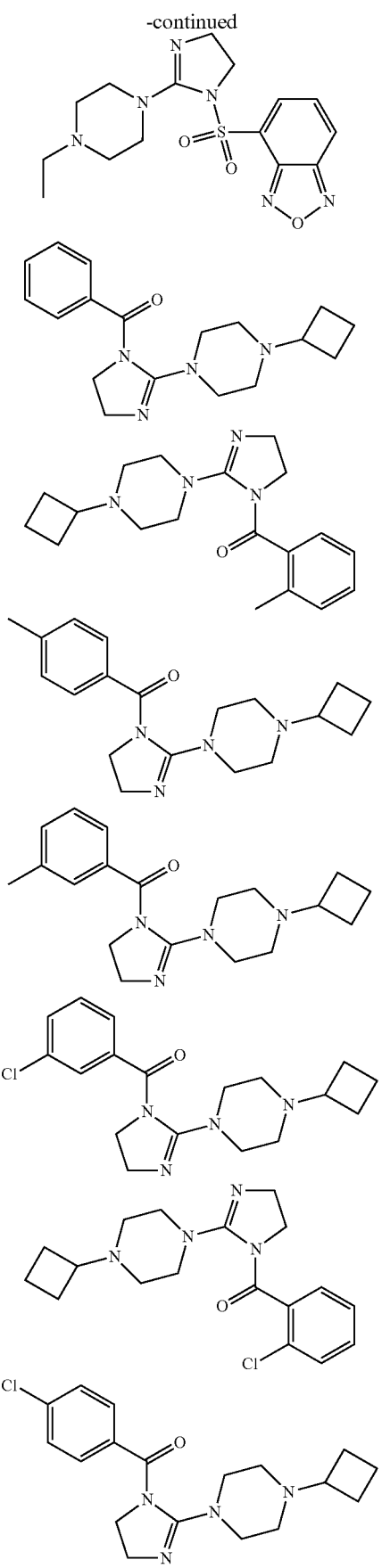

211
-continued
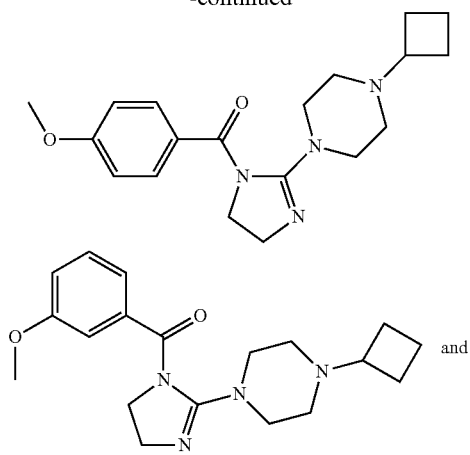
and
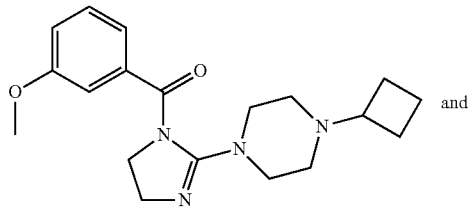
212
-continued
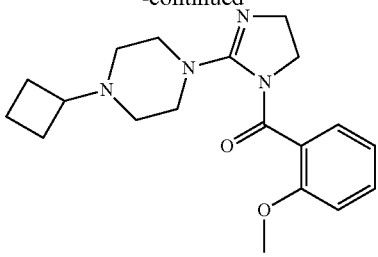
or a salt thereof.
16. A pharmaceutical composition comprising a compound as described in claim 1, or a pharmaceutically acceptable salt thereof, and a pharmaceutically acceptable adjuvant, carrier, or vehicle.
* * * * *

UNITED STATES PATENT AND TRADEMARK OFFICE
CERTIFICATE OF CORRECTION

PATENT NO. : 10,202,354 B2
APPLICATION NO. : 15/643805
DATED : February 12, 2019
INVENTOR(S) : Brian K. Albrecht et al.

Page 1 of 1

It is certified that error appears in the above-identified patent and that said Letters Patent is hereby corrected as shown below:

On the Title Page

Item (72), Inventors, please delete "James Richard Jr. Kiefer," and insert -- James Richard Kiefer Jr., --;

In the Claims

Column 181, Line 4, Claim 1, please delete "or R$_4$ and R$^5$" and insert -- or R$^4$ and R$^5$ --;

Column 182, Line 23, Claim 1, please delete "4-(i        sopropyl)phenyl" and insert -- 4-(isopropyl)phenyl --;

Column 185, Line 46, Claim 10, please delete "-N        (R$^b$)-S(O)-R$^b$" and insert -- -N(R$^b$)-S(O)-R$^b$ --;

Column 202, Lines 20-30, Claim 15, please delete the following compound:

" 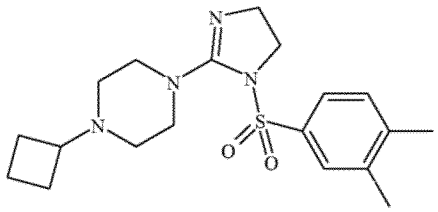 " and insert -- 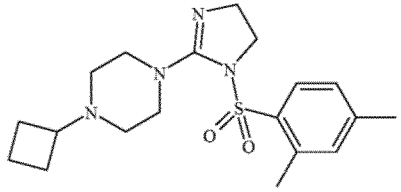 -- therefor.

Signed and Sealed this
Thirtieth Day of April, 2019

Andrei Iancu
*Director of the United States Patent and Trademark Office*